US007998485B2

(12) United States Patent
Nauwynck et al.

(10) Patent No.: US 7,998,485 B2
(45) Date of Patent: Aug. 16, 2011

(54) SIALOADHESIN-RELATED COMPOSITIONS AND METHODS

(75) Inventors: Hans Nauwynck, Zomergem (BE); Peter Delputte, Gent Oost-Vlaanderen (BE)

(73) Assignee: Universiteit Gent, Ghent (BE)

( * ) Notice: Subject to any disclaimer, the term of this patent is extended or adjusted under 35 U.S.C. 154(b) by 50 days.

(21) Appl. No.: 12/227,106

(22) PCT Filed: May 11, 2007

(86) PCT No.: PCT/IB2007/004499
§ 371 (c)(1),
(2), (4) Date: Nov. 7, 2008

(87) PCT Pub. No.: WO2008/093166
PCT Pub. Date: Aug. 7, 2008

(65) Prior Publication Data
US 2009/0104147 A1      Apr. 23, 2009

Related U.S. Application Data

(60) Provisional application No. 60/799,566, filed on May 11, 2006.

(51) Int. Cl.
*A61K 39/385* (2006.01)
*A61K 39/39* (2006.01)
*A61K 39/145* (2006.01)
*C12N 15/00* (2006.01)
(52) U.S. Cl. ............. 424/192.1; 424/193.1; 424/196.11; 424/210.1; 424/278.1; 435/317.1; 435/440
(58) Field of Classification Search .................. None
See application file for complete search history.

(56) References Cited

U.S. PATENT DOCUMENTS

| 6,756,044 B1 * | 6/2004 | Roelvink et al. ............ 424/281.1 |
| 2003/0157113 A1 | 8/2003 | Tenman |
| 2007/0231266 A1 | 10/2007 | Low et al. |
| 2008/0138396 A1 | 6/2008 | Low et al. |

FOREIGN PATENT DOCUMENTS

| WO | WO 91/15232 | * | 10/1991 |
| WO | WO 92/16212 | * | 10/1992 |
| WO | WO 94/00143 | * | 1/1994 |
| WO | WO 95/22618 |   | 8/1995 |
| WO | WO 98/06733 |   | 2/1998 |
| WO | WO 99/61463 |   | 5/1999 |
| WO | WO 99/61463 |   | 12/1999 |
| WO | WO 01/12646 |   | 2/2001 |
| WO | WO 01/36005 |   | 5/2001 |
| WO | WO 01/60850 |   | 8/2001 |
| WO | 02087424 A |   | 11/2002 |
| WO | WO 02/087424 |   | 11/2002 |
| WO | 2004100983 A |   | 11/2004 |
| WO | WO 2004/100983 A |   | 11/2004 |
| WO | WO 2005/042573 | * | 5/2005 |
| WO | WO 2007/022494 |   | 2/2007 |
| WO | WO 2007/056525 |   | 5/2007 |

OTHER PUBLICATIONS

Hartnell et al (Blood 97:288-296, 2001).*
Vanderheijden et al (Journal of Virology 77:8207-8215, 2003).*
Deputte et al., Porcine Arterivirus infection of alveolar macrophages in mediated by sialic acid on the virus, Journal of Virology, Aug. 2004, pp. 8094-8101, vol. 78, No. 15.
Crocker et al., Sialoadhesin Binds Preferentially to Cells of the Granulocytic Lineage, Journal of Clinical Investigation, 1995, pp. 635-643, vol. 95, No. 2.
Kalovidouris et al., Constructing carbohydrate-based multivalent scaffolds for studying carbohydrate-protein interactions, Database Dissabs, Oct. 13, 2003.
Ducreux et al., The inhibitory potencies of monoclonal antibodies to the macrophage adhesion molecule sialoadhesin are greatly increased following PEGylation, Bioconjugate Chemistry, Oct. 1, 2008, pp. 2088-2094, vol. 19. No. 10.
PCT International Search Report, PCT/IB2007/004499, dated Oct. 1, 2009.
PCT International Preliminary Report on Patentability, PCT/IB2007/004499, dated Oct. 13, 2009.
U.S. Appl. No. 11/781,558, filed Jul. 23, 2007, Pensaert et al., Nucleic Acid Encoding Polypeptide Involved in Cellular Entrance of the PRRS Virus.
U.S. Appl. No. 12/452,675, filed Jan. 13, 2010, Delputte et al., Permissive Cells and Uses Thereof.
Deputte et al., Porcine Arterivirus infection of alveolar macrophages in mediated by sialic acid on the virus, Journal of Virology, Aug. 2004, pp. 8094-8101, vol. 78, No. 15.
Crocker et al., Sialoadhesin Binds Preferentially to Cells of the Granulocytic Lineage, Journal of Clinical Investigation, 1995, pp. 635-643, vol. 95, No. 2.
Ducreux et al., The inhibitory potencies of monoclonal antibodies to the macrophage adhesion molecule sialoadhesin are greatly increased following PEGylation, Bioconjugate Chemistry, Oct. 1, 2008, pp. 2088-2094, vol. 19, No. 10.
Duan, et al.: Identification of a Putative Receptor for Procine Reproductive and Respiratory Synddrome Virus on Procine Alveolar Macrophages; Journal of Virology; May 1998; vol. 72, No. 5; pp. 4520-4523.

(Continued)

*Primary Examiner* — Mary E Mosher
(74) *Attorney, Agent, or Firm* — TraskBritt

(57) ABSTRACT

Methods of delivering a cargo moiety to a cell is provided according to embodiments of the present invention which includes contacting a cell expressing sialoadhesin with a conjugate including a sialoadhesin binding moiety and a cargo moiety. The sialoadhesin binding moiety binds to the sialoadhesin expressed by the cell and is internalized along with the cargo, delivering the cargo moiety to the cell. Particular methods provided by the present invention include induction or enhancement of sialoadhesin expression in a cell which naturally produces little or no sialoadhesin. Induction or enhancement of sialoadhesin expression includes transfection of a sialoadhesin expression construct and/or administration of an agent effective to induce or enhance sialoadhesin expression. Methods and compositions for stimulating an immune response in a subject are detailed. Particular methods and compositions for stimulating an immune response to a virus are provided by the present invention.

38 Claims, 7 Drawing Sheets

OTHER PUBLICATIONS

Bullido et al., Monoclonal antibodies specific for porcine monocytes/macrophages: macrophage heterogeneity in the pig evidenced by the expression of surface antigens, Tissue Antigens, 1997, pp. 403-414, vol. 49.

Crocker et al., Purification and properties of sialoadhesin, a sialic acid-binding receptor of murine tissue macrophages, The EMBO Journal, 1991, pp. 1661-1669, vol. 10, No. 7.

Crocker et al., Sialoadhesin, a macrophage sialic acid binding receptor for haemopoietic cells with 17 immunoglobulin-like domains, The EMBO Journal, 1994, pp. 4490-4503, vol. 13, No. 19.

Crocker et al., Mouse Macrophage Hemagglutinin (Sheep Erythrocyte Receptor) with Specificity for Sialylated Glycoconjugates Characterized by a Monoclonal Antibody, J. Exp. Med., Apr. 1989, pp. 1333-1346, vol. 169, The Rockefeller University Press.

Crocker et al., Properties and Distribution of a Lectin-like Hemagglutinin Differentially Expressed by Murine Stromal Tissue Macrophages, J. Exp. Med., Dec. 1986, pp. 1862-1875, vol. 164, The Rockefeller University Press.

Duan et al., Identification of a Putative Receptor for Porcine Reproductive and Respiratory Syndrome Virus on Porcine Alveolar Macrophages, Journal of Virology, May 1998, pp. 4520-4523, vol. 72, No. 5.

Nath et al., Macrophage-tumour cell interactions: identification of MUC1 on breast cancer cells as a potential counter-receptor for the macrophage-restricted receptor, sialoadhesin, Imunology, 1999, pp. 213-219.

Nauwynck et al., Virus production and viral antigen expression in porcine blood monocytes inoculated with pseudorabies virus, Arch Virol, 1994, pp. 69-79, vol. 137.

Pescovitz et al., Preparation and Characterization of Monoclonal Antibodies Reactive with Porcine PBL, The Journal of Immunology, Jul. 1984, pp. 368-375.

Van Der Stede et al., Enhanced induction of the IgA response in pigs by calcitriol after intramuscular immunization, Vaccine, 2001, pp. 1870-1878, vol. 19.

Van Reeth et al., Investigations of the efficacy of European H1N1- and H3N2-based swine influenza vaccines against the novel H1N2 subtype, The Veterinary Records, Jul. 5, 2003, pp. 9-13, vol. 153.

Verdonck et al., Fimbriae of enterotoxigenic *Escherichia coli* function as a mucosal carrier for a coupled heterologous antigen, Journal of Controlled Release, 2005, pp. 243-258, vol. 104.

* cited by examiner

US 7,998,485 B2

SIALOADHESIN-RELATED COMPOSITIONS AND METHODS

REFERENCE TO RELATED APPLICATIONS

This application is a national phase entry under 35 U.S.C. §371 of International Patent Application PCT/IB2007/004499, filed May 11, 2007, published in English as International Patent Publication WO 2008/093166 A2 on Aug. 7, 2008, which application claims priority to U.S. Provisional Patent Application Ser. No. 60/799,566, filed May 11, 2006, the entire content of which is incorporated herein by reference.

FIELD OF THE INVENTION

The present invention relates generally to compositions and methods for targeted cargo delivery to a cell. In particular, the present invention relates to compositions and methods for targeted cargo delivery to a sialoadhesin-expressing cell.

BACKGROUND OF THE INVENTION

Specific delivery of a substance to a targeted cell is desirable for various purposes, including pharmacological intervention as well as clinical and research bioassays.

Targeted delivery is particularly desirable where exposure of non-targeted cells to a substance to be delivered is preferably avoided, such as where exposure of non-targeted cells can result in undesirable side effects. For example, a therapeutic intervention may require elimination, inhibition, stimulation and/or activation of a particular cell or cell type. In such a situation, it is advantageous to deliver a substance effective to achieve a desired result preferentially to a targeted cell in order to avoid an undesirable side effect such as inhibition or stimulation of non-targeted cells and cell types. Targeted delivery also allows use of less of the substance to be delivered to achieve a desired effect.

There is a continuing need for compositions and methods for achieving targeted delivery of a substance to a cell.

SUMMARY OF THE INVENTION

A method of delivering a cargo moiety to a cell is provided according to embodiments of the present invention which includes contacting a cell expressing sialoadhesin with a conjugate including a sialoadhesin binding moiety and a cargo moiety. The sialoadhesin binding moiety binds to the sialoadhesin expressed by the cell and is internalized along with the cargo moiety, thereby delivering the cargo moiety to the cell. Cells naturally expressing sialoadhesin are known, particularly including macrophages. Particular methods provided by the present invention include induction or enhancement of sialoadhesin expression in a cell which naturally produces little or no sialoadhesin. Induction or enhancement of sialoadhesin expression includes transfection of a sialoadhesin expression construct and/or administration of an agent effective to induce or enhance sialoadhesin expression. Expression of sialoadhesin is determined by any of various methods including binding of sialoadhesin-specific antibodies, detection of sialoadhesin encoding mRNA and the like.

In particular embodiments, the sialoadhesin binding moiety is an antibody which binds substantially specifically to sialoadhesin. Such antibodies include, but are not limited to, mouse anti-porcine sialoadhesin mAb 41D3, mouse anti-human sialoadhesin mAb 7D2 and mouse anti-porcine sialoadhesin mAb MCA2316.

In further embodiments of a method according to the present invention a sialoadhesin binding moiety is a sialoadhesin ligand.

A cargo moiety included in a conjugate is a stimulator of a response in the cell in particular embodiments. For example, in one embodiment, a conjugate is a stimulator of an immune response in the cell. In further particular embodiments, a conjugate which stimulates an immune response in the cell stimulates an immune response in a subject. Thus, a cargo moiety may be an antigen.

Also provided are embodiments of the present invention in which the cargo moiety is an inhibitor of the cell. For example, a cargo moiety included in a conjugate is a cytotoxic agent in particular embodiments. A cytotoxic agent is exemplified by, but not limited to, a ribosome inactivating protein. A specific cytotoxic agent which is a ribosome inactivating protein is saporin.

In further embodiments, a cargo moiety is an antimicrobial agent. An antimicrobial agent included in a conjugate is effective to inhibit a microbe such as, but not limited to, a bacterium, a virus, a fungus or a protozoan.

A cytokine is a cargo moiety in certain embodiments of an inventive method. Optionally, the cargo moiety is a nucleic acid. A delivered nucleic acid is optionally an expression construct. Further optionally an expression construct is included in a vector, such as, but not limited to, a bacterial plasmid or a viral vector. A nucleic acid cargo is optionally an antisense construct such as, but not limited to, an antisense oligonucleotide, an siRNA, an shRNA or an expression vector for expressing an antisense nucleic acid.

Where a cargo moiety is an antigen, the antigen is optionally a protein, a peptide, a glycoprotein or a glycopeptide. Such antigens may be synthetic, such as, but not limited to, recombinantly produced or chemically synthesized proteins or peptides; or natural, such as, but not limited to, an antigen isolated from a cell, virus or organism. In particular embodiments, a cargo which is an antigen is a viral protein, a viral peptide, a viral glycoprotein or a viral glycopeptide.

In particular embodiments, an antigen conjugated to a sialoadhesin binding moiety is an influenza virus haemagglutinin or an antigenic portion thereof. A specific antigenic portion of an influenza virus haemagglutinin is encoded by SEQ ID No. 3 or a homologue thereof. In particular embodiments, a virus haemagglutinin included in a conjugate of the present invention is an influenza virus haemagglutinin of SEQ ID No. 4 or a homologue thereof.

A cell contacted by a conjugate for delivery of a cargo to the cell is in vitro, or in vivo.

In further embodiments of methods according to the present invention a cell is treated with a cytokine effective to induce or enhance expression of sialoadhesin in the cell. For example, a cell treated with a cytokine effective to induce or enhance expression of sialoadhesin is a monocyte, a monocyte cell line, a macrophage and a macrophage cell line. In particular embodiments, a human cell and/or a human-derived cell line is treated with a cytokine effective to induce or enhance expression of sialoadhesin. An example of a human-derived cell line is human monocyte cell line THP-1. In further particular embodiments, a porcine cell and/or a porcine-derived cell line is treated with a cytokine effective to induce or enhance expression of sialoadhesin. Suitable cytokines effective to induce or enhance expression of sialoadhesin include interferon alpha (IFN-alpha), and a combination of tumor necrosis factor-alpha (TNF-alpha) and interferon-gamma (IFN-gamma).

Compositions are provided according to the present invention which include a sialoadhesin binding moiety conjugated to a cargo moiety. The sialoadhesin binding moiety is an antibody or a sialoadhesin ligand in particular embodiments of a composition of the present invention.

A method of stimulating an immune response in a subject to a viral antigen is provided according to the present invention which includes administering a composition including a sialoadhesin binding moiety conjugated to a viral antigen to a subject. In particular embodiments, a cargo which is a viral antigen is a viral protein, a viral peptide, a viral glycoprotein or a viral glycopeptide.

In particular embodiments, a viral antigen conjugated to a sialoadhesin binding moiety is an influenza virus haemagglutinin or an antigenic portion thereof. A specific antigenic portion of an influenza virus haemagglutinin is encoded by SEQ ID No. 3.

Also provided are methods and compositions in which a viral antigen conjugated to a sialoadhesin binding moiety is a Porcine Reproductive and Respiratory Syndrome virus, a Porcine Reproductive and Respiratory Syndrome virus protein or an antigenic portion of a Porcine Reproductive and Respiratory Syndrome virus protein.

Optionally a sialoadhesin binding moiety is an antibody or a sialoadhesin ligand. Specific antibodies included in a conjugate according to the present invention include monoclonal antibody 41D3, monoclonal antibody 7D2 and monoclonal antibody MCA2316.

A conjugate including a sialoadhesin binding moiety and a cargo is produced by chemical bonding between the sialoadhesin binding moiety and cargo in particular embodiments. In further embodiments, a conjugate including a sialoadhesin binding moiety and a cargo is produced by recombinant techniques, including expression of a fusion protein.

In particular embodiments, a method of stimulating an immune response according to the present invention includes administering an amount of a cytokine effective to induce or enhance expression of sialoadhesin in a cytokine responsive cell in the subject. A specific cytokine effective to induce or enhance expression of sialoadhesin in an INF-alpha responsive cell is INF-alpha. A, INF-alpha responsive cell is identified by methods known in the art including, but not limited to, detection of an INF-alpha receptor. Particular INF-alpha responsive cells include monocytes, such as, but not limited to, human monocytes, and monocyte-derived cell lines, such as, but not limited to, human monocyte cell line THP-1. A macrophage is a further example of a INF-alpha responsive cell.

A method of stimulating an immune response to an antigen in a subject is provided according to embodiments of the present invention which includes administering a composition including a sialoadhesin binding moiety conjugated to an antigen to a subject.

In further embodiments of the present invention, a method of screening a compound for sialoadhesin binding activity and/or sialoadhesin binding stimulated cell internalization activity is provided which includes administering a cytokine effective to induce or enhance sialoadhesin expression; administering the compound; and performing an assay for specific binding of the compound to sialoadhesin and/or performing an assay for sialoadhesin binding stimulated cell internalization activity. In particular embodiments, the cytokine effective to induce or enhance sialoadhesin expression is INF-alpha. A compound is illustratively an anti-sialoadhesin antibody or a sialoadhesin ligand. Examples of assays to determine specific binding of the compound include incubation of the compound with the cell under typical sialoadhesin binding moiety binding conditions, such as under substantially physiological conditions, and detection of binding. Detection of binding may include, for instance, detection of a reporter bound to the compound. Detection of internalization of the compound is illustratively accomplished by permeabilization of a cell and incubation with a reagent that binds to the compound, such as, but not limited to, an antibody, followed by detection of the reagent.

A method of transfecting a cell is provided which includes administering a sialoadhesin binding moiety conjugated to an expression construct to a cell expressing sialoadhesin. The cell expressing sialoadhesin is a cell transfected with a sialoadhesin expression construct in particular embodiments. In further embodiments, the cell is a cell line stably expressing sialoadhesin. In yet further embodiments, the cell is treated with a cytokine to induce or enhance sialoadhesin expression.

A kit for delivering a cargo to a cell is provided by the present invention which includes a cell expressing sialoadhesin and a sialoadhesin binding moiety. Optionally, a provided kit includes a reagent for use in conjugation of a cargo to the sialoadhesin binding moiety. A cell included in an inventive kit is optionally a cell line. In a further option the sialoadhesin binding moiety included in the kit is conjugated to a cargo. In particular embodiments, the cargo conjugated to the sialoadhesin binding moiety is an expression construct.

A method of treating a pathological condition in a subject is provided including
administering a therapeutically effective amount of a sialoadhesin binding moiety conjugated to a therapeutic cargo moiety to the subject, wherein the therapeutic cargo moiety is delivered to a sialoadhesin expressing cell in the subject, thereby treating the pathological condition. In particular embodiments, the therapeutic cargo moiety is an inhibitor of the cell, such as, but not limited to, a cytotoxic agent. An example of an inhibitor is saporin. A pathological condition treated according to an inventive method is characterized by presence of a pathogen in the cell in particular embodiments. In further embodiments, the pathological condition is an autoimmune disease or cancer. An included cargo moiety is an inhibitor of macrophage activation and/or inflammation in embodiments for treating autoimmune disease. Such inhibitors include, but are not limited to, an inhibitor of macrophage activation and/or inflammation such as IL-10, TGF-beta, 6-(methylsulfinyl)hexyl isothiocyanate, a sesquiterpene chromones, and a combination thereof.

DETAILED DESCRIPTION OF THE INVENTION

Figure 1:
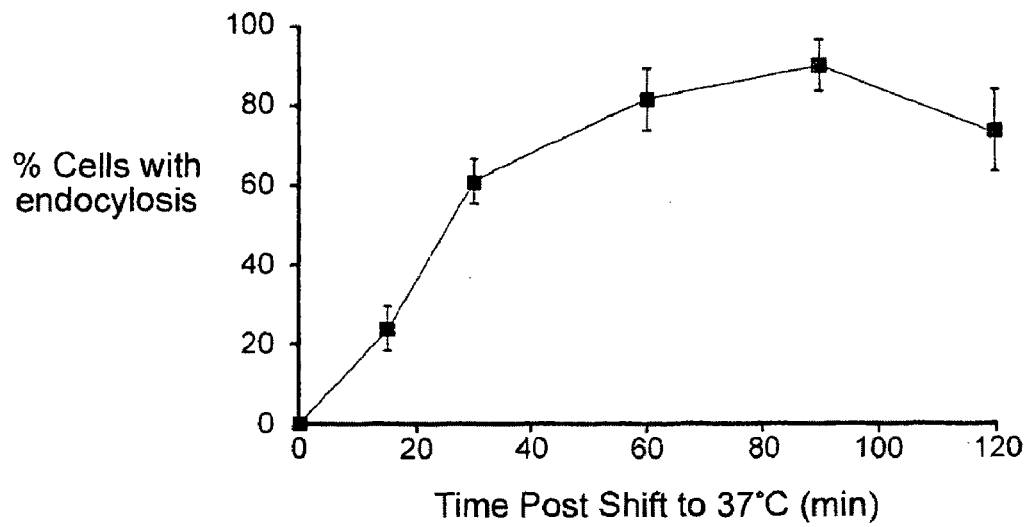
FIG. 1 is a graph illustrating specific binding and internalization of a sialoadhesin binding moiety at different times after incubation of macrophages at 37° C. with mAb 41D3.

Few effective targeted delivery compositions and methods are capable of delivering a desired cargo to a targeted cell. A particular receptor, sialoadhesin (Sn), is identified as a target for targeted delivery compositions and methods according to the present invention.

Sialoadhesin, also called sheep erythrocyte receptor (SER) or sialic acid binding immunoglobulin-like lectin 1 (Siglec-1) belongs the Siglec family of 1-type lectins and is expressed exclusively on subsets of macrophages that are found mostly in spleen, lymph nodes, bone marrow, liver, colon and lungs but not on blood monocytes as described in Crocker, P. R., et al., 1991, Embo J 10:1661-9; Crocker, P. R., et al., 1994, Embo J 13:4490-503; Duan, X., et al., 1998, J Virol 72:4520-3; Hartnell, A., et al., 2001, Blood 97:288-96; and Vanderheijden, N., et al., 2003, J Virol 77:8207-15. High Sn expression has also been detected on inflammatory macrophages in tissues from patients with rheumatoid arthritis, and on infiltrating macrophages that make close contact with breast carcinoma cells as described in Hartnell, A., et al., 2001, Blood 97:288-96; and Nath, D., et al., 1999, Immunology 98:213-9. Sialoadhesin (Sn) was initially identified as a sialic acid dependent-sheep erythrocyte receptor (SER) on resident bone marrow cells of mice, and is now also characterized in a number of mammals including human, rat and swine, described in Crocker, P. R., and S. Gordon, 1989, J Exp Med 169:1333-46; Crocker, P. R., and S. Gordon, 1986, J Exp Med 164:1862-75; and Vanderheijden, N., et al., 2003, J Virol 77:8207-15.

A conjugate composition is provided according to the present invention which includes a sialoadhesin binding moiety conjugated to a cargo moiety. Conjugate compositions including a sialoadhesin binding moiety conjugated to a cargo moiety may be used to deliver a cargo moiety to a sialoadhesin expressing cell.

The term "nucleic acid" as used herein refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid. It is appreciated that, due to the degeneracy of the genetic code, multiple nucleic acids encode an identical polypeptide.

The terms "protein," "polypeptide" and "peptide" are used interchangeably herein to refer to two or more amino acids linked by peptide bonds. The term protein includes modified proteins and peptides exemplified by, but not limited to, glycosylated, phosphorylated, ubiquitinated, myristoylated, palmitoylated, and acetylated proteins and peptides.

The term "expression construct" refers to a recombinant or synthetic nucleic acid including a nucleic acid encoding a protein, and one or more regulatory nucleic acid sequences operably linked to the nucleic acid encoding the protein that direct transcription of at least the nucleic acid encoding the protein in a cell.

The term "transfection" refers to introduction of an exogenous nucleic acid into a cell.

The term "operably linked" refers to a nucleic acid in functional relationship with a second nucleic acid. In general, operably linked nucleic acids are contiguous. An exception is operable linkage of an enhancer, which may be non-contiguous and in functional relationship with another nucleic acid.

The term "vaccine" refers to a pharmaceutical composition including at least one antigen that stimulates an immune response in a subject.

The term "vaccination" refers to administration of a vaccine to stimulate an immune response in a subject. Vaccination of a subject may be performed to prevent or treat a disease in the subject.

The term "antigen" refers to a molecule that includes one or more epitopes that stimulate an antigen-specific response by a component of a host immune system, such as an immune cell. An antigen can include peptide, proteins, glycoproteins, polysaccharides, lipids, gangliosides, portions thereof, and combinations thereof.

The term "stimulation of an immune response" refers to eliciting or enhancement of an immune response.

The term "homologue" refers to a protein characterized by an amino acid sequence and/or structural homology to a reference protein. In general, a homologue of the reference protein is at least 50%, preferably at least 75%, more preferably at least 80%, 85%, 90%, 91%, 92%, 93%, 94%, 95%, 96%, 97%, 98%, 99%, or greater, identical to the reference protein. A homologue is illustratively an orthologue of the reference protein isolated from another species. A homologue includes a protein having one or more amino acid substitutions, deletions or insertions compared with the reference protein.

The term "biologically active homologue" of a reference protein refers to a protein characterized by an amino acid sequence and/or structural homology to the reference protein which has substantially similar functional, structural, and/or biochemical properties compared to the reference protein, particularly the naturally occurring reference protein.

One type of homologue is a conservatively modified protein and/or fragment thereof. A conservatively modified protein or fragment thereof is a protein or peptide which includes substitution of an amino acid with a chemically similar amino acid. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate and glutamate; basic amino acids include histidine, lysine and arginine; aliphatic amino acids include isoleucine, glycine, leucine and valine; aromatic amino acids include phenylalanine, tyrosine and tryptophan; polar amino acids include aspartate, glutamate, histidine, lysine, asparagine, glutamine, arginine, serine, threonine and tyrosine; hydrophobic amino acids include alanine, cysteine, phenylalanine, glycine, isoleucine, leucine, methionine, proline, valine, tyrosine and tryptophan; and hydrophilic amino acids include asparagine, aspartate, glutamine, glutamate, histidine, serine and threonine. Amino acids may also be described in terms of relative size, alanine, cysteine, aspartate, glycine, asparagine, proline, threonine, serine, valine, all typically considered to be small.

Percent identity is determined by comparison of amino acid or nucleic acid sequences, including a reference sequence and a putative homologue sequence. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S, Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, publicly available from the National Center for Biotechnology Information, for instance at http://www.ncbi.nlm.nih.gov.

Sialoadhesin Binding Moiety

A sialoadhesin binding moiety binds specifically to sialoadhesin. The term "binds specifically" as used herein is intended to indicate that a sialoadhesin binding moiety included in an inventive conjugate interacts preferentially with sialoadhesin and does not significantly interact with other proteins or other molecules. A sialoadhesin binding moiety conjugated to a cargo moiety has sialoadhesin-specific binding activity and thus confers sialoadhesin-specific binding activity on an inventive conjugate. In particular, a sialoadhesin binding moiety conjugated to a cargo moiety binds to an extracellular portion of sialoadhesin expressed by a cell. Further, a sialoadhesin binding moiety binds specifically with sialoadhesin present in the cell membrane of a target cell and stimulates uptake of an inventive conjugate into the cell In one embodiment, a sialoadhesin binding moiety is an antibody. The term "antibody" refers to polyclonal antibodies, monoclonal antibodies (mAbs), chimeric antibodies, humanized antibodies, as well as antigen binding antibody fragments and molecules having antigen binding functionality.

The term "antibody" includes an intact immunoglobulin having four polypeptide chains, two heavy (H) chains and two light (L) chains linked by disulfide bonds. The term "antibody" also includes sialoadhesin binding antibody fragments illustratively including, but not limited to, such fragments as an Fab fragment, an Fab' fragment, an F(ab')2 fragment, an Fd fragment, an Fv fragment, an scFv fragment, and a domain antibody (dAb).

An anti-sialoadhesin antibody and/or sialoadhesin binding antibody fragment included in a conjugate of the present invention is capable of binding sialoadhesin and stimulating uptake of the conjugate into the cell.

An antibody or antibody fragment included in a conjugate according to the invention specifically binds to sialoadhesin. A preferred sialoadhesin binding moiety binds sialoadhesin with greater affinity than it binds another member of the Siglec family.

A preferred sialoadhesin binding moiety included in an inventive conjugate is characterized by specific binding activity for sialoadhesin of at least about $1 \times 10^5$ $M^{-1}$. In further embodiments, a preferred sialoadhesin binding moiety has a specific binding affinity for sialoadhesin of at least about $1 \times 10^6$ $M^{-1}$. In still further embodiments, a preferred sialoadhesin binding moiety has a specific binding affinity for sialoadhesin of at least about $1 \times 10^7$ $M^{-1}$.

Anti-sialoadhesin antibodies and sialoadhesin binding antibody fragments may be provided by any method, illustratively including, but not limited to, immunization, isolation and purification, enzymatic cleavage of an intact immunoglobulin, chemical synthesis of a desired sialoadhesin binding peptide or protein, production by recombinant nucleic acid technology. Combinations of such methods may also be used.

An anti-sialoadhesin antibody can be made by immunization using as an antigen a full length sialoadhesin or a peptide fragment of sialoadhesin. Such proteins and peptides may be, illustratively a human, pig, sheep, rat, mouse, or other sialoadhesin protein or peptide. Exemplary human, mouse and porcine sialoadhesin protein sequences and nucleic acid sequences encoding human, mouse and porcine sialoadhesins included herein as SEQ ID No. 5, SEQ ID No. 6, SEQ ID No. 7, SEQ ID No. 8, SEQ ID No. 9, and SEQ ID No. 10.

Extracellular portions of sialoadhesin from various species have been characterized, as have sialic acid binding sites, as exemplified in Nath, D. et al., J. Biol. Chem., 270:26184-26191, 1995; Vinson, M. et al., J. Biol. Chem., 271:9267-9272, 1996; Hartnell, A. et al., Blood, 97:288-296; and Vanderheijden, N. et al., 2003, J. Virol. 77:8207-15. For example, an extracellular portion of human sialoadhesin extends from amino acid 1-1642, an extracellular portion of porcine sialoadhesin extends from amino acid 1-1643 and an extracellular portion of mouse sialoadhesin extends from amino acid 1-1638, each with reference to the sequences described herein. A sialoadhesin fragment used as an antigen in preparation of a sialadhesin binding antibody preferably includes one or more Ig-like domains.

Antigens may be prepared by any of various methods, including isolation from natural sources, recombinant production or by chemical synthetic techniques. Sialoadhesin proteins and peptides for use as antigens in preparation of a sialadhesin binding antibody are similarly prepared by any of various techniques.

A peptide portion of a sialoadhesin or other antigen may be made more immunogenic if desired by linkage to a carrier molecule such bovine serum albumin or keyhole limpet hemocyanin. Such a linkage may be accomplished by any of various techniques, illustratively including, but not limited to, conjugation and expression of a fusion protein.

Recombinantly expressed proteins and peptides, such as, but not limited to, sialoadhesin and sialoadhesin fragments, may be tagged to allow for easier isolation. For instance, such proteins and peptides may be Fc-tagged.

Antibodies, antigen binding fragments and methods for their generation are known in the art and such antibodies, antigen binding fragments and methods are described in further detail, for instance, in Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002, particularly chapter 11; J. D. Pound (Ed.) Immunochemical Protocols, Methods in Molecular Biology, Humana Press; 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975).

The term "antigen" in the context of making a sialoadhesin binding moiety refers to sialoadhesin or an antigenic peptide portion thereof. In a particular embodiment, an antigenic portion of sialoadhesin includes a portion of sialoadhesin present external to a cell expressing sialoadhesin. Such a portion preferably includes a sialic acid binding domain.

An antibody which is a sialoadhesin binding moiety may be made using a native sialoadhesin, such as exemplified by amino acid sequences appended hereto, and/or peptide fragments thereof, as an antigen. An antibody which is a sialoadhesin binding moiety may be also be made using a sialoadhesin homologue, modified sialoadhesin and/or fragment thereof as an antigen.

In a specific embodiment, a sialoadhesin binding moiety is a monoclonal antibody 41D3. Monoclonal antibody 41D3 (mAb 41D3) is a mouse monoclonal anti-porcine sialoadhesin antibody. Monoclonal antibody 41D3 is described in Vanderheijden, N. et al., 2003, J Virol 77:8207-15; and in Duan, X. et al., 1998, J Virol 72:4520-3. A hybridoma producing monoclonal antibody 41D3 was deposited with the CNCM (Collection Nationale de Cultures-de Microorganisms) at the Institute Pasteur, 28, Rue du Docteur Roux, F-75724 Paris Cedex 15 and given Accession number I-2719.

In a further specific embodiment, a sialoadhesin binding moiety is mouse monoclonal antibody 7D2 (mAb 7D2) which binds human sialoadhesin. MAb 7D2 was raised against an Fc fusion protein containing the N-terminal four domains of human sialoadhesin. MAb 7D2 is further described in Hartnell, A. et al., Blood, 97:288-96, 2001 and is commercially available.

Another specific example of a sialoadhesin binding moiety is mouse anti-porcine sialoadhesin monoclonal antibody MCA2316 described, for example, in Bullido, R., Tissue Antigens, 1997, 49(4):403-13 and commercially available.

A sialoadhesin binding moiety is a sialoadhesin ligand in a further embodiment of a conjugate composition according to the present invention. As noted above, sialoadhesin is a sialic acid-binding immunoglobulin-like lectin. Sialoadhesin binds sialic acid, and in particular, α2-3 sialic acid residues and some α2-6 and α2-8 sialic acid residues. Such sialic acid residues illustratively include Siaα2-3Galβ1-3GalNAc; Siaα2-3Galβ1-3GlcNAc; and Siaα2-3Galβ1-4GlcNAc, Siaα2-6Galβ1-3GalNAc and Siaα2-8Neu5Acα2-3Galβ1-3GalNAc. Thus, in an embodiment in which a sialoadhesin binding moiety is a sialoadhesin ligand, a sialoadhesin binding moiety preferably includes a sialylated organic structure such as, but not limited to, a sialylated protein or peptide, lipid, and/or carbohydrate.

In a further embodiment, a sialoadhesin binding moiety includes a natural sialylated ligand for sialoadhesin. A natural sialylated ligand for sialoadhesin is a sialylated structure which occurs naturally and binds sialoadhesin in vivo. Natural sialylated ligands illustratively include CD43, galactose-type C-type lectin 1, and MUC1 antigen. A natural sialylated ligand of sialoadhesin may be isolated from a natural source or recombinantly produced for inclusion in a conjugate composition according to the present invention.

A further natural sialoadhesin ligand is a porcine arterivirus protein.

Cargo Moiety

As noted above, a conjugate composition according to the present invention includes a sialoadhesin binding moiety and a cargo moiety. A cargo moiety is a substance to be delivered to a target cell.

In one embodiment, a cargo moiety is a stimulator of a response in a target cell. For instance, a cargo moiety is optionally a stimulator of an immune response in a macrophage. A cargo moiety may also be a stimulator of nitric oxide production in a target cell.

Examples of cargo moieties which are macrophage stimulators illustratively include interleukin-4, interleukin-10, interleukin-13, macrophage stimulating protein, CD40 ligand, and interferon-gamma. Additional stimulators include lipoteichoic acid, murarnyl tripeptide TNF-alpha, GM-CSF, a lipopolysaccharide and an extracellular matrix protein.

In a particular example, a cargo moiety which is a stimulator of an immune response is an antigen. An antigen included in an inventive conjugate may be any type of antigen, illustratively including, but not limited to, a peptide, a protein, a lipid, a carbohydrate, and combinations of these or other antigenic substances. An antigen may be derived from any source and thus may be an isolated natural substance, a recombinantly produced substance, a chemically synthesized substance, or otherwise provided. The identity of the antigen will depend on the desired result. In general, an antigen is included as a cargo moiety to be delivered to an antigen presenting cell in order to stimulate the immune system of a subject to produce an immune response to the antigen.

In a specific embodiment, an antigen included as a cargo moiety is a porcine arterivirus peptide or protein.

Also provided is a conjugate including a cargo moiety which is an inhibitor of a target cell. Exemplary inhibitors include inhibitors of macrophage activation, inhibitors of inflammation and general cell inhibitors.

Inhibitors of macrophage activation and inflammation are useful as cargo moieties to decrease macrophage activation and inflammation where problematic, such as in autoimmune diseases illustratively including, but not limited to, endotoxemia, multiple sclerosis, rheumatoid arthritis, and lupus erythematosus. Inhibitors of macrophage activation and inflammation include anti-inflammatory cytokines and anti-inflammatory compounds such as, but not limited to, IL-10, TGF-beta, 6-(methylsulfinyl)hexyl isothiocyanate, and sesquiterpene chromones including those isolated from Ferula fukanensis.

In a further embodiment, a cargo moiety which is an inhibitor of a target cell is a cytotoxic agent. A cytotoxic agent may be included in an inventive conjugate for delivery to a cell in order to inhibit or destroy the cell. For example, a macrophage may be targeted for inhibition of destruction by a cytotoxic agent in order to inhibit a macrophage activity, such as an inflammatory activity. In a further example, a cytotoxic agent is delivered to a sialoadhesin expressing cell in order to inhibit a microbial infection. A cytotoxic agent may be any cytotoxic agent which can be conjugated with a sialoadhesin binding moiety to produce a conjugate according to the invention.

Exemplary cytotoxic cargo moieties are drugs used as anti-tumoral agents. Anti-tumoral agents are described, for example, in Goodman et al., Goodman and Gilman's The Pharmacological Basis of Therapeutics, 8th Ed., Macmillan Publishing Co., 1990.

Such drugs illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, droloxifene, dromostanolone, duazomycin, edatrexate, eflornithine, elsamitrucin, enloplatin, enpromate, epipropidine, epirubicin, erbulozole, esorubicin, estramustine, estramustine, etanidazole, etoposide, etoposide, etoprine, fadrozole, fazarabine, fenretinide, floxuridine, fludarabine, fluorouracil, fluorocitabine, fosquidone, fostriecin, fulvestrant, gemcitabine, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-I a, interferon gamma-I b, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, puromycin, pyrazofurin, riboprine, rogletimide, safingol, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vindesine, vinepidine, vinglycinate, vinleurosine, vinorelbine, vinrosidine, vinzolidine, vorozole, zeniplatin, zinostatin, zoledronate, and zorubicin. A cytotoxic cargo moiety may also be a pharmaceutically acceptable salts, esters, amides, hydrates, and/or prodrug of any of these or other cytotoxins.

In a further specific example, a cytotoxic cargo moiety is the cytotoxic ribosome-inactivating protein saporin.

In some embodiments, a toxic agent may be included to inhibit or destroy a pathological microbial organism associated with the cell. For example, bacteria, viruses and protozoa are known to be sequestered within certain cells. Pathogens, illustratively including, but not limited to, *Trypanosoma cruzi, Mycobacterium tuberculosis, Salmonella* sp., *Neisseria meningitidis*, HIV, and Ross River virus, can hide in macrophages from the host's immune system and thereby cause persistent infections as described in Aquaro, S., et al., 2002, Antiviral Res 55:209-25; Brodsky, I. E., et al., 2005, Mol Microbiol 55:954-72; Jones, C., et al., 2003, Mol Microbiol 49:1213-25; Monack, D. M., et al., 2004, J Exp Med 199:231-41; Monteiro, V. G., et al., 2005, Parasitol Res 97:380-5; Rengarajan, J., et al., 2005, Proc Natl Acad Sci U S A 102:8327-32; and Way, S. J., et al., 2002, Virology 301: 281-92. A fungus is a further example of a pathogen which may be present in a host immune system. Thus, in one embodiment of a conjugate composition according to the present invention, a toxic agent effective to inhibit an organism is a cargo moiety delivered to a cell infected by the organism. Such toxic agents illustratively include an antibacterial agent, an antiviral agent, an antifungal agent and an antiprotozoal agent.

Specific examples of antibacterial agents include tetracyclines such as, but not limited to, doxycycline, tetracycline oxytetracycline, demeclocycline, and minocycline; beta-lactams such as, but not limited to, penicillins and cephalosporins; aminoglycosides such as, but not limited to, gentamycin, neomycin and streptomycin; macrolides such as, but not limited to, azithromycin, clarithromycin, lincomycin and erythromycin; nitroimidazoles such as, but not limited to, metronidazole and tinidazole; quinolones such as, but not limited to, cinoxacin, ciprofloxacin, norfloxacin, ofloxacin, and levofloxacin; rifampin, vancomycin, and clindamycin.

Specific examples of antiviral agents include abacavir, acyclovir, amprenavir, aplaviroc, atazanavir, brecanavir, darunavir, delavirdine, dexelvucitabine, didanosine, disoproxil, efavirenz, emtricitabine, enfuvirtide, etravirine, famciclovir, fosamprenavir, ganciclovir, indinavir, lamivudine, lopinavir, maraviroc, nelfinavir, nevirapine, ritonavir, saquinavir, stavudine, tenofovir fumarate, tipranavir, vicriviroc, zalcitabine, and zidovudine.

Specific examples of antiprotozoal agents include azanidazole, chloroquine, metronidazole, nimorazole, omidazole, secnidazole, sinefungin, tenonitrozole, temidazole, tinidazole.

Examples of antifungal agents include azoles illustratively including, but not limited to, miconazole, ketonazole, itraconazole, fluconazole, voriconazole, posaconazole, ravuconazole, terconazole, clotrimazole, sertaconazole, econazole, and fenticonazole; and polyenes illustratively including, but not limited to, natamycin, filipin, nystatin and amphotericin B.

A cargo moiety is a nucleic acid in particular embodiments. A cargo nucleic acid may be DNA, RNA, a polynucleotide, an oligonucleotide, an antisense polynucleotide or oligonucleotide, or siRNA for example. The nucleic acid may encode a protein or peptide, such as an mRNA. A cargo nucleic acid may be linear, circular, supercoiled, single stranded, or double, triple or quadruple stranded In particular embodiments, a cargo nucleic acid includes an expression construct. Delivery of a conjugate including a sialoadhesin binding moiety and a cargo nucleic acid expression construct to a cell expressing sialoadhesin allows expression of an expression construct encoded protein or peptide in the cell.

In further embodiments, a cargo moiety which is an inhibitor or stimulator of a target cell may be a nucleic acid. A nucleic acid inhibitor may encode an inhibitor or stimulator for example. Alternatively, the nucleic acid itself may act as a stimulator or inhibitor.

A nucleic acid cargo is an inhibitor in one embodiment, delivered to a sialoadhesin expressing cell in order to inhibit expression of a protein, and/or transcription and/or translation of a nucleic acid. Illustrative examples of nucleic acid inhibitors include siRNA, an antisense polynucleotide, an antisense oligonucleotide, and a ribozyme. Nucleic acid inhibitors may contain naturally occurring nucleic acids and/or may contain modified nucleic acids such as, but not limited to, phosphorothioates.

Preparation of Nucleic Acid Inhibitors Such as these are Known in the Art, as Described for example in Crooke, S. T., Antisense Drug Technology: Principles, Strategies, and Applications, CRC Press, 2001; and Engelke, D., RNA Interference (RNAi): The Nuts & Bolts of siRNA Technology, DNA Press, 2004.

A nucleic acid inhibitor is delivered to inhibit a desired target in a sialoadhesin expressing cell in vitro, ex vivo and/or in vivo, particularly a macrophage. For example, a nucleic acid inhibitor of function or synthesis of a microbial protein or nucleic acid infecting the sialoadhesin expressing cell is delivered to inhibit microbial infection.

In a further example, a nucleic acid inhibitor is delivered to inhibit a process or function of the sialoadhesin expressing cell. For example, it may be desired to inhibit or eliminate a cell expressing sialoadhesin. Inflammation and/or macrophage activation are processes or functions of a sialoadhesin expressing cell that may be inhibited. An inhibitory nucleic acid cargo, such as a nucleotide analog, may be delivered to inhibit or eliminate such a cell.

A nucleic acid cargo is a stimulator in one embodiment, delivered to a sialoadhesin expressing cell in vitro, ex vivo and/or in vivo in order to stimulate a process or function of the sialoadhesin expressing cell. For example, a nucleic acid cargo includes a plasmid encoding a peptide or protein to which an immune response is desired. The plasmid cargo is delivered to a sialoadhesin expressing macrophage in an organism wherein the peptide or protein is produced and stimulates an immune response.

A plasmid encoding a peptide or protein is preferably an expression construct containing a nucleic acid encoding the peptide or protein along with one or more regulatory nucleic acid sequences required or desirable for expression of the peptide or protein. Such regulatory sequences illustratively include a promoter, an enhancer, a splicing signal, a transcription start site, a transcription termination signal, a polyadenylation signal, an internal ribosome entry site (IRES) and combinations thereof. Suitable promoters include constitutively active promoters, inducible promoters and cell-type specific promoters.

A nucleic acid cargo may be conjugated to a sialoadhesin binding moiety directly or indirectly.

For example, a nucleic acid may be conjugated to a sialoadhesin binding moiety forming a bond between the nucleic acid and the sialoadhesin binding moiety. For example, a carbodiimide, such as 1-ethyl-3-[3-dimethylaminopropyl] carbodiimide hydrochloride (EDC), may be used to form a phosphate ester with a 5' terminal phosphate group present on a nucleic acid and then coupled with an amine group of a sialoadhesin binding moiety to produce a conjugate including a phosphoramidate linkage.

In a further embodiment, a nucleic acid is indirectly conjugated to a sialoadhesin binding moiety, such as through a linker or other molecule. For example, a sialoadhesin binding moiety may be conjugated to a positively charged protein. The positively charged protein may be brought into contact with a nucleic acid to allow charge-based bonding between the positively charged protein and the negatively charged nucleic acid. Examples of positively charged proteins in this context include protamine and polylysine.

A cargo moiety optionally includes a microorganism and/or an antigenic molecule derived from such an organism. For example, a cargo moiety may be a virus, a bacterium, a protozoan, and/or an antigenic molecule derived from such an organism. A microorganism included in such a conjugate is preferably killed or inactivated.

In a preferred embodiment, a viral cargo moiety is an intact virus or portion thereof conjugated to a sialoadhesin binding antibody. Such a virus may be any type of virus, including viruses useful in stimulating an antigenic response to the virus.

In particular embodiments, a virus included in a conjugate as a cargo moiety is a swine viral disease virus. Swine viral disease viruses include Porcine Reproductive and Respiratory Syndrome virus (PRRSV), Porcine circovirus type 2, Parvovirus and Pseudorabies virus. In particular embodiments, a swine viral disease virus is included as a cargo moiety in a conjugate according to the present invention for administration to stimulate an immune response to the virus. A particular swine viral disease virus protein or antigenic portion of a swine viral disease virus protein is included in a conjugate according to the present invention as a cargo moiety in particular embodiments. For example, a PRRSV membrane protein GP3, GP4, GP5 or Matrix (M) and/or an antigenic portion thereof is a cargo moiety in some embodiments of an inventive conjugate. In further embodiments, a cargo moiety is a Porcine circovirus type 2 Capsid protein (CAP), a Parvovirus Capsid protein VP2 and/or a Pseudorabies virus gB, gC and/or gD protein, and/or an antigenic portion thereof. A combination of viral proteins and/or antigenic portions thereof is optionally included as a cargo moiety in embodiments of a conjugate of the present invention.

PRRSVs are exemplified by European type PRRSV Lelystad virus, Accession No. M96262 and American type PRRSV VR-2332, Accession No. U87392.

In further embodiments, a virus included in a conjugate as a cargo moiety is a human viral disease virus. Human viral disease viruses Herpes simplex virus type 1, Herpes simplex virus type 2, Varicella Zoster Virus, Cytomegalovirus, Measles virus, Mumps virus, Rubella virus, Hepatitis A virus, Hepatitis B virus, Hepatitis C virus, Human immunodeficiency virus (HIV), Poliovirus, Human papillomavirus, and Coronaviruses. In particular embodiments, a human viral disease virus is included as a cargo moiety in a conjugate according to the present invention for administration to stimulate an immune response to the virus. A particular human viral disease virus protein or antigenic portion of a human viral disease virus protein is included in a conjugate according to the present invention as a cargo moiety in particular embodiments. For example, a cargo moiety is optionally a Herpes simplex virus type 1 gB, gC and/or gD protein; a Herpes simplex virus type 2 gB, gC and/or gD protein; a Varicella Zoster Virus gH:gL complex, gB, and/or gC protein; a Cytomegalovirus gM:gN complex and/or gB protein; a Measles virus Hemagglutinin protein (H) and/or fusion protein (F); a Mumps virus Hemagglutinin-Neuraminidase protein (HN) and/or fusion protein (F); a Rubella virus Envelope protein E1 and/or E2; a Hepatitis A virus Capsid protein VP1 and/or VP2; a Hepatitis B virus Envelope protein S, M, L and/or HbsAb; a Hepatitis C virus Envelope glycoproteins E1 and/or E2; a Human immunodeficiency virus (HIV) gp120; a Poliovirus VP1, VP2 and/or VP3 protein; a Human papillomavirus L1 protein; a Coronavirus spike protein, such as, but not limited to, SARS Coronavirus Spike protein (S); and/or an antigenic portion of any of these. In particular embodiments, Human papillomavirus L1 protein is a Human papillomavirus type 16, 18, 6 and/or 11 L1 protein and/or an antigenic portion thereof. A combination of viral proteins is optionally included as a cargo moiety in embodiments of a conjugate of the present invention.

Influenza viruses are a major cause of human and animal disease. Influenza viruses are classed and named according to the specific characteristics of two proteins on the surface of the virus, haemagglutinin (also called hemagglutinin) and neuraminidase. At least sixteen different influenza virus subtypes have been identified according to haemagglutin protein characteristics. These subtypes are called H1, H2, H3, H4, H5, H6, H7, H8, H9, H10, H11, H12, H13, H14, H15 and H16. Numerous influenza virus strains of each subtype have been identified and many have been characterized by nucleic acid sequencing and/or protein sequencing of the viral glycoprotein haemagglutinin. Nucleotide and protein sequences of the influenza virus protein haemagglutinin are known in the art and are available to the public via the National Center for Biotechnology Information (NCBI) Entrez protein and nucleotide search and retrieval system which have been compiled from a variety of sources, including GenBank, RefSeq, and PDB, and including SwissProt, PIR, PRF, PDB, genpept and translations from annotated coding regions in GenBank and RefSeq under accession numbers included herein. The protein and nucleic acid sequences associated with the accession numbers included herein characterize influenza virus haemagglutinins suitable for inclusion as a cargo moiety in conjugates according to the present invention.

In particular, protein sequences of influenza virus subtype H1 haemagglutinin suitable for inclusion as a cargo moiety in conjugates according to the present invention have the following accession numbers and are available to the public via the National Center for Biotechnology Information (NCBI) Entrez protein search and retrieval system:

AAF87274; AAF87282; AAF87284; AAN64900; AAN64902; AAN83988; AAQ10372; AAQ10387; AAQ10394; AAT81327; AAT81329; AAT81330; AAT81336; AAT81338; ABB19551; ABB19618; ABB79979; ABC02277; ABD62781; ABD94965; ABD95075; ABD95152; ABD95229; ABD95284; ABD95306; ABF47869; ABF82896; ABG66974; ABI21200; ABI21222; ABJ09327; ABK40028; ABO21716; ABO21724; ABO32992; ABP49327; ABP49382; ABP49481; BAE53729; BAE96533; BAE96534; BAE96536; BAF03629; CAA40728; AAF87278; AAF87279; AAF87280; AAF87281; AAN64903; AAN64904; AAN64905; AAQ10390; AAQ10391; AAR90881; AAT81331; AAT81332; AAT81333; AAT81334; AAT81335; AAT93388; AAY56898; ABA43189; ABB19562; ABB21772; ABC86237; ABD61518; ABD62843; ABD79255; ABD94987; ABD95240; ABD95251; ABD95273; ABF47891; ABF82662; ABF82684; ABF82841; ABF82863; ABF82918; ABI84478; ABI84948; ABI93028; ABJ16686; ABK40006; ABK40557; ABN50917; ABN51066; ABN51088; ABO21709; ABO21723; CAA40730; CAA86563; CAA91082; AAA16808; AAA16813; AAA16880; AAA19935; AAA43142; AAA43153; AAA43168; AAA43170; AAA43171; AAA43175; AAA43231; AAA43240; AAC57415; AAK40318; AAK51344; AAK51345; AAK51347; AAN46827; AAN64894; AAN64896; AAP69688; AAP69691; AAP79971; AAU09400; ABA08519; ABA42247; ABB03123; ABB04972; ABB80045; ABB84190; ABB86887; ABD77675; ABD78071; ABD94789; ABE12248; ABF47693; ABG72868; ABG72869; ABG79952; ABI54437; ABI54444; ABI54445; ABO21730; ABO21731; ABO33006; ABO52038; ABO52258; ABP49305; ABP49360; BAF31892; CAA86560; CAA86561; CAA86562; CAC18524; AAA43158; AAA43169; AAA43173; AAA43176; AAA43190; AAA43194; AAA43225; AAA43232; AAA43283; AAK40314; AAK40315; AAK51348; AAN64897; AAN64898; AAN64899; AAP79977; AAX56530; AAZ79549; ABA08497; ABA12707; ABA42258; ABB51962; ABB53603; ABB82194; ABB82205; ABB82216; ABB86877; ABB86917; ABB86929; ABB86937; ABB86946; ABC40522; ABD77708; AAA43661; AAA43680; AAF06945; AAF06946; AAF87275; AAF87276; AAF87283; AAN64901; AAQ10369; AAQ10373; AAQ10380; AAQ10385; AAQ10386; AAQ10388; AAQ10395; AAQ10396; AAT81328; AAT81337; AAT81339; AAT81340; AAT85679; ABA12729; ABB19571; ABB19607; ABB19628; ABB20429; ABB79990; ABC40631; ABD61540; ABD61735; ABD62061; ABD79101; ABD85261; ABD95053; ABD95064; ABD95086; ABD95163; ABD95218; ABD95295; ABF71860; ABF82852; ABF82874; ABF82885; ABF82907; ABI92379; ABI96088; ABI96091; ABI96093; ABI96097; ABI96098; ABI96101; ABI96107; ABI96108; ABI96111; ABJ09151; ABJ53493; ABK40510; ABK40579; ABK40601; ABM22246; ABO38384; ABO38406; BAA96109; BAA96114; BAA96115; BAA96122; BAA96124; BAA96125; CAA35094; AAA58799; AAA58801; AAA65544; AAA65546; AAA65551; AAA65553; AAA65554; AAA74285; AAA74289; AAA74291; AAA74293; AAA74299; AAA91616; AAA92279; AAB03291; AAB27052; AAB29091; AAB39351; AAB50958; AAB50966; AAG22555; ABD77917; ABD77928; ABD77950; ABD78038; ABD94778; ABE12634; ABE26991; ABF47583; ABG48049; ABG72867; ABI20826; ABI51313; ABI54438; ABI84617; ABI92302; ABI95250; ABI96094; ABI96095; ABI96096; ABI96104; ABI96105; ABI96106; ABJ53427; ABJ53504; ABK40689; ABM22224; ABO38318; ABO38340; ABO44046; BAA96111; BAA96112; BAA96117; BAA96118; BAA96121; BAA96126; BAA96127; BAA96128; BAA96131; BAF47397; AAA65547; AAA65548; AAA65549; AAA65550; AAA65556; AAA65557; ABG37362; ABG66973; ABG66975; ABI21211; ABI21233; ABJ16609; ABM21960; ABM66864; ABN50928; ABN51077; ABN59423; ABN59434; ABO21725; ABO52104; ABP49316; ABP49338; ABP49349; BAE53730; BAE96535; BAE96537; BAE96541; BAE96542; BAF03627; CAA40729; CAA82950; CAA91083; AAA16779; AAA16809; AAA16812; AAA16879; AAA16905; AAA43161; AAA43167; AAA43172; AAA43206; AAA43209; AAA43233; AAA43234; AAA43238; AAC53845;

AAC53846; AAC57166; AAK40317; AAK51342; AAK51343; AAK51346; AAF06947; AAF75994; AAF80098; AAF80099; AAF87277; AAQ10367; AAQ10368; AAQ10389; AAQ10392; AAQ10393; AAZ38627; ABA42575; ABB19574; ABB19667; ABD63063; ABD79112; ABD85123; ABD94976; ABD94998; ABD95130; ABD95141; ABD95262; ABF47880; ABF82673; ABF82819; ABF82830; ABF82929; ABG66976; ABG66977; ABG88344; ABK39995; ABK40534; ABK40546; ABK40568; ABN50756; ABN50900; ABO33025; ABO52280; ABP49393; ABP49448; BAE96538; BAE96539; BAE96540; CAA40731; CAA42444; AAL60444; AAL87869; AAL87871; AAM76686; AAM76689; AAM76690; AAP34322; AAP69678; AAP69679; AAP69681; AAZ74374; ABA08464; ABA18037; ABB19518; ABB19529; ABB19540; ABC66233; ABC66236; ABD77719; ABD77807; ABD77818; ABD77972; ABD94811; ABD95328; ABD95339; ABE11657; ABE11723; ABE11812; ABE11922; ABE12032; ABF21277; ABG26243; ABG26791; ABG26813; ABG26824; ABG26945; ABG67477; ABI21530; ABI21552; ABI21574; ABI22109; ABI30367; ABI96117; ABI96118; ABI96123; AAK67338; AAA72339; AAA74296; AAA74297; AAA74298; AAA79714; AAA79727; AAB03292; AAB39352; AAB50960; AAB50961; AAB50962; AAB50963; AAB50964; AAB50965; AAL60449; AAL87868; AAM22277; AAM22278; AAM76691; AAP34323; AAP34324; AAT65329; AAZ83977; ABA06510; ABA42324; ABC66239; ABD78093; ABD95350; ABD95712; ABE11668; ABE11690; ABE11834; ABE11856; ABE11878; ABE11889; ABF21278; ABF47561; ABF82940; ABG26835; ABG88300; ABG88311; ABG88333; ABG88542; ABI85225; AAK51352; AAN64893; AAN64895; AAP69687; AAP69692; AAP79964; AAZ79392; AAZ79538; ABA12715; ABA42280; ABB03134; ABB03145; ABB86899; ABB86907; ABC40533; ABD77939; ABD94800; ABF47605; ABF47704; ABG72870; ABG88256; ABI20848; ABI54442; ABI54443; ABI54446; ABI95217; ABI96089; ABI96090; ABI96092; ABI96099; ABI96100; ABI96102; ABI96109; ABI96110; ABO38065; ABO38362; ABO38373; ABO38395; BAA96110; BAA96113; BAA96116; BAA96123; CAA24272; CAA35097; AAA58800; ABI96114; ABI96115; ABI96120; ABI96121; ABI96122; ABI96127; ABI96130; ABI96137; ABI96140; ABI96141; ABI96145; ABI96146; ABI96147; ABI96150; ABK79959; ABL67253; ABM22202; ABO37988; ABO38010; ABO38021; AAB52910; AAB81460; AAB81463; AAD25308; AAK67319; AAK67320; AAK67325; AAK67326; AAK67327; AAK67328; AAK67335; AAK67336; AAK67337; AAK67344; AAK70451; AAK70452; AAK70453; AAK70458; AAK70459; AAK71687; AAK73325; AAK73326; AAK73331; AAK73332; AAK73333; AAA65545; AAA65552; AAA65555; AAA74286; AAA74290; AAA74292; AAA74300; AAA99877; AAB39851; AAB50957; AAB50959; AAL60443; AAL87870; AAM76687; AAM76688; AAP69676; AAP69677; AAP69680; AAP69682; ABA18145; ABB19507; ABB53729; ABB53740; ABC66234; ABC66235; ABD77730; ABD77796; ABD77961; ABD77983; ABD78082; ABD78104; ABD95317; ABE11701; ABE11712; ABE11734; ABE11823; ABE11900; ABE11942; ABF21274; ABF21276; ABF47572; ABG26242; ABG26244; ABG26245; ABG26780; AAK73334; AAK73341; AAK73342; AAK73343; AAK73344; AAL29701; AAL29707; AAO65612; AAV68006; AAW50829; AAW50830; AAW50831; AAW50832; AAY42117; AAY42118; AAY42121; AAY42122; AAZ17358; AAZ17359; AAZ79604; ABA87057; ABB02792; ABB02814; ABB02913; ABB02936; ABB83026; ABB83127; ABC66240; ABD59849; ABD60944; ABD60955; ABD78016; ABD94756; ABD95042; ABD95119; ABD95174; ABF47638; ABF47660; ABF47715; ABF47759; ABF47770; ABF47792; ABF47814; ABG37395; ABG47807; ABI96124; ABI96126; ABI96134; ABI96143; ABI96144; ABI96151; ABI96153; ABK79948; ABK80036; ABK80047; ABM22169; ABO38032; ABO52225; BAA00308; BAA00718; BAA00720; BAA01280; BAA21641; AAB52905; AAB52907; AAB57740; AAB81456; AAB81457; AAB81459; AAC14275; AAD25304; AAD25305; AAD25307; AAK67322; AAK67324; AAK67329; AAK67332; AAK67338; AAK67339; AAK67341; AAK67343; AAK70449; AAK70450; AAK70456; AAK73322; AAK73324; AAK73328; AAK73330; AAK73338; AAK73340; ABI21541; ABI21563; ABI30378; ABI85231; ABI96116; ABI96119; ABI96125; ABI96132; ABI96135; ABI96142; ABI96152; ABJ09184; ABK80025; ABO38043; BAA00309; BAA00719; BAA02765; BAA21642; AAB52904; AAB52906; AAB52908; AAB81458; AAD05215; AAD17229; AAD25303; AAD25306; AAD25312; AAK67321; AAK67323; AAK67330; AAK67331; AAK67333; AAK67340; AAK67342; AAK70455; AAK70457; AAK70464; AAK73321; AAK73323; AAK73327; AAK73329; AAK73336; AAK73337; AAK73339; AAL29694; AAK73345; AAL02002; AAL29695; AAL29702; AAL29708; AAL29710; AAL29711; AAL47668; AAO65768; AAW50828; AAW50836; AAY42114; AAY42115; AAZ15839; AAZ15840; AAZ15842; AAZ83253; ABA87080; ABA87231; ABB03101; ABB53707; ABB83015; ABC66243; ABC66246; ABD15515; ABD60779; ABD60856; ABD60878; ABD60900; ABD60933; ABD60966; ABD94943; ABD95020; ABD95097; ABD95207; ABF47748; ABI83825; ABF47847; ABG80183; ABG88212; ABI30565; ABI55088; ABI96154; ABI96160; ABI96166; ABG47829; ABI20870; ABI54447; ABI95272; ABI96155; ABI96156; ABI96157; ABI96162; ABI96163; ABI96171; ABI96172; ABI96173; ABJ51891; ABM22279; ABM66886; ABM66908; ABN51143; ABO32948; ABO32970; ABO32981; BAC82844; BAC82847; BAC82848; BAC82853; BAC82854; BAC82860; BAC82869; BAC82870; BAC82880; BAC82889; BAC82890; BAC82898; BAD02346; CAC86333; CAC86334; CAC86621; CAD29905; CAD29906; CAD29915; CAD29916; CAD29921; CAD29922; CAD29923; CAD29931; CAD29932; CAD29941; AAL29696; AAL29697; AAL29703; AAL29709; AAL29712; AAL29713; AAL47667; AAO88265; AAT00437; AAT00438; AAV67984; AAW22156; AAW50827; AAW50834; AAW50835; AAW50837; AAW56635; AAY42116; AAZ15838; AAZ15841; AAZ15843; ABA87045; ABA87091; ABB02825; ABB80103; ABB83138; ABC66244; ABC66245; ABD15258; ABD59847; ABD60867; ABD60889; ABD60911; ABD95108; ABD95185; ABD95196; ABF47726; ABF47737; ABF47836; ABG88201; ABI96159; ABI96161; ABI96165; ABI96167; ABI96168; ABI96169; ABI96170; ABJ51892; ABJ51894; ABJ51895; ABJ53449; ABK40634;

ABK57093; ABL67055; ABL67066; ABL67209; ABM22026; ABM22268; ABN50940; ABN50962; ABN50973; ABO44123; BAC82843; BAC82850; BAC82851; BAC82857; BAC82859; BAC82866; BAC82867; BAC82873; BAC82876; BAC82877; BAC82879; BAC82886; BAC82887; BAC82893; BAC82896; BAC82897; BAD02356; CAC86337; CAC86605; CAC86608; CAC86609; CAC86617; CAC86618; CAC86620; CAC86625; CAD29902; CAD29909; CAD29912; CAD29918; ABJ16719; ABJ51890; ABJ51893; ABK57092; ABL67187; ABM22257; ABO44134; ABP49217; BAC82842; BAC82849; BAC82852; BAC82858; BAC82864; BAC82865; BAC82868; BAC82874; BAC82875; BAC82878; BAC82884; BAC82885; BAC82888; BAC82894; BAC82895; CAC86336; CAC86606; CAC86607; CAC86610; CAC86611; CAC86616; CAC86619; CAD29900; CAD29901; CAD29903; CAD29910; CAD29911; CAD29917; CAD29919; CAD29926; CAD29927; CAD29933; CAD29936; CAD29937; CAD29939; CAD29943; CAD29946; CAD29947; CAD29924; CAD29925; CAD29928; CAD29934; CAD29935; CAD29938; CAD29944; CAD29945; CAD29948; CAD35680; CAD35682; CAD57617; CAD57619; CAA86567; CAA91080; CAA91081; AAA16778; AAA16810; AAA16811; AAA16814; AAA16815; AAA19934; AAA43157; AAA43166; AAA43235; AAA43236; AAC57167; AAC57168; AAC57169; AAK40313; AAK40316; AAK51341; AAK51349; AAK51350; AAK51351; AAN64892; AAP69685; AAP69686; AAP69689; AAP69690; AAU25851; ABA08475; ABA08486; ABA08508; ABA12696; ABA42236; ABB96487; ABC41714; ABD78060; ABE27153; ABF47671; ABG72863; ABG72864; ABG72865; ABG72866; ABI20837; ABI20859; ABI54439; ABI54440; ABI54441; ABI84855; ABI92181; ABI92313; ABI95294; ABI96103; ABJ53438; ABJ53515; ABK40590; ABM22213; ABM22235; ABO32678; ABO38329; ABO38351; ABO52797; BAA96119; BAA96120; BAA96129; BAA96130; AAA67181; AAA67182; AAA67183; AAA74287; AAA74288; AAA74294; AAA74295; AAA92280; AAB39353; AAL87865; AAL87866; AAL87867; AAL87872; AAM75158; AAP34325; AAP60036; AAP60037; AAP69673; AAP69674; AAP69675; AAP69683; AAP69684; AAZ83299; AAZ85126; ABA06542; ABC66232; ABC66237; ABC66238; ABD77994; ABE11679; ABE11845; ABE11867; ABF21272; ABG26246; ABG37120; ABG67491; ABG88322; ABG88553; ABI21519; ABI96112; ABI96113; ABI96128; ABI96129; ABI96138; ABI96139; ABI96148; ABI96149; ABJ16675; ABK40039; ABK40050; ABK79970; ABL67264; ABM22180; ABM22191; ABN59401; ABN59412; ABO37999; ABO38054; BAA00721; BAA00722; BAA01027; BAA02766; BAA02767; BAA02768; BAA02769; BAA05874; BAA06719; AAB52909; AAB81461; AAB81462; AAD05216; CAD29942; CAD35678; CAD35679; CAD35686; CAD35687; CAD35688; CAD57616; CAD57620; CAD57623; CAD35681; CAD35683; CAD35684; CAD57618; AAD05217; AAD05218; AAD05219; AAD17218; AAD17219; AAD25301; AAD25302; AAD25309; AAD25310; AAD25311; AAK67334; AAK70454; AAK73320; AAK73335; AAL15459; AAL29693; AAL29698; AAL29699; AAL29700; AAL29704; AAL29705; AAL29706; AAL29714; AAL29715; AAO65769; AAT00436; AAT12706; AAW50833; AAY42119; AAY42120; AAY78939; AAZ15844; ABB02781; ABB02803; ABB02924; ABC42750; ABC66241; ABC66242; ABD59848; ABD78005; ABD78027; ABD95009; ABD95031; ABF47627; ABF47649; ABF47781; ABF47803; ABF47955; ABG37384; ABG47818; ABG47840; ABG80172; ABI21189; ABI95261; ABI95283; ABI96158; ABI96164; ABI96174; ABJ16642; ABJ16653; ABJ16664; ABJ16730; ABM22158; ABM22290; ABM66897; ABM67051; ABN50951; ABO32959; BAC82845; BAC82846; BAC82855; BAC82856; BAC82861; BAC82862; BAC82863; BAC82871; BAC82872; BAC82881; BAC82882; BAC82883; BAC82891; BAC82892; CAC86335; CAC86612; CAC86613; CAC86614; CAC86615; CAC86622; CAC86623; CAC86624; CAD29898; CAD29899; CAD29904; CAD29907; CAD29908; CAD29913; CAD29914; CAD29920; CAD29929; CAD29930; CAD29940; CAD29958; CAD35685; CAD57621 and CAD57622.

Protein sequences of influenza virus subtype H2 haemagglutinin suitable for inclusion as a cargo moiety in conjugates according to the present invention have the following accession numbers and are available to the public via the National Center for Biotechnology Information (NCBI) Entrez protein search and retrieval system:

BAC43764; BAF02312; AAO46270; AAO46271; AAO46272; AAO46273; AAO46274; AAO46275; AAO46276; AAO46277; AAO46278; AAO46279; AAO46280; AAO46281; AAO46282; AAO46283; AAO46284; AAO46285; AAO46286; AAO46287; AAO46288; AAO46289; AAO46290; AAO46291; AAO46292; AAO46293; AAO46294; AAO46295; AAO46296; AAO46297; AAO46298; AAO46299; AAO46300; AAO46301; AAO46302; AAO46303; AAO46304; AAO46305; AAS57527; AAS57528; AAS57529; AAS57530; AAT65325; AAT65327; AAT65331; AAT65348; AAT65351; AAV91219; ABB17150; ABB17670; ABB17681; ABB17692; ABB17703; ABB17714; ABB18378; ABB17725; ABB17736; ABB17756; ABB17813; ABB18025; ABB18036; ABB18047; ABB18058; ABB18069; ABB18080; ABB19639; ABB20141; ABB20229; ABB20240; ABB20466; ABB20509; ABI84382; ABI84384; ABI84450; ABI84458; ABI84459; ABI84588; ABI84744; ABI84755; ABI84959; ABI85183; ABL67022; ABM21949; ABO38098; ABO38296; ABO38307; ABO38701; ABO38712; ABO38723; ABO38734; ABO44057; ABO44090; ABO44101; ABO52236; ABO52247; ABO52302; ABO52379; ABP49437; ABP49459; ABP49470; BAA02770; BAA02771; BAA02772; BAA02773; BAA02774; BAA02775; AAY23639; AAY23640; AAY28987; AAY87410; AAY87419; ABF21270; ABF21275; AAA43185; AAA43196; AAA43089; AAA43090; AAA43659; AAA43243; AAA43117; AAA43284; AAA43450; AAA43096; AAA43247; AAA43248; AAA43088; AAA43345; AAA43576; AAA43578; AAA43658; AAA43660; AAA43662; AAA43678; AAA64362; AAA64364; AAA64365; AAA64363; AAA64366; BAF33428; BAF33438; BAF33398; BAF33408; BAF34322; BAF34377; BAF47131; BAF48641; BAF49415; AAD43235; AAD43236; AAD43237; AAD43238; AAD43239; AAD43240; AAD43241; AAD43242; AAD43243; AAD43244; AAD43245; AAD43246; AAD43247; AAD43248; AAD43249; AAK14980; AAF82100; AAF82101; AAF82102; AAF82103;

AAF82104; AAF82105; AAF82106; AAF82107; AAF82108; AAF82109; AAF82110; AAF82111; AAF82112; AAN83926; AAN83927; AAN83928; AAN83929; AAN83930; AAN83931; AAO46268 and AAO46269.

Protein sequences of influenza virus subtype H3 haemagglutinin suitable for inclusion as a cargo moiety in conjugates according to the present invention have the following accession numbers and are available to the public via the National Center for Biotechnology Information (NCBI) Entrez protein search and retrieval system:

BAA77284; BAA77285; BAA77286; BAA77287; BAA77288; BAA77289; BAA77290; BAA77291; BAA77292; BAA77293; BAA77294; BAA86062; BAA86063; BAA86064; BAA86065; BAA96300; BAA96301; BAA96302; BAA96303; BAE75900; BAE75901; BAE75902; BAE75903; BAE75904; BAE75905; BAE75906; BAE75907; BAE75908; BAE75909; BAE75910; BAE75911; BAE75912; BAE75913; BAE75914; BAE75915; BAE75916; BAE75917; BAE75918; BAE75919; BAE54256; BAE54257; BAE54258; BAE54259; BAE54260; BAE54261; BAE54262; BAE75854; BAE94240; BAE94241; BAE94242; BAE94243; BAE94244; BAE94245; BAE94246; BAE94247; BAE94248; BAE94249; BAE94250; BAE94251; BAE94568; BAE94569; BAE94570; BAE96004; BAE96005; BAE96006; BAE96007; BAF46357; BAF46358; BAF46359; BAF46360; BAF46361; BAF46362; BAF46363; BAF46364; BAF46365; BAF46366; BAF46367; BAF46375; BAF46376; BAF46377; BAF46378; BAF46379; BAF46380; BAF46381; BAF46382; BAF46383; BAF46384; BAF46317; BAF46318; BAF46319; BAF46320; BAF46325; BAF46326; BAF46327; BAF46328; BAF46329; BAF46330; BAF46331; BAF46338; BAF46339; BAF46340; BAF46341; BAF46342; BAF46343; BAF46344; BAF47998; BAF47999; BAF48000; BAF48001; BAF48002; BAF48003; BAF48004; BAF48005; BAF48006; BAF48007; BAF48008; BAF48009; BAF48010; BAF48011; BAF48012; BAF48013; BAF48014; BAF48015; BAF48016; BAF48017; BAF48018; BAF48019; BAF48020; BAF48021; BAF48022; BAF48023; BAF48024; BAF48025; BAF48026; BAF48027; BAF48028; BAF48029; BAF48030; BAF48031; BAF48032; BAF48033; BAF48034; BAF48035; BAF48036; BAF48037; BAF48038; BAF48039; BAF33059; BAF34375; BAF34924; BAF37221; BAF43466; BAF46752; BAF46760; BAF46902; BAF46910; BAF48361; AAB66723; AAB66724; AAB66725; AAB66726; AAB66727; AAB66728; AAB66729; AAB66730; AAB66731; AAB66732; AAB66733; AAB66734; AAB66735; AAB66736; AAB66737; AAB66738; AAB66739; AAB66740; AAB66741; AAB66742; AAB66743; AAB66744; AAB66745; AAB66746; AAB66747; AAB66748; AAB66749; AAB66750; AAB66751; AAB66752; AAB66753; AAB66754; AAB66755; AAB66756; AAB66757; AAB66758; AAB66759; AAB66760; AAB66761; AAB66762; AAB66763; AAB66764; AAB66765; AAB66766; AAB66767; AAB66768; AAB66769; AAB66770; AAB66771; AAB66772; AAB66773; AAB66774; AAB66775; AAB66776; AAB66777; AAB66778; AAB66779; AAB66780; AAB66781; AAB66782; AAB66783; AAB66784; AAB66785; AAB66786; AAB66787; AAB66788; AAB66789; AAB66790; AAB66791; AAB66792; AAB66793; AAB66794; AAB66795; AAB66796; AAB66797; AAB66798; AAB66799; AAB66800; AAB66801; AAB66802; AAB66803; AAB66804; AAB66805; AAB66806; AAB66807; AAB66808; AAB66809; AAB66810; AAB63681; AAB63682; AAB63683; AAB63684; AAB63685; AAB63686; AAB63687; AAB63688; AAB63689; AAB63690; AAB63691; AAB63692; AAB63693; AAB63694; AAB63695; AAB63696; AAB63697; AAB63698; AAB63699; AAB63700; AAB63701; AAB63702; AAB63703; AAB63704; AAB63705; AAB63706; AAB63707; AAB63708; AAB63709; AAB63710; AAB63711; AAB63712; AAB63713; AAB63714; AAB63715; AAB63716; AAB63717; AAB63718; AAB63719; AAB63720; AAB63721; AAB63722; AAB63723; AAB63724; AAB63725; AAB63726; AAB63727; AAB63728; AAB63729; AAB63730; AAB63731; AAB63732; AAB63733; AAB63734; AAB63735; AAB63736; AAB63737; AAB63738; AAB63739; AAB63740; AAB63741; AAB63742; AAB63743; AAB63744; AAB63745; AAB63746; AAB63747; AAB63748; AAB63749; AAB63750; AAB63751; AAB63752; AAB63753; AAB63754; AAB63755; AAB63756; AAB63757; AAB63758; AAB63759; AAB63760; AAB63761; AAB63762; AAB63763; AAB63764; AAB63765; AAB63766; AAB63767; AAB69773; AAB69774; AAB69775; AAB69776; AAB69777; AAB69778; AAB69779; AAB69780; AAB69781; AAB69782; AAB69783; AAB69784; AAB69785; AAB69786; AAB69787; AAB69788; AAB69789; AAB69790; AAB69791; AAB69792; AAB69793; AAB69794; AAB69795; AAB69796; AAB69797; AAB69798; AAB69799; AAB69800; AAB69801; AAB69802; AAB69803; AAB69804; AAB69805; AAB69806; AAB69807; AAB69808; AAB69809; AAB69810; AAB69811; AAB69812; AAB69813; AAB69814; AAB69815; AAB69816; AAB69817; AAB69818; AAB69819; AAB69820; AAB69821; AAB69822; AAB69823; AAB69824; AAB69825; AAB69826; AAB69827; AAB69828; AAB69829; AAB69830; AAB69831; AAB69832; AAB69833; AAB69834; AAB69835; AAB69836; AAB69837; AAB69838; AAB69839; AAB69840; AAB69841; AAB69842; AAB69843; AAB69844; AAB69845; AAB69846; AAB69847; AAB69848; AAB69849; AAB69850; AAB69851; AAC59602; AAC59603; AAC59604; AAC63474; AAC63475; AAC63476; AAC63477; AAC63478; AAC31556; AAC36729; AAC36730; AAC36731; AAC36732; AAC36733; AAC36734; AAC36735; AAC36736; AAC36737; AAC36738; AAC78086; AAC78087; AAC78088; AAC78089; AAC78090; AAC78091; AAC78092; AAC78093; AAC78094; AAC78095; AAC78096; AAC78097; AAC78098; AAC83790; AAC83791; AAC83792; AAC83793; AAC83794; AAC83795; AAC83796; AAC83797; AAC83798; AAC83799; AAC83800; AAF06948; AAF06949; AAF06950; AAD34847; AAD34848; AAD34849; AAD34850; AAD34851; AAD34852; AAD34853; AAD34854; AAD34855; AAD34856; AAD34857; AAD51239; AAD51240; AAD51241; AAD51242; AAF16416; AAF16417; AAF16418; AAF16419; AAF16420; AAF16421; AAF16422; AAF16423; AAF16424; AAF16425; AAF16426; AAF16427; AAF16428; AAF16429; AAF16430; AAF16431; AAF16432; AAF16433; AAF16434; AAF16435;

AAF16436; AAF16437; AAF16438; AAF16439; AAK67179; AAK67180; AAK67181; AAK67182;
AAF16440; AAF16441; AAF16442; AAF16443; AAK67183; AAK67184; AAK67185; AAK67186;
AAF16444; AAF16445; AAF16446; AAF16447; AAK67187; AAK67188; AAK67189; AAK67190;
AAF16448; AAF16449; AAF16450; AAF16451; AAK67191; AAK67192; AAK67193; AAK67194;
AAF16452; AAF16453; AAF16454; AAF16455; AAK67195; AAK67196; AAK67197; AAK67198;
AAF16456; AAF16457; AAF16458; AAF16459; AAK67199; AAK67200; AAK67201; AAL30462;
AAF16460; AAF16461; AAF16462; AAF16463; AAL30463; AAL30464; AAL60147; AAL60148;
AAF16464; AAF16465; AAF16466; AAF16467; AAL60149; AAL60150; AAL60151; AAL60152;
AAF16468; AAF16469; AAF16470; AAF16471; AAL60153; AAL77301; AAL77302; AAL77303;
AAF16472; AAF16473; AAF16474; AAF16475; AAL77304; AAL77305; AAL77306; AAL77307;
AAF16476; AAF16477; AAF16478; AAF16479; AAL77308; AAL77309; AAL77310; AAL77311;
AAF16480; AAF16481; AAF16482; AAF16483; AAL77312; AAL77313; AAL77314; AAL77315;
AAF16484; AAF16485; AAF16486; AAF16487; AAL77316; AAL77317; AAL77318; AAL77319;
AAF16488; AAF16489; AAF16490; AAF16491; AAL77320; AAL77321; AAL77322; AAL77323;
AAF16492; AAF16493; AAF16494; AAF16495; AAL77324; AAL77325; AAL77326; AAL77327;
AAF16496; AAF16497; AAF16498; AAF16499; AAL77328; AAL77329; AAL62329; AAM46871;
AAF16500; AAF16501; AAF16502; AAF16503; AAM46872; AAM46873; AAM46874; AAM46875;
AAF16504; AAF16505; AAF16506; AAF16507; AAM46876; AAM46877; AAM46878; AAM46879;
AAF16508; AAF16509; AAF16510; AAF16511; AAM46880; AAM46881; AAM46882; AAM46883;
AAF16512; AAF16513; AAF16514; AAF16515; AAM46884; AAM46885; AAM46886; AAM46887;
AAF16516; AAF16517; AAF16518; AAF22345; AAM46888; AAM46889; AAM46890; AAM46891;
AAF22346; AAF22347; AAF22348; AAF22349; AAM82560; AAM82561; AAM82562; AAM88280;
AAF22350; AAF22351; AAF22352; AAF22353; AAM88283; AAN01150; AAN01151; AAN01152;
AAF18089; AAF18090; AAF18091; AAF18092; AAN01153; AAN01154; AAN01155; AAN01156;
AAF18093; AAF13705; AAF13706; AAF19421; AAN01157; AAN01158; AAN01159; AAN01160;
AAL59048; AAL59049; AAL59050; AAL59051; AAN01161; AAN01162; AAN01163; AAN01164;
AAO15354; AAO15355; AAO15356; AAO15357; AAN01165; AAN01166; AAN01167; AAQ10355;
AAF60285; AAG01749; AAG01758; AAG01767; AAQ10356; AAQ10357; AAQ10358; AAQ10359;
AAG01776; AAG01785; AAK49194; AAK49195; AAQ10360; AAQ10361; AAQ10362; AAQ10363;
AAK49196; AAK49197; AAK49198; AAK49199; AAQ10364; AAQ10365; AAQ10366; AAQ10370;
AAK49200; AAK49201; AAK49202; AAK49203; AAQ10371; AAQ10374; AAQ10375; AAQ10376;
AAK49204; AAG10735; AAG10736; AAG10737; AAQ10377; AAQ10378; AAQ10379; AAQ10381;
AAG10738; AAG10739; AAG10740; AAG33221; AAQ10382; AAQ10383; AAQ10384; AAQ10397;
AAG33222; AAG33223; AAG33224; AAG47797; AAQ10398; AAQ10399; AAQ10400; AAQ10401;
AAG47798; AAG47799; AAG47800; AAG47801; AAQ10402; CAA11167; CAA11168; CAA11169;
AAG47802; AAG47803; AAG47804; AAG47805; CAA11170; CAA11171; CAA11172; CAC81013;
AAG47806; AAG47807; AAG47808; AAG47809; CAC81016; CAC81017; CAC81018; CAC40044;
AAG47810; AAG47811; AAG47812; AAG47813; CAC40045; CAC40046; CAC40047; CAC40048;
AAG47814; AAG47815; AAG47816; AAG47817; CAC40049; CAC40050; CAC40051; CAC36995;
AAG47818; AAG47819; AAG49302; AAG49303; CAC37007; CAC37327; CAC86626; CAD20322;
AAG49304; AAG49305; AAG49306; AAG49307; CAD20336; CAD44999; CAG27339; CAG27340;
AAG49308; AAG49309; AAG49310; AAG49311; CAG27341; CAG27342; CAG28960; CAG28961;
AAG49312; AAG49313; AAG49314; AAG49335; CAG28962; CAG34129; CAH56424; CAJ32551;
AAG49336; AAG49337; AAG49338; AAG49339; CAJ32558; CAD22811; CAD22818; AAK53066;
AAK51718; AAL18558; AAL18559; AAL18560; AAK62039; AAK62040; AAK62041; AAK62042;
AAL18561; AAL18562; AAL18563; AAL18564; AAK62043; AAL06634; AAL06635; AAL06636;
AAL18565; AAL18566; AAL18567; AAL18568; AAL06637; AAL06638; AAN17779; AAN63953;
AAL18569; AAL18570; AAL18571; AAL18572; AAN63954; AAN63955; AAN63956; AAN63957;
AAL18573; AAL18574; AAL18575; AAL18576; AAN63958; AAN83932; AAN83933; AAN83934;
AAL18577; AAL18578; AAL18579; AAL18580; AAN83935; AAN83936; AAN83937; AAN83938;
AAL18581; AAL18582; AAL18583; AAL18584; AAN83939; AAN83940; AAN83941; AAN83942;
AAL18585; AAL18586; AAL18587; AAL18588; AAN83943; AAN83944; AAN83945; AAN83946;
AAL18589; AAL18590; AAL18591; AAL18592; AAN83947; AAN83948; AAN83949; AAN83950;
AAL18593; AAL18594; AAL18595; AAL18596; AAN83951; AAN83952; AAN83953; AAN83954;
AAL18597; AAL18598; AAK82853; AAK82854; AAN83955; AAN83956; AAN83957; AAN83958;
AAK82855; AAK82856; AAK82857; AAK82858; AAN83959; AAN83960; AAN83961; AAP21996;
AAK82859; AAK82860; AAK82861; AAK82862; AAP21997; AAP23238; AAQ18434; AAQ18435;
AAK82863; AAK82864; AAK82865; AAK82866; AAP79943; AAP79947; AAP79953; AAP79961;
AAK82867; AAK82868; AAK82869; AAK52910; AAP79966; AAP79973; AAP79975; AAR12332;
AAK52911; AAK52912; AAK54141; AAK54142; AAR12333; AAR12334; AAR12335; AAR12336;
AAK54143; AAK54144; AAK54145; AAK54146; AAR12337; AAR12338; AAR12339; AAR12340;
AAK54147; AAK54148; AAK54149; AAK54150; AAR12341; AAR12342; AAR12343; AAR12344;
AAK54151; AAK63816; AAK63817; AAK63818; AAR12345; AAR12346; AAR12347; AAR12348;
AAK63819; AAK63820; AAK63821; AAK63822; AAR12349; AAQ86988; AAQ85081; AAQ85082;
AAK63823; AAK63824; AAK63825; AAK63826; AAQ85083; AAQ85084; AAQ85085; AAQ85086;
AAK67171; AAK67172; AAK67173; AAK67174; AAQ85087; AAQ85088; AAQ85089; AAQ85090;
AAK67175; AAK67176; AAK67177; AAK67178; AAQ85091; AAT12703; AAT12704; AAR90879;

AAQ90291; AAQ92920; AAQ92921; AAQ92922; AAQ92923; AAQ92924; AAQ92925; AAQ92926; AAQ92927; AAQ92928; AAQ92929; AAQ92930; AAQ92931; AAR25201; AAR33033; AAT07998; AAT08000; AAT08002; AAT08004; AAT12654; AAT12655; AAT12656; AAT12657; AAT12658; AAT12659; AAT12660; AAT12661; AAT12662; AAT12663; AAT12664; AAT12665; AAT12666; AAT12667; AAT12668; AAT12669; AAT12670; AAT12671; AAT12672; AAT12673; AAT12674; AAT12675; AAT12676; AAS93870; AAS93871; AAS93872; AAS93873; AAS93874; AAS93875; AAS93876; AAS93877; AAS93878; AAS93879; AAS93880; AAS93881; AAS93882; AAS93883; AAS93884; AAT09637; AAT09638; AAT09639; AAT81341; AAT81342; AAT81343; AAT81344; AAT81345; AAT81346; AAT81347; AAT81348; AAT81349; AAT81350; AAT81351; AAT81352; AAT81353; AAT81354; AAT81355; AAT81356; AAT81357; AAT81358; AAT81359; AAT81360; AAT81361; AAT81362; AAU25861; AAU25871; AAT79527; AAT79528; AAT79529; AAT65319; AAT65321; AAT65324; AAT65333; AAT65334; AAT65345; AAT65349; AAT51806; AAT51807; AAT51808; AAT51809; AAT51810; AAT51811; AAT51812; AAT51813; AAT51814; AAT51815; AAT51816; AAT51817; AAT51818; AAT51819; AAT51820; AAT51821; AAT51822; AAT51823; AAT51824; AAT51825; AAT51826; AAT51827; AAT51828; AAT51829; AAT51830; AAT51831; AAT51832; AAT51833; AAT51834; AAT51835; AAT51836; AAT51837; AAT51838; AAT51839; AAT51840; AAT51841; AAT51842; AAT51843; AAT51844; AAT51845; AAT51846; AAT51847; AAT51848; AAT51849; AAT51850; AAT51851; AAT51852; AAT51853; AAT51854; AAT51855; AAT51856; AAT51857; AAT51858; AAT51859; AAT64666; AAT64667; AAT64668; AAT64669; AAT64670; AAT64671; AAT64672; AAT64673; AAT64674; AAT64675; AAT64676; AAT64677; AAT64678; AAT64679; AAT64680; AAT64681; AAT64682; AAT64683; AAT64684; AAT64685; AAT64686; AAT64687; AAT64688; AAT64689; AAT64690; AAT64691; AAT64692; AAT64693; AAT64694; AAT64695; AAT64696; AAT64697; AAT64698; AAT64699; AAT64700; AAT64701; AAT64702; AAT64703; AAT64704; AAT64705; AAT64706; AAT64707; AAT64708; AAT64709; AAT64710; AAT64711; AAT64712; AAT64713; AAT64714; AAT64715; AAT64716; AAT64717; AAT64718; AAT64719; AAT64720; AAT64721; AAT64722; AAT64723; AAT64724; AAT64725; AAT64726; AAT64727; AAT64728; AAT64729; AAT64730; AAT64731; AAT64732; AAT64733; AAT64734; AAT64735; AAT64736; AAT64737; AAT64738; AAT64739; AAT64740; AAT64741; AAT64742; AAT64743; AAT64744; AAT64745; AAT64746; AAT64747; AAT64748; AAT64749; AAT64750; AAT64751; AAT64752; AAT64753; AAT64754; AAT64755; AAT64756; AAT64757; AAT64758; AAT64759; AAT64760; AAT64761; AAT64762; AAT64763; AAT64764; AAT64765; AAT64766; AAT64767; AAT64768; AAT64769; AAT64770; AAT64771; AAT64772; AAT64773; AAT64774; AAT64775; AAT64776; AAT64777; AAT64778; AAT64779; AAT64780; AAT64781; AAT64782; AAT64783; AAT64784; AAT64785; AAT64786; AAT64787; AAT64788; AAT64789; AAT64790; AAT64791; AAT64792; AAT64793; AAT64794; AAT64795; AAT64796; AAT64797; AAT64798; AAT64799; AAT64800; AAT64801; AAT64802; AAT64803; AAT64804; AAT64805; AAT64806; AAT64807; AAT64808; AAT64809; AAT64810; AAT64811; AAT64812; AAT64813; AAT64814; AAT64815; AAT64816; AAT64817; AAT64818; AAT64819; AAT64820; AAT64821; AAT64822; AAT64823; AAT64824; AAT64825; AAT64826; AAT64827; AAT64828; AAT64829; AAT64830; AAT64831; AAT64832; AAT64833; AAT64834; AAT64835; AAT64836; AAT64837; AAT64838; AAT64839; AAT64840; AAT64841; AAT64842; AAT64843; AAT64844; AAT64845; AAT64846; AAT64847; AAT64848; AAT64849; AAT64850; AAT64851; AAT64852; AAT64853; AAT64854; AAT64855; AAT64856; AAT64857; AAT64858; AAT64859; AAT64860; AAT64861; AAT64862; AAT64863; AAT64864; AAT64865; AAT64866; AAT64867; AAT64868; AAT64869; AAT64870; AAT64871; AAT64872; AAT64873; AAT64874; AAT64875; AAT64876; AAT64877; AAT64878; AAT64879; AAT64880; AAT64881; AAT64882; AAT64883; AAT64884; AAT64885; AAT64886; AAU07825; AAU07826; AAU07827; AAU07828; AAU07829; AAU07830; AAU07831; AAU09399; AAW24444; AAW24445; AAW24446; AAW24447; AAW24448; AAW24449; AAW24450; AAW24451; AAU11522; AAU25949; AAV80797; AAV80798; AAW65986; AAW65987; AAW65988; AAW65989; AAW65990; AAW34374; AAW34375; AAW34376; AAW34377; AAW34378; AAW50838; AAW50839; AAW50840; AAW50841; AAX23575; AAW78047; AAW78048; AAW78049; AAW78050; AAW78051; AAW78052; AAX77666; AAX77667; AAX77668; AAX77669; AAX77670; AAX77671; AAX77672; AAX77673; AAX77674; AAX14851; AAX47732; AAX47733; AAX47734; AAX47735; AAX47736; AAX47737; AAX47738; AAX47739; AAX47740; AAX47741; AAX47742; AAX47743; AAX47744; AAX47745; AAX47746; AAX47747; AAX47748; AAX47749; AAX47750; AAX47751; AAX47752; AAX47753; AAX47754; AAX47755; AAX47756; AAX47757; AAX49559; AAX49562; AAY85891; AAY85892; AAY85893; AAY85894; AAY85895; AAY85896; AAY85897; AAY85898; AAY85899; AAY85900; AAY85901; AAY85902; AAY85903; AAY85904; AAY85905; AAY85906; AAY85907; AAY85908; AAY85909; AAY85910; AAY85911; AAX63815; AAX63816; AAX63817; AAX63818; AAX63819; AAX63820; AAX63821; AAX63822; AAX63823; AAX63824; AAX63825; AAX63826; AAX63827; AAX63828; AAY42043; AAY42044; AAY42045; AAY42046; AAY42047; AAY42048; AAY42049; AAY42050; AAY42051; AAY42052; AAY42053; AAY42054; AAY42055; AAY42056; AAY42057; AAY42058; AAY42059; AAY42060; AAY42061; AAY42062; AAY42063; AAY42064; AAY42065; AAY42066; AAY42067; AAX84524; AAX84525; AAX84526; AAX84527; AAX84528; AAX84529; AAX84530; AAX84531; AAX84532; AAX84533; AAX84534; AAX84535; AAX84536; AAX84537; AAX84538; AAX84539; AAX84540; AAX84541; AAX84542; AAX84543; AAX84544; AAX84545; AAX84546; AAX84547; AAX84548; CAL40875; AAX11455; AAX11475; AAX11485; AAX11495; AAX56420; AAX11505; AAY28295; AAX11515; AAX11565; AAX11575; AAX11585; AAX11595; AAX11605; AAX11615; AAX11635; AAX12731; AAX11465; AAY28571; AAX12751; AAX11525; AAX11535; AAX11545; AAX11555; AAX11625; AAX12741; AAX12761; AAX12771; AAX12781; AAX12791; AAX12801; AAX12811; AAX34061; AAX35821; AAX35831; AAX38237; AAX35841; AAX35851; AAX47525; AAX56490; AAX47515; AAX35861; AAX47535; AAX35871; AAX56380; AAX56390; AAX56400; AAX56410; AAX56430; AAX56440; AAX56450; AAX56460; AAX56470; AAX56480; AAX56500; AAX56510; AAX56520; AAX56540; AAX56550; AAX56560; AAX56570; AAX56580; AAX56590; AAX56600; AAX57644; AAX57654; AAX57664; AAX57674; AAX57684;

AAX57694; AAX57704; AAX57714; AAX57733; ABA43178; ABA42291; ABA43336; ABA43200;
AAX57734; AAX57744; AAX57754; AAX57764; ABA42302; ABA42313; ABA42335; ABA42346;
AAX57774; AAX57784; AAX57794; AAX57804; ABA42989; ABA42357; ABA42368; ABA42379;
AAX57814; AAX57824; AAX57834; AAX57844; ABA42390; ABA42401; ABA42412; ABA42443;
AAX57854; AAX57864; AAX57874; AAX57884; ABA42454; ABA42465; ABA42476; ABA42487;
AAX57894; AAX57904; AAX57914; AAX57924; ABA42498; ABA42978; ABA42939; ABA42928;
AAX57934; AAX57944; AAX76623; AAX76633; ABA42509; ABA42520; ABA42531; ABA42542;
AAX76643; AAX76653; AAX76663; AAY59035; ABA42553; ABA42564; ABA87242; ABA87253;
AAX76673; AAX76683; AAX76693; AAX76703; ABB96509; ABB02836; ABB02847; ABB02858;
AAX76713; AAY28375; AAX76723; AAX76733; ABB02869; ABB02880; ABB02891; ABB02902;
AAX76743; AAX76753; AAX76763; AAY18086; ABB04283; ABB04294; ABB04305; ABB04316;
AAY18096; AAY18611; AAY18585; AAY18106; ABB04327; ABB04338; ABB04349; ABB04360;
AAY18116; AAY18564; AAY18126; AAY18136; ABB04371; ABB02947; ABB02958; ABB02969;
AAY18146; AAY18156; AAY18166; AAY18176; ABB02980; ABB02991; ABB03002; ABB03013;
AAY18186; AAY18196; AAY27863; AAY28385; ABB03024; ABB03035; ABB03046; ABB03057;
AAY27843; AAY28561; AAY28345; AAY28395; ABB03068; ABB03079; ABB03090; ABB03112;
AAY27853; AAY28325; AAY27959; AAY27994; ABB04906; ABB04917; ABB04928; ABB04939;
AAY28004; AAY28014; AAY28265; AAY28275; ABB04950; ABB04961; ABB04983; ABB05183;
AAY28285; AAY28363; AAY28648; AAY28305; ABB05194; ABB05205; ABB05216; ABB04994;
AAY28315; AAY28335; AAY28355; AAY28638; ABB05005; ABB19704; ABB19712; ABB19723;
AAY28405; AAY28486; AAY28521; AAY28531; ABB19744; ABB19758; ABB86785; ABB86796;
AAY28541; AAY28628; AAY28551; AAY28618; ABB87034; ABB87377; ABB87388; ABB87399;
AAY28581; AAY28591; AAY28608; AAY44610; ABB87410; ABB87421; ABB87429; ABB87440;
AAY44906; AAY44620; AAY44621; AAY44631; ABB87451; ABB87462; ABB87789; ABB88149;
AAY44896; AAY44641; AAY44796; AAY44795; ABB88150; ABB88152; ABB88162; ABB88173;
AAY44785; AAY44775; AAY44765; AAY44755; ABB88183; ABB88256; ABB88309; ABB88342;
AAY44651; AAY44661; AAY46371; AAY46381; ABB88369; ABB46547; ABB46392; ABB46403;
AAY47013; AAY47023; AAY47052; AAY46391; ABB46414; ABB46425; ABB46436; ABB46447;
AAY47075; AAY47085; AAY46416; AAY46426; ABB46458; ABB53614; ABB53625; ABB53652;
AAY46436; AAY64192; AAY64202; AAY64212; ABB53663; ABB53674; ABB53685; ABB53696;
AAY64252; AAY64272; AAY64292; AAY64222; ABB53718; ABB53751; ABB54514; ABB52376;
AAY64312; AAY64232; AAY64242; AAY64322; ABB77853; ABB59996; ABB77864; ABC50167;
AAY64262; AAY64282; AAY64342; AAY64302; ABC50178; ABC50189; ABB79716; ABB60007;
AAY64352; AAY64332; AAY64392; AAY64362; ABB79731; ABB80034; ABB80023; ABB79788;
AAY64372; AAY64382; AAY64402; AAY98770; ABB79799; ABB79810; ABB79957; ABB79968;
AAY98037; AAY98047; AAY98187; AAY98057; ABB80001; ABB80012; ABB80137; ABB80148;
AAY98067; AAY98077; AAY98087; AAY98097; ABB80159; ABB80081; ABB80092; ABB80185;
AAY98107; AAY98117; AAY98127; AAY98137; ABB80196; ABB80207; ABB80229; ABB80492;
AAY98147; AAY98157; AAY98167; AAY98177; ABB80503; ABB80514; ABB80748; ABB80218;
AAY98195; AAY98217; AAY98207; AAY98237; ABB80529; ABB80641; ABB80661; ABB80240;
AAY98227; AAY98247; AAY98319; AAY98329; ABB80251; ABB80672; ABB80682; ABB80693;
AAY98339; AAY98353; AAY98366; AAY98376; ABB80704; ABB80737; ABB80715; ABB80724;
AAY98386; AAY98396; AAY98406; AAZ38539; ABB82183; ABB82227; ABB96319; ABB96330;
AAZ38561; AAZ38462; AAZ38473; AAZ38484; ABB96341; ABB96352; ABB96363; ABB96374;
AAZ38495; AAZ38506; AAZ38517; AAZ38528; ABB96395; ABB96498; ABB96520; ABB96531;
AAZ38583; AAZ38605; AAZ38550; AAZ38572; ABC02234; ABC02288; ABC02299; ABC02332;
AAZ38594; AAZ38616; AAZ38638; AAZ38650; ABC02321; ABC02255; ABC02266; ABC02310;
AAZ43370; AAZ43383; AAZ43394; AAZ43405; ABC39805; ABC40642; ABC40544; ABC40555;
AAZ74386; AAZ74352; AAZ74363; AAZ74430; ABC40608; ABC40619; ABC41692; ABC41703;
AAZ74397; AAZ74408; AAZ74419; AAZ74441; ABC41725; ABC41952; ABC41736; ABC41953;
AAZ74452; AAZ74507; AAZ74463; AAZ74474; ABC41964; ABC42014; ABC42114; ABC42125;
AAZ74485; AAZ74496; AAZ74529; AAZ74518; ABC42136; ABC42147; ABC42929; ABC42940;
AAZ74540; AAZ74573; AAZ74606; AAZ74551; ABC42158; ABC42169; ABC42180; ABC42192;
AAZ74595; AAZ74562; AAZ74584; AAZ74617; ABC42951; ABC42307; ABC42318; ABC42346;
AAZ79505; AAZ79516; AAZ79527; AAZ79560; ABC42461; ABC42962; ABC42494; ABC42505;
AAZ79571; AAZ79582; AAZ79626; AAZ79944; ABC42516; ABC42527; ABC42973; ABC42984;
AAZ79593; AAZ79615; AAZ79627; AAZ79941; ABC42995; ABC43006; ABC43017; ABC42574;
AAZ79963; AAZ79974; AAZ79985; AAZ80017; ABC43028; ABC43039; ABC43050; ABC43061;
AAZ79996; AAZ80007; AAZ80030; AAZ83288; ABC43072; ABC43083; ABC43094; ABC43105;
AAZ83242; AAZ83312; AAZ83266; AAZ83277; ABC43116; ABC42585; ABC42596; ABC43127;
AAZ83323; AAZ83371; AAZ83382; AAZ83649; ABC42607; ABC42618; ABC42629; ABC43138;
AAZ83688; ABA12740; ABA12751; ABA12762; ABC43149; ABC42640; ABC43160; ABC42651;
ABA12780; ABA12773; ABA16214; ABA18048; ABC43171; ABC43182; ABC42662; ABC42673;
ABA18134; ABA18156; ABA18026; ABA18123; ABC42684; ABC43475; ABC42695; ABC43486;
ABA26799; ABA26700; ABA26711; ABA26722; ABC43497; ABC43508; ABC42706; ABC42717;
ABA26733; ABA26744; ABA26755; ABA26766; ABC42728; ABC42739; ABC42761; ABC42772;
ABA26777; ABA26788; ABA42269; ABA43167; ABC42783; ABC42794; ABC42805; ABC43519;

ABC43530; ABC42816; ABC43541; ABC42827; ABE13076; ABE13323; ABE13471; ABE13555;
ABC42838; ABC42849; ABC43552; ABC42860; ABE13595; ABE13606; ABE13617; ABE13628;
ABC42871; ABC42882; ABC42893; ABC46554; ABE13639; ABE13652; ABE13824; ABE14019;
ABC46565; ABC46576; ABC54668; ABC54679; ABE14030; ABE14041; ABE14052; ABE14063;
ABC50200; ABC50211; ABC50222; ABC50233; ABE14124; ABE14464; ABE14840; ABE15578;
ABC50244; ABC50255; ABC50266; ABC50277; ABF47550; ABF47594; ABF47616; ABF47858; ABF47902;
ABC50288; ABC50299; ABC50310; ABC50321; ABI47947; ABI48006; ABF82651; ABF83447; ABF82695;
ABC50332; ABC50343; ABC50354; ABC50365; ABF82706; ABG26758; ABG26769; ABG26802;
ABC50376; ABC50387; ABC50398; ABC50409; ABG26846; ABG26857; ABG26868; ABG26879;
ABC50420; ABC67319; ABC67817; ABC68233; ABG26890; ABG26901; ABG26912; ABG26923;
ABC67850; ABC67883; ABC67894; ABC67967; ABG26934; ABG26956; ABG37131; ABG37142;
ABC67978; ABC67454; ABC67989; ABC68000; ABG37153; ABG37164; ABG37175; ABG37186;
ABC68049; ABC68060; ABC67471; ABC68071; ABG37197; ABG37208; ABG37219; ABG37230;
ABC68093; ABC67543; ABC67554; ABC68082; ABG37241; ABG37252; ABG37263; ABG37274;
ABC67565; ABC67576; ABC67587; ABC67598; ABG37285; ABG37296; ABG37307; ABG37318;
ABC67609; ABC67620; ABC67631; ABC67642; ABG37329; ABG37340; ABG37351; ABG37373;
ABC67653; ABC67664; ABC67675; ABC67686; ABG37406; ABG37417; ABG37428; ABG37439;
ABC67697; ABC67708; ABC67719; ABC67733; ABG37450; ABG37461; ABG37472; ABG37483;
ABC67806; ABC67828; ABC67839; ABC67861; ABG37494; ABG37505; ABG37516; ABG37527;
ABC67872; ABC68222; ABC84389; ABC84400; ABG37538; ABG37549; ABG37560; ABG37571;
ABC86148; ABC84411; ABC86124; ABC86040; ABG37582; ABG37593; ABG37604; ABG37615;
ABC84422; ABC86029; ABC86018; ABC84433; ABG47851; ABG47862; ABG47873; ABG47884;
ABC86007; ABC85996; ABC85985; ABC85974; ABG47895; ABG47906; ABG47917; ABG47928;
ABC84444; ABC85963; ABC85952; ABD38134; ABG47939; ABG47950; ABG47961; ABG47972;
ABC85941; ABC85930; ABC85919; ABC85908; ABG47983; ABG47994; ABG48005; ABG48016;
ABC85897; ABC85886; ABC85875; ABC84498; ABG48027; ABG48038; ABG48060; ABG48071;
ABC84509; ABC85864; ABC85853; ABC85842; ABG48082; ABG48093; ABG48104; ABG48115;
ABC84520; ABC85831; ABC85765; ABC85820; ABG48126; ABG48137; ABG48148; ABG48159;
ABC85809; ABC85798; ABC84531; ABC84542; ABG48170; ABG48181; ABG48192; ABG48203;
ABC86137; ABC85787; ABC85776; ABC85754; ABG48214; ABG48225; ABG48236; ABG48247;
ABC84560; ABC84571; ABD15526; ABD15537; ABG48258; ABG48269; ABG48280; ABG48291;
ABD16538; ABD16527; ABD16516; ABD16560; ABG48302; ABG48313; ABG48324; ABG48335;
ABD16505; ABD16494; ABD16483; ABD16472; ABG48346; ABG48357; ABG48368; ABG67135;
ABD16358; ABD16347; ABD16336; ABD16325; ABG67146; ABG67667; ABG67157; ABG67168;
ABD16314; ABD16303; ABD16549; ABD16762; ABG67179; ABG67190; ABG67201; ABG67212;
ABD17334; ABD17323; ABC97374; ABD16751; ABG67223; ABG67234; ABG67245; ABG67502;
ABD16740; ABD16729; ABD16718; ABD16593; ABG67513; ABG67524; ABG67535; ABG67546;
ABD16582; ABD16571; ABD16292; ABD15790; ABG67557; ABG67568; ABG67579; ABG67590;
ABD15779; ABD15768; ABD15757; ABD15746; ABG67601; ABG67612; ABG67623; ABG67634;
ABD15735; ABD15724; ABD15713; ABD15702; ABG67645; ABG67656; ABG79941; ABG79963;
ABD15691; ABD15680; ABD15669; ABD15658; ABG79974; ABG79985; ABG79996; ABG80007;
ABD15647; ABD15504; ABD15493; ABD15482; ABG80018; ABG80029; ABG80040; ABG80051;
ABD15471; ABD15460; ABD15449; ABD15625; ABG80062; ABG80073; ABG80084; ABG80095;
ABD15614; ABD15603; ABD15592; ABD15581; ABG80106; ABG80117; ABG80128; ABG80139;
ABD15570; ABD15559; ABD15548; ABD15636; ABG80150; ABG80161; ABG80194; ABG80205;
ABD60790; ABD60801; ABD61293; ABD60812; ABG80216; ABG80227; ABG80238; ABG80249;
ABD61304; ABD60823; ABD61529; ABD61757; ABG80260; ABG80271; ABG80282; ABG80293;
ABD61777; ABD61315; ABD61326; ABE12078; ABG80304; ABG80315; ABG80326; ABG80337;
ABD60834; ABD61337; ABD61348; ABD61359; ABG80348; ABG80359; ABG80370; ABG80381;
ABD61370; ABD61381; ABD60845; ABD61392; ABG80392; ABG80403; ABG80414; ABG80425;
ABD61403; ABD61260; ABD61271; ABD60922; ABG80436; ABG88289; ABG88355; ABG88366;
ABD61282; ABD61551; ABD61249; ABE12532; ABG88377; ABG88388; ABG88399; ABG88410;
ABE12623; ABD62833; ABD62794; ABD77598; ABG88421; ABG88432; ABG88443; ABG88454;
ABD77609; ABD77620; ABD77631; ABD77642; ABG88465; ABG88476; ABG88487; ABG88498;
ABD77653; ABD77664; ABD79123; ABD79134; ABG88509; ABG88520; ABG88531; ABG88564;
ABD79145; ABD77686; ABE12645; ABD77697; ABG88575; ABG88586; ABG88597; ABG88608;
ABD79156; ABD79167; ABD79178; ABD77741; ABG88619; ABG88630; ABG88641; ABG88652;
ABD77752; ABD77763; ABD77774; ABD77785; ABG88663; ABG88674; ABG88685; ABG88696;
ABD79032; ABD77829; ABD79189; ABD77840; ABG88707; ABG88718; ABG88729; ABG88740;
ABD79200; ABD79211; ABD77851; ABD79222; ABG88751; ABG88762; ABG88773; ABG88784;
ABD77862; ABD77873; ABD79233; ABD77884; ABG88795; ABG88806; ABG88817; ABI20793;
ABD77895; ABD79244; ABD77906; ABD78049; ABI20815; ABI20881; ABI20892; ABI20903; ABI20914;
ABD78115; ABD78126; ABD94734; ABD94745; ABI20925; ABI20936; ABI20947; ABI20958; ABI20969;
ABD94767; ABD94822; ABD94833; ABD94844; ABI21736; ABI20980; ABI20991; ABI21002; ABI21013;
ABD94855; ABD94866; ABD94877; ABD94888; ABI21024; ABI21035; ABI21046; ABI21057; ABI21068;
ABD94899; ABD94910; ABD94921; ABD94932; ABI21079; ABI21090; ABI30444; ABI21101; ABI21112;
ABD94954; ABE11911; ABE12123; ABE27164; ABI21123; ABI26646; ABI21134; ABI21145; ABI21156;

ABI21167; ABI21178; ABI21244; ABI21255; ABI21266; ABI21277; ABI21288; ABI21299; ABI21310; ABI21321; ABI21332; ABI21343; ABI21354; ABI21365; ABI21376; ABI21387; ABI21398; ABI21409; ABI21420; ABI21431; ABI21442; ABI21453; ABI21464; ABI21475; ABI21486; ABI21497; ABI22159; ABI21508; ABI30389; ABI30400; ABI30411; ABI30422; ABI30433; ABI30455; ABI30466; ABI30477; ABI30488; ABI30499; ABI30510; ABI30521; ABI30532; ABI30543; ABI30554; ABI30576; ABI30587; ABI30598; ABI30609; ABI30620; ABI30733; ABI30744; ABI30755; ABI30766; ABI30777; ABI30788; ABI30799; ABI30810; ABI30821; ABI30832; ABI30843; ABI30854; ABI30865; ABI30876; ABI84400; ABI84412; ABI84471; ABI84486; ABI84577; ABI84806; ABI84938; ABI92258; ABI92269; ABI92280; ABI92291; ABI92324; ABI92335; ABI92346; ABI92357; ABI92368; ABI92390; ABI92401; ABI92412; ABI92423; ABI92434; ABI92445; ABI92456; ABI92467; ABI92478; ABI92489; ABI92500; ABI92511; ABI92522; ABI92533; ABI92544; ABI92555; ABI92566; ABI92577; ABI92588; ABI92599; ABI92610; ABI92621; ABI92632; ABI92643; ABI92654; ABI92665; ABI92676; ABI92687; ABI92698; ABI92709; ABI92720; ABI92731; ABI92742; ABI92753; ABI92764; ABI92775; ABI92786; ABI92797; ABI92808; ABI92819; ABI92830; ABI92841; ABI92852; ABI92863; ABI92874; ABI92885; ABI92896; ABI92907; ABI92918; ABI92929; ABI92940; ABI92951; ABI92962; ABI92973; ABI92984; ABI92995; ABI93006; ABI93017; ABI93039; ABI93050; ABI93061; ABI93072; ABI93083; ABI93094; ABI93105; ABI93116; ABI95474; ABK79937; ABI95228; ABI95239; ABI95305; ABJ09096; ABJ09107; ABJO9118; ABJO9140; ABJ09162; ABJ09173; ABJ09195; ABJ09206; ABJ09217; ABJ09228; ABJ09239; ABJ09250; ABJ09261; ABJ09272; ABJ09283; ABJ09294; ABJ09305; ABJ09316; ABJ09338; ABJ09349; ABJ09360; ABJ09371; ABJ09382; ABJ16587; ABJ16598; ABJ16620; ABJ16631; ABJ16697; ABJ16708; ABJ16741; ABJ16752; ABJ16763; ABJ16774; ABJ16785; ABJ53460; ABJ53471; ABJ53482; ABK39951; ABK39962; ABK39973; ABK39984; ABK40017; ABK40061; ABK40075; ABK40612; ABK40623; ABK40645; ABK40656; ABK40667; ABK40678; ABK40700; ABK40711; ABK40722; ABK40733; ABK40744; ABK79981; ABK79992; ABK80014; ABK80058; ABK80069; ABK80080; ABK80091; ABK80102; ABK80113; ABK80124; ABK80300; ABK80135; ABK80146; ABK80157; ABK80168; ABK80179; ABK80190; ABK80201; ABK80212; ABK80223; ABK80234; ABK80245; ABK80256; ABK80267; ABK80278; ABK80289; ABK80311; ABL67044; ABL67110; ABL67132; ABL67165; ABL67176; ABL67198; ABL67220; ABL67841; ABL67275; ABL67286; ABL67297; ABL67308; ABL67319; ABL67330; ABL67341; ABL67352; ABL67363; ABL67374; ABL67385; ABL67396; ABL67407; ABL67418; ABL75563; ABM21938; ABM22015; ABM22037; ABM22059; ABM22070; ABM22081; ABM22092; ABM22103; ABM22114; ABM22125; ABO32816; ABM22136; ABM22147; ABM22301; ABM22312; ABM22323; ABM22334; ABM22345; ABM22356; ABM22367; ABM66853; ABM66875; ABM66919; ABM66930; ABM66941; ABM66952; ABM66963; ABM66974; ABM66985; ABM66996; ABM67007; ABM67018; ABM67029; ABM67040; ABN50767; ABN50984; ABN50995; ABN51010; ABN51021; ABN51032; ABN51043; ABN51054; ABN51099; ABN51110; ABN51121; ABN51132; ABN51154; ABN59390; ABO32656; ABO32667; ABO32692; ABO32751; ABO32762; ABO32775; ABO32790; ABO32803; ABO32827; ABO32838; ABO32849; ABO32860; ABO32871; ABO32882; ABO32893; ABO32904; ABO32915; ABO32926; ABO32937; ABO033036; ABO33047; ABO33058; ABO33069; ABO38076; ABO38087; ABO38230; ABO38241; ABO38252; ABO38274; ABO38285; ABO38417; ABO44035; ABO44068; ABO44079; ABO51829; ABO51862; ABO51884; ABO76913; ABO52071; ABO52126; ABO52214; ABO52291; ABO52313; ABO52324; ABO52335; ABO52346; ABO52357; ABO52368; ABO52423; ABO52522; ABO52566; ABO52577; ABO52588; ABO52599; ABO52632; ABO52643; ABO52676; ABO64343; ABO76946; ABO76957; ABP49184; ABP49371; ABP49404; ABP49415; ABP49426; ABP49492; ABP49503; ABP49514; BAA00769; BAA00770; BAA00771; BAA00772; BAA01025; BAA01026; BAA02776; BAA02777; BAA02778; BAA02779; BAA04707; BAA04708; BAA04709; BAA04710; BAA04711; BAA04712; BAA04713; BAA04714; BAA04715; BAA04716; BAA04717; BAA04718; BAA04719; BAA21644; BAA21645; BAA21646; BAA21647; BAA21648; BAA33866; BAA33938; BAA33939; BAA33940; BAA33941; BAA33942; BAA33943; BAA33944; BAA33945; BAA33946; BAA33947; BAA07844; BAA07845; BAA07846; BAA07847; BAA07848; BAA07849; BAA07850; BAA08713; BAA08714; BAA21070; BAA08715; BAA08716; BAA08717; BAA08718; BAA21071; BAA08719; BAA13091; AAY23641; AAY23642; AAY25498; AAY46201; AAY46202; AAY58320; AAZ06795; AAZ32943; AAZ32944; AAZ32945; AAZ32946; AAZ32947; AAZ32948; AAZ32949; AAZ32950; AAZ32951; AAZ32952; AAZ32953; AAZ29151; AAZ29152; AAZ29153; AAZ29154; AAZ29155; AAZ29156; AAZ29157; AAZ29158; AAZ29159; AAZ29160; AAZ29161; AAZ29162; AAZ29163; AAZ29164; AAZ29165; AAZ29166; AAZ29167; AAZ29168; AAZ29169; AAZ29170; AAZ29171; AAZ29172; AAZ29173; AAZ29174; AAZ29175; AAZ29176; AAZ29177; AAZ29178; AAZ29179; AAZ29180; AAZ29181; AAZ29182; AAZ29183; AAZ29184; AAZ29185; AAZ29186; AAZ29187; AAZ29188; AAZ29189; AAZ29190; AAZ29191; AAZ29192; ABA39842; ABA39843; ABA39844; ABA39845; ABA39846; ABA39847; ABA39848; ABA39849; ABA39850; AAZ57437; AAZ74350; ABA46957; ABA41538; ABA27432; ABA27440; AAZ91962; AAZ91963; AAZ91964; ABA60253; ABA60254; ABA60255; ABA60256; ABA60257; ABA60258; ABA60259; ABA60260; ABA60261; ABA60262; ABA60263; ABA60264; ABA60265; ABA60266; ABA60267; ABA60268; ABA60269; ABA60270; ABA60271; ABA60272; ABA60273; ABA60274; ABA60275; ABA60276; ABA60277; ABA60278; ABA60279; ABA60280; ABA60281; ABA60282; ABA60283; ABA60284; ABA60285; ABA60286; ABA60287; ABA60288; ABA60289; ABA60290; ABA60291; ABA60292; ABA60293; ABA60294; ABA60295; ABA60296; ABA60297; ABA60298; ABA60299; ABA60300; ABA60301; ABA60302; ABA60303; ABA60304; ABA60305; ABA60306; ABA60307; ABA60308; ABA60309; ABA06580; ABA06581; ABA06582; ABA06583; ABA06584; ABA06585; ABA60900; ABA60901; ABA60902; ABA60903; ABA60904; ABA60905; ABA60906;

ABA60907; ABA60908; ABA60909; ABA60910; ABA60911; ABA60912; ABA60913; ABA60914; ABA60915; ABA60916; ABA60917; ABA60918; ABA60919; ABA60920; ABA60921; ABA60922; ABA60923; ABA60924; ABA60925; ABA60926; ABA60927; ABA60928; ABA60929; ABA60930; ABA60931; ABA60932; ABA60933; ABA60934; ABA60935; ABA60936; ABA60937; ABA60938; ABA60939; ABA60940; ABA60941; ABA60942; ABA60943; ABA60944; ABA60945; ABA60946; ABA60947; ABA60948; ABA60949; ABA60950; ABA60951; ABA60952; ABA60953; ABA60954; ABA60955; ABA60956; ABA60957; ABA60958; ABA60959; ABA60960; ABA60961; ABA60962; ABA60963; ABA60964; ABA60965; ABA60966; ABA60967; ABA60968; ABA60969; ABA60970; ABA60971; ABA60972; ABA60973; ABA60974; ABA60975; ABA60976; ABA60977; ABA60978; ABA60979; ABA60980; ABA60981; ABA60982; ABA60983; ABA60984; ABA60985; ABA60986; ABA60987; ABA60988; ABA60989; ABA60990; ABA60991; ABA60992; ABA60993; ABA60994; ABA60995; ABA60996; ABA60997; ABA60998; ABA60999; ABA61000; ABA61001; ABA61002; ABA61003; ABA61004; ABA61005; ABA61006; ABA61007; ABA61008; ABA61009; ABA61010; ABA61011; ABA61012; ABA61013; ABA61014; ABA61015; ABA61016; ABA61017; ABA61018; ABA61019; ABA61020; ABA61021; ABA61022; ABA61023; ABA61024; ABA61025; ABA61026; ABA61027; ABA61028; ABA61029; ABA61030; ABA61031; ABA61032; ABA61033; ABA61034; ABA61035; ABA61036; ABA61037; ABA61038; ABA61039; ABA61040; ABA61041; ABA61042; ABA61043; ABA61044; ABA61045; ABB17173; ABB71825; ABB71826; ABB71827; ABB71828; ABB71829; ABB71830; ABB71831; ABB71832; ABB71833; ABB51981; ABB51982; ABB51983; ABB51961; ABB51963; ABB51964; ABB76697; ABB76698; ABB76699; ABB76700; ABB84191; ABB84192; ABB84193; ABB84194; ABB84195; ABB84196; ABB84197; ABB84198; ABB84199; ABB84200; ABB84201; ABB84202; ABC59709; ABC66247; ABC66248; ABC66249; ABC66250; ABC66251; ABC66252; ABC66253; ABC66254; ABC66255; ABC66256; ABC66257; ABC66258; ABD59850; ABD59851; ABD59852; ABD59853; ABD59854; ABD59855; ABD59856; ABD59857; ABD85122; ABF17954; ABF17955; ABF17956; ABF17957; ABF17958; ABF17959; ABE73114; ABE73115; ABF21268; ABF21269; ABF21271; ABF21273; ABF21281; ABG26247; ABG26248; ABG26249; ABG26250; ABG26251; ABG26252; ABG26253; ABG26254; ABG26255; ABG26256; ABG02860; ABG02861; ABG02862; ABG02863; ABH00993; ABH00994; ABH00995; ABH00996; ABH00997; ABH00998; ABH00999; ABH01000; ABHO1001; ABHO1002; ABHO1003; ABHO1004; ABHO1005; ABHO1006; ABHO1007; ABHO1008; ABHO1009; ABHO1010; ABHO1011; ABHO1012; ABHO1013; ABHO1014; ABHO1015; ABHO1016; ABHO1017; ABHO1018; ABHO1019; ABHO1020; ABHO1021; ABHO1022; ABI22056; ABI22057; ABI22058; ABI22059; ABI22060; ABI22061; ABI22062; ABI22063; ABI22064; ABI22065; ABI22066; ABI22067; ABI22068; ABI22069; ABI22070; ABI22071; ABI22072; ABI22073; ABI22074; ABI22075; ABI22076; ABI22077; ABI22078; ABI22079; ABI22080; ABI22081; ABI22082; ABI22083; ABI22084; ABI22085; ABI22086; ABI22087; ABI22088; ABI22089; ABI22090; ABI22091; ABI22092; ABI22093; ABI22094; ABI22095; ABI22096; ABI22097; ABI22098; ABI22099; ABI22100; ABI22101; ABI22102; ABI54388; ABI54389; ABJ51896; ABI49169; ABI49170; ABI49171; ABI49172; ABI49173; ABI49174; ABI49175; ABI49176; ABI49177; ABI49178; ABI49179; ABI49180; ABI49181; ABI49182; ABI49183; ABI49184; ABI51314; ABI51315; ABI51316; ABI55257; ABI55258; ABI55259; ABI55260; ABI55261; ABI55262; ABI55263; ABI55264; ABI55265; ABI55266; ABI55267; ABI55268; ABI55269; ABI55270; ABI55271; ABI55272; ABI55273; ABI55274; ABI55275; ABI55276; ABI55277; ABI55278; ABJ53158; ABM47075; ABK60213; ABK60214; ABK60215; ABL86145; ABM98421; ABM98422; ABO10165; ABO10166; ABO10167; ABO10168; ABO10169; ABO10170; ABO10171; ABO10172; ABO10173; ABO10174; ABO10175; ABO10182; ABO20947; ABO20952; ABO20953; ABO20954; ABO20955; ABO20956; ABO20957; ABO20958; ABO21717; ABO21718; ABO21719; ABO21720; ABO21721; ABO21722; ABO21726; ABO21727; ABO21728; ABO21729; ABO20959; ABO20960; ABO21733; ABO37477; ABO37478; ABO37479; ABO37480; ABO37481; ABO37482; ABO37483; ABO37484; ABO37485; ABO37486; ABO37487; ABO37488; ABO37489; ABO37490; ABO37491; ABO37492; ABO37493; ABO37494; ABO37495; ABO37496; ABO37497; ABO37498; ABO37499; ABO37500; ABO37501; ABO37502; ABO37503; ABO37504; ABO37505; ABO37506; ABO37507; ABO37508; ABO37509; ABO37510; ABO37511; ABO37512; ABO37513; ABO37514; ABO37515; ABO37516; ABO37517; ABO37518; ABO37519; ABO37520; ABO37522; ABO37523; ABO37524; ABO37525; ABO37526; ABO37527; ABO37528; ABO37529; ABO37530; ABO37531; ABO37532; ABO37533; ABO37534; ABO37535; ABO37536; ABO37537; ABO37538; ABO37539; ABO37540; ABO37541; ABO37542; ABO37543; ABO37544; ABO37545; ABO37546; ABO37547; ABO37548; ABO37549; ABO37550; ABO37551; ABO37552; ABO37553; ABO37554; ABO37555; ABO37556; ABO37557; ABO37558; ABO37559; ABO37560; ABO37561; ABO37562; ABO37563; ABO37564; ABO37565; ABO37566; ABO37567; ABO37568; ABO37569; ABO37570; ABO37571; ABO37572; ABO37573; ABO37574; ABO37575; ABO37576; ABO37577; ABO37578; ABO37579; ABO37580; ABO37581; ABO37582; ABO37583; ABO37584; ABO37585; ABO37586; ABO37587; ABO37588; ABO37589; ABO37590; ABO37591; ABO37592; ABO37593; ABO37594; ABO37595; ABO37596; ABO37597; ABO37598; ABO37599; ABO37600; ABO37601; ABO37602; ABO37603; ABO37604; ABO37605; ABO37606; ABO37607; ABO37608; ABO37609; ABO37610; ABO37611; ABO37612; ABO37613; ABO37614; ABO37615; ABO37616; ABO37617; ABO37618; ABO37619; ABO37620; ABO37621; ABO37622; ABO37623; ABO37624; ABO37625; ABO37626; ABO37627; ABO37628; ABO37629; ABO37630; ABO37631; ABO37632; ABO37633; ABO37634; ABO37635; ABO37636; ABO37637; ABO37638; ABO37639; ABO37640; ABO37641; ABO37642; ABO37643; ABO37644; ABO37645; ABO37646; ABO37647; ABO37648; ABO37649;

ABO37650; ABO37651; ABO37652; ABO37653; ABO37654; ABO37655; ABO37656; ABO37657; ABO37658; ABO37659; ABO37660; ABO37661; ABO37662; ABO37663; ABO37664; ABO37665; ABO37666; ABO37667; ABO37668; ABO37669; ABO37670; ABO37671; ABO37672; ABO37673; ABO37674; ABO37675; ABO37676; ABO37677; ABO37678; ABO37679; ABO37680; ABO37681; ABO37682; ABO37683; ABO37684; ABO37685; ABO37686; ABO37687; ABO37688; ABO37689; ABO37690; ABO37691; ABO37692; ABO37693; ABO37694; ABO37695; ABO37696; ABO37697; ABO37698; ABO37699; ABO37700; ABO37701; ABO37702; ABO37703; ABO37704; ABO37705; ABO37706; ABO37707; ABO37708; ABO37709; ABO37710; ABO37711; ABO37712; ABO37713; ABO37714; ABO37715; ABO37716; ABO37717; ABO37718; ABO37719; ABO37720; ABO37721; ABO37722; ABO37723; ABO37724; ABO37725; ABO37726; ABO37727; ABO37728; ABO37729; ABO37730; ABO37731; ABO37732; ABO37733; ABO37734; ABO37735; ABO37736; ABO37737; ABO37738; ABO37739; ABO37740; ABO37741; ABO37742; ABO37743; ABO37744; ABO37745; ABO37746; ABO37747; ABO37748; ABO37749; ABO37750; ABO37751; ABO37752; ABO37753; ABO37754; ABO37755; ABO37756; ABO37757; ABO37758; ABO37759; ABO37760; ABO37761; ABO37762; ABO37763; ABO37764; ABO37765; ABO37766; ABO37768; ABO37769; ABO37770; ABO37771; ABO37772; ABO37773; ABO37774; ABO37775; ABO37776; ABO37777; ABO37778; ABO37779; ABO37780; ABO37781; ABO37782; ABO37783; ABP35587; ABP35588; ABP35589; ABP35590; ABP35591; ABP35592; ABP35593; ABP35594; ABP35595; ABP35596; ABP35597; ABP35598; ABP35599; ABP35600; ABP35601; ABP35602; AAA43178; AAA43182; AAA43187; AAA43200; AAA43184; AAA43195; AAA62328; AAA62335; AAA62329; AAA62331; AAA62327; AAA62330; AAA62339; AAA62338; AAA62332; AAA43230; AAA43229; AAA43228; AAA43227; AAA43226; ABG66978; ABE73717; ABG66979; ABG66980; ABG66981; ABG57281; ABG57282; ABG57283; ABG57284; AAA62470; AAA64229; AAA64228; AAB36975; AAB36976; AAB36977; AAB36978; AAB36979; AAB36980; AAB19009; AAB19010; AAB19011; AAB19012; AAB19013; AAB19014; AAB19015; AAB19016; AAB19017; AAB19018; AAB19019; AAB19020; AAB19021; AAB19022; AAB19023; AAB19024; AAB19025; AAB19028; AAB19026; AAB19027; AAA43143; AAA43144; AAA43145; AAA43146; AAA43147; AAA43148; AAA43149; AAA43211; AAA43212; AAA43275; AAA43114; AAA43105; AAA43111; AAA43100; AAA43107; AAA43101; AAA43109; AAA43110; AAA43112; AAA43102; AAA43103; AAO49821; AAA43163; AAA43164; AAA43099; AAA43239; AAA43155; AAA43156; AAA43162; AAA43165; AAA43151; ABF60581; ABF60577; ABF60576; ABF60580; ABF60579; ABF60578; AAB27733; AAB33340; AAA85781; AAA18781; AAA18782; AAC79579; AAA87553; AABQ9413; AABO9414; AABO9415; AAB09416; AABO9417; AABO9418; AABO9419; AAB09420; AAB09421; AAA92927; AAB02560; AAD00123; AAD00124; AAC80152; AAD00125; AAD00126; AAC80153; AAD00127; AAD00128; AAC80154; AAF24003; AAC08288; AAC08289; AAC08290; AAC08291; AAC08292; AAC08293; AAC08294; AAC08295; AAC08296; AAC08297; AAB58297; CAA24269; CAA24270; CAA24271; CAA24273; CAA24281; CAA24290; CAA24291; CAA29337; CAA48482; CAA51904; CAA51905; CAA51906; CAA53437; CAA59412; CAA59413; CAA59414; CAA59415; CAA59416; CAA59417; CAA64893; CAA64894; CAA74382; CAA74383; CAA74384; CAA74385; CAA74386; CAA74387; CAA74388; CAA86526; CAA86527; CAA86528; CAA86529; CAA86530; CAA86531; CAA86532; CAA86533; CAA86534; CAA86535; CAA86536; CAA86537; CAA86538; CAA86539; CAA86540; CAA86541; CAA86542; CAA86543; CAA86544; CAA86545; CAA86546; CAA86547; CAA86548; CAA86549; CAA86550; CAA86551 and CAA86552.

Protein sequences of influenza virus subtype H4 haemagglutinin suitable for inclusion as a cargo moiety in conjugates according to the present invention have the following accession numbers and are available to the public via the National Center for Biotechnology Information (NCBI) Entrez protein search and retrieval system:

BAF43432; BAF43456; ABB87539; ABB87550; ABB87561; ABB87572; ABB87583; ABB87594; ABB87604; ABB87615; ABB87626; ABB87637; ABB87648; ABB87656; ABB87667; ABB87678; ABB87689; ABB87700; ABB88194; ABB88267; ABB88298; ABI47995; ABI48017; ABG88223; ABG88234; ABI92225; ABI84388; ABI84423; ABI84483; ABI84604; ABI84643; ABI84795; ABI84885; ABI84894; ABI84905; ABI92203; ABI92214; ABI97487; ABL67033; ABL67088; ABO51840; ABO51851; ABO51873; ABO51895; ABO51906; ABO51928; ABO51939; ABO51950; ABO52192; ABO52500; ABO52511; ABO52533; ABO52654; ABO52665; ABO52687; BAA14332; AAY88147; AAY88148; AAY88149; AAY88150; AAY88151; AAY88152; AAY88153; AAY88154; AAY88155; AAY88156; AAY88157; AAY88158; AAY88159; AAY88160; AAY88161; AAY88162; AAY88163; AAY88164; AAY88165; AAY88166; AAY88167; ABB80525; ABC59902; ABI17551; ABJ53168; AAA43179; AAA43216; AAA43217; AAA43218; AAA43219; AAA43220; AAA43221; AAA43222; AAA43223; AAA43224; BAF43458; BAF46756; BAF46758; BAF46904; BAF48476; BAF48478; AAG17427; AAG17429; AAF99711; CAD45001; CAD45000; AAN83962; AAN83963; AAN83964; AAN83965; AAN83966; AAN83967; AAN83968; AAN83969; AAN83970; AAN83971; AAT09640; AAT09641; AAT09642; AAT65318; AAT65320; AAT65322; AAT65335; AAT65336; AAT65338; AAT65346; AAT65347; ABB19802; ABB19847; ABB19867; ABB19878; ABB19886; ABB20362; ABB20372; ABB87473; ABB87484; ABB87495; ABB87506; ABB90165; ABB87517 and ABB87528.

Protein sequences of influenza virus subtype H5 haemagglutinin suitable for inclusion as a cargo moiety in conjugates according to the present invention have the following accession numbers and are available to the public via the National Center for Biotechnology Information (NCBI) Entrez protein search and retrieval system:

AB166862; AB188816; AB188824; AB189053; AB189061; AB212054; AB212280; AB212649; AB233319; AB233320; AB233321; AB233322; AB239125; AB241614; AB241615; AB241616; AB241617; AB241618; AB241619; AB241620; AB241621; AB241622; AB241623; AB241624;

AB241625; AB241626; AB259712; AB261853; AB263192;
AB263752; AB275420; AB275421; AB275422; AB275423;
AB275424; AB275425; AB275426; AB275427; AB275428;
AB275429; AB275430; AB275431; AB275432; AB275433;
AB275434; AB284324; AB295603; AF028709; AF036356;
AF046080; AF046088; AF046096; AF046097; AF046098;
AF046099; AF046100; AF057291; AF082034; AF082035;
AF082036; AF082037; AF082038; AF082039; AF082040;
AF082041; AF082042; AF082043; AF084279; AF084280;
AF084281; AF084532; AF098537; AF098538; AF098539;
AF098540; AF098541; AF098542; AF098543; AF098544;
AF098545; AF098546; AF100179; AF100180; AF102671;
AF102672; AF102673; AF102674; AF102675; AF102676;
AF102677; AF102678; AF102679; AF102680; AF102681;
AF102682; AF144305; AF148678; AF164655; AF164656;
AF164657; AF164658; AF164659; AF164660; AF164661;
AF164662; AF164663; AF164664; AF164665; AF194169;
AF194990; AF194991; AF194992; AF216713; AF216721;
AF216729; AF216737; AF290443; AF303057; AF364334;
AF377870; AF398417; AF398418; AF420254; AF439407;
AF439408; AF468837; AF501234; AF501235; AF509016;
AF509017; AF509018; AF509019; AF509020; AF509021;
AF509022; AF509023; AF509024; AF509025; AF509026;
AF509027; AF509028; AF509029; AF509030; AF509031;
AF509032; AF509033; AF509034; AF509035; AF509036;
AF509037; AF509038; AF509039; AJ305306; AJ621807;
AJ621811; AJ632268; AJ632269; AJ715872; AJ867074;
AJ971297; AJ971298; AJ972673; AM087222; AM183669;
AM183670; AM183671; AM183672; AM183673;
AM183674; AM183675; AM183676; AM183677;
AM231714; AM236074; AM262541; AM262542;
AM262543; AM262546; AM262547; AM262553;
AM262572; AM397634; AM400972; AM400973;
AM400974; AM400975; AM400976; AM400977;
AM400978; AM400979; AM400980; AM400981;
AM403460; AM403461; AM403462; AM403463;
AM403464; AM403465; AM403466; AM403467;
AM403468; AM403469; AM403470; AM403471;
AM403472; AM403473; AM403474; AM403475;
AM408209; AM408210; AM408211; AM408212;
AM408213; AM408214; AM408215; AM408216;
AM492165; AY059474; AY059475; AY059476; AY059477;
AY059478; AY059479; AY059480; AY059481; AY059482;
AY075027; AY075030; AY075033; AY221521; AY221522;
AY221523; AY221524; AY221525; AY221526; AY221527;
AY221528; AY221529; AY296064; AY296065; AY296066;
AY296067; AY296068; AY296069; AY296070; AY296071;
AY296072; AY296073; AY296074; AY296075; AY296076;
AY296077; AY296078; AY296079; AY296080; AY296081;
AY296082; AY296083; AY296084; AY296085; AY296086;
AY497063; AY497064; AY497065; AY497066; AY497067;
AY497068; AY497069; AY497070; AY497071; AY497072;
AY497073; AY497074; AY497075; AY497076; AY497077;
AY497078; AY497079; AY497080; AY497081; AY497082;
AY497083; AY497084; AY497085; AY497086; AY497087;
AY497088; AY497089; AY497090; AY497091; AY497092;
AY497093; AY497094; AY497095; AY497096; AY500365;
AY518362; AY526745; AY531029; AY534913; AY534914;
AY535020; AY535021; AY535022; AY535023; AY536212;
AY552000; AY552001; AY553784; AY553785; AY553786;
AY553787; AY553788; AY553789; AY553790; AY553791;
AY553792; AY553793; AY553794; AY553795; AY553796;
AY553797; AY553798; AY553799; AY553800; AY553801;
AY553802; AY553803; AY553804; AY553805; AY553806;
AY553807; AY553808; AY553809; AY553810; AY553811;
AY555150; AY555153; AY573917; AY574187; AY574190;
AY575869; AY575870; AY575871; AY575872; AY575873;
AY575874; AY575875; AY575876; AY575877; AY575878;
AY575879; AY575880; AY576927; AY576930; AY577314;
AY585357; AY585358; AY585359; AY585360; AY585361;
AY585362; AY585363; AY585364; AY585365; AY585366;
AY585367; AY585368; AY585369; AY585370; AY585371;
AY585372; AY585373; AY585374; AY585375; AY585376;
AY585377; AY590563; AY590568; AY590569; AY590570;
AY590571; AY590572; AY590577; AY609312; AY623430;
AY626143; AY627885; AY639405; AY646167; AY646175;
AY646424; AY649382; AY651320; AY651321; AY651322;
AY651323; AY651324; AY651325; AY651326; AY651327;
AY651328; AY651329; AY651330; AY651331; AY651332;
AY651333; AY651334; AY651335; AY651336; AY651337;
AY651338; AY651339; AY651340; AY651341; AY651342;
AY651343; AY651344; AY651345; AY651346; AY651347;
AY651348; AY651349; AY651350; AY651351; AY651352;
AY651353; AY651354; AY651355; AY651356; AY651357;
AY651358; AY651359; AY651360; AY651361; AY651362;
AY651363; AY651364; AY651365; AY651366; AY651367;
AY651368; AY651369; AY651370; AY651371; AY651372;
AY651373; AY653200; AY676033; AY676034; AY676035;
AY676036; AY679514; AY684706; AY684894; AY720942;
AY720945; AY720950; AY724782; AY724783; AY724785; AY724787;
AY724789; AY724791; AY724793; AY724795; AY728892;
AY728894; AY737289; AY737296; AY737304; AY741213;
AY741215; AY741217; AY741219; AY741221; AY747609;
AY747617; AY770079; AY770991; AY779048; AY779050;
AY786078; AY818135; AY818136; AY818137; AY830774;
AY834279; AY842935; AY849793; AY854190; AY861372;
AY866475; AY950230; AY950231; AY950232; AY950233;
AY950234; AY950235; AY950236; AY972539; AY972540;
AY972541; AY972542; AY995883; AY995884; AY995885;
AY995886; AY995887; AY995888; AY995889; AY995890;
AY995891; AY995892; AY995893; AY995894; AY995895;
AY995896; AY995897; AY995898; CY005575; CY005918;
CY005926; CY005927; CY005969; CY006028; CY006036;
CY006040; CY011248; CY014168; CY014177; CY014185;
CY014193; CY014197; CY014198; CY014199; CY014200;
CY014201; CY014202; CY014203; CY014204; CY014205;
CY014206; CY014207; CY014208; CY014209; CY014210;
CY014211; CY014212; CY014213; CY014272; CY014280;
CY014288; CY014296; CY014303; CY014311; CY014368;
CY014376; CY014384; CY014393; CY014401; CY014409;
CY014417; CY014425; CY014433; CY014441; CY014449;
CY014457; CY014465; CY014477; CY014481; CY014489;
CY014497; CY014510; CY014518; CY014529; CY014537;
CY014543; CY014580; CY014615; CY014640; CY014642;
CY014717; CY014722; CY014726; CY014849; CY014872;
CY014984; CY015073; CY015081; CY015089; CY015115;
CY016276; CY016284; CY016292; CY016300; CY016611;
CY016779; CY016787; CY016795; CY016803; CY016811;
CY016819; CY016827; CY016835; CY016843; CY016851;
CY016859; CY016867; CY016875; CY016883; CY016891;
CY016899; CY016907; CY016915; CY016923; CY016931;
CY016939; CY016947; CY017027; CY017035; CY017043;
CY017051; CY017059; CY017067; CY017179; CY017187;
CY017403; CY017638; CY017646; CY017654; CY017662;
CY017670; CY017678; CY017688; CY018949; CY019352;
CY019360; CY019368; CY019376; CY019384; CY019392;
CY019400; CY019408; CY019416; CY019424; CY019432;
CY020229; CY020349; CY020621; CY020629; CY020637;
CY020645; CY020653; CY020661; CY020669; CY020677;
CY020693; CY020701; CY020709; CY021373; CY021381;
CY021389; CY021397; CY021517; CY021525; DQ003215;
DQ007623; DQ017270; DQ017271; DQ017272;
DQ017273; DQ017274; DQ017275; DQ017276;
DQ017277; DQ017278; DQ017279; DQ017280;

DQ017281; DQ017282; DQ017283; DQ017284; DQ497661; DQ497662; DQ497663; DQ497664;
DQ017285; DQ017286; DQ017287; DQ017288; DQ497665; DQ497666; DQ497667; DQ497668;
DQ017289; DQ017290; DQ017291; DQ017292; DQ497669; DQ497670; DQ497671; DQ497672;
DQ017293; DQ017294; DQ017295; DQ017296; DQ497673; DQ497674; DQ497675; DQ497676;
DQ017297; DQ017298; DQ017299; DQ017300; DQ497677; DQ497678; DQ497679; DQ497680;
DQ017301; DQ017302; DQ017303; DQ017304; DQ497681; DQ497682; DQ497683; DQ497684;
DQ017305; DQ017306; DQ017307; DQ017308; DQ497685; DQ497686; DQ497687; DQ497688;
DQ023145; DQ076201; DQ080022; DQ083550; DQ497689; DQ497690; DQ497691; DQ497692;
DQ083551; DQ083552; DQ083553; DQ083554; DQ497693; DQ497694; DQ497695; DQ497696;
DQ083555; DQ083556; DQ083557; DQ083558; DQ497697; DQ497698; DQ497699; DQ497700;
DQ083559; DQ083560; DQ083561; DQ083562; DQ497701; DQ497702; DQ497703; DQ497704;
DQ083563; DQ083564; DQ083565; DQ083566; DQ497705; DQ497706; DQ497707; DQ497708;
DQ083567; DQ083568; DQ083569; DQ083570; DQ497709; DQ497710; DQ497711; DQ497712;
DQ083571; DQ083572; DQ083573; DQ083574; DQ497713; DQ497714; DQ497715; DQ497716;
DQ083575; DQ083576; DQ083577; DQ083578; DQ497717; DQ497718; DQ497719; DQ497720;
DQ083579; DQ083580; DQ083581; DQ083582; DQ497721; DQ497722; DQ497723; DQ497724;
DQ083583; DQ083584; DQ083585; DQ092869; DQ497725; DQ497726; DQ497727; DQ497728;
DQ095612; DQ095613; DQ095614; DQ095615; DQ497729; DQ515984; DQ530173; DQ535724;
DQ095616; DQ095617; DQ095618; DQ095619; DQ643809; DQ643982; DQ644955; DQ644956;
DQ095620; DQ095621; DQ095622; DQ095623; DQ644957; DQ644958; DQ644959; DQ650659;
DQ095624; DQ095625; DQ095626; DQ095627; DQ650663; DQ659113; DQ659326; DQ659327;
DQ095628; DQ095629; DQ095630; DQ095631; DQ659679; DQ661910; DQ666146; DQ673901;
DQ099755; DQ099756; DQ099757; DQ099758; DQ676830; DQ676834; DQ676838; DQ676840;
DQ099759; DQ099760; DQ100554; DQ100555; DQ767725; DQ826532; DQ835313; DQ836043;
DQ100556; DQ100557; DQ104701; DQ122147; DQ837587; DQ837588; DQ837589; DQ837590;
DQ137873; DQ153251; DQ153252; DQ182483; DQ838508; DQ838509; DQ838516; DQ838517;
DQ188905; DQ188906; DQ188907; DQ188908; DQ840519; DQ840533; DQ842487; DQ842489;
DQ190857; DQ190858; DQ190859; DQ190860; DQ845348; DQ851561; DQ852600; DQ861291;
DQ190861; DQ191688; DQ191689; DQ201829; DQ861999; DQ862000; DQ862001; DQ862002;
DQ211922; DQ211923; DQ211924; DQ211925; DQ862003; DQ863503; DQ864711; DQ864715;
DQ212792; DQ230521; DQ230522; DQ231240; DQ864716; DQ864717; DQ864718; DQ864719;
DQ231241; DQ231242; DQ236077; DQ236085; DQ864720; DQ864721; DQ885610; DQ885612;
DQ251447; DQ251796; DQ251797; DQ251798; DQ885614; DQ885616; DQ885618; DQ914808;
DQ251799; DQ251800; DQ256383; DQ279301; DQ914814; DQ991231; DQ992714; DQ992715;
DQ309440; DQ320137; DQ320875; DQ320876; DQ992716; DQ992717; DQ992718; DQ992719;
DQ320877; DQ320878; DQ320879; DQ320880; DQ992720; DQ992721; DQ992722; DQ992723;
DQ320881; DQ320882; DQ320883; DQ320884; DQ992724; DQ992725; DQ992726; DQ992727;
DQ320885; DQ320886; DQ320887; DQ320888; DQ992728; DQ992729; DQ992730; DQ992731;
DQ320889; DQ320890; DQ320891; DQ320892; DQ992732; DQ992733; DQ992734; DQ992735;
DQ320893; DQ320894; DQ320895; DQ320896; DQ992736; DQ992737; DQ992738; DQ992739;
DQ320897; DQ320898; DQ320899; DQ320900; DQ992740; DQ992741; DQ992742; DQ992743;
DQ320901; DQ320902; DQ320903; DQ320904; DQ992744; DQ992745; DQ992746; DQ992747;
DQ320905; DQ320906; DQ320907; DQ320908; DQ992748; DQ992749; DQ992750; DQ992751;
DQ320909; DQ320910; DQ320911; DQ320912; DQ992752; DQ992753; DQ992754; DQ992755;
DQ320913; DQ320914; DQ320915; DQ320916; DQ992756; DQ992757; DQ992758; DQ992759;
DQ320917; DQ320918; DQ320919; DQ320920; DQ992760; DQ992761; DQ992762; DQ992763;
DQ320921; DQ320922; DQ320923; DQ320924; DQ992764; DQ992765; DQ992766; DQ992767;
DQ320925; DQ320926; DQ320927; DQ320928; DQ992768; DQ992769; DQ992770; DQ992771;
DQ320929; DQ320930; DQ320931; DQ320932; DQ992772; DQ992773; DQ992774; DQ992775;
DQ320933; DQ320934; DQ320935; DQ320936; DQ992776; DQ992777; DQ992778; DQ992779;
DQ320937; DQ320938; DQ320939; DQ320940; DQ992780; DQ992781; DQ992782; DQ992783;
DQ323672; DQ334760; DQ334768; DQ334776; DQ992784; DQ992785; DQ992786; DQ992787;
DQ340848; DQ343150; DQ343151; DQ343152; DQ992788; DQ992789; DQ992790; DQ992791;
DQ343502; DQ356886; DQ358746; DQ360835; DQ992792; DQ992793; DQ992794; DQ992795;
DQ363918; DQ363923; DQ364996; DQ365004; DQ992796; DQ992797; DQ992798; DQ992799;
DQ366306; DQ366314; DQ366322; DQ366330; DQ992800; DQ992801; DQ992802; DQ992803;
DQ366338; DQ371928; DQ371929; DQ371930; DQ992804; DQ992805; DQ992806; DQ992807;
DQ372591; DQ387854; DQ389158; DQ399540; DQ992808; DQ992809; DQ992810; DQ992811;
DQ399547; DQ406728; DQ407519; DQ412997; DQ992812; DQ992813; DQ992814; DQ992815;
DQ434889; DQ435200; DQ435201; DQ435202; DQ992816; DQ992817; DQ992818; DQ992819;
DQ440535; DQ447199; DQ449031; DQ449632; DQ992820; DQ992821; DQ992822; DQ992823;
DQ449640; DQ453141; DQ458992; DQ464354; DQ992824; DQ992825; DQ992826; DQ992827;
DQ464377; DQ497642; DQ497643; DQ497644; DQ992828; DQ992829; DQ992830; DQ992831;
DQ497645; DQ497646; DQ497647; DQ497648; DQ992832; DQ992833; DQ992834; DQ992835;
DQ497649; DQ497650; DQ497651; DQ497652; DQ992836; DQ992837; DQ992838; DQ992839;
DQ497653; DQ497654; DQ497655; DQ497656; DQ992840; DQ992841; DQ992842; DQ992843;
DQ497657; DQ497658; DQ497659; DQ497660; DQ992844; DQ992845; DQ992846; DQ992847;

DQ992848; DQ992849; DQ992850; DQ992851; DQ992852; DQ992853; DQ992854; DQ992855; DQ992856; DQ992857; DQ992858; DQ992859; DQ992860; DQ992861; DQ992862; DQ992863; DQ992864; DQ992865; DQ992866; DQ992867; DQ992868; DQ992869; DQ992870; DQ992871; DQ992872; DQ992873; DQ992874; DQ992875; DQ992876; DQ992877; DQ992878; DQ992879; DQ992880; DQ992881; DQ992882; DQ992883; DQ992884; DQ992885; DQ992886; DQ992887; DQ992888; DQ992889; DQ992890; DQ992891; DQ992892; DQ992893; DQ992894; DQ992895; DQ992896; DQ992897; DQ992898; DQ992899; DQ992900; DQ992901; DQ992902; DQ992903; DQ992904; DQ992905; DQ992906; DQ992907; DQ992908; DQ992909; DQ992910; DQ992911; DQ992912; DQ992913; DQ992914; DQ992915; DQ992916; DQ992917; DQ992918; DQ992919; DQ992920; DQ992921; DQ992922; DQ992923; DQ992924; DQ992925; DQ992926; DQ992927; DQ992928; DQ992929; DQ992930; DQ992931; DQ992932; DQ992933; DQ992934; DQ992935; DQ992936; DQ992937; DQ992938; DQ992939; DQ992940; DQ992941; DQ992942; DQ992943; DQ992944; DQ992945; DQ992946; DQ992947; DQ992948; DQ992949; DQ992950; DQ992951; DQ992952; DQ992953; DQ992954; DQ992955; DQ992956; DQ992957; DQ992958; DQ992959; DQ992960; DQ992961; DQ992962; DQ992963; DQ992964; DQ992965; DQ992966; DQ992967; DQ992968; DQ992969; DQ992970; DQ992971; DQ992972; DQ992973; DQ992974; DQ992975; DQ992976; DQ992977; DQ992978; bQ992979; DQ992980; DQ992981; DQ992982; DQ992983; DQ992984; DQ992985; DQ992986; DQ992987; DQ992988; DQ992989; DQ992990; DQ992991; DQ992992; DQ992993; DQ992994; DQ992995; DQ992996; DQ992997; DQ992998; DQ992999; DQ993000; DQ993001; DQ993002; DQ993003; DQ993004; DQ993005; DQ993006; DQ993007; DQ993008; DQ993009; DQ993010; DQ993011; DQ993012; DQ993013; DQ993014; DQ993015; DQ993016; DQ993017; DQ993018; DQ993019; DQ993020; DQ993021; DQ993022; DQ993023; DQ993024; DQ993025; DQ993026; DQ993027; DQ993028; DQ993029; DQ993030; DQ993031; DQ993032; DQ993033; DQ993034; DQ993035; DQ993036; DQ993037; DQ993038; DQ993039; DQ993040; DQ993041; DQ993042; DQ993043; DQ993044; DQ993045; DQ993046; DQ993047; DQ993048; DQ993049; DQ993050; DQ993051; DQ993052; DQ993053; DQ993054; DQ993055; DQ993056; DQ993057; DQ993058; DQ993059; DQ993060; DQ993061; DQ993062; DQ993063; DQ993064; DQ993065; DQ993066; DQ993067; DQ993068; DQ993069; DQ993070; DQ993071; DQ993072; DQ993073; DQ993074; DQ993075; DQ993076; DQ993077; DQ993078; DQ993079; DQ993080; DQ993081; DQ993082; DQ993083; DQ993084; DQ993085; DQ993086; DQ993087; DQ993088; DQ993089; DQ993090; DQ993091; DQ993092; DQ993093; DQ993094; DQ993095; DQ993096; DQ993097; DQ993098; DQ993099; DQ993100; DQ993101; DQ993102; DQ993103; DQ993104; DQ993105; DQ993106; DQ993107; DQ993108; DQ993109; DQ993110; DQ993111; DQ993112; DQ993113; DQ993114; DQ993115; DQ993116; DQ993117; DQ997076; DQ997087; DQ997094; DQ997102; DQ997111; DQ997122; DQ997123; DQ997133; DQ997163; DQ997182; DQ997218; DQ997219; DQ997253; DQ997262; DQ997268; DQ997276; DQ997283; DQ997308; DQ997325; DQ997352; DQ997355; DQ997361; DQ997370; DQ997377; DQ997392; DQ997396; DQ997405; DQ997410; DQ997513; DQ997522; DQ997531; DQ997538; DQ997547; DQ999872; DQ999880; DQ999887; EF041479; EF042614; EF042615; EF042616; EF042617; EF042618; EF042619; EF042620; EF042621; EF042622; EF042623; EF042624; EF061116; EF090647; EF090648; EF090649; EF090650; EF107522; EF110518; EF110519; EF124794; EF165048; EF165049; EF165050; EF165051; EF165052; EF165053; EF165054; EF165055; EF165056; EF165057; EF165058; EF165059; EF165060; EF165061; EF165062; EF165063; EF165064; EF165065; EF165066; EF200512; EF200513; EF205154; EF205155; EF205156; EF205157; EF205158; EF205159; EF205160; EF382359; EF395844; EF395845; EF419242; EF419243; EF441263; EF441276; EF441277; EF441278; EF441279; EF441280; EF441281; EF446771; EF446779; EF447430; EF451059; EF456780; EF456781; EF456795; EF456798; EF456799; EF456802; EF456803; EF456805; EF467862; EF469650; EF469651; EF469652; EF469653; EF469654; EF469655; EF469656; EF469657; EF469658; EF469659; EF469660; EF473068; EF473069; EF473070; EF473073; EF473074; EF473075; EF473080; EF473081; EF474450; J02160; J04325; L46585; L46586; L46587; M10243; M18001; M18450; M18451; M30122; S68489; U05330; U05331; U05332; U20460; U20472; U20473; U20474; U20475; U28919; U28920; U37165; U37166; U37167; U37168; U37169; U37170; U37171; U37172; U37173; U37174; U37175; U37176; U37177; U37178; U37179; U37180; U37181; U37182; U67783; U69277; U79448; U79449; U79450; U79451; U79452; U79453; U79454; U79455; U79456; X07826 and X07869.

Protein sequences of influenza virus subtype H6 haemagglutinin suitable for inclusion as a cargo moiety in conjugates according to the present invention have the following accession numbers and are available to the public via the National Center for Biotechnology Information (NCBI) Entrez protein search and retrieval system:

BAF36386; BAF41914; CAC83641; CAC83642; CAC83644; CAC83645; CAC83646; CAC81274; CAC81276; CAC81279; CAC84237; CAC84238; CAC84239; CAC84240; CAC84241; CAC84242; CAC84243; CAC84244; CAD20327; CAD45192; CAD45193; CAD45194; CAD45195; CAD45196; CAD45197; CAD45198; CAG27343; CAG27344; CAG27345; CAG27346; CAG27347; AAT65326; AAT65328; AAT65330; AAT65332; AAT65340; AAT65341; AAT65342; AAT65343; AAT65344; AAT65350; AAV91218; AAX07773; AAV41833; AAW78053; AAX78820; ABB18391; ABB18402; ABB18476; ABB18951; ABB18962; ABB18973; ABB18978; ABB18994; ABB19011; ABB19020; ABB19026; ABB19032; ABB19042; ABB19055; ABB19072; ABB19083; ABB19094; ABB19101; ABB19107; ABB19118; ABB19129; ABB19140; ABB19151; ABB19162; ABB19173; ABB19184; ABB19195; ABB19206; ABB19217; ABB19228; ABB19239; ABB19360; ABB19371; ABB19382; ABB19393; ABB19404; ABB19585; ABB19596; ABB19947; ABB20283; ABB20294; ABB20387; ABB21783; ABO52005; ABG88267; ABI20804; ABI30356; ABI84387; ABI84457; ABI84466; ABI84473; ABI84516; ABI84663;

ABI84827; ABI84838; ABI84866; ABI84916; ABI84927; ABI85172; ABI92192; ABI92236; ABI92247; ABI95151; ABI95162; ABI95173; ABI95184; ABI95195; ABJ16576; ABL67154; ABL75574; ABM21971; ABM21993; ABM22004; ABO51917; ABO51961; ABO51972; ABO51983; ABO51994; ABO52016; ABO52027; ABO52049; ABO52159; ABO52181; ABO52203; ABO52478; ABO52489; ABO76979; ABP49283; BAA14333; AAZ04680; AAZ04681; AAZ04682; AAZ04683; AAZ04684; AAZ04685; AAZ04686; AAZ04687; AAZ04688; AAZ04689; AAZ04690; AAZ04691; AAZ04692; AAZ04693; AAZ04694; AAZ04695; AAZ04696; AAZ04697; AAZ04698; AAZ04699; AAZ04700; AAZ04701; AAZ04702; AAZ04703; AAZ04704; AAZ04706; AAZ04707; AAZ04708; AAZ04709; AAZ04710; AAZ04711; AAZ04712; AAZ04713; AAZ04714; AAZ04715; ABB88830; ABD35522; ABD35523; ABD35524; ABD35525; ABD35526; ABD35527; ABD35528; ABD35529; ABD35530; ABD35531; ABD35532; ABD35533; ABD35534; ABD35535; ABD35536; ABD35537; ABD35538; ABD35539; ABD35540; ABD35541; ABD35542; ABD35543; ABD35544; ABD35545; ABD35546; ABD35547; ABD35548; ABD35549; ABD35550; ABD35551; ABD35552; ABD35553; ABD35554; ABD35555; ABD35556; ABD35557; ABD65973; ABD65981; ABD65988; ABH03489; ABH03497; AAA43198; BAF47393; BAF47395; BAF47399; BAF48480; BAF48639; BAF49413; AAF04721; AAF87507; AAG38550; AAG38551; AAG38552; AAM69944; AAM69945; AAM69946; AAM69947; AAM69948; AAM69949; AAM69950; AAM69951; AAM69962; AAM69973; AAM69983; AAM69993; AAM70005; AAM70007; AAO33479; AAO33480; AAO33481; AAO33482; AAO33483; AAO33484; AAO33485; AAO33486; AAO33487; AAO33488; CAC81746; CAC81747; CAC84981; CAC84982; CAC85087; CAC84852; CAC84860; CAC85080; CAC85081; CAC85082; CAC85083; CAC85084 and CAC85085.

Protein sequences of influenza virus subtype H7 haemagglutinin suitable for inclusion as a cargo moiety in conjugates according to the present invention have the following accession numbers and are available to the public via the National Center for Biotechnology Information (NCBI) Entrez protein search and retrieval system:

BAE96029; AAD26924; AAG10680; AAL37237; AAL37238; AAL37239; AAL37240; AAL37241; AAL37242; AAK58912; AAK58913; AAK58914; AAK58915; AAK58916; AAK58917; AAK58918; AAK58919; AAK58920; AAK58921; AAK58922; AAK58923; AAK58924; AAK58925; AAK58926; AAK58927; AAK58928; AAK58929; AAK58930; AAK58931; AAK58932; AAK58933; AAK58934; AAK58935; AAK58936; AAK58937; AAK58938; AAK58939; AAK58940; AAK58941; AAK58942; AAK58943; AAK58944; AAK58945; AAK58946; AAK58947; AAK58948; AAK58949; AAK58950; AAK58951; AAM19228; AAM19229; AAM19230; AAM19231; AAM19232; AAM19233; AAM19234; AAM19235; AAM19236; CAD33826; CAD37074; CAD38049; CAD38050; CAD38051; CAD38052; CAD38053; CAD38054; CAD38282; CAD38283; CAD38284; CAD38285; CAD38286; CAD38287; CAD38288; CAE45011; CAE48276; CAF04466; CAF33017; CAF33020; CAG27348; CAG27349; CAG28943; CAG28944; CAG28945; CAG28956; CAG28957; CAG28958; CAG28959; CAJ32548; CAJ32557; AAO86904; AAO86905; AAO86906; AAO86907; AAO86908; AAO86909; AAO86910; AAO86911; AAO86912; AAO86913; AAO86914; AAO86915; AAO86916; AAO86917; AAO86918; AAO86919; AAO86920; AAO86921; AAO86922; AAO86923; AAO86924; AAO86925; AAO86926; AAO86927; AAO86928; AAO86929; AAO86930; AAO86931; AAO86932; AAO86933; AAO86934; AAO86935; AAO86936; AAO86937; AAO86938; AAO86939; AAO86940; AAO86941; AAO86942; AAO86943; AAO86944; AAO86945; AAO86946; AAO86947; AAO86948; AAO86949; AAO86950; AAO86951; AAO86952; AAQ77402; AAQ77403; AAQ77404; AAQ77405; AAQ77406; AAQ77407; AAR02636; AAR02637; AAR02638; AAR02639; AAR02640; AAR02641; AAR02642; AAR02643; AAQ90292; AAS68158; AAT37403; AAT37404; AAT37405; AAT37406; AAT02538; AAT38819; AAT66415; AAT78582; AAT70170; AAT69348; AAV74187; AAU00821; AAU25838; AAU25943; AAU85295; AAU33999; AAU44367; AAU50675; AAV98693; AAV98694; AAV98695; AAY20940; AAY46207; AAY46208; AAY46209; AAY46210; AAY46211; AAY46212; AAY46213; AAY46214; AAY46215; AAY46216; AAY46217; AAY46218; AAY46219; AAY46220; AAY46221; ABB87303; ABB87751; ABB87762; ABB87773; ABB87784; ABB87800; ABB87822; ABB87833; ABB87854; ABB88289; ABB88359; ABI84433; ABI84462; ABI84599; ABI84602; ABI84683; ABI84694; ABI84849; ABI84981; ABI85000; ABI85011; ABI85029; ABI85038; ABI85084; ABI95206; ABM21982; ABO44145; ABO44156; ABO44167; ABO44178; ABO44189; ABO45248; ABO52060; ABO52698; ABO52709; ABO52764; ABO52775; ABO52786; ABO76990; ABO77001; ABO77012; ABO77056; ABO77067; ABO77078; ABO77089; ABP49206; ABP49228; AAY21164; AAY87433; AAY87443; ABF69256; ABG57088; ABG57089; ABG57090; ABG57091; ABG57092; ABG57093; ABH04379; ABH04385; ABH05673; ABI26074; ABI26075; ABJ90226; ABJ90237; ABJ90248; ABJ90259; ABJ90270; ABJ90280; ABO21714; ABO21715; AAA43192; AAR96248; AAA56803; AAA92244; AAA92245; AAA92246; AAA43152; AAA43154; AAA43150; AAA43237; AAA43087; AAA43174; AAC54376; AAC54377; AAC54379; AAC54380; AAC54381; AAC54382; AAC54383; AAC54384; AAC54385; AAC54386; AAC54387; AAC54388; AAC54389; CAA43815; CAA44429; CAA44430; CAA44431; CAA44432; CAA44433; CAA44434; CAA44435; CAA44436; CAA44437; CAA78263; CAA87393; BAE96040; BAE96041; BAE96042; BAE96043; BAE96044; BAE96045; BAF02913; BAF02930; BAF02931; BAF02932; BAF02933; BAF02934; BAF03206; BAF03525; BAF03526; BAF49200; BAF49202; BAF49411; AAC40998; AAC40999; AAD19847; AAD19848; AAD26922; AAD26923; AAD26925; AAD26926; AAD26927; AAD26928; AAD26929; AAD26930; AAD26931; AAD26932; AAD26933; AAD26934; AAD26935; AAD26936; AAD26937; AAD26938; AAD26939; AAD26940; AAD26941; AAD37422; AAG10650; AAG10651; AAG10652; AAG10653; AAG10654; AAG10655; AAG10656; AAG10657; AAG10658; AAG10659; AAG10660; AAG10661; AAG10662; AAG10663; AAG10664; AAG10665; AAG10666;

AAG10667; AAG10668; AAG10669; AAG10670; AAG10671; AAG10672; AAG10673; AAG10674; AAG10675; AAG10676; AAG10677; AAG10678 and AAG10679.

Protein sequences of influenza virus subtype H8 haemagglutinin suitable for inclusion as a cargo moiety in conjugates according to the present invention have the following accession numbers and are available to the public via the National Center for Biotechnology Information (NCBI) Entrez protein search and retrieval system:

BAF43468; AAG38554; AAG38555; AAG38556; ABB87722; ABB87729; ABB87740; ABI84428; ABI84519; ABI85240; ABL67099; BAA14334; ABK32094 and AAA43177.

Protein sequences of influenza virus subtype H9 haemagglutinin suitable for inclusion as a cargo moiety in conjugates according to the present invention have the following accession numbers and are available to the public via the National Center for Biotechnology Information (NCBI) Entrez protein search and retrieval system:

AAA43208; AAD48995; AAD48996; AAD48997; AAD48998; AAD48999; AAD49000; AAF00701; AAF00702; AAF00703; AAF00704; AAF00705; AAF00706; AAF00707; AAF00708; AAF00709; AAF00710; AAF00711; AAF00712; AAF15580; AAF15581; AAF15582; AAF15583; AAF69255; AAF69256; AAF69257; AAF69258; AAF69259; AAF69260; AAF69261; AAF69262; AAG48164; AAG48165; AAG48166; AAG48167; AAG48168; AAG48169; AAG48170; AAG48171; AAG53035; AAG53036; AAG53037; AAG53038; AAG53039; AAG53040; AAG53041; AAG53042; AAG53043; AAG53044; AAG53045; AAG53046; AAG53047; AAG53048; AAG53049; AAG53050; AAG53051; AAG53052; AAG53053; AAG53054; AAG53055; AAG53056; AAG53057; AAG53058; AAG53059; AAG53060; AAG53061; AAG53062; AAG53063; AAG53064; AAG53065; AAG53066; AAG53067; AAG53068; AAG53069; AAK62979; AAK64189; AAL14080; AAL14081; AAL30486; AAL30487; AAL32475; AAL32476; AAL32477; AAL32478; AAL32479; AAL65235; AAL65236; AAL65237; AAL65238; AAL65239; AAL65240; AAL65241; AAL65242; AAL65243; AAL65244; AAL65245; AAL65246; AAL65247; AAL65248; AAL65249; AAL65250; AAL65251; AAL65252; AAL65253; AAL65254; AAL65255; AAL65256; AAL65257; AAL65258; AAM03341; AAM03342; AAN05676; AAN05677; AAN05678; AAN05679; AAN05680; AAN05681; AAN05682; AAN05683; AAN05684; AAN05685; AAN83972; AAN83973; AAN83974; AAN83975; AAN83976; AAN83977; AAN83978; AAN83979; AAN83980; AAN83981; AAN83982; AAN83983; AAN83984; AAN83985; AAN83986; AAN83987; AAO46077; AAO46078; AAO46079; AAO46080; AAO46081; AAO46082; AAO46083; AAO46084; AAO46085; AAO46086; AAO47744; AAO47745; AAO47746; AAO47747; AAO47748; AAO47749; AAO47750; AAO47751; AAO47752; AAP23303; AAP41031; AAP41032; AAP41033; AAP41034; AAP41035; AAP47821; AAP49029; AAP49030; AAP49031; AAP49032; AAP49033; AAP49034; AAP49035; AAP49036; AAP49037; AAP49038; AAP49039; AAP49040; AAP49041; AAP49042; AAP49043; AAP49044; AAP49045; AAP49046; AAP49047; AAP97867; AAQ04843; AAQ04844; AAQ04845; AAQ04846; AAQ04847; AAQ04848; AAQ04849; AAQ04850; AAQ04851; AAQ04852; AAQ04853; AAQ04854; AAQ04855; AAQ04856; AAQ04857; AAQ04858; AAQ04859; AAQ04860; AAQ04861; AAQ04862; AAQ04863; AAQ63104; AAQ63105; AAQ63106; AAQ63107; AAQ63108; AAQ63109; AAQ63110; AAQ63111; AAQ63112; AAQ63113; AAQ63114; AAQ63115; AAQ63116; AAQ63117; AAQ63118; AAQ63119; AAQ67246; AAQ97375; AAQ97376; AAQ97377; AAQ97378; AAQ97379; AAR08917; AAR08918; AAR98872; AAS48376; AAS48377; AAS48378; AAS48379; AAS48380; AAS48381; AAS48382; AAS48383; AAS48384; AAS48385; AAS48386; AAS48387; AAS48388; AAS48389; AAS48390; AAS48391; AAS48392; AAT12413; AAT37508; AAT45076; AAT65317; AAT65323; AAT65337; AAT65339; AAT70836; AAU00107; AAU00108; AAU00109; AAU11147; AAU11148; AAU11149; AAU11150; AAU11151; AAU11152; AAU11153; AAU11154; AAU11155; AAU11156; AAU11157; AAU11158; AAU11159; AAU11160; AAU11161; AAU11162; AAU11163; AAU11164; AAU11165; AAV30213; AAV52598; AAV52599; AAV52600; AAV52601; AAV52602; AAV52603; AAV52604; AAV52605; AAV67992; AAV68000; AAV68014; AAV68022; AAV68030; AAV68031; AAV68032; AAV68037; AAW29075; AAW29076; AAW29077; AAW29078; AAW29079; AAW29080; AAW50825; AAW50826; AAW78038; AAW78039; AAW78040; AAW78041; AAW78042; AAW78043; AAW78044; AAW78045; AAW78046; AAX32895; AAX32896; AAX51299; AAY27556; AAY52492; AAY52493; AAY52494; AAY52495; AAY52496; AAY52497; AAY52498; AAY52499; AAY52500; AAY52501; AAY52502; AAY52503; AAY52504; AAY52505; AAY52506; AAY52507; AAY52508; AAY52509; AAY52510; AAY52511; AAY52512; AAY52513; AAY52514; AAY52515; AAY52516; AAY52517; AAY52518; AAY52519; AAZ14102; AAZ14103; AAZ14104; AAZ14105; AAZ14106; AAZ14107; AAZ14108; AAZ14109; AAZ14110; AAZ14111; AAZ14112; AAZ14113; AAZ14114; AAZ14115; AAZ14116; AAZ14117; AAZ14118; AAZ14119; AAZ14120; AAZ14121; AAZ14122; AAZ14123; AAZ14124; AAZ14125; AAZ14126; AAZ14127; AAZ14128; AAZ14129; AAZ14977; AAZ14978; AAZ14979; AAZ14980; AAZ14981; AAZ14982; AAZ14983; AAZ14984; AAZ14985; AAZ14986; AAZ14987; AAZ14988; AAZ14989; AAZ14990; AAZ14991; AAZ14992; AAZ14993; AAZ14994; AAZ14995; AAZ14996; AAZ14997; AAZ14998; AAZ14999; AAZ15000; AAZ15001; AAZ15002; AAZ15003; AAZ15004; AAZ15005; AAZ15006; AAZ15007; AAZ15008; AAZ15009; AAZ15010; AAZ15011; AAZ15012; AAZ15013; AAZ15014; ABB03902; ABB17027; ABB17191; ABB19481; ABB19693; ABB20314; ABB20324; ABB20444; ABB51137; ABB58945; ABB58946; ABB58947; ABB58948; ABB58949; ABB58950; ABB58951; ABB58952; ABB58953; ABB58954; ABB58955; ABB87163; ABB87314; ABB87366; ABB87864; ABB87875; ABB87886; ABB87896; ABB87907; ABB87918; ABB87929; ABB87939; ABB87950; ABB88247; ABB88390; ABB90182; ABB90203; ABB90214; ABC48798; ABC48808; ABC48818; ABC48828; ABC48838; ABD61024; ABE02148; ABE27712; ABE27713; ABE27714; ABE27715; ABE27716;

ABE27717; ABE27718; ABE28413; ABF56623; ABF56632; ABF56641; ABG27038; ABG27042; ABG27051; ABG27056; ABH12262; ABI17549; ABI17550; ABI84463; ABI84523; ABI94767; ABI94782; ABI96694; ABI96715; ABI96777; ABI97307; ABJ15706; ABK00113; ABK00119; ABK00143; ABK41621; ABK59023; ABM21875; ABM21876; ABM21877; ABM21878; ABM21879; ABM21880; ABM21881; ABM46227; ABM46228; ABM46229; ABM46230; ABM46231; ABM46232; ABM46233; ABM46234; ABM46235; ABM46236; ABM46237; ABM46238; ABM46239; ABM46240; ABM46241; ABM46242; ABM46243; ABM46244; ABM46245; ABM46246; ABM46247; ABM46248; ABM46249; ABM46250; ABM46251; ABM46252; ABM46253; ABM46254; ABM46255; ABM46256; ABM46257; ABM46258; ABM46259; ABM46260; ABM46261; ABM46262; ABM46263; ABM46264; ABM46265; ABM46266; ABM46267; ABM46268; ABM46269; ABM46270; ABM46271; ABM46272; ABM46273; ABM46274; ABM46275; ABM46276; ABM46277; ABM46278; ABM46279; ABM46280; ABM46281; ABM46282; ABM46283; ABM46284; ABM46285; ABM46286; ABM46287; ABM46288; ABM46289; ABM46290; ABM46291; ABM46292; ABM46293; ABM46294; ABM46295; ABM46296; ABM46297; ABM46298; ABM46299; BAA14335; BAB39511; BAB39512; BAB85614; BAB85615; BAB85616; BAB85617; BAB85618; BAD01514; BAD01515; BAD01516; BAD01517; BAD01518; BAE96033; BAF34373; BAF46427; BAF46437; BAF46447; BAF46457; BAF46467; BAF46477; BAF46487; BAF46497; BAF46507; BAF46517; BAF46527; BAF48357; CAB95856; CAB95857; CAC19694; CAD60401; CAD60402; CAD60403; CAH04111; CAH04112; CAH04113; CAH04114; CAH04115; CAH04116; CAH04117; CAH04118; CAH04119; CAH04120; CAJ32552; CAJ32553; CAL15444 and CAL15445.

Protein sequences of influenza virus subtype H10 haemagglutinin suitable for inclusion as a cargo moiety in conjugates according to the present invention have the following accession numbers and are available to the public via the National Center for Biotechnology Information (NCBI) Entrez protein search and retrieval system:

BAF03631; BAF31846; ABB87989; ABB88000; ABB88011; ABB88022; ABB88033; ABB88044; ABI84469; ABI84499; ABI84534; ABI84626; ABL67143; ABO52082; ABO52093; ABO52115; ABD23975; AAA43186; AAA79774; AAA79775; BAF43464; BAF46762; BAF46908; BAF47127; BAF48645; AAG33016; CAJ32549; CAJ32550; ABB87206; ABB87217; ABB87325; ABB87844; ABB87956; ABB87967 and ABB87978.

Protein sequences of influenza virus subtype H11 haemagglutinin suitable for inclusion as a cargo moiety in conjugates according to the present invention have the following accession numbers and are available to the public via the National Center for Biotechnology Information (NCBI) Entrez protein search and retrieval system:

BAF34926; BAF43435; ABD91535; ABD66294; ABD66295; ABD66296; ABD66297; ABD66298; ABF22671; ABM54148; AAA43188; AAA43191; AAA43183; AAA43203; AAA43181; BAF47125; BAF47129; BAF48643; BAF49417; AAG38553; AAV91221; ABB87228; ABB87239; ABB88055; ABB88066; ABB88077; ABB88088; ABI84440; ABI84442; ABI84545; ABI84556; ABI84600; ABI84723; ABJ53570; ABL67121; ABL67231; ABL75585; ABO52137; ABO52148; ABO52170; ABO52390; ABO52401; ABO52412; ABO52434; ABO52445; ABO52456; ABO52544; ABO52555; ABO76924; ABO76935; ABO76968; ABP49195; ABP49239; ABP49250; ABP49261; ABP49272; ABP49294; BAA14336; AAY85533; ABC59903; ABD91532; ABD91533 and ABD91534.

Protein sequences of influenza virus subtype H12 haemagglutinin suitable for inclusion as a cargo moiety in conjugates according to the present invention have the following accession numbers and are available to the public via the National Center for Biotechnology Information (NCBI) Entrez protein search and retrieval system:

BAF43416; BAF43433; AAG38557; AAG38558; AAG38559; CAL15446; ABB87195; ABB87249; ABB88099; ABB88110; ABB88121; ABG88278; ABI84446; ABI84489; ABJ09129; ABL67077; ABL67242; ABO52610; ABO52621; BAA14337; ABI17552 and AAA43180.

Protein sequences of influenza virus subtype H13 haemagglutinin suitable for inclusion as a cargo moiety in conjugates according to the present invention have the following accession numbers and are available to the public via the National Center for Biotechnology Information (NCBI) Entrez protein search and retrieval system:

BAF37821; BAF38383; BAF46906; CAJ32554; CAJ32555; AAV91212; AAV91213; ABB86511; ABB87334; ABB87345; ABB87811; ABI84452; ABI84566; ABI84601; BAA14338; ABG57285; AAA43213; AAA43214 and AAA43215.

Protein sequences of influenza virus subtype H14 haemagglutinin suitable for inclusion as a cargo moiety in conjugates according to the present invention have the following accession numbers and are available to the public via the National Center for Biotechnology Information (NCBI) Entrez protein search and retrieval system:

BAF43460 and ABI84453.

Protein sequences of influenza virus subtype H15 haemagglutinin suitable for inclusion as a cargo moiety in conjugates according to the present invention have the following accession numbers and are available to the public via the National Center for Biotechnology Information (NCBI) Entrez protein search and retrieval system:

ABB88138; ABB88320; ABB88331; AAA96134; ABB90704; BAF48363; ABB88132 and AAA92247.

Protein sequences of influenza virus subtype H16 haemagglutinin suitable for inclusion as a cargo moiety in conjugates according to the present invention have the following accession numbers and are available to the public via the National Center for Biotechnology Information (NCBI) Entrez protein search and retrieval system:

ABB87356; ABI84447; ABI85221; AAV91214; AAV91215; AAV91216 and AAV91217.

Nucleic acid sequences encoding influenza virus subtype H1 haemagglutinins suitable for inclusion as a cargo moiety in conjugates according to the present invention have the following accession numbers and are available to the public via the National Center for Biotechnology Information (NCBI) Entrez nucleotide search and retrieval system:

AF222026; AF222034; AF222036; AF503481; AF503483; AY180460; AF534030; AF534045; AF534052; AY604795; AY604797; AY604798; AY604804; AY604806; CY004490; CY004539; CY006355; CY006779; CY009324; CY010092; CY010172; CY010228; CY010284; CY010324; CY010340; CY010996; CY011208; M59325; CY013565; CY013581; CY016563; CY017139; EF462556; EF462564;

CY020173; CY021709; CY021749; CY021821; AB243744; AB255389; AB255390; AB255392; AB271115; X57491; AF222030; AF222031; AF222032; AF222033; AF503484; AF503485; AF503486; AF534048; AF534049; AY377936; AY604799; AY604800; AY604801; AY604802; AY604803; AY684125; DQ058215; CY003016; CY004498; CY005866; CY008148; CY009204; CY009276; CY009628; CY010108; CY010292; CY010300; CY010316; CY011012; CY011072; CY011088; CY011168; CY011184; CY011224; CY014627; CY014968; CY016052; CY016699; CY017123; CY017219; CY019763; CY019867; CY019883; EF467821; EF462563; X57493; Z46437; Z54288; L20111; L20113; L25072; U11858; L33780; L19022; L19016; L19014; M38312; L19006; L19024; K01331; U85986; AY029292; AF320059; AF320060; AF320062; AY129156; AF503475; AF503477; AY299509; AY297156; AY303741; AY701753; CY002672; CY002984; CY003688; CY003761; CY006419; DQ265706; DQ280203; CY009444; CY009868; CY009964; CY010556; CY010868; DQ666649; DQ666650; CY012440; DQ978382; DQ978389; DQ978390; EF462570; EF462571; CY020181; CY020861; CY021029; CY021693; CY021733; AB274304; Z46434; Z46435; Z46436; AJ289702; L19028; L19019; L19018; L19008; L19027; J02144; L19017; L19026; L24362; AY029288; AY029289; AF320063; AF503478; AF503479; AF503480; AY303747; CY000449; CY002360; CY002648; CY002688; CY003024; DQ249260; CY006107; CY003833; CY006667; CY006675; DQ280195; DQ280227; DQ280236; DQ280243; DQ280250; CY006867; CY009532; M34335; M33748; AF131993; AF131994; AF222027; AF222028; AF222035; AF503482; AF534027; AF534031; AF534038; AF534043; AF534044; AF534046; AF534053; AF534054; AY604796; AY604805; AY604807; AY604808; AY682833; CY002704; CY004504; CY004531; CY004546; CY005735; CY006363; CY003769; CY009220; CY009332; DQ397950; CY009452; DQ431990; CY010156; CY010164; CY010180; CY010236; CY010276; CY010332; M81707; CY011176; CY011192; CY011200; CY011216; CY015580; CY016308; CY016311; CY016313; CY016317; CY016318; CY016321; CY016327; CY016328; CY016331; CY016435; CY017003; CY017195; CY017235; CY017251; CY019101; CY020469; CY020485; AB043478; AB043483; AB043484; AB043491; AB043493; AB043494; X17221; J04572; J04574; L33480; L33482; L33487; L33489; L33490; L33755; L33743; L33745; L33747; L33753; U11703; U08903; U53162; S62154; S67220; U80948; U45451; U46943; AF305218; CY009756; CY009764; CY009780; CY009844; CY009956; CY010572; CY010740; CY010780; CY011952; DQ666648; CY013271; DQ981739; DQ978383; CY014733; CY015524; CY016228; CY016314; CY016315; CY016316; CY016324; CY016325; CY016326; CY016955; CY017011; CY017315; CY019085; CY020421; CY020437; CY020509; AB043480; AB043481; AB043486; AB043487; AB043490; AB043495; AB043496; AB043497; AB043500; AB294217; L33483; L33484; L33485; L33486; L33492; L33493; CY011584; M59324; M59326; CY013573; CY013589; CY016643; CY018885; CY019205; CY019771; CY019875; CY019963; CY019971; EF462565; CY020917; CY021701; CY021717; CY021725; AB243745; AB255391; AB255393; AB255397; AB255398; AB271113; X57492; Z30276; Z54289; L20109; L20112; L20110; L25071; M73975; L19015; L19549; M38353; K01330; J02176; L19025; L19013; L19023; U03719; U03720; U72666; AY029291; AF320057; AF320058; AF320061; AF131995; AF250124; AF268312; AF268313; AF222029; AF534025; AF534026; AF534047; AF534050; AF534051; CY001952; CY003288; CY004507; CY004592; CY009212; CY009596; DQ447187; CY010100; CY010116; CY010212; CY010220; CY010308; CY011004; CY011080; CY011152; CY011160; CY011232; M59327; M59328; CY012888; CY017115; CY017203; CY017211; CY017227; CY019739; CY019755; CY020189; CY021053; CY021757; CY021797; AB255394; AB255395; AB255396; X57494; X59778; AF398875; AF455679; AF455681; AF494246; AF494249; AF494250; AY289927; AY299499; AY299500; AY299502; CY002152; CY002616; CY002800; CY004466; CY004474; CY004482; DQ335992; DQ335995; CY009540; CY009612; CY009620; CY009796; CY009980; CY010356; CY010364; CY010380; CY010428; CY010444; CY010524; CY010540; DQ508897; DQ534416; CY011280; CY011296; CY011304; CY011392; CY012296; CY013821; CY013837; CY013853; CY013597; CY013871; CY016337; CY016338; CY016343; U02085; L09063; L33750; L33751; L33752; U37727; U38242; U53163; U80949; U46020; U46021; U46782; U46783; U46941; U46942; AF398878; AF455678; AY095226; AY095227; AF494251; AY289928; AY289929; AY633212; CY002536; CY002632; CY003000; DQ335998; CY009884; CY010372; CY009916; CY010388; CY010404; CY010460; CY010476; CY010492; CY010500; DQ508905; CY010764; CY011240; CY011312; CY012856; CY012864; CY012880; CY013032; CY015163; AF320067; AF503474; AF503476; AY299508; AY297157; AY303734; DQ139320; CY002352; CY002696; CY002992; CY003696; CY003704; DQ280212; DQ280219; CY006875; CY009772; CY009972; CY010804; CY010876; DQ666651; CY012824; CY013287; DQ978387; DQ978388; DQ978391; CY016196; CY016309; CY016310; CY016312; CY016319; CY016320; CY016322; CY016329; CY016330; CY020293; CY020453; CY020461; CY020477; AB043479; AB043482; AB043485; AB043492; V01088; X17224; J04573; CY016334; CY016335; CY016340; CY016341; CY016342; CY016347; CY016350; CY016357; CY016360; CY016361; CY016365; CY016366; CY016367; CY016370; CY017371; CY017869; CY019069; CY020237; CY020253; CY020261; U47310; AF026157; AF026160; AF091313; AF362778; AF362779; AF362784; AF362785; AF362786; AF362787; AF362794; AF362795; AF362796; AF362803; AF386775; AF386776; AF386777; AF386782; AF386783; AY038014; AY038338; AY038339; AY038344; AY038345; AY038346; L33481; L33488; L33491; L33756; L33744; L33746; L33754; L19005; K00992; U44482; U45452; AF398874; AF455680; AF494247; AF494248; AY299497; AY299498; AY299501; AY299503; CY002808; CY004458; CY006187; CY006195; DQ335993; DQ335994; CY009548; CY009604; CY009788; CY009804; CY009876; CY009892; CY010348; CY010412; CY010420; CY010436; CY010452; CY010508; CY010532; DQ508873; DQ508889; CY010772; DQ534415; DQ534417; DQ534418; CY011272; AY038347; AY038354; AY038355; AY038356; AY038357; AY060038; AY060044; AY233393; AY790289; AY851464; AY851465; AY851466; AY851467; AY971006; AY971007; AY971010; AY971011; DQ100426; DQ100427; CY002392; CY003296; CY003376; CY003392; CY003464; CY003480; CY006395; CY006403; DQ335999; DQ415318; CY009292; CY009316; CY009828; CY009940; CY010148; CY010204; CY010244; CY010828; CY010844; CY010884; CY010916; CY010924; CY010940; CY010956; CY011608; CY011776; CY016344; CY016346; CY016354; CY016363; CY016364; CY016371; CY016373; CY017363; CY017427; CY017435; CY019045; CY020269; CY021005; D00406; D00837; D00839; D10477; D29656; U47305; U47307; U96766; AF026153; AF026154; AF026156; AF055426; AF091309; AF091310; AF091312; AF362781; AF362783; AF362788; AF362791; AF362797; AF362798; AF362800; AF362802;

AF386773; AF386774; AF386780; AY038335; AY038337; AY038341; AY038343; AY038351; AY038353; CY013829; CY013845; CY013879; CY015167; CY016336; CY016339; CY016345; CY016352; CY016355; CY016362; CY016372; CY016459; CY017419; CY020277; D00407; D00838; D13570; D29657; U47304; U47306; U47308; AF026155; AF085413; AF117241; AF091308; AF091311; AF091317; AF362780; AF362782; AF362789; AF362790; AF362792; AF362799; AF362801; AF386779; AF386781; AF387491; AY038334; AY038336; AY038340; AY038342; AY038349; AY038350; AY038352; AY060031; AY038358; AF408859; AY060032; AY060039; AY060045; AY060047; AY060048; AY063229; AY184805; AY851463; AY851471; AY971003; AY971004; DQ118159; DQ118160; DQ118162; CY002528; CY003304; CY003328; CY003672; CY006171; CY006387; DQ336002; DQ336005; CY008524; CY008996; CY009172; CY009188; CY009228; CY009284; CY009340; CY010076; CY010132; CY010188; CY010268; CY010908; CY010964; CY010980; CY012608; CY011040; CY014007; DQ986134; CY016374; CY016380; CY016386; CY011792; CY013303; DQ978392; CY016244; CY016375; CY016376; CY016377; CY016382; CY016383; CY016391; CY016392; CY016393; DQ973300; CY019125; CY019221; CY019237; CY019923; CY020141; CY020157; CY020165; AB117167; AB117170; AB117171; AB117176; AB117177; AB117183; AB117192; AB117193; AB117203; AB117212; AB117213; AB117221; AB126622; AJ412708; AJ412709; AJ344013; AJ457868; AJ457869; AJ457878; AJ457879; AJ457884; AJ457885; AJ457886; AJ457894; AJ457895; AJ457904; AY060033; AY060034; AY060040; AY060046; AY060049; AY060050; AY063228; AF342821; AY590823; AY590824; AY790267; AY701755; AY851462; AY851469; AY851470; AY851472; AY861443; AY971005; DQ118158; DQ118161; DQ118163; CY003312; CY003320; CY003400; CY006427; CY006411; DQ336003; DQ336004; CY008988; DQ415316; CY009180; CY009196; CY009236; CY010196; CY010252; CY010260; CY010892; CY010900; CY010972; CY012800; CY016379; CY016381; CY016385; CY016387; CY016388; CY016389; CY016390; DQ973301; DQ973303; DQ973304; CY016971; CY017275; EF101749; CY017717; CY017725; CY017829; CY018933; CY019117; CY019779; CY019795; CY019803; CY020565; AB117166; AB117173; AB117174; AB117180; AB117182; AB117189; AB117190; AB117196; AB117199; AB117200; AB117202; AB117209; AB117210; AB117216; AB117219; AB117220; AB126630; AJ412712; AJ344002; AJ344019; AJ344020; AJ344009; AJ344010; AJ344012; AJ344022; AJ457865; AJ457872; AJ457875; AJ457881; CY016723; DQ973299; DQ973302; EF101741; CY017813; CY019109; CY020573; CY021629; AB117165; AB117172; AB117175; AB117181; AB117187; AB117188; AB117191; AB117197; AB117198; AB117201; AB117207; AB117208; AB117211; AB117217; AB117218; AJ412711; AJ344017; AJ344018; AJ344021; AJ344003; AJ344008; AJ344011; AJ457863; AJ457864; AJ457866; AJ457873; AJ457874; AJ457880; AJ457882; AJ457889; AJ457890; AJ457896; AJ457899; AJ457900; AJ457902; AJ457906; AJ457909; AJ457910; AJ457887; AJ457888; AJ457891; AJ457897; AJ457898; AJ457901; AJ457907; AJ457908; AJ457911; AJ489854; AJ489856; AJ517814; AJ517816; Z46441; Z54286; Z54287; L20106; L20117; L20116; L20108; L20107; U11857; L19021; L19011; L19020; L19012; U72667; U72668; U72669; AY029287; AY029290; AF320056; AF320064; AF320065; AF320066; AF503473; AY299506; AY299507; AY297154; AY297155; AY619961; CY002624; CY002640; CY002664; CY002680; CY003008; CY006747; CY006915; CY009860; CY010580; CY010852; DQ666644; DQ666645; DQ666646; DQ666647; CY013279; CY013295; DQ978384; DQ978385; DQ978386; CY014901; CY015443; CY015532; CY016260; CY016323; CY016963; CY017019; CY017243; CY019077; CY019093; CY019997; CY020429; CY020445; CY021037; AB043488; AB043489; AB043498; AB043499; U04857; U04858; U04859; L33757; L33758; L33748; L33749; U08904; U80950; AF455675; AF455676; AF455677; AF455682; AF389118; AY289930; AY282756; AY282757; AY299494; AY299495; AY299496; AY299504; AY299505; CY002568; CY002400; CY002656; DQ335991; DQ335996; DQ335997; CY009812; CY010396; CY010468; CY010484; DQ508857; DQ534419; CY011408; CY012304; CY012872; CY013040; CY013813; CY016332; CY016333; CY016348; CY016349; CY016358; CY016359; CY016368; CY016369; CY016691; CY017147; CY017155; CY017379; CY017877; CY019053; CY019061; CY019947; CY019955; CY020245; CY020285; D00840; D00841; D10163; D13571; D13572; D13573; D13574; D28518; D31949; U47309; AF026158; AF026159; AF085414; AJ457905; AJ489852; AJ489853; AJ489860; AJ489861; AJ489862; AJ517813; AJ517817; AJ517820; AJ489855; AJ489857; AJ489858; AJ517815; AF085415; AF085416; AF085417; AF116575; AF116576; AF091306; AF091307; AF091314; AF091315; AF091316; AF362793; AF386778; AY038333; AY038348; AY052778; AY060030; AY060035; AY060036; AY060037; AY060041; AY060042; AY060043; AY060051; AY060052; AY184806; AY590822; AY377929; AY851468; AY971008; AY971009; CY001680; DQ118164 and CY003368.

Nucleic acid sequences encoding influenza virus subtype H2 haemagglutinins suitable for inclusion as a cargo moiety in conjugates according to the present invention have the following accession numbers and are available to the public via the National Center for Biotechnology Information (NCBI) Entrez nucleotide search and retrieval system:

AB056699; AB266382; AY209954; AY209955; AY209956; AY209957; AY209958; AY209959; AY209960; AY209961; AY209962; AY209963; AY209964; AY209965; AY209966; AY209967; AY209968; AY209969; AY209970; AY209971; AY209972; AY209973; AY209974; AY209975; AY209976; AY209977; AY209978; AY209979; AY209980; AY209981; AY209982; AY209983; AY209984; AY209985; AY209986; AY209987; AY209988; AY209989; AY422014; AY422015; AY422016; AY422017; AY633180; AY633196; AY633228; AY633364; AY633388; AY684893; CY003847; CY003855; CY003863; CY003871; CY003879; CY003887; CY003907; CY003914; CY003922; CY003936; CY003944; CY003952; CY003960; CY003968; CY003976; CY003984; CY003992; CY004554; CY005413; CY005538; CY005546; CY005765; CY005808; CY01456; CY014558; CY014601; CY014608; CY014609; CY014710; CY014821; CY014829; CY014976; CY015135; CY017693; CY018877; CY020317; CY020373; CY020381; CY020389; CY020397; CY020405; CY020413; CY020517; CY020541; CY020549; CY021013; CY021021; CY021069; CY021125; CY021789; CY021805; CY021813; D13575; D13576; D13577; D13578; D13579; D13580; DQ006282; DQ006283; DQ009917; DQ017486; DQ017493; DQ508841; DQ508881; J02127; J02154; L11125; L11126; L11127; L11128; L11129; L11130; L11131; L11132; L11133; L11134; L11135; L11136; L11137; L11138; L11139; L11140; L11141; L11142; L20406; L20407; L20408; L20409; L20410; AB275406; AB275414; AB275620; AB275628; AB275861; AB276115; AB292785; AB296074; AB298281; AF116197; AF116198; AF116199; AF116200; AF116201; AF116202; AF116203; AF116204; AF116205; AF116206; AF116207; AF116208;

AF116209; AF116210; AF116211; AF231356; AF270716; AF270717; AF270718; AF270719; AF270720; AF270721; AF270722; AF270723; AF270724; AF270725; AF270726; AF270727; AF270728; AY180398; AY180399; AY180400; AY180401; AY180402; AY180403; AY209952 and AY209953.

Nucleic acid sequences encoding influenza virus subtype H3 haemagglutinins suitable for inclusion as a cargo moiety in conjugates according to the present invention have the following accession numbers and are available to the public via the National Center for Biotechnology Information (NCBI) Entrez nucleotide search and retrieval system:

AB013806; AB013807; AB013808; AB013809; AB013810; AB013811; AB013812; AB013813; AB014060; AB014061; AB014062; AB019354; AB019355; AB019356; AB019357; AB043705; AB043706; AB043707; AB043708; AB221016; AB221017; AB221018; AB221019; AB221020; AB221021; AB221022; AB221023; AB221024; AB221025; AB221026; AB221027; AB221028; AB221029; AB221030; AB221031; AB221032; AB221033; AB221034; AB221035; AB243867; AB243868; AB243869; AB243870; AB243871; AB243872; AB243873; AB246366; AB259101; AB259102; AB259103; AB259104; AB259105; AB259106; AB259107; AB259108; AB259109; AB259110; AB259111; AB259112; AB259739; AB259740; AB259741; AB262301; AB262302; AB262303; AB262304; AB270992; AB270993; AB270994; AB270995; AB270996; AB270997; AB270998; AB270999; AB271000; AB271001; AB271002; AB271489; AB271490; AB271491; AB271492; AB271493; AB271494; AB271495; AB271496; AB271497; AB271498; AB271503; AB271504; AB271505; AB271506; AB271511; AB271512; AB271513; AB271514; AB271515; AB271516; AB271517; AB271524; AB271525; AB271526; AB271527; AB271528; AB271529; AB271530; AB271809; AB271810; AB271811; AB271812; AB271813; AB271814; AB271815; AB271816; AB271817; AB271818; AB271819; AB271820; AB271821; AB271822; AB271823; AB271824; AB271825; AB271826; AB271827; AB271828; AB271829; AB271830; AB271831; AB271832; AB271833; AB271834; AB271835; AB271836; AB271837; AB271838; AB271839; AB271840; AB271841; AB271842; AB271843; AB271844; AB271845; AB271846; AB271847; AB271848; AB271849; AB271850; AB275283; AB276113; AB277754; AB284320; AB289341; AB292402; AB292410; AB292660; AB292668; AB295605; AF008656; AF008657; AF008658; AF008659; AF008660; AF008661; AF008662; AF008663; AF008664; AF008665; AF008666; AF008667; AF008668; AF008669; AF008670; AF008671; AF008672; AF008673; AF008674; AF008675; AF008676; AF008677; AF008678; AF008679; AF008680; AF008681; AF008682; AF008683; AF008684; AF008685; AF008686; AF008687; AF008688; AF008689; AF008690; AF008691; AF008692; AF008693; AF008694; AF008695; AF008696; AF008697; AF008698; AF008699; AF008700; AF008701; AF008702; AF008703; AF008704; AF008705; AF008706; AF008707; AF008708; AF008709; AF008710; AF008711; AF008712; AF008713; AF008714; AF008715; AF008716; AF008717; AF008718; AF008719; AF008720; AF008721; AF008722; AF008723; AF008724; AF008725; AF008726; AF008727; AF008728; AF008729; AF008730; AF008731; AF008732; AF008733; AF008734; AF008735; AF008736; AF008737; AF008738; AF008739; AF008740; AF008741; AF008742; AF008743; AF008744; AF008745; AF008746; AF008747; AF008748; AF008749; AF008750; AF008751; AF008752; AF008753; AF008754; AF008755; AF008756; AF008757; AF008758; AF008759; AF008760; AF008761; AF008762; AF008763; AF008764; AF008765; AF008766; AF008767; AF008768; AF008769; AF008770; AF008771; AF008772; AF008773; AF008774; AF008775; AF008776; AF008777; AF008778; AF008779; AF008780; AF008781; AF008782; AF008783; AF008784; AF008785; AF008786; AF008787; AF008788; AF008789; AF008790; AF008791; AF008792; AF008793; AF008794; AF008795; AF008796; AF008797; AF008798; AF008799; AF008800; AF008801; AF008802; AF008803; AF008804; AF008805; AF008806; AF008807; AF008808; AF008809; AF008810; AF008811; AF008812; AF008813; AF008814; AF008815; AF008816; AF008817; AF008818; AF008819; AF008820; AF008821; AF008822; AF008823; AF008824; AF008825; AF008826; AF008827; AF008828; AF008829; AF008830; AF008831; AF008832; AF008833; AF008834; AF008835; AF008836; AF008837; AF008838; AF008839; AF008840; AF008841; AF008842; AF008843; AF008844; AF008845; AF008846; AF008847; AF008848; AF008849; AF008850; AF008851; AF008852; AF008853; AF008854; AF008855; AF008856; AF008857; AF008858; AF008859; AF008860; AF008861; AF008862; AF008863; AF008864; AF008865; AF008866; AF008867; AF008868; AF008869; AF008870; AF008871; AF008872; AF008873; AF008874; AF008875; AF008876; AF008877; AF008878; AF008879; AF008880; AF008881; AF008882; AF008883; AF008884; AF008885; AF008886; AF008887; AF008888; AF008889; AF008890; AF008891; AF008892; AF008893; AF008894; AF008895; AF008896; AF008897; AF008898; AF008899; AF008900; AF008901; AF008902; AF008903; AF008904; AF008905; AF008906; AF008907; AF008908; AF008909; AF017270; AF017271; AF017272; AF038266; AF038267; AF038268; AF038269; AF038270; AF079570; AF087700; AF087701; AF087702; AF087703; AF087704; AF087705; AF087706; AF087707; AF087708; AF087709; AF092052; AF092053; AF092054; AF092055; AF092056; AF092057; AF092058; AF092059; AF092060; AF092061; AF092062; AF092063; AF092064; AF096306; AF096307; AF096308; AF096309; AF096310; AF096311; AF096312; AF096313; AF096314; AF096315; AF096316; AF131996; AF131997; AF131998; AF139930; AF139931; AF139932; AF139933; AF139934; AF139935; AF139936; AF139937; AF139938; AF139939; AF139940; AF153232; AF153233; AF153234; AF153235; AF180564; AF180565; AF180566; AF180567 AF180568; AF180569; AF180570: AF180571; AF180572; AF180573; AF180574; AF180575; AF180576; AF180577; AF180578; AF180579; AF180580; AF180581; AF180582; AF180583; AF180584; AF180585; AF180586; AF180587; AF180588; AF180589; AF180590; AF180591; AF180592; AF180593; AF180594; AF180595; AF180596; AF180597; AF180598; AF180599; AF180600; AF180601; AF180602; AF180603; AF180604; AF180605; AF180606; AF180607; AF180608; AF180609; AF180610; AF180611; AF180612; AF180613; AF180614; AF180615; AF180616; AF180617; AF180618; AF180619; AF180620; AF180621; AF180622; AF180623; AF180624; AF180625; AF180626; AF180627; AF180628; AF180629; AF180630; AF180631; AF180632; AF180633; AF180634; AF180635; AF180636; AF180637; AF180638; AF180639; AF180640; AF180641; AF180642; AF180643; AF180644; AF180645; AF180646; AF180647; AF180648; AF180649; AF180650; AF180651; AF180652; AF180653; AF180654; AF180655; AF180656; AF180657; AF180658; AF180659; AF180660; AF180661; AF180662; AF180663; AF180664; AF180665; AF180666; AF197241; AF197242; AF197243; AF197244; AF197245; AF197246; AF197247; AF197248; AF197249; AF201842; AF201843; AF201844; AF201845; AF201846; AF201874; AF201875; AF204238; AF213900; AF213901; AF213902; AF213903; AF225542; AF225543; AF225544; AF225545; AF233691; AF251395; AF251403; AF251411; AF251419; AF251427; AF255019; AF255020; AF255021;

AF255022; AF255023; AF255024; AF255025; AF255026; AF255027; AF255028; AF255029; AF268123; AF268124; AF268125; AF268126; AF268127; AF268128; AF297094; AF297095; AF297096; AF297097; AF311676; AF311677; AF311678; AF311679; AF311680; AF311681; AF311682; AF311683; AF311684; AF311685; AF311686; AF311687; AF311688; AF311689; AF311690; AF311691; AF311692; AF311693; AF311694; AF311695; AF311696; AF311697; AF311698; AF315559; AF315560; AF315561; AF315562; AF315563; AF315564; AF315565; AF315566; AF315567; AF315568; AF315569; AF315570; AF315571; AF316817; AF316818; AF316819; AF316820; AF316821; AF348176; AF357929; AF357930; AF357931; AF357932; AF357933; AF357934; AF357935; AF357936; AF357937; AF357938; AF357939; AF357940; AF357941; AF357942; AF357943; AF357944; AF357945; AF357946; AF357947; AF357948; AF357949; AF357950; AF357951; AF357952; AF357953; AF357954; AF357955; AF357956; AF357957; AF357958; AF357959; AF357960; AF357961; AF357962; AF357963; AF357964; AF357965; AF357966; AF357967; AF357968; AF357969; AF362804; AF362805; AF362806; AF362807; AF362808; AF362809; AF362810; AF362811; AF362812; AF362813; AF362814; AF362815; AF362816; AF362817; AF362818; AF362819; AF362820; AF363502; AF363503; AF363504; AF368436; AF368437; AF368438; AF368439; AF368440; AF368441; AF368442; AF368443; AF368444; AF368445; AF368446; AF382318; AF382319; AF382320; AF382321; AF382322; AF382323; AF382324; AF382325; AF382326; AF382327; AF382328; AF386604; AF386605; AF386606; AF386607; AF386608; AF386609; AF386610; AF386611; AF386612; AF386613; AF386614; AF386615; AF386616; AF386617; AF386618; AF386619; AF386620; AF386621; AF386622; AF386623; AF386624; AF386625; AF386626; AF386627; AF386628; AF386629; AF386630; AF386631; AF386632; AF386633; AF386634; AF400752; AF400753; AF400754; AF405206; AF405207; AF405208; AF405209; AF405210; AF405211; AF405212; AF442455; AF442456; AF442457; AF442458; AF442459; AF442460; AF442461; AF442462; AF442463; AF442464; AF442465; AF442466; AF442467; AF442468; AF442469; AF442470; AF442471; AF442472; AF442473; AF442474; AF442475; AF442476; AF442477; AF442478; AF442479; AF442480; AF442481; AF442482; AF442483; AF450246; AF501515; AF501516; AF501517; AF501518; AF501519; AF501520; AF501521; AF501522; AF501523; AF501524; AF501525; AF501526; AF501527; AF501528; AF501529; AF501530; AF501531; AF501532; AF501533; AF501534; AF501535; AF525217; AF525218; AF525219; AF525686; AF525799; AF533712; AF533713; AF533714; AF533715; AF533716; AF533717; AF533718; AF533719; AF533720; AF533721; AF533722; AF533723; AF533724; AF533725; AF533726; AF533727; AF533728; AF533729; AF534013; AF534014; AF534015; AF534016; AF534017; AF534018; AF534019; AF534020; AF534021; AF534022; AF534023; AF534024; AF534028; AF534029; AF534032; AF534033; AF534034; AF534035; AF534036; AF534037; AF534039; AF534040; AF534041; AF534042; AF534055; AF534056; AF534057; AF534058; AF534059; AF534060; AJ223192; AJ223193; AJ223194; AJ223195; AJ223196; AJ223197; AJ252129; AJ252130; AJ252131; AJ252132; AJ293926; AJ293927; AJ293928; AJ293929; AJ293930; AJ293931; AJ293932; AJ293933; AJ311454; AJ311466; AJ311511; AJ344023; AJ427297; AJ4217304; AJ506781; AJ697863; AJ697864; AJ697865; AJ697866; AJ704814; AJ704815; AJ704816; AJ746251; AJ841293; AM087217; AM087224; AX350190; AX350204; AY032978; AY035588; AY035589; AY035590; AY035591; AY035592; AY048077; AY048078; AY048079; AY048080; AY048081; AY137206; AY138513; AY138515; AY138516; AY138517; AY138518; AY138519; AY180404; AY180405; AY180406; AY180407; AY180408; AY180409; AY180410; AY180411; AY180412; AY180413; AY180414; AY180415; AY180416; AY180417; AY180418; AY180419; AY180420; AY180421; AY180422; AY180423; AY180424; AY180425; AY180426; AY180427; AY180428; AY180429; AY180430; AY180431; AY180432; AY180433; AY262744; AY262745; AY271794; AY273167; AY273168; AY303713; AY303717; AY303723; AY303731; AY303736; AY303743; AY303745; AY363509; AY363510; AY363511; AY363512; AY363513; AY363514; AY363515; AY363516; AY363517; AY363518; AY363519; AY363520; AY363521; AY363522; AY363523; AY363524; AY363525; AY363526; AY377129; AY377537; AY377538; AY377539; AY377540; AY377541; AY377542; AY377543; AY377544; AY377545; AY377546; AY377547; AY377924; AY377927; AY377933; AY383755; AY389349; AY389350; AY389351; AY389352; AY389353; AY389354; AY389355; AY389356; AY389357; AY389358; AY389359; AY389360; AY462237; AY479982; AY531031; AY531033; AY531035; AY531037; AY531039; AY531040; AY531041; AY531042; AY531043; AY531044; AY531045; AY531046; AY531047; AY531048; AY531049; AY531050; AY531051; AY531052; AY531053; AY531054; AY531055; AY531056; AY531057; AY531058; AY531059; AY531060; AY531061; AY589647; AY589648; AY589649; AY589650; AY589651; AY589652; AY589653; AY589654; AY589655; AY589656; AY589657; AY589658; AY589659; AY589660; AY589661; AY596799; AY596800; AY596801; AY604809; AY604810; AY604811; AY604812; AY604813; AY604814; AY604815; AY604816; AY604817; AY604818; AY604819; AY604820; AY604821; AY604822; AY604823; AY604824; AY604825; AY604826; AY604827; AY604828; AY604829; AY604830; AY619969; AY619977; AY625729; AY625730; AY625731; AY633132; AY633148; AY633172; AY633244; AY633252; AY633340; AY633372; AY633996; AY633997; AY633998; AY633999; AY634000; AY634001; AY634002; AY634003; AY634004; AY634005; AY634006; AY634007; AY634008; AY634009; AY634010; AY634011; AY634012; AY634013; AY634014; AY634015; AY634016; AY634017; AY634018; AY634019; AY634020; AY634021; AY634022; AY634023; AY634024; AY634025; AY634026; AY634027; AY634028; AY634029; AY634030; AY634031; AY634032; AY634033; AY634034; AY634035; AY634036; AY634037; AY634038; AY634039; AY634040; AY634041; AY634042; AY634043; AY634044; AY634045; AY634046; AY634047; AY634048; AY634049; AY660991; AY660992; AY660993; AY660994; AY660995; AY660996; AY660997; AY660998; AY660999; AY661000; AY661001; AY661002; AY661003; AY661004; AY661005; AY661006; AY661007; AY661008; AY661009; AY661010; AY661011; AY661012; AY661013; AY661014; AY661015; AY661016; AY661017; AY661018; AY661019; AY661020; AY661021; AY661022; AY661023; AY661024; AY661025; AY661026; AY661027; AY661028; AY661029; AY661030; AY661031; AY661032; AY661033; AY661034; AY661035; AY661036; AY661037; AY661038; AY661039; AY661040; AY661041; AY661042; AY661043; AY661044; AY661045; AY661046; AY661047; AY661048; AY661049; AY661050; AY661051; AY661052; AY661053; AY661054; AY661055; AY661056; AY661057; AY661058; AY661059; AY661060; AY661061; AY661062; AY661063; AY661064; AY661065; AY661066; AY661067; AY661068; AY661069; AY661070; AY661071; AY661072; AY661073; AY661074; AY661075; AY661076; AY661077; AY661078; AY661079; AY661080; AY661081; AY661082; AY661083; AY661084; AY661085; AY661086; AY661087; AY661088; AY661089; AY661090; AY661091; AY661092; AY661093;

AY661094; AY661095; AY661096; AY661097; AY661098; AY661099; AY661100; AY661101; AY661102; AY661103; AY661104; AY661105; AY661106; AY661107; AY661108; AY661109; AY661110; AY661111; AY661112; AY661113; AY661114; AY661115; AY661116; AY661117; AY661118; AY661119; AY661120; AY661121; AY661122; AY661123; AY661124; AY661125; AY661126; AY661127; AY661128; AY661129; AY661130; AY661131; AY661132; AY661133; AY661134; AY661135; AY661136; AY661137; AY661138; AY661139; AY661140; AY661141; AY661142; AY661143; AY661144; AY661145; AY661146; AY661147; AY661148; AY661149; AY661150; AY661151; AY661152; AY661153; AY661154; AY661155; AY661156; AY661157; AY661158; AY661159; AY661160; AY661161; AY661162; AY661163; AY661164; AY661165; AY661166; AY661167; AY661168; AY661169; AY661170; AY661171; AY661172; AY661173; AY661174; AY661175; AY661176; AY661177; AY661178; AY661179; AY661180; AY661181; AY661182; AY661183; AY661184; AY661185; AY661186; AY661187; AY661188; AY661189; AY661190; AY661191; AY661192; AY661193; AY661194; AY661195; AY661196; AY661197; AY661198; AY661199; AY661200; AY661201; AY661202; AY661203; AY661204; AY661205; AY661206; AY661207; AY661208; AY661209; AY661210; AY661211; AY695084; AY695085; AY695086; AY695087; AY695088; AY695089; AY695090; AY701752; AY702440; AY702441; AY702442; AY702443; AY702444; AY702445; AY702446; AY702447; AY714347; AY738729; AY779253; AY779254; AY851473; AY851474; AY851475; AY851476; AY851477; AY852273; AY852274; AY852275; AY852276; AY852277; AY854046; AY854047; AY854048; AY854049; AY855341; AY862607; AY862608; AY862609; AY862610; AY862611; AY862612; AY884276; AY884277; AY884278; AY884279; AY884280; AY884281; AY884282; AY884283; AY884284; AY919314; AY945263; AY945264; AY945265; AY945266; AY945267; AY945268; AY945269; AY945270; AY945271; AY945272; AY945273; AY945274; AY945275; AY945276; AY945277; AY945278; AY945279; AY945280; AY945281; AY945282; AY945283; AY945284; AY945285; AY945286; AY945287; AY945288; AY947474; AY947476; AY961997; AY961998; AY961999; AY962000; AY962001; AY962002; AY962003; AY962004; AY962005; AY962006; AY962007; AY962008; AY962009; AY962010; AY962011; AY962012; AY962013; AY962014; AY962015; AY962016; AY962017; AY963782; AY963783; AY963784; AY963785; AY963786; AY963788; AY963789; AY963790; AY963791; AY963792; AY963793; AY963794; AY963795; AY963796; AY968017; AY968018; AY968019; AY968020; AY968021; AY968022; AY968023; AY968024; AY968025; AY968026; AY968027; AY968028; AY968029; AY968030; AY968031; AY968032; AY968033; AY968034; AY968035; AY968036; AY968037; AY968038; AY968039; AY968040; AY968041; AY972827; AY972828; AY972829; AY972830; AY972831; AY972832; AY972833; AY972834; AY972835; AY972836; AY972837; AY972838; AY972839; AY972840; AY972841; AY972842; AY972843; AY972844; AY972845; AY972846; AY972847; AY972848; AY972849; AY972850; AY972851; CS406467; CY000001; CY000009; CY000017; CY000025; CY000033; CY000041; CY000049; CY000057; CY000065; CY000073; CY000081; CY000089; CY000097; CY000105; CY000113; CY000121; CY000129; CY000137; CY000145; CY000153; CY000161; CY000169; CY000177; CY000185; CY000193; CY000201; CY000209; CY000217; CY000225; CY000233; CY000241; CY000249; CY000257; CY000265; CY000273; CY000281; CY000289; CY000297; CY000305; CY000313; CY000321; CY000329; CY000337; CY000345; CY000353; CY000361; CY000369; CY000377; CY000385; CY000393; CY000401; CY000409; CY000417; CY000425; CY000433; CY000441; CY000457; CY000465; CY000473; CY000481; CY000489; CY000497; CY000505; CY000513; CY000521; CY000529; CY000537; CY000545; CY000553; CY000561; CY000569; CY000584; CY000585; CY000593; CY000601; CY000609; CY000617; CY000625; CY000633; CY000641; CY000649; CY000657; CY000665; CY000673; CY000681; CY000689; CY000697; CY000705; CY000713; CY000721; CY000729; CY000737; CY000745; CY000753; CY000761; CY000769; CY000777; CY000785; CY000793; CY000801; CY000809; CY000817; CY000825; CY000833; CY000841; CY000849; CY000857; CY000865; CY000873; CY000881; CY000889; CY000901; CY000909; CY000917; CY000925; CY000933; CY000941; CY000949; CY000957; CY000965; CY000973; CY000981; CY000989; CY000997; CY001005; CY001013; CY001021; CY001029; CY001037; CY001045; CY001053; CY001061; CY001064; CY001072; CY001080; CY001088; CY001096; CY001104; CY001112; CY001120; CY001128; CY001136; CY001144; CY001152; CY001160; CY001168; CY001176; CY001184; CY001197; CY001205; CY001213; CY001221; CY001229; CY001237; CY001245; CY001253; CY001261; CY001269; CY001277; CY001285; CY001293; CY001301; CY001309; CY001317; CY001325; CY001333; CY001341; CY001349; CY001357; CY001365; CY001373; CY001381; CY001397; CY001405; CY001413; CY001421; CY001429; CY001437; CY001445; CY001453; CY001461; CY001469; CY001477; CY001485; CY001493; CY001504; CY001512; CY001520; CY001528; CY001536; CY001544; CY001552; CY001560; CY001568; CY001576; CY001584; CY001592; CY001600; CY001608; CY001616; CY001624; CY001632; CY001640; CY001648; CY001656; CY001664; CY001672; CY001688; CY001696; CY001704; CY001712; CY001720; CY001728; CY001736; CY001744; CY001752; CY001760; CY001768; CY001776; CY001784; CY001792; CY001800; CY001808; CY001816; CY001824; CY001832; CY001840; CY001848; CY001856; CY001864; CY001872; CY001880; CY001888; CY001896; CY001904; CY001912; CY001920; CY001928; CY001936; CY001944; CY001960; CY001968; CY001976; CY001984; CY001992; CY002000; CY002008; CY002016; CY002024; CY002032; CY002040; CY002048; CY002056; CY002064; CY002072; CY002080; CY002088; CY002096; CY002104; CY002112; CY002120; CY002128; CY002136; CY002144; CY002160; CY002168; CY002176; CY002184; CY002192; CY002200; CY002208; CY002216; CY002224; CY002232; CY002240; CY002248; CY002256; CY002264; CY002272; CY002280; CY002288; CY002296; CY002304; CY002312; CY002328; CY002336; CY002344; CY002368; CY002376; CY002384; CY002408; CY002416; CY002424; CY002432; CY002440; CY002448; CY002456; CY002464; CY002472; CY002480; CY002488; CY002496; CY002504; CY002512; CY002520; CY002544; CY002552; CY002560; CY002576; CY002584; CY002592; CY002600; CY002608; CY002712; CY002720; CY002728; CY002736; CY002744; CY002752; CY002760; CY002768; CY002776; CY002784; CY002816; CY002904; CY002905; CY002906; CY002914; CY002922; CY002930; CY002938; CY002946; CY002954; CY002962; CY003032; CY003040; CY003048; CY003056; CY003064; CY003072; CY003080; CY003088; CY003096; CY003104; CY003112; CY003120; CY003123; CY003136; CY003144; CY003152; CY003160; CY003168; CY003176; CY003184; CY003192; CY003200; CY003208; CY003216; CY003224; CY003232; CY003240; CY003248; CY003256; CY003264; CY003272; CY003280; CY003336; CY003344; CY003352; CY003408; CY003416; CY003424; CY003432; CY003440; CY003448; CY003456; CY003488; CY003496; CY003504; CY003512; CY003520; CY003528; CY003536; CY003544; CY003552; CY003560; CY003568;

CY003576; CY003584; CY003592; CY003600; CY003608; CY003616; CY003624; CY003632; CY003640; CY003648; CY003656; CY003664; CY003680; CY003712; CY003720; CY003728; CY003736; CY003744; CY003752; CY003777; CY003785; CY003793; CY003801; CY003809; CY003817; CY003825; CY004657; CY004662; CY004670; CY004692; CY004702; CY005915; CY005916; CY005917; CY005935; CY005936; CY005937; CY005938; CY005939; CY005940; CY005941; CY005942; CY005943; CY005977; CY006011; CY006012; CY006013; CY006014; CY006015; CY006016; CY006026; CY006031; CY006035; CY006038; CY006043; CY006044; CY006052; CY006060; CY006068; CY006076; CY006084; CY006092; CY006115; CY006123; CY006131; CY006139; CY006147; CY006155; CY006163; CY006179; CY006203; CY006211; CY006219; CY006227; CY006235; CY006243; CY006251; CY006259; CY006267; CY006275; CY006283; CY006291; CY006299; CY006307; CY006315; CY006323; CY006331; CY006339; CY006347; CY006371; CY006379; CY006435; CY006443; CY006451; CY006459; CY006467; CY006475; CY006483; CY006491; CY006499; CY006507; CY006515; CY006523; CY006531; CY006539; CY006547; CY006555; CY006563; CY006571; CY006579; CY006587; CY006595; CY006603; CY006611; CY006619; CY006627; CY006635; CY006659; CY006683; CY006691; CY006699; CY006707; CY006715; CY006723; CY006731; CY006739; CY006755; CY006763; CY006771; CY006787; CY006795; CY006803; CY006811; CY006819; CY006827; CY006835; CY006843; CY006851; CY006859; CY006883; CY006891; CY006899; CY006907; CY006923; CY006931; CY006939; CY006947; CY006955; CY006963; CY006971; CY006979; CY006987; CY006995; CY007003; CY007011; CY007019; CY007027; CY007035; CY007043; CY007051; CY007059; CY007067; CY007075; CY007083; CY007091; CY007099; CY007107; CY007115; CY007123; CY007131; CY007139; CY007147; CY007155; CY007163; CY007171; CY007179; CY007187; CY007195; CY007203; CY007211; CY007219; CY007227; CY007235; CY007243; CY007251; CY007259; CY007267; CY007275; CY007283; CY007291; CY007299; CY007307; CY007315; CY007323; CY007331; CY007339; CY007347; CY007355; CY007363; CY007371; CY007379; CY007387; CY007395; CY007403; CY007411; CY007419; CY007427; CY007435; CY007443; CY007451; CY007459; CY007467; CY007475; CY007483; CY007491; CY007499; CY007507; CY007515; CY007523; CY007531; CY007539; CY007547; CY007555; CY007563; CY007571; CY007579; CY007587; CY007595; CY007603; CY007611; CY007619; CY007627; CY007635; CY007643; CY007651; CY007659; CY007667; CY007675; CY007683; CY007691; CY007699; CY007707; CY007715; CY007723; CY007731; CY007739; CY007747; CY007755; CY007763; CY007771; CY007779; CY007787; CY007795; CY007803; CY007811; CY007819; CY007827; CY007835; CY007843; CY007851; CY007859; CY007867; CY007875; CY007883; CY007891; CY007899; CY007907; CY007915; CY007923; CY007931; CY007939; CY007947; CY007955; CY007963; CY007971; CY007979; CY007987; CY007995; CY008003; CY008011; CY008019; CY008027; CY008035; CY008043; CY008051; CY008059; CY008067; CY008075; CY008083; CY008091; CY008099; CY008107; CY008115; CY008123; CY008131; CY008139; CY008156; CY008164; CY008172; CY008180; CY008196; CY008204; CY008212; CY008220; CY008228; CY008236; CY008244; CY008252; CY008260; CY008268; CY008276; CY008284; CY008292; CY008300; CY008308; CY008316; CY008324; CY008332; CY008340; CY008348; CY008356; CY008364; CY008372; CY008380; CY008388; CY008396; CY008404; CY008412; CY008420; CY008428; CY008436; CY008444; CY008452; CY008460; CY008468; CY008476; CY008484; CY008492; CY008500; CY008508; CY008516; CY008532; CY008540; CY008548; CY008556; CY008564; CY008572; CY008580; CY008588; CY008596; CY008604; CY008612; CY008620; CY008628; CY008636; CY008644; CY008652; CY008660; CY008668; CY008676; CY008684; CY008692; CY008700; CY008708; CY008716; CY008724; CY008732; CY008740; CY008748; CY008756; CY008764; CY008772; CY008780; CY008788; CY008796; CY008804; CY008812; CY008820; CY008828; CY008836; CY008844; CY008852; CY008860; CY008868; CY008876; CY008884; CY008892; CY008900; CY008908; CY008916; CY008924; CY008932; CY008940; CY008948; CY008956; CY008964; CY008972; CY008980; CY009004; CY009012; CY009020; CY009028; CY009036; CY009044; CY009052; CY009060; CY009068; CY009076; CY009084; CY009092; CY009100; CY009108; CY009116; CY009124; CY009132; CY009140; CY009148; CY009156; CY009164; CY009244; CY009252; CY009260; CY009268; CY009300; CY009308; CY009348; CY009356; CY009372; CY009380; CY009388; CY009396; CY009404; CY009412; CY009420; CY009428; CY009436; CY009460; CY009468; CY009476; CY009484; CY009492; CY009500; CY009508; CY009516; CY009524; CY009556; CY009564; CY009572; CY009580; CY009588; CY009636; CY009644; CY009652; CY009660; CY009668; CY009676; CY009684; CY009692; CY009700; CY009708; CY009716; CY009724; CY009732; CY009740; CY009748; CY009852; CY009900; CY009908; CY009924; CY009932; CY009948; CY009988; CY009996; CY010004; CY010012; CY010020; CY010028; CY010036; CY010044; CY010052; CY010060; CY010068; CY010084; CY010516; CY010548; CY010564; CY010588; CY010596; CY010604; CY010612; CY010620; CY010628; CY010636; CY010644; CY010652; CY010660; CY010668; CY010676; CY010684; CY010692; CY010700; CY010708; CY010716; CY010724; CY010732; CY010748; CY010756; CY010796; CY010812; CY010988; CY011020; CY011028; CY011048; CY011064; CY011120; CY011128; CY011136; CY011256; CY011264; CY011288; CY011320; CY011328; CY011336; CY011344; CY011352; CY011360; CY011368; CY011376; CY011384; CY011400; CY011416; CY011424; CY011432; CY011440; CY011448; CY011456; CY011464; CY011472; CY011480; CY011488; CY011496; CY011504; CY011512; CY011520; CY011528; CY011536; CY011544; CY011552; CY011560; CY011568; CY011576; CY011592; CY011616; CY011624; CY011632; CY011640; CY011648; CY011656; CY011664; CY011672; CY011680; CY011688; CY011696; CY011704; CY011712; CY011720; CY011728; CY011736; CY011744; CY011752; CY011760; CY011768; CY011808; CY011816; CY011824; CY011832; CY011840; CY011848; CY011856; CY011864; CY011872; CY011880; CY011888; CY011896; CY011904; CY011912; CY011920; CY011928; CY011936; CY011944; CY011960; CY011968; CY011976; CY011984; CY011992; CY012000; CY012008; CY012016; CY012024; CY012032; CY012040; CY012048; CY012056; CY012064; CY012072; CY012080; CY012088; CY012096; CY012104; CY012112; CY012120; CY012128; CY012136; CY012144; CY012152; CY012160; CY012168; CY012176; CY012184; CY012200; CY012208; CY012216; CY012224; CY012232; CY012240; CY012248; CY012256; CY012264; CY012272; CY012280; CY012288; CY012312; CY012320; CY012328; CY012336; CY012344; CY012352; CY012360; CY012368; CY012376; CY012384; CY012392; CY012400; CY012408; CY012416; CY012424; CY012432; CY012448; CY012456; CY012464; CY012472; CY012480; CY012488; CY012496; CY012504; CY012512; CY012520; CY012528; CY012536; CY012544; CY012552; CY012560; CY012568; CY012576; CY012584; CY012592; CY012616; CY012624; CY012632; CY012640; CY012648;

CY012656; CY012664; CY012672; CY012680; CY012688;
CY012696; CY012704; CY012712; CY012720; CY012728;
CY012736; CY012744; CY012752; CY012760; CY012768;
CY012776; CY012784; CY012792; CY012848; CY012896;
CY012904; CY012912; CY012920; CY012928; CY012936;
CY012944; CY012952; CY012960; CY012968; CY012976;
CY012984; CY012992; CY013000; CY013008; CY013016;
CY013024; CY013048; CY013056; CY013064; CY013072;
CY013080; CY013088; CY013096; CY013104; CY013112;
CY013120; CY013128; CY013136; CY013144; CY013152;
CY013160; CY013168; CY013176; CY013184; CY013192;
CY013200; CY013208; CY013216; CY013224; CY013232;
CY013240; CY013263; CY013311; CY013319; CY013327;
CY013335; CY013343; CY013351; CY013359; CY013367;
CY013375; CY013383; CY013389; CY013397; CY013405;
CY013413; CY013421; CY013429; CY013437; CY013445;
CY013453; CY013461; CY013469; CY013477; CY013485;
CY013493; CY013501; CY013509; CY013517; CY013525;
CY013533; CY013541; CY013549; CY013605; CY013613;
CY013621; CY013629; CY013637; CY013645; CY013653;
CY013661; CY013669; CY013677; CY013685; CY013693;
CY013701; CY013709; CY013717; CY013725; CY013733;
CY013741; CY013749; CY013757; CY013765; CY013773;
CY013781; CY013789; CY013797; CY013805; CY013887;
CY013895; CY013903; CY013911; CY013919; CY013927;
CY013935; CY013943; CY013951; CY013959; CY013967;
CY013975; CY013983; CY013991; CY013999; CY014015;
CY014023; CY014031; CY014039; CY014047; CY014055;
CY014063; CY014071; CY014079; CY014087; CY014095;
CY014103; CY014111; CY014119; CY014127; CY014135;
CY014143; CY014151; CY014159; CY014548; CY014571;
CY014621; CY014633; CY014702; CY014865; CY014961;
CY015492; CY015500; CY015508; CY015516; CY015540;
CY015548; CY015556; CY015564; CY015572; CY015588;
CY015596; CY015604; CY015612; CY015620; CY015628;
CY015636; CY015644; CY015652; CY015660; CY015668;
CY015676; CY015684; CY015692; CY015700; CY015708;
CY015716; CY015724; CY015732; CY015740; CY015748;
CY015756; CY015764; CY015772; CY015780; CY015788;
CY015796; CY015804; CY015812; CY015820; CY015828;
CY015836; CY015844; CY015852; CY015860; CY015868;
CY015876; CY015884; CY015892; CY015900; CY015908;
CY015916; CY015924; CY015932; CY015940; CY015948;
CY015956; CY015964; CY015972; CY015980; CY015988;
CY015996; CY016004; CY016012; CY016020; CY016028;
CY016036; CY016044; CY016060; CY016068; CY016076;
CY016084; CY016092; CY016100; CY016108; CY016116;
CY016140; CY016180; CY016204; CY016212; CY016268;
CY016395; CY016403; CY016411; CY016427; CY016443;
CY016451; CY016467; CY016475; CY016483; CY016491;
CY016499; CY016507; CY016515; CY016523; CY016531;
CY016539; CY016547; CY016555; CY016571; CY016579;
CY016587; CY016595; CY016603; CY016627; CY016635;
CY016651; CY016659; CY016707; CY016715; CY016739;
CY016747; CY016755; CY016763; CY016771; CY016979;
CY016987; CY016995; CY017083; CY017091; CY017099;
CY017107; CY017131; CY017163; CY017171; CY017259;
CY017267; CY017283; CY017291; CY017299; CY017307;
CY017323; CY017331; CY017339; CY017347; CY017355;
CY017387; CY017395; CY017411; CY017443; CY017451;
CY017459; CY017467; CY017475; CY017483; CY017491;
CY017499; CY017507; CY017515; CY017523; CY017531;
CY017539; CY017547; CY017555; CY017563; CY017571;
CY017579; CY017587; CY017595; CY017603; CY017611;
CY017619; CY017627; CY017709; CY017757; CY017773;
CY017797; CY017805; CY017821; CY017837; CY017861;
CY017885; CY017893; CY017901; CY017909; CY017917;
CY017925; CY017933; CY017941; CY017949; CY017957;
CY017965; CY017973; CY017981; CY017989; CY017999;
CY018869; CY018925; CY018941; CY018957; CY018965;
CY018973; CY018981; CY018989; CY018997; CY019005;
CY019013; CY019021; CY019029; CY019141; CY019149;
CY019157; CY019165; CY019173; CY019181; CY019189;
CY019197; CY019213; CY019245; CY019253; CY019261;
CY019269; CY019277; CY019285; CY019293; CY019301;
CY019309; CY019317; CY019325; CY019333; CY019747;
CY019811; CY019819; CY019827; CY019835; CY019843;
CY019851; CY019859; CY019891; CY019899; CY019907;
CY019915; CY019931; CY019939; CY019981; CY019989;
CY020005; CY020013; CY020021; CY020029; CY020037;
CY020045; CY020053; CY020061; CY020069; CY020077;
CY020085; CY020093; CY020101; CY020109; CY020117;
CY020125; CY020133; CY020197; CY020205; CY020213;
CY020221; CY020301; CY020309; CY020325; CY020333;
CY020341; CY020357; CY020365; CY020493; CY020501;
CY020525; CY020533; CY020717; CY020741; CY020757;
CY020877; CY020893; CY020933; CY020997; CY021061;
CY021077; CY021085; CY021093; CY021101; CY021109;
CY021117; CY021157; CY021229; CY021261; CY021269;
CY021277; CY021285; CY021309; CY021317; CY021341;
CY021429; CY021453; CY021461; CY021597; CY021741;
CY021765; CY021773; CY021781; CY021829; CY021837;
CY021845; D00929; D00930; D00931; D00932; D10161;
D10162; D13581; D13582; D13583; D13584; D21171;
D21172; D21173; D21174; D21175; D21176; D21177;
D21178; D21179; D21180; D21181; D21182; D21183;
D30662; D30663; D30664; D30665; D30668; D30669;
D30677; D30678; D30679; D30680; D30681; D30682;
D30683; D30684; D30685; D30686; D43786; D43787;
D43788; D43789; D43790; D43791; D43792; D49959;
D49960; D49961; D49962; D49963; D49964; D49965;
D49966; D49967; D86469; DQ006284; DQ006285;
DQ007622; DQ021910; DQ021911; DQ059385;
DQ066936; DQ086157; DQ086158; DQ086159;
DQ086160; DQ086161; DQ089634; DQ089635;
DQ089636; DQ089637; DQ089638; DQ089639;
DQ114496; DQ114497; DQ114498; DQ114499;
DQ114500; DQ114501; DQ114502; DQ114503;
DQ114504; DQ114505; DQ114506; DQ114507;
DQ114508; DQ114509; DQ114510; DQ114511;
DQ114512; DQ114513; DQ114514; DQ114515;
DQ114516; DQ114517; DQ114518; DQ114519;
DQ114520; DQ114521; DQ114522; DQ114523;
DQ114524; DQ114525; DQ114526; DQ114527;
DQ114528; DQ114529; DQ114530; DQ114531;
DQ114532; DQ114533; DQ114534; DQ114535;
DQ114536; DQ114537; DQ124157; DQ124189;
DQ124190; DQ124191; DQ124192; DQ124193;
DQ124194; DQ124195; DQ124196; DQ132433;
DQ141307; DQ145537; DQ146419; DQ150425;
DQ150433; DQ159065; DQ159066; DQ159067;
DQ167251; DQ167252; DQ167253; DQ167254;
DQ167255; DQ167256; DQ167257; DQ167258;
DQ167259; DQ167266; DQ167261; DQ167262;
DQ167263; DQ167264; DQ167265; DQ167266;
DQ167267; DQ167268; DQ167269; DQ167270;
DQ167271; DQ167272; DQ167273; DQ167274;
DQ167275; DQ167276; DQ167277; DQ167278;
DQ167279; DQ167280; DQ167281; DQ167282;
DQ167283; DQ167284; DQ167285; DQ167286;
DQ167287; DQ167288; DQ167289; DQ167290;
DQ167291; DQ167292; DQ167293; DQ167294;
DQ167295; DQ167296; DQ167297; DQ167298;
DQ167299; DQ167300; DQ167301; DQ167302;

DQ167303; DQ167304; DQ167305; DQ167306; DQ883582; DQ883583; DQ883584; DQ883585;
DQ167307; DQ174263; DQ174264; DQ174265; DQ883586; DQ883587; DQ883588; DQ883589;
DQ174266; DQ174267; DQ174268; DQ179382; DQ883590; DQ883591; DQ883592; DQ883593;
DQ179383; DQ179384; DQ179385; DQ179386; DQ883594; DQ883595; DQ883596; DQ883597;
DQ179387; DQ179388; DQ179389; DQ179390; DQ883598; DQ883599; DQ883600; DQ883601;
DQ179391; DQ179392; DQ179393; DQ179394; DQ883602; DQ883603; DQ883604; DQ883605;
DQ179395; DQ179396; DQ179397; DQ179398; DQ883606; DQ883607; DQ883608; DQ883609;
DQ179399; DQ179400; DQ179401; DQ179402; DQ883610; DQ883611; DQ883612; DQ883613;
DQ179403; DQ179404; DQ179405; DQ179406; DQ883614; DQ883615; DQ883616; DQ883617;
DQ179407; DQ179408; DQ179409; DQ179410; DQ883618; DQ883619; DQ883620; DQ883621;
DQ179411; DQ179412; DQ179413; DQ179414; DQ883622; DQ883623; DQ883624; DQ883625;
DQ179415; DQ179416; DQ179417; DQ179418; DQ883626; DQ883627; DQ883628; DQ923506;
DQ179419; DQ179420; DQ179421; DQ179422; DQ923507; DQ973305; DQ975252; DQ975253;
DQ179423; DQ179424; DQ179425; DQ179426; DQ975254; DQ975255; DQ975256; DQ975257;
DQ179427; DQ179428; DQ179429; DQ179430; DQ975258; DQ975259; DQ975260; DQ975261;
DQ179431; DQ179432; DQ179433; DQ179434; DQ975262; DQ975263; DQ975264; DQ975265;
DQ179435; DQ179436; DQ179437; DQ179438; DQ975266; DQ975267; DQ981740; DQ981741;
DQ179439; DQ179440; DQ179441; DQ179442; DQ981742; DQ983746; DQ983747; DQ983748;
DQ179443; DQ179444; DQ179445; DQ179446; DQ983749; DQ983750; DQ983751; DQ983752;
DQ179447; DQ179448; DQ179449; DQ179450; DQ983753; DQ983754; DQ983755; DQ983756;
DQ179451; DQ179452; DQ179453; DQ179454; DQ983757; DQ983758; DQ983759; DQ983760;
DQ179455; DQ179456; DQ179457; DQ179458; DQ983761; DQ983762; DQ983763; DQ983764;
DQ179459; DQ179460; DQ179461; DQ179462; DQ983765; DQ983766; DQ983767; EF041487; EF117330;
DQ179463; DQ179464; DQ179465; DQ179466; EF118172; EF118173; EF118174; EF151958; EF199897;
DQ179467; DQ179468; DQ179469; DQ179470; EF199898; EF456782; EF456783; EF456784; EF456785;
DQ179471; DQ179472; DQ179473; DQ179474; EF456786; EF456787; EF456788; EF456789; EF456790;
DQ179475; DQ179476; DQ179477; DQ179478; EF456791; EF456792; EF456797; EF462544; EF462549;
DQ179479; DQ179480; DQ179481; DQ179482; EF462550; EF462551; EF462552; EF462553; EF462554;
DQ179483; DQ179484; DQ179485; DQ179486; EF462555; EF462557; EF462558; EF462559; EF462560;
DQ179487; DQ179488; DQ179489; DQ179490; EF462561; EF462562; EF462566; EF462567; EF462568;
DQ179491; DQ179492; DQ179493; DQ179494; EF462569; EF467799; EF467800; EF467827; EF473329;
DQ179495; DQ179496; DQ179497; DQ179498; EF473330; EF473331; EF473332; EF473333; EF473334;
DQ179499; DQ179500; DQ179501; DQ179502; EF473335; EF473336; EF473337; EF473338; EF473339;
DQ179503; DQ179504; DQ179505; DQ179506; EF473340; EF473341; EF473342; EF473343; EF473344;
DQ179507; DQ179508; DQ179509; DQ179510; EF473345; EF473346; EF473347; EF473348; EF473349;
DQ179511; DQ179512; DQ179513; DQ179514; EF473350; EF473351; EF473352; EF473353; EF473354;
DQ179515; DQ179516; DQ179517; DQ179518; EF473355; EF473356; EF473357; EF473358; EF473359;
DQ179519; DQ179520; DQ179521; DQ179522; EF473360; EF473362; EF473363; EF473364; EF473365;
DQ179523; DQ179524; DQ179525; DQ179526; EF473366; EF473367; EF473368; EF473369; EF473370;
DQ179527; DQ222913; DQ227423; DQ227424; EF473371; EF473372; EF473373; EF473375; EF473376;
DQ227425; DQ227426; DQ227427; DQ227428; EF473377; EF473378; EF473379; EF473380; EF473381;
DQ227429; DQ227430; DQ227431; DQ241761; EF473382; EF473383; EF473384; EF473385; EF473386;
DQ241762; DQ241763; DQ249259; DQ249261; EF473387; EF473388; EF473389; EF473390; EF473391;
DQ249262; DQ256372; DQ256373; DQ256374; EF473392; EF473393; EF473394; EF473395; EF473396;
DQ256375; DQ265707; DQ265708; DQ265709; EF473398; EF473399; EF473400; EF473401; EF473402;
DQ265710; DQ265711; DQ265712; DQ265713; EF473403; EF473404; EF473405; EF473406; EF473408;
DQ265714; DQ265715; DQ265716; DQ265717; EF473409; EF473410; EF473411; EF473412; EF473413;
DQ265718; DQ335771; DQ336006; DQ336007; EF473414; EF473415; EF473416; EF473417; EF473418;
DQ336008; DQ336009; DQ336010; DQ336011; EF473419; EF473420; EF473421; EF473422; EF473423;
DQ336012; DQ336013; DQ336014; DQ336015; EF473424; EF473425; EF473426; EF473427; EF473428;
DQ336016; DQ336017; DQ415319; DQ415320; EF473429; EF473430; EF473431; EF473432; EF473433;
DQ415321; DQ415322; DQ415323; DQ415324; EF473434; EF473435; EF473436; EF473437; EF473438;
DQ415325; DQ415326; DQ447186; DQ469962; EF473439; EF473440; EF473441; EF473442; EF473443;
DQ469970; DQ469978; DQ469986; DQ469994; EF473444; EF473445; EF473446; EF473447; EF473449;
DQ470002; DQ487340; DQ487341; DQ508825; EF473450; EF473451; EF473452; EF473453; EF473454;
DQ508833; DQ508849; DQ508865; DQ508929; EF473455; EF473456; EF473457; EF473458; EF473459;
DQ534420; DQ534421; DQ534422; DQ534423; EF473460; EF473461; EF473462; EF473463; EF473464;
DQ534424; DQ534425; DQ534426; DQ534427; EF473465; EF473466; EF473467; EF473468; EF473469;
DQ534428; DQ534429; DQ632594; DQ632595; EF473470; EF473471; EF473472; EF473473; EF473474;
DQ632596; DQ632597; DQ865945; DQ865946; EF473475; EF473476; EF473477; EF473478; EF473479;
DQ865947; DQ865948; DQ865949; DQ865950; EF473480; EF473481; EF473482; EF473483; EF473484;
DQ865951; DQ865952; DQ865953; DQ865954; EF473485; EF473486; EF473487; EF473488; EF473489;
DQ865955; DQ865956; DQ865957; DQ865958; EF473490; EF473491; EF473492; EF473493; EF473494;
DQ865959; DQ865960; DQ865961; DQ865962; EF473495; EF473496; EF473497; EF473498; EF473499;
DQ865963; DQ865964; DQ865965; DQ865966; EF473500; EF473504; EF473505; EF473506; EF473507;
DQ865967; DQ865968; DQ865969; DQ865970; EF473508; EF473509; EF473510; EF473511; EF473512;
DQ865971; DQ865972; DQ865973; DQ865974; EF473513; EF473514; EF473515; EF473516; EF473517;

EF473518; EF473519; EF473520; EF473521; EF473522; EF473523; EF473524; EF473525; EF473526; EF473527; EF473528; EF473529; EF473530; EF473531; EF473532; EF473533; EF473534; EF473535; EF473536; EF473537; EF473538; EF473539; EF473540; EF473541; EF473542; EF473543; EF473544; EF473545; EF473546; EF473547; EF473548; EF473549; EF473550; EF473551; EF473552; EF473553; EF473555; EF473556; EF473557; EF473558; EF473559; EF473560; EF473561; EF473562; EF473563; EF473564; EF473565; EF473566; EF473567; EF473568; EF473569; EF473570; EF473571; EF473572; EF473573; EF473574; EF473575; EF473576; EF473577; EF473578; EF473579; EF473581; EF473582; EF473583; EF473584; EF473585; EF473586; EF473588; EF473589; EF473590; EF473591; EF473592; EF473593; EF473594; EF473595; EF473596; EF473597; EF473598; EF473599; EF473600; EF473601; EF473602; EF473603; EF473604; EF473605; EF473607; EF473608; EF473609; EF473611; EF473612; EF473613; EF473614; EF473615; EF473616; EF473617; EF473618; EF473619; EF473620; EF473621; EF473622; EF473623; EF473624; EF473625; EF473626; EF473627; EF473628; EF473629; EF473630; EF473632; EF473633; EF473634; EF473635; EF473636; EF473638; EF473639; EF473640; EF473641; EF473642; EF473643; EF473644; EF473645; EF473646; EF473647; EF473648; EF541428; EF541429; EF541430; EF541431; EF541432; EF541433; EF541434; EF541435; EF541436; EF541437; EF541438; EF541439; EF541440; EF541441; EF541442; EF541443; J02090; J02092; J02132; J02538; K03335; K03338; L18994; L18996; L18997; L18998; L19000; L19001; L19002; L19003; L19004; L19412; L19413; L19414; L19415; L19416; L20101; L20102; L20103; L20104; L20105; L20114; L20115; L20118; L20119; L27597; L31949; L32024; L39913; L39914; L39915; L39916; L39917; L39918; L75975; L75976; L75977; L75978; L75979; L75980; L75981; L75982; L75983; L75984; L75985; L75986; L75987; L75988; L75989; L75990; L75991; L76035; L76036; L76037; M16737; M16738; M16739; M16740; M16741; M16742; M16743; M19056; M19057; M21648; M24718; M24719; M24720; M24721; M24722; M24723; M24724 M24725; M24726; M24727; M24728; M25044; M25434; M29257; M54895; M55059; M57630; M57631; M57632; M57644; M65018; M73771; M73772; M73773; M73774; M73775; M73776; S64310; S77429; U07146; U08858; U08859; U08905; U26830; U48439; U48440; U48441; U48442; U48443; U48444; U48445; U48446; U48447; U49722; U58195; U65552; U65553; U65554; U65555; U65556; U65557; U65558; U65559; U65560; U77830; U77831; U77832; U77833; U77834; U77835; U77836; U77837; U77838; U77839; U77840; U97740; V01085; V01086; V01087; V01089; V01098; V01103; X05907; X68437; X73489; X73490; X73491; X75800; X85085; X85086; X85087; X85088; X85089; X85090; X95637; X95638; Y14053; Y14055; Y14056; Y14057; Y14058; Y14059; Y14060; Z46391; Z46392; Z46393; Z46394; Z46395; Z46396; Z46397; Z46398; Z46399; Z46400; Z46401; Z46402; Z46403; Z46404; Z46405; Z46406; Z46407; Z46408; Z46409; Z46410; Z46411; Z46412; Z46413; Z46414; Z46415; Z46416 and Z46417.

Nucleic acid sequences encoding influenza virus subtype H4 haemagglutinins suitable for inclusion as a cargo moiety in conjugates according to the present invention have the following accession numbers and are available to the public via the National Center for Biotechnology Information (NCBI) Entrez nucleotide search and retrieval system:

AB288842; AB289331; CY005952; CY005953; CY005954; CY005955; CY005956; CY005957; CY005958; CY005959; CY005961; CY005962; CY005963; CY005964; CY005965; CY005966; CY005967; CY005968; CY006017; CY006027; CY006030; CY011036; CY011056; CY012808; CY012816; CY013248; CY014562; CY014579; CY014630; CY014723; CY014751; CY014857; CY014922; CY014929; CY014937; CY015459; CY015467; CY016148; CY017701; CY017741; CY020725; CY020733; CY020749; CY020765; CY020773; CY020789; CY020797; CY020805; CY020981; CY021213; CY021221; CY021237; CY021325; CY021333; CY021349; D90302; DQ021848; DQ021849; DQ021850; DQ021851; DQ021852; DQ021853; DQ021854; DQ021855; DQ021856; DQ021857; DQ021858; DQ021859; DQ021860; DQ021861; DQ021862; DQ021863; DQ021864; DQ021865; DQ021866; DQ021867; DQ021868; DQ236166; DQ327834; DQ787806; EF041495; J02102; M25283; M25284; M25285; M25286; M25287; M25288; M25289; M25290; M25291; AB289333; AB292406; AB292408; AB292662; AB295609; AB295611; AF285883; AF285885; AF290436; AJ506780; AJ506782; AY180434; AY180435; AY180436; AY180437; AY180438; AY180439; AY180440; AY180441; AY180442; AY180443; AY596802; AY596803; AY596804; AY633124; AY633141; AY633156; AY633260; AY633268; AY633284; AY633348; AY633356; CY004847; CY004911; CY004925; CY004933; CY004939; CY005672; CY005679; CY005944; CY005945; CY005946; CY005947; CY005948; CY005950 and CY005951.

Nucleic acid sequences encoding influenza virus subtype H5 haemagglutinins suitable for inclusion as a cargo moiety in conjugates according to the present invention have the following accession numbers and are available to the public via the National Center for Biotechnology Information (NCBI) Entrez nucleotide search and retrieval system:

BAD89305; BAD89315; BAD89325; BAD89335; BAD89345; BAE07201; BAE07155 BAE47131; BAE48315; BAE48316; BAE48317; BAE48318; BAE46949; BAE48684; BAE48685; BAE48686; BAE48687; BAE48688; BAE48689; BAE48690; BAE48691; BAE48692; BAE48693; BAE48694; BAE48695; BAE48696; BAE94699; BAF37962; BAE96567; BAE96961; BAF49662; BAF49663; BAF49664; BAF49665; BAF49666; BAF49667; BAF49668; BAF49669; BAF49670; BAF49671; BAF49672; BAF49673; BAF49674; BAF49675; BAF49676; BAF37387; BAF48359; AAC40508; AAC34263; AAC32078; AAC32088; AAC32098; AAC32099; AAC32100; AAC32101; AAC32102; AAC14418; AAD13566; AAD13567; AAD13568; AAD13569; AAD13570; AAD13571; AAD13572; AAD13573; AAD13574; AAD13575; AAF74329; AAF74330; AAF74331; AAD52043; AAF02300; AAF02301; AAF02302; AAF02303; AAF02304; AAF02305; AAF02306; AAF02307; AAF02308; AAF02309; AAF04719; AAF04720; AAD21153; AAD21154; AAD21155; AAD21156; AAD21157; AAD21158; AAD21159; AAD21160; AAD21161; AAD21162; AAD21163; AAD21164; AAD51927; AAD37782; AAF89536; AAF89537; AAF89538; AAF89539; AAF89540; AAF89541; AAF89542; AAF89543; AAF89544; AAF89545; AAF89546; AAG28424; AAG60347; AAG60348; AAG60349; AAG01195; AAG01205; AAG01215; AAG01225; AAF99718; AAG38534; AAK38298; AAK57506;

AAL59142; AAL59143; AAL16033; AAL84323; AAL84324; AAM49555; AAM22457; AAM22458; AAO52859; AAO52860; AAO52861; AAO52862; AAO52863; AAO52864; AAO52865; AAO52866; AAO52867; AAO52868; AAO52869; AAO52870; AAO52871; AAO52872; AAO52873; AAO52874; AAO52875; AAO52876; AAO52877; AAO52878; AAO52879; AAO52880; AAO52881; AAO52882; CAC28131; CAF21870; CAF21874; CAG14996; CAG14997; CAG29661; CAI29278; CAI96162; CAI96163; CAI99404; CAJ32556; CAJ75440; CAJ75441; CAJ75442; CAJ75443; CAJ75444; CAJ75445; CAJ75446; CAJ75447; CAJ75448; CAJ77761; CAJ84721; CAK18565; CAK18566; CAK18567; CAK18570; CAK18571; CAK18577; CAK18596; CAL37103; CAL51387; CAL51388; CAL51389; CAL51390; CAL51391; CAL51392; CAL51393; CAL51394; CAL51395; CAL51396; CAL48277; CAL48276; CAL48275; CAL48274; CAL48273; CAL48272; CAL48271; CAL48270; CAL48269; CAL48268; CAL48267; CAL48279; CAL48278; CAL48266; CAL48265; CAL48280; CAL59784; CAL59783; CAL59782; CAL59781; CAL59780; CAL59779; CAL59786; CAL59785; CAM33521; AAL31380; AAL31381; AAL31382; AAL31383; AAL31384; AAL31385; AAL31386; AAL31387; AAL31388; AAL75839; AAL75843; AAL75847; AAO46797; AAO46798; AAO46799; AAO46800; AAO46801; AAO46802; AAO46803; AAO46804; AAO46805; AAP71989; AAP71990; AAP71991; AAP71992; AAP71993; AAP71994; AAP71995; AAP71996; AAP71997; AAP71998; AAP71999; AAP72000; AAP72001; AAP72002; AAP72003; AAP72004; AAP72005; AAP72006; AAP72007; AAP72008; AAP72009; AAP72010; AAP72011; AAR88808; AAR88809; AAR88810; AAR88811; AAR88812; AAR88813; AAR88814; AAR88815; AAR88816; AAR88817; AAR88818; AAR88819; AAR88820; AAR88821; AAR88822; AAR88823; AAR88824; AAR88825; AAR88826; AAR88827; AAR88828; AAR88829; AAR88830; AAR88831; AAR88832; AAR88833; AAR88834; AAR88835; AAR88836; AAR88837; AAR88838; AAR88839; AAR88840; AAR88841; AAS07023; AAR99628; AAR98819; AAT07996; AAS50166; AAS50167; AAS57873; AAS57874; AAS57875; AAS57876; AAS45134; AAS84275; AAS84276; AAS84247; AAS84248; AAS84249; AAS84250; AAS84251; AAS84252; AAS84253; AAS84254; AAS84255; AAS84256; AAS84257; AAS84258; AAS84259; AAS84260; AAS84261; AAS84262; AAS84263; AAS84264; AAS84265; AAS84266; AAS84267; AAS84268; AAS84269; AAS84270; AAS84271; AAS84272; AAS84273; AAS84274; AAS65615; AAS65618; AAS87596; AAS87577; AAS87580; AAT39065; AAT39066; AAT39067; AAT39068; AAT39073; AAT39074; AAT39075; AAT39076; AAT39077; AAT39078; AAT39079; AAT39080; AAS79356; AAS79359; AAS89004; AAT12022; AAT12023; AAT12024; AAT12025; AAT12026; AAT12027; AAT12028; AAT12029; AAT12030; AAT12031; AAT12032; AAT12033; AAT12034; AAT12035; AAT12036; AAT12037; AAT12038; AAT12039; AAT12040; AAT12041; AAT12042; AAS89267; AAS89268; AAS89269; AAS89270; AAS89271; AAS89272; AAS89273; AAT37563; AAT90337; AAV34704; AAV32636; AAT65209; AAT70210; AAT70218; AAT72505; AAV65826; AAT73260; AAT73261; AAT73262; AAT73263; AAT73264; AAT73265; AAT73266; AAT73267; AAT73268; AAT73269; AAT73270; AAT73271; AAT73272; AAT73273; AAT73274; AAT73275; AAT73276; AAT73277; AAT73278; AAT73279; AAT73280; AAT73281; AAT73282; AAT73283; AAT73284; AAT73285; AAT73286; AAT73287; AAT73288; AAT73289; AAT73290; AAT73291; AAT73292; AAT73293; AAT73294; AAT73295; AAT73296; AAT73297; AAT73298; AAT73299; AAT73300; AAT73301; AAT73302; AAT73303; AAT73304; AAT73305; AAT73306; AAT73307; AAT73308; AAT73309; AAT73310; AAT73311; AAT73312; AAT73313; AAT76166; AAV97601; AAV97602; AAV97603; AAV97604; AAT84153; AAT90832; AAV91220; AAV73972; AAV73975; AAV73980; AAW59548; AAW59550; AAW59552; AAW59554; AAW59556; AAW59558; AAW59559; AAU08349; AAU08351; AAW59390; AAW59398; AAW59408; AAW19638; AAW19640; AAW19642; AAW19644; AAW19646; AAV30828; AAV30836; AAV48546; AAV41002; AAV48778; AAV48780; AAV74400; AAW80717; AAW80718; AAW80719; AAV91149; AAV97886; AAW30657; AAX47288; AAW72226; AAX59694; AAW66002; AAX53504; AAX53505; AAX53506; AAX53507; AAX53508; AAX53509; AAX53510; AAX83395; AAX83396; AAX83397; AAX83398; AAY57183; AAY57184; AAY57185; AAY57186; AAY57187; AAY57188; AAY57189; AAY57190; AAY57191; AAY57192; AAY57193; AAY57194; AAY57195; AAY57196; AAY57197; AAY57198; ABB20262; ABB87042; ABB87281; ABB87292; ABB87711; ABB88278; ABB88348; ABB88379; ABG88245; ABI36041; ABI36012; ABI36023; ABI36034; ABI36040; ABI36042; ABI36043; ABI36044; ABI36045; ABI36046; ABI36047; ABI36048; ABI36049; ABI36050; ABI36051; ABI36052; ABI36053; ABI36054; ABI36055; ABI36056; ABI36057; ABI36144; ABI36155; ABI36166; ABI36177; ABI36187; ABI36198; ABI36275; ABI36286; ABI36295; ABI36307; ABI36318; ABI36329; ABI36340; ABI36351; ABI36362; ABI36373; ABI36384; ABI36395; ABI36406; ABI36423; ABI36428; ABI36439; ABI36450; ABI36469; ABI36480; ABI49396; ABI49407; ABI49415; ABI84424; ABI84465; ABI84495; ABI84497; ABI84598; ABI84603; ABI84608; ABI84706; ABI84784; ABI84816; ABI84970; ABI85095; ABI85106; ABI85117; ABI85155; ABI95316; ABI95327; ABI95338; ABI95349; ABJ16565; ABJ16796; ABJ16807; ABJ16818; ABJ16928; ABJ16917; ABJ16829; ABJ16939; ABJ51728; ABJ51717; ABJ51706; ABJ51695; ABJ51739; ABJ51684; ABJ51673; ABJ16950; ABJ16840; ABJ16851; ABJ16862; ABJ16873; ABJ16884; ABJ16895; ABJ16906; ABJ53526; ABJ53537; ABJ53548; ABJ53594; ABJ53583; ABJ53559; ABK40087; ABK40492; ABK80003; ABL07008; ABL07019; ABL07030; ABL31744; ABL31755; ABL31766; ABL31780; ABM22048; ABM90434; ABM90445; ABM90456; ABM90467; ABM90478; ABM90489; ABM90500; ABM90511; ABM90522; ABM90533; ABM90544; ABO37977; ABO38263; ABO44200; ABO44211; ABO44222; ABO44233; ABO44244; ABO44255; ABO44266; ABO44277; ABO44288; ABO44299; ABO44310; ABO52720; ABO52731; ABO52742; ABO52753; ABO77034; ABO77045; AAY21163; AAY25499; AAY46328; AAY46329; AAY46330; AAY46331; AAY46332; AAY46333; AAY46334; AAY46335; AAY46336; AAY46337; AAY46338; AAY46339; AAY46340; AAY46341; AAY46342; AAY46343; AAY46344; AAY46345; AAY46346; AAY46347; AAY46348; AAY46349; AAY46350; AAY46351; AAY46352; AAY46353; AAY46354; AAY46355;

AAY46356; AAY46357; AAY46358; AAY46359; ABE97583; ABE97584; ABE97585; ABE97586;
AAY46360; AAY46361; AAY46362; AAY46363; ABE97587; ABE97588; ABE97589; ABE97590;
AAY46364; AAY46365; AAY46366; AAY56367; ABE97591; ABE97592; ABE97593; ABE97594;
AAY68363; AAY78953; AAZ29946; AAZ29947; ABE97595; ABE97596; ABE97597; ABE97598;
AAZ29948; AAZ29949; AAZ29950; AAZ29951; ABE97599; ABE97600; ABE97601; ABE97602;
AAZ29952; AAZ29953; AAZ29954; AAZ29955; ABE97603; ABE97604; ABE97605; ABE97606;
AAZ29956; AAZ29957; AAZ29958; AAZ29959; ABE97607; ABE97608; ABE97609; ABE97610;
AAZ29960; AAZ29961; AAZ29962; AAZ29963; ABE97611; ABE97612; ABE97613; ABE97614;
AAZ29964; AAZ29965; AAZ29966; AAZ29967; ABE97615; ABE97616; ABE97617; ABE97618;
AAZ29968; AAZ29969; AAZ29970; AAZ29971; ABE97619; ABE97620; ABE97621; ABE97622;
AAZ29972; AAZ29973; AAZ29974; AAZ29975; ABE97623; ABE97624; ABE97625; ABE97626;
AAZ29976; AAZ29977; AAZ29978; AAZ29979; ABE97627; ABE97628; ABE97629; ABE97630;
AAZ29980; AAZ29981; AAZ76389; ABE68921; ABE97631; ABE97632; ABE97633; ABE97634;
ABE68922; AAZ16275; ABE68923; ABE68924; ABF56528; ABF58847; ABF56648; ABG23657;
ABE68925; ABE68926; AAZ16276; AAZ16277; ABF61761; ABG20463; ABG20464; ABG20465;
ABE68927; AAZ16278; AAZ16279; ABE68928; ABG20466; ABG20467; ABG38185; ABG38189;
ABE68929; AAZ16280; ABE68930; ABE68931; ABF72802; ABF93440; ABF93441; ABG49439;
ABE68932; AAZ16281; AAZ16282; AAZ72734; ABF84066; ABG45944; ABG75543; ABG20468;
AAZ72735; AAZ72736; AAZ72737; AAZ72738; ABG20472; ABG20476; ABG20478; ABG35546;
AAZ72739; AAZ17522; AAZ17523; AAZ17524; ABG65732; ABI16504; ABG65733; ABG67711;
AAZ23154; AAZ80486; AAZ78315; ABA29447; ABG67712; ABG67713; ABG67714; ABG57086;
AAZ82496; AAZ82497; ABA70758; ABB00917; ABG57087; ABG57094; ABG57095; ABG78549;
ABB00918; ABB00919; ABB00920; ABA39516; ABG78567; ABI34140; ABI34142; ABG67978;
ABA39517; ABA39518; ABA39519; ABA39520; ABG75831; ABG75616; ABI23979; ABG81037;
ABA87102; ABA87103; ABA54915; ABA55714; ABG81038; ABG81039; ABG81040; ABG81041;
ABA55715; ABA55716; ABA55717; ABB00582; ABI18096; ABH85395; ABH09484; ABH09485;
ABB43058; ABB43059; ABB22773; ABB22774; ABH09486; ABH09487; ABH09488; ABH09489;
ABB22775; ABB43119; ABB43127; ABB83598; ABH09490; ABJ98523; ABJ98525; ABJ98527; ABJ98529;
ABB58817; ABB58818; ABB58819; ABB58820; ABJ98531; ABI34124; ABK34764; ABJ88847; ABJ96647;
ABB58821; ABB80546; ABB86287; ABC47656; ABJ96648; ABJ96649; ABJ96650; ABJ96651; ABJ96652;
ABC59833; ABC66517; ABC66518; ABC66519; ABJ96653; ABJ96654; ABJ96655; ABJ96656; ABJ96657;
ABC66520; ABC66521; ABC66522; ABC66523; ABJ96658; ABJ96659; ABJ96660; ABJ96661; ABJ96662;
ABC66524; ABC66525; ABC66526; ABC66527; ABJ96663; ABJ96664; ABJ96665; ABJ96666; ABJ96667;
ABC66528; ABC66529; ABC66530; ABC66531; ABJ96668; ABJ96669; ABJ96670; ABJ96671; ABJ96672;
ABC66532; ABC66533; ABC66534; ABC66535; ABJ96673; ABJ96674; ABJ96675; ABJ96676; ABJ96677;
ABC66536; ABC66537; ABC66538; ABC66539; ABJ96678; ABJ96679; ABJ96680; ABJ96681; ABJ96682;
ABC66540; ABC66541; ABC66542; ABC66543; ABJ96683; ABJ96684; ABJ96685; ABJ96686; ABJ96687;
ABC66544; ABC66545; ABC66546; ABC66547; ABJ96688; ABJ96689; ABJ96690; ABJ96691; ABJ96692;
ABC66548; ABC66549; ABC66550; ABC66551; ABJ96693; ABJ96694; ABJ96695; ABJ96696; ABJ96697;
ABC66552; ABC66553; ABC66554; ABC66555; ABJ96698; ABJ96699; ABJ96700; ABJ96701; ABJ96702;
ABC66556; ABC66557; ABC66558; ABC66559; ABJ96703; ABJ96704; ABJ96705; ABJ96706; ABJ96707;
ABC66560; ABC66561; ABC66562; ABC66563; ABJ96708; ABJ96709; ABJ96710; ABJ96711; ABJ96712;
ABC66564; ABC66565; ABC66566; ABC66567; ABJ96713; ABJ96714; ABJ96715; ABJ96716; ABJ96717;
ABC66568; ABC66569; ABC66570; ABC66571; ABJ96718; ABJ96719; ABJ96720; ABJ96721; ABJ96722;
ABC66572; ABC66573; ABC66574; ABC66575; ABJ96723; ABJ96724; ABJ96725; ABJ96726; ABJ96727;
ABC66576; ABC66577; ABC66578 ABC66579; ABJ96728; ABJ96729; ABJ96730; ABJ96731; ABJ96732;
ABC66580: ABC66581: ABC66582; ABC48787; ABJ96733; ABJ96734; ABJ96735; ABJ96736; ABJ96737;
ABC69216; ABC69224; ABC69232; ABC70167; ABJ96738; ABJ96739; ABJ96740; ABJ96741; ABJ96742;
ABC69148; ABC69149; ABC69150; ABC70712; ABJ96743; ABJ96744; ABJ96745; ABJ96746; ABJ96747,
ABC72082; ABC87315; ABC72655; ABD32123; ABJ96748; ABJ96749; ABJ96750; ABJ96751; ABJ96752;
ABD32128; ABC88573; ABC88583; ABD14806; ABJ96753; ABJ96754; ABJ96755; ABJ96756; ABJ96757;
ABD14807; ABD14808; ABD14809; ABD14810; ABJ96758; ABJ96759; ABJ96760; ABJ96761; ABJ96762;
ABD28180; ABD28181; ABD28182; ABD16284; ABJ96763; ABJ96764; ABJ96765; ABJ96766; ABJ96767;
ABD46889; ABD49489; ABD60336; ABD60345; ABJ96768; ABJ96769; ABJ96770; ABJ96771; ABJ96772;
ABD46740; ABD73284; ABD52284; ABD65415; ABJ96773; ABJ96774; ABJ96775; ABJ96776; ABJ96777;
ABD66291; ABD66292; ABD66293; ABD73804; ABJ96778; ABJ96779; ABJ96780; ABJ96781; ABJ96782;
ABD85144; ABD83818; ABD92945; ABD92953; ABJ96783; ABJ96784; ABJ96785; ABJ96786; ABJ96787;
ABD85374; ABD95991; ABE26829; ABE01046; ABJ96788; ABJ96789; ABJ96790; ABJ96791; ABJ96792;
ABE97547; ABE97548; ABE97549; ABE97550; ABJ96793; ABJ96794; ABJ96795; ABJ96796; ABJ96797;
ABE97551; ABE97552; ABE97553; ABE97554; ABJ96798; ABJ96799; ABJ96800; ABJ96801; ABJ96802;
ABE97555; ABE97556; ABE97557; ABE97558; ABJ96803; ABJ96804; ABJ96805; ABJ96806; ABJ96807;
ABE97559; ABE97560; ABE97561; ABE97562; ABJ96808; ABJ96809; ABJ96810; ABJ96811; ABJ96812;
ABE97563; ABE97564; ABE97565; ABE97566; ABJ96813; ABJ96814; ABJ96815; ABJ96816; ABJ96817;
ABE97567; ABE97568; ABE97569; ABE97570; ABJ96818; ABJ96819; ABJ96820; ABJ96821; ABJ96822;
ABE97571; ABE97572; ABE97573; ABE97574; ABJ96823; ABJ96824; ABJ96825; ABJ96826; ABJ96827;
ABE97575; ABE97576; ABE97577; ABE97578; ABJ96828; ABJ96829; ABJ96830; ABJ96831; ABJ96832;
ABE97579; ABE97580; ABE97581; ABE97582; ABJ96833; ABJ96834; ABJ96835; ABJ96836; ABJ96837;

ABJ96838; ABJ96839; ABJ96840; ABJ96841; ABJ96842; ABJ96843; ABJ96844; ABJ96845; ABJ96846; ABJ96847; ABJ96848; ABJ96849; ABJ96850; ABJ96851; ABJ96852; ABJ96853; ABJ96854; ABJ96855; ABJ96856; ABJ96857; ABJ96858; ABJ96859; ABJ96860; ABJ96861; ABJ96862; ABJ96863; ABJ96864; ABJ96865; ABJ96866; ABJ96867; ABJ96868; ABJ96869; ABJ96870; ABJ96871; ABJ96872; ABJ96873; ABJ96874; ABJ96875; ABJ96876; ABJ96877; ABJ96878; ABJ96879; ABJ96880; ABJ96881; ABJ96882; ABJ96883; ABJ96884; ABJ96885; ABJ96886; ABJ96887; ABJ96888; ABJ96889; ABJ96890; ABJ96891; ABJ96892; ABJ96893; ABJ96894; ABJ96895; ABJ96896; ABJ96897; ABJ96898; ABJ96899; ABJ96900; ABJ96901; ABJ96902; ABJ96903; ABJ96904; ABJ96905; ABJ96906; ABJ96907; ABJ96908; ABJ96909; ABJ96910; ABJ96911; ABJ96912; ABJ96913; ABJ96914; ABJ96915; ABJ96916; ABJ96917; ABJ96918; ABJ96919; ABJ96920; ABJ96921; ABJ96922; ABJ96923; ABJ96924; ABJ96925; ABJ96926; ABJ96927; ABJ96928; ABJ96929; ABJ96930; ABJ96931; ABJ96932; ABJ96933; ABJ96934; ABJ96935; ABJ96936; ABJ96937; ABJ96938; ABJ96939; ABJ96940; ABJ96941; ABJ96942; ABJ96943; ABJ96944; ABJ96945; ABJ96946; ABJ96947; ABJ96948; ABJ96949; ABJ96950; ABJ96951; ABJ96952; ABJ96953; ABJ96954; ABJ96955; ABJ96956; ABJ96957; ABJ96958; ABJ96959; ABJ96960; ABJ96961; ABJ96962; ABJ96963; ABJ96964; ABJ96965; ABJ96966; ABJ96967; ABJ96968; ABJ96969; ABJ96970; ABJ96971; ABJ96972; ABJ96973; ABJ96974; ABJ96975; ABJ96976; ABJ96977; ABJ96978; ABJ96979; ABJ96980; ABJ96981; ABJ96982; ABJ96983; ABJ96984; ABJ96985; ABJ96986; ABJ96987; ABJ96988; ABJ96989; ABJ96990; ABJ96991; ABJ96992; ABJ96993; ABJ96994; ABJ96995; ABJ96996; ABJ96997; ABJ96998; ABJ96999; ABJ97000; ABJ97001; ABJ97002; ABJ97003; ABJ97004; ABJ97005; ABJ97006; ABJ97007; ABJ97008; ABJ97009; ABJ97010; ABJ97011; ABJ97012; ABJ97013; ABJ97014; ABJ97015; ABJ97016; ABJ97017; ABJ97018; ABJ97019; ABJ97020; ABJ97021; ABJ97022; ABJ97023; ABJ97024; ABJ97025; ABJ97026; ABJ97027; ABJ97028; ABJ97029; ABJ97030; ABJ97031; ABJ97032; ABJ97033; ABJ97034; ABJ97035; ABJ97036; ABJ97037; ABJ97038; ABJ97039; ABJ97040; ABJ97041; ABJ97042; ABJ97043; ABJ97044; ABJ97045; ABJ97046; ABJ97047; ABJ97048; ABJ97049; ABJ97050; ABK00133; ABI94741; ABI94747; ABI94754; ABI94764; ABI96729; ABI96730; ABI96741; ABJ09476; ABI96767; ABJ09545; ABI96701; ABJ16473; ABJ15720; ABI98911, ABI09528; ABI198919; ABI97335; ABJ52562; ABJ80592; ABK00083; ABK00087; ABK00096; ABI98929; ABK00132; ABI97303; ABJ09511; ABJ09498; ABJ09466; ABJ09518; ABJ09488; ABK00104; ABI98938; ABK13783; ABK13784; ABK13782; ABJ53148; ABK32775; ABK32776; ABK32777; ABK32778; ABK32779; ABK32780; ABK32781; ABK32782; ABK34511; ABK34512; ABK34513; ABJ90343; ABK79301; ABK79302; ABK79303; ABK79304; ABL10088; ABL74499; ABL74500; ABL75919; ABL63754; ABL63755; ABL63756; ABL63757; ABL63758; ABL63759; ABL63760; ABL63761; ABL63762; ABL63763; ABL63764; ABL63765; ABL63766; ABL63767; ABL63768; ABL63769; ABL63770; ABL63771; ABL63772; ABM54179; ABM54180; ABO76638; ABO76639; ABO76640; ABO76641; ABO76642; ABO76643; ABO76644; ABM92273; ABN54791; ABN54792; ABO14789; ABO14790; ABO30505; ABN70706; ABN70707; ABN70708; ABN70709; ABN70710; ABN70711; ABO13912; ABO13920; ABO38179; ABO20946; ABO10162; ABO10163; ABO10181; ABO10183; ABO10184; ABO10185; ABO10186; ABO10187; ABO20962; ABO64687; ABO64688; ABO64689; ABO64690; ABO64691; ABO64692; ABO64693; ABO64694; ABO64695; ABO64696; ABO64697; ABO30353; ABO30354; ABO30355; ABO30359; ABO30360; ABO30361; ABO30346; ABO30347; ABO31434; AAA43199; AAA43094; AAL34297; AAL34298; AAL34299; AAA43159; AAA43160; AAA43082; AAA43083; AAA43205; AAB29507; AAB82064; AAA74909; AAA74910; AAC54378; AAC54390; AAC54391; AAC54392; AAC54393; AAB49654; AAB49655; AAB19072; AAB19073; AAB19074; AAB19075; AAB19076; AAB19077; AAB19078; AAB19079; AAB19080; AAB19081; AAB19082; AAB19083; AAB19084; AAB19085; AAB19086; AAB19087; AAB19088; AAB19089; AAC58999; AAB39639; AAC58990; AAC58991; AAC58992; AAC58993; AAC58994; AAC58995; AAC58996; AAC58997; AAC58998; CAA30680 and CAA30719.

Nucleic acid sequences encoding influenza virus subtype H6 haemagglutinins suitable for inclusion as a cargo moiety in conjugates according to the present invention have the following accession numbers and are available to the public via the National Center for Biotechnology Information (NCBI) Entrez nucleotide search and retrieval system:

AB278600; AB286875; AJ410532; AJ410533; AJ410534; AJ410535; AJ410536; AJ410537; AJ410538; AJ410539; AJ410540; AJ410541; AJ410542; AJ410543; AJ410544; AJ410545; AJ410546; AJ410547; AJ427308; AJ507203; AJ507204; AJ507205; AJ507206; AJ507207; AJ507208; AJ507209; AJ697867; AJ697868; AJ697869; AJ697870; AJ697871; AY633188; AY633204; AY633220; AY633236; AY633300; AY633308; AY633316; AY633324; AY633332; AY633380; AY684892; AY703832; AY773907; AY862613; AY968676; CY004034; CY004035; CY004036; CY004037; CY004038; CY004039; CY004043; CY004054; CY004066; CY004072; CY004076; CY004080; CY004086; CY004094; CY004114; CY004129; CY004137; CY004142; CY004146; CY004154; CY004162; CY004170; CY004178; CY004186; CY004194; CY004202; CY004210; CY004218; CY004226; CY004234; CY004242; CY004250; CY004258; CY004266; CY004274; CY004282; CY004515; CY004523; CY005106; CY00597; CY005605; CY005691; CY005881; CY0111122; CY012832; CY013255; CY013863; CY014561; CY014607; CY014616; CY014623; CY014656; CY014764; CY014880; CY014888; CY014909; CY014945; CY014953; CY015127; CY015451; CY015476; CY015484; CY016124; CY016132; CY016156; CY016164; CY016172; CY016619; CY017789; CY018007; CY018893; CY018909; CY018917; CY020781; CY020813; CY020821; CY020829; CY020837; CY020845; CY020853; CY020869; CY020957; CY020973; CY020989; CY021197; CY021205; CY021477; CY021677; D90303; DQ021649; DQ021650; DQ021651; DQ021652; DQ021653; DQ021654; DQ021655; DQ021656; DQ021657; DQ021658; DQ021659; DQ021660; DQ021661; DQ021662; DQ021663; DQ021664; DQ021665; DQ021666; DQ021667; DQ021668; DQ021669; DQ021670; DQ021671; DQ021672; DQ021673; DQ021675; DQ021676; DQ021677; DQ021678; DQ021679; DQ021680; DQ021681; DQ021682; DQ021683; DQ021684; DQ285546; DQ376618; DQ376619; DQ376620; DQ376621; DQ376622; DQ376623; DQ376624; DQ376625; DQ376626; DQ376627; DQ376628; DQ376629; DQ376630; DQ376631; DQ376632; DQ376633; DQ376634; DQ376635; DQ376636; DQ376637;

DQ376638; DQ376639; DQ376640; DQ376641; DQ376642; DQ376643; DQ376644; DQ376645; DQ376646; DQ376647; DQ376648; DQ376649; DQ376650; DQ376651; DQ376652; DQ376653; DQ408509; DQ408517; DQ408524; DQ822190; DQ822198; J02158; AB294213; AB294215; AB294219; AB295615; AB296072; AB298279; AF100181; AF250479; AF310983; AF310984; AF310985; AF457663; AF457664; AF457665; AF457666; AF457667; AF457668; AF457669; AF457670; AF457679; AF457688; AF457696; AF457704; AF457713; AF457715; AF474029; AF474030; AF474031; AF474032; AF474033; AF474034; AF474035; AF474036; AF474037; AF474038; AJ410519; AJ410520; AJ410521; AJ410522; AJ410523; AJ410524; AJ410525; AJ410526; AJ410527; AJ410528; AJ410529; AJ410530 and AJ410531.

Nucleic acid sequences encoding influenza virus subtype H7 haemagglutinins suitable for inclusion as a cargo moiety in conjugates according to the present invention have the following accession numbers and are available to the public via the National Center for Biotechnology Information (NCBI) Entrez nucleotide search and retrieval system:

AB262459; AF072385; AF202256; AF322021; AF322022; AF322023; AF322024; AF322025; AF322026; AF364133; AF364134; AF364135; AF364136; AF364137; AF364138; AF364139; AF364140; AF364141; AF364142; AF364143; AF364144; AF364145; AF364146; AF364147; AF364148; AF364149; AF364150; AF364151; AF364152; AF364153; AF364154; AF364155; AF364156; AF364157; AF364158; AF364159; AF364160; AF364161; AF364162; AF364163; AF364164; AF364165; AF364166; AF364167; AF364168; AF364169; AF364170; AF364171; AF364172; AF497551; AF497552; AF497553; AF497554; AF497555; AF497556; AF497557; AF497558; AF497559; AJ489520; AJ491720; AJ493212; AJ493213; AJ493214; AJ493215; AJ493216; AJ493217; AJ493466; AJ493467; AJ493468; AJ493469; AJ493470; AJ493471; AJ493472; AJ580353; AJ584647; AJ620350; AJ627491; AJ627493; AJ697872; AJ697873; AJ704797; AJ704798; AJ704799; AJ704810; AJ704811; AJ704812; AJ704813; AM087214; AM087223; AY240877; AY240878; AY240879; AY240880; AY240881; AY240882; AY240883; AY240884; AY240885; AY240886; AY240887; AY240888; AY240889; AY240890; AY240891; AY240892; AY240893; AY240894; AY240895; AY240896; AY240897; AY240898; AY240899; AY240900; AY240901; AY240902; AY240903; AY240904; AY240905; AY240906; AY240907; AY240908; AY240909; AY240910; AY240911; AY240912; AY240913; AY240914; AY240915; AY240916; AY240917; AY240918; AY240919; AY240920; AY240921; AY240922; AY240923; AY240924; AY240925; AY303630; AY303631; AY303632; AY303633; AY303634; AY303635; AY338455; AY338456; AY338457; AY338458; AY338459; AY338460; AY338461; AY338462; AY383756; AY559235; AY586408; AY586409; AY586410; AY586411; AY596307; AY611524; AY644402; AY646078; AY648287; AY650270; AY672090; AY724257; AY724684; AY725855; AY730057; AY731820; AY734541; AY736323; AY831668; AY831669; AY831670; AY943924; AY999977; AY999978; AY999979; AY999980; AY999981; AY999982; AY999983; AY999984; AY999985; AY999986; AY999987; AY999988; AY999989; AY999990; AY999991; CY005928; CY005973; CY005974; CY005975; CY005976; CY005978; CY005980; CY005981; CY005983; CY006029; CY006037; CY014587; CY014612; CY014718; CY014721; CY014778; CY014786; CY014896; CY014992; CY015006; CY015014; CY015027; CY015033; CY015065; CY016188; CY018901; CY020581; CY020589; CY020597; CY020605; CY020613; CY020685; CY020885; CY021357; CY021365; CY021405; CY021413; CY021421; CY021485; CY021493; CY021501; CY021533; CY021541; CY021549; CY021557; CY021621; CY021637; DQ003216; DQ017504; DQ017513; DQ525411; DQ838510; DQ838511; DQ838512; DQ838513; DQ838514; DQ838515; DQ870888; DQ870894; DQ873807; DQ907527; DQ907528; DQ991304; DQ991312; DQ991320; DQ991328; DQ991336; DQ991343; EF467825; EF467826; J02164; K00429; L37794; L43913; L43914; L43915; M17735; M17736; M24457; M24458; M31689; M58657; U20458; U20459; U20461; U20462; U20463; U20464; U20465; U20466; U20467; U20468; U20469; U20470; U20471; X61627; X62552; X62553; X62554; X62555; X62556; X62557; X62558; X62559; X62560; Z12617; Z47199; AB262468; AB262469; AB262470; AB262471; AB262472; AB262473; AB268557; AB269692; AB269693; AB269694; AB269695; AB269696; AB269872; AB270592; AB270593; AB297923; AB297925; AB298277; AF028020; AF028021; AF071775; AF071776; AF072383; AF072384; AF072386; AF072387; AF072388; AF072389; AF072390; AF072391; AF072392; AF072393; AF072394; AF072395; AF072396; AF072397; AF072398; AF072399; AF072400; AF072401; AF072402; AF149295; AF202226; AF202227; AF202228; AF202229; AF202230; AF202231; AF202232; AF202233; AF202234; AF202235; AF202236; AF202237; AF202238; AF202239; AF202240; AF202241; AF202242; AF202243; AF202244; AF202245; AF202246; AF202247; AF202248; AF202249; AF202250; AF202251; AF202252; AF202253; AF202254 and AF202255.

Nucleic acid sequences encoding influenza virus subtype H8 haemagglutinins suitable for inclusion as a cargo moiety in conjugates according to the present invention have the following accession numbers and are available to the public via the National Center for Biotechnology Information (NCBI) Entrez nucleotide search and retrieval system:

AB289343; AF310987; AF310988; AF310989; CY005970; CY005971; CY005972; CY014583; CY014659; CY015173; CY017749; D90304; EF061122 and J02089.

Nucleic acid sequences encoding influenza virus subtype H9 haemagglutinins suitable for inclusion as a cargo moiety in conjugates according to the present invention have the following accession numbers and are available to the public via the National Center for Biotechnology Information (NCBI) Entrez nucleotide search and retrieval system:

J02166; AF156385; AF156386; AF156387; AF156388; AF156389; AF156390; AF156373; AF156374; AF156375; AF156376; AF156377; AF156378; AF156379; AF156380; AF156381; AF156382; AF156383; AF156384; AF186266; AF186267; AF186268; AF186269; AF203008; AF203009; AF203010; AF203011; AF203012; AF203013; AF203014; AF203015; AF222606; AF222607; AF222608; AF222609; AF222610; AF222611; AF222612; AF222613; AF218086; AF218087; AF218088; AF218089; AF218090; AF218091; AF218092; AF218093; AF218094; AF218095; AF218096; AF218097; AF218098; AF218099; AF218100; AF218101; AF218102; AF218103; AF218104; AF218105; AF218106; AF218107; AF218108; AF218109; AF218110; AF218111; AF218112; AF218113; AF218114; AF218115; AF218116; AF218117; AF218118; AF218119; AF218120; AF384557; AY036880; AF222810; AF222811; AF400776; AF400777; AY043014; AY043015; AY043017; AY043018; AY043019; AF461509; AF461510; AF461511; AF461512; AF461513; AF461514; AF461515; AF461516; AF461517; AF461518; AF461519; AF461520; AF461521; AF461522; AF461523; AF461524; AF461525; AF461526; AF461527; AF461528; AF461529; AF461530; AF461531; AF461532; AY083840; AY083841; AF536689; AF536690; AF536691; AF536692; AF536693; AF536694; AF536695; AF536696; AF536697;

AF536698; AY180444; AY180445; AY180446; AY180447; AY180448; AY180449; AY180450; AY180451; AY180452; AY180453; AY180454; AY180455; AY180456; AY180457; AY180458; AY180459; AY206671; AY206672; AY206673; AY206674; AY206675; AY206676; AY206677; AY206678; AY206679; AY206680; AY198313; AY198314; AY198315; AY198316; AY198317; AY198318; AY198319; AY198320; AY198321; AY281745; AY264870; AY264871; AY264872; AY264875; AY264876; AY294658; AF523372; AF523373; AF523374; AF523375; AF523376; AF523377; AF523378; AF523379; AF523380; AF523381; AF523382; AF523383; AF523384; AF523385; AF523386; AF523387; AF523388; AF523389; AF523390; AY336597; AF508554; AF508555; AF508556; AF508557; AF508558; AF508559; AF508560; AF508561; AF508562; AF508563; AF508564; AF508565; AF508566; AF508567; AF508568; AF508569; AF508570; AF508571; AF508572; AF508573; AF508574; AY345925; AY345926; AY345927; AY345928; AY345929; AY345930; AY345931; AY345932; AY345933; AY345934; AY345935; AY345936; AY345937; AY345938; AY345939; AY345940; AY364228; AY330332; AY330333; AY330334; AY330335; AY330336; AY435039; AY435040; AY513715; AY548499; AY548500; AY548501; AY548502; AY548503; AY548504; AY548505; AY548506; AY548507; AY548508; AY548509; AY548510; AY548511; AY548512; AY548513; AY548514; AY548515; AY603067; AY549889; AY623810; AY633116; AY633164; AY633276; AY633292; AY652980; AY594194; AY594195; AY594196; AY664660; AY664661; AY664662; AY664663; AY664664; AY664665; AY664666; AY664667; AY664668; AY664669; AY664670; AY664671; AY664672; AY664673; AY664674; AY664675; AY664676; AY664677; AY664678; AY743216; AY768552; AY768553; AY768554; AY768555; AY768556; AY768557; AY768558; AY768559; AY790275; AY790283; AY790297; AY790305; AY790313; AY790314; AY790315; AY790320; AY738451; AY738452; AY738453; AY738454; AY738455; AY738456; AY851460; AY851461; AY862598; AY862599; AY862600; AY862601; AY862602; AY862603; AY862604; AY862605; AY862606; AY937403; AY937404; AY949989; DQ003335; DQ064354; DQ064355; DQ064356; DQ064357; DQ064358; DQ064359; DQ064360; DQ064361; DQ064362; DQ064363; DQ064364; DQ064365; DQ064366; DQ064367; DQ064368; DQ064369; DQ064370; DQ064371; DQ064372; DQ064373; DQ064374; DQ064375; DQ064376; DQ064377; DQ064378; DQ064379; DQ064380; DQ067444; DQ108905; DQ108906; DQ108907; DQ108908; DQ108909; DQ108910; DQ108911; DQ108912; DQ108913; DQ108914; DQ108915; DQ108916; DQ108917; DQ108918; DQ108919; DQ108920; DQ108921; DQ108922; DQ108923; DQ108924; DQ108925; DQ108926; DQ108927; DQ108928; DQ108929; DQ108930; DQ108931; DQ108932; DQ104448; DQ104449; DQ104450; DQ104451; DQ104452; DQ104453; DQ104454; DQ104455; DQ104456; DQ104457; DQ104458; DQ104459; DQ104460; DQ104461; DQ104462; DQ104463; DQ104464; DQ104465; DQ104466; DQ104467; DQ104468; DQ104469; DQ104470; DQ104471; DQ104472; DQ104473; DQ104474; DQ104475; DQ104476; DQ104477; DQ104478; DQ104479; DQ104480; DQ104481; DQ104482; DQ104483; DQ104484; DQ104485; DQ225271; DQ227352; DQ223544; CY004420; CY004642; CY005632; CY005639; CY005746; DQ234277; DQ226106; DQ226107; DQ226108; DQ226109; DQ226110; DQ226111; DQ226112; DQ226113; DQ226114; DQ226115; DQ226116; CY005919; CY005929; CY005934; CY005984; CY005985; CY005986; CY005987; CY005988; CY005989; CY005990; CY005991; CY005992; CY006025; CY006042; CY006018; CY006021; CY006023; DQ299829; DQ299837; DQ299845; DQ299853; DQ299861; DQ390215; DQ464352; DQ473608; DQ473609; DQ473610; DQ473611; DQ473612; DQ473613; DQ473614; DQ465400; DQ485208; DQ485216; DQ485224; DQ681203; DQ681207; DQ681216; DQ681221; DQ885991; DQ787797; DQ787802; CY014613; CY014663; DQ997505; DQ997481; DQ997474; DQ997437; DQ997460; DQ997187; DQ997465; DQ997490; DQ997451; DQ997419; DQ997448; EF070733; EF063510; EF063511; EF063512; EF063513; EF063514; EF063515; EF063516; EF154907; EF154908; EF154909; EF154910; EF154911; EF154912; EF154913; EF154914; EF154915; EF154916; EF154917; EF154918; EF154919; EF154920; EF154921; EF154922; EF154923; EF154924; EF154925; EF154926; EF154927; EF154928; EF154929; EF154930; EF154931; EF154932; EF154933; EF154934; EF154935; EF154936; EF154937; EF154938; EF154939; EF154940; EF154941; EF154942; EF154943; EF154944; EF154945; EF154946; EF154947; EF154948; EF154949; EF154950; EF154951; EF154952; EF154953; EF154954; EF154955; EF154956; EF154957; EF154958; EF154959; EF154960; EF154961; EF154962; EF154963; EF154964; EF154965; EF154966; EF154967; EF154968; EF154969; EF154970; EF154971; EF154972; EF154973; EF154974; EF154975; EF154976; EF154977; EF154978; EF154979; D90305; AB049159; AB049160; AB080224; AB080225; AB080226; AB080227; AB080228; AB125927; AB125928; AB125929; AB125930; AB125931; AB262463; AB276111; AB256666; AB256674; AB256682; AB256690; AB256698; AB256706; AB256714; AB256722; AB256730; AB256738; AB256746; AB295601; AJ404626; AJ404627; AJ291392; AJ536330; AJ536331; AJ536332; AJ781818; AJ781819; AJ781820; AJ781821; AJ781822; AJ781823; AJ781824; AJ781825; AJ781826; AJ781827; AM087218; AM087219; AM286688 and AM286689.

Nucleic acid sequences encoding influenza virus subtype H10 haemagglutinins suitable for inclusion as a cargo moiety in conjugates according to the present invention have the following accession numbers and are available to the public via the National Center for Biotechnology Information (NCBI) Entrez nucleotide search and retrieval system:

AB271117; AB274041; CY005996; CY005997; CY005998; CY005999; CY006000; CY006001; CY014619; CY014644; CY014671; CY014739; CY017781; CY020901; CY020909; CY020925; DQ374399; J02110; M21646; M21647; AB289339; AB292412; AB292666; AB292781; AB296078; AF311750; AM087215; AM087216; CY005921; CY005922; CY005930; CY005982; CY005993; CY005994 and CY005995.

Nucleic acid sequences encoding influenza virus subtype H111 haemagglutinins suitable for inclusion as a cargo moiety in conjugates according to the present invention have the following accession numbers and are available to the public via the National Center for Biotechnology Information (NCBI) Entrez nucleotide search and retrieval system:

AB277756; AB288845; DQ424861; DQ435281; DQ435282; DQ435283; DQ435284; DQ435285; DQ482667; EF200063; J02100; J02106; J02107; J02108; J02161; AB292779; AB292783; AB296076; AB298283; AF310986; AY684895; CY005923; CY005924; CY006000; CY006003; CY006004; CY006005; CY014593; CY014595; CY014679; CY014687; CY014719; CY014806; CY017075; CY017765; CY017845; CY018015; CY020941; CY020949;

CY020965; CY021133; CY021141; CY021149; CY021165; CY021173; CY021181; CY021245; CY021253; CY021437; CY021445; CY021469; CY021613; CY021645; CY021653; CY021661; CY021669; CY021685; D90306; DQ080993; DQ327835; DQ424858; DQ424859 and DQ424860.

Nucleic acid sequences encoding influenza virus subtype H12 haemagglutinins suitable for inclusion as a cargo moiety in conjugates according to the present invention have the following accession numbers and are available to the public via the National Center for Biotechnology Information (NCBI) Entrez nucleotide search and retrieval system:

AB288334; AB288843; AF310990; AF310991; AF310992; AM286685; CY005920; CY005925; CY006006; CY006007; CY006008; CY012840; CY014598; CY014636; CY016419; CY017733; CY017853; CY021293; CY021301; D90307; DQ787811 and J02104.

Nucleic acid sequences encoding influenza virus subtype H13 haemagglutinins suitable for inclusion as a cargo moiety in conjugates according to the present invention have the following accession numbers and are available to the public via the National Center for Biotechnology Information (NCBI) Entrez nucleotide search and retrieval system:

AB284988; AB285094; AB292664; AM087220; AM087221; AY684886; AY684887; CY005914; CY005931; CY005932; CY005979; CY014603; CY014694; CY014720; D90308; K00383; M26089; M26090 and M26091.

Nucleic acid sequences encoding influenza virus subtype H14 haemagglutinins suitable for inclusion as a cargo moiety in conjugates according to the present invention have the following accession numbers and are available to the public via the National Center for Biotechnology Information (NCBI) Entrez nucleotide search and retrieval system:

AB289335 and CY014604.

Nucleic acid sequences encoding influenza virus subtype H15 haemagglutinins suitable for inclusion as a cargo moiety in conjugates according to the present invention have the following accession numbers and are available to the public via the National Center for Biotechnology Information (NCBI) Entrez nucleotide search and retrieval system:

CY006010; CY006033; CY006034; L43917; CY006032; AB295613; CY006009 and L43916.

Nucleic acid sequences encoding influenza virus subtype H16 haemagglutinins suitable for inclusion as a cargo moiety in conjugates according to the present invention have the following accession numbers and are available to the public via the National Center for Biotechnology Information (NCBI) Entrez nucleotide search and retrieval system:

CY005933; CY014599; CY015160; AY684888; AY684889; AY684890 and AY684891.

Thus, a nucleic acid sequence encoding an influenza virus haemagglutinin is optionally included as a cargo moiety.

In particular embodiments, influenza virus haemagglutinin protein or an antigenic portion thereof is included in a conjugate composition for administration to a subject to enhance an immune response to influenza virus.

In other embodiments, the virus conjugated to a sialoadhesin binding antibody may be used as a gene transfer vector in order to express a desired nucleic acid in a target cell. Such viruses are known in the art and include herpes viruses, adenoviruses and adeno-associated viruses, for example.

In further embodiments, a viral cargo moiety is a virus or portion thereof expressing no non-viral proteins. A cargo moiety virus is a porcine arterivirus in one embodiment.

Conjugation

A cargo moiety is conjugated to a sialoadhesin binding moiety by any of various methods. The conjugation method chosen will depend on the chemical identity of the cargo and the sialoadhesin binding moiety.

A conjugate according to embodiments of the present invention encompasses a sialoadhesin binding moiety and a cargo linked together by chemical bonding, covalent or non-covalent, as well as by recombinant techniques including production of a fusion protein, such as a conjugate produced using a nucleic acid expression construct encoding a sialoadhesin binding moiety and a cargo.

In particular embodiments, a cargo moiety and a sialoadhesin binding moiety are chemically linked via free functional groups on these moieties. Such functional groups illustratively include amino, carboxyl, hydroxyl, and sulfhydryl groups.

A linkage between a cargo moiety and a sialoadhesin binding moiety is illustratively an ester, an ether, a carbamate, a carbonate, a disulfide, a peptide, and an amide. The term "linkage" refers to a bond or group formed by chemical reaction between the two moieties such that the moieties are covalently coupled, directly or indirectly.

In one embodiment, a linkage between a sialoadhesin binding moiety and a cargo moiety is labile in an intracellular environment, such that the sialoadhesin binding moiety and cargo moiety may be separated following cell uptake. For instance, a linkage may be susceptible to hydrolysis, enzymatic cleavage, or other form of cleavage, such that the cargo moiety provides a desired effect following such separation from the sialoadhesin binding moiety. An ester linkage is one example of a linkage susceptible to hydrolysis in a cell. A disulfide linkage is a further example of a linkage susceptible to cleavage following cell uptake. In other embodiments, a cargo moiety provides a desired effect while conjugated to the sialoadhesin binding moiety.

In one embodiment, more than one cargo moiety may be included in a conjugate composition. Further, more than one sialoadhesin binding moiety may be included in a conjugate composition.

Where one or both of the sialoadhesin binding moiety and the cargo moiety include a peptide and/or protein, functional group of a cargo moiety and a sialoadhesin binding moiety used to conjugate these moieties can be at N- or C-terminus or at between the termini of one or both peptides or proteins.

A protective group may be added to a sialoadhesin binding moiety and/or cargo moiety in a process to form a conjugate according to the present invention. Such groups, their generation and use are described in Protective Groups in Organic Synthesis by T. W. Greene and P. G. M. Wuts, John Wiley & Sons, 1999.

Conjugation chemistries used in conjugation of a cargo moiety and a sialoadhesin binding moiety illustratively include coupling agents such as, but not limited to, glutaraldehyde, carbodiimide, succinimde esters, benzidine, periodate, isothionate and combinations of these.

A conjugate according to the present invention is optionally produced using recombinant techniques. For example, in particular embodiments, a conjugate is an expression product of nucleic acid construct including an expression construct encoding a fusion protein, the fusion protein including a sialoadhesin binding moiety or portion thereof and a cargo moiety linked directly to the sialoadhesin binding moiety or portion thereof or through an intermediate linker.

In particular embodiments, an expression construct encoding a fusion protein encodes an anti-sialoadhesin antibody or a fragment of an anti-sialoadhesin antibody. Thus, in particular embodiments, an expression construct encodes a fusion protein including a nucleic acid which encodes a cargo moiety and an anti-sialoadhesin antibody or portion thereof. For example, an expression construct encoding a fusion protein according to the present invention encodes a cargo attached to a portion of an anti-sialoadhesin antibody including a variable region of an anti-sialoadhesin antibody such as, but not limited to, a heavy chain variable region and/or a light chain variable region, a single chain VL-VH region, and/or an H chain C region in particular embodiments.

In particular embodiments, an expression construct encoding a fusion protein encodes a cargo moiety and mAb 41D3 or a portion of mAb 41D3. In further particular embodiments, an expression construct encoding a fusion protein encodes an influenza virus haemagglutinin and mAb 41D3 or a portion of mAb 41D3.

In particular embodiments, an expression construct encoding a fusion protein encodes a cargo moiety and mAb 7D2 or a portion of mAb 7D2. In further particular embodiments, an expression construct encoding a fusion protein encodes an influenza virus haemagglutinin and mAb 7D2 or a portion of mAb 7D2.

In particular embodiments, an expression construct encoding a fusion protein encodes a cargo moiety and mAb MCA2316 or a portion of mAb MCA2316. In further particular embodiments, an expression construct encoding a fusion protein encodes an influenza virus haemagglutinin and mAb MCA2316 or a portion of mAb MCA2316.

Cloning and expression of nucleic acids encoding antibody regions and fusion proteins including an antibody region are known in the art as exemplified in J. D. Pound (Ed.) Immunochemical Protocols, Methods in Molecular Biology, Humana Press; 2nd ed., 1998, chapter 43; R. Kontermann and S. Dübel (Eds.), Antibody Engineering, Springer Lab Manuals, Springer, 2001; and B. K. C. Lo (Ed.), Antibody Engineering Methods and Protocols, Methods in Molecular Biology, Humana Press, 2003.

A cargo moiety and a sialoadhesin binding moiety may be linked directly to form a conjugate. Alternatively, a linker may be bound to both a cargo moiety and to a sialoadhesin binding moiety, such that these moieties are indirectly linked through the linker. A linker may be a homo bifunctional linker or a hetero-bifunctional linker, depending on the identity of the moieties to be conjugated. Further, a linker may be multifunctional so as to link more than one cargo moiety and/or more than one sialoadhesin binding moiety.

In general, a linker has about 1-20 backbone carbon atoms. However, a linker may be larger or smaller.

Optionally, a linker is encoded by a nucleic acid in an expression construct.

A linker may be a natural or synthetic polymer in some embodiments. For example, suitable polymers include agarose, carboxymethylcellulose, cellulose, dextran, and polyaminopolystyrene. A preferred polymer is polyacrylamide, PEO (polyethylene) or PEG (polyethylene glycol) spacer.

In one embodiment, a sialoadhesin binding moiety including a sialic acid and/or sialylated structure may be conjugated to a cargo moiety directly or indirectly. For example, a sialic acid residue may be conjugated to a lipid-containing cargo moiety to form a glycolipid conjugate composition and/or to a protein or peptide cargo moiety by N-linkage or O-linkage to form a glycopeptide or glycoprotein conjugate according to the present invention. A sialic acid residue may also be conjugated to a linker.

Pharmaceutical Compositions and Administration

A conjugate of the present invention can be administered to a subject alone or as part of a pharmaceutical composition. Inventive conjugate compositions are suitable for administration to patients by a variety of routes illustratively including, but not limited to, intravenous, oral, parenteral, intramuscular, subcutaneous and mucosal.

An inventive pharmaceutical composition includes a conjugate according to the present invention and a pharmaceutically acceptable carrier. The term "pharmaceutically acceptable" refers to a material which can be administered to a subject along with an inventive conjugate composition without causing significant undesirable biological effects and without interacting in a deleterious manner with any other component of the pharmaceutical composition.

Pharmaceutical compositions suitable for administration illustratively include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers; diluents; solvents; or vehicles include water, ethanol, polyols such as, but not limited to, propylene glycol, polyethylene glycol, glycerol, and the like, suitable mixtures thereof; vegetable oils such as, but not limited to, olive oil; and injectable organic esters such as, but not limited to, ethyloleate. Proper fluidity can be maintained, for example, by the use of a coating such as, but not limited to, lecithin, by the maintenance of the required particle size in the case of dispersions, and by the use of surfactants.

Compositions suitable for injection optionally include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as, but not limited to, ethyl oleate. Proper fluidity can be maintained, for example, by the use of a coating such as, but not limited to, lecithin, by the maintenance of the required particle size in the case of dispersions and by the use of surfactants.

Pharmaceutical compositions according to the present invention may also contain adjuvants such as, but not limited to, preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of an injectable pharmaceutical form can be brought about by the use of agents delaying absorption, for example, aluminum monostearate and gelatin.

Further exemplary adjuvants include immunostimulating adjuvants such as, but not limited to, Freund's complete adjuvant; Freund's incomplete adjuvant; aluminum hydroxide such as commercially available as Alhydrogel, Accurate Chemical & Scientific Co, Westbury, N.Y.; and Gerbu adjuvant, available from C-C Biotech, Poway, Calif.

Solid dosage forms for oral administration include capsules, tablets, pills, powders, and granules. In such solid dosage forms, an inventive conjugate is admixed with at least one inert customary excipient (or carrier) such as, but not limited to, sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as, but not limited to, tablets, dragees, capsules, pills, and granules can be prepared with coatings and shells, such as, but not limited to, enteric coatings and others well known in the art. They may contain opacifying agents, and can also be of such composition that they release the active compound or compounds in a certain part of the intestinal tract in a delayed manner. Microencapsulated formulations of an inventive conjugate are also contemplated.

Liquid dosage forms for oral administration include pharmaceutically acceptable emulsions, solutions, suspensions, syrups, and elixirs. In addition to a conjugate according to the present invention, the liquid dosage forms may contain inert diluents commonly used in the art, such as, but not limited to, water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, a pharmaceutical composition according to the present invention can also include adjuvants, such as, but not limited to, wetting agents, emulsifying and suspending agents, sweetening, flavoring, and perfuming agents.

Suspensions, in addition to an inventive conjugate, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Further specific details of pharmaceutical formulation can be found in Pharmaceutical Dosage Forms: Tablets, eds. H. A. Lieberman et al., New York: Marcel Dekker, Inc., 1989; L. V. Allen, Jr. et al., Ansel's Pharmaceutical Dosage Forms and Drug Delivery Systems, 8th Ed., Philadelphia, Pa., Lippincott, Williams & Wilkins, 2004; and Remington, The Science and Practice of Pharmacy, 21$^{st}$ ed., Lippincott, Williams & Wilkins, Philadelphia, Pa., 2006.

An inventive conjugate is optionally delivered in conjunction with a non-conjugated therapeutic and/or diagnostic agent in one embodiment. A therapeutic and/or diagnostic agent suitable in this regard illustratively includes an analgesic, an antibiotic, an antibody, an antigen, an anti-inflammatory, an anti-tumoral agent, an antiviral, a gamma or beta radiation emitting species, an enzyme, and a hormone. In addition, two or more conjugate compositions may be administered to a subject.

The dosage of an inventive pharmaceutical composition will vary based on factors such as, but not limited to, the route of administration; the age, health, and weight of the subject to whom the composition is to be administered; the nature and extent of the subject's symptoms, if any, and the effect desired. Usually a daily dosage of an inventive conjugate is in the range of about 0.001 to 100 milligrams per kilogram of a subject's body weight. A daily dose may be administered as two or more divided doses to obtain the desired effect. An inventive pharmaceutical composition may also be formulated for sustained release to obtain desired results.

For example, a parenteral composition suitable for administration by injection includes 1% by weight of an inventive conjugate in buffered saline.

Methods

A method of delivering a cargo moiety to a cell is provided which includes contacting a cell expressing sialoadhesin with a conjugate according to the present invention. The sialoadhesin binding moiety present in the conjugate binds to the sialoadhesin expressed by the cell and the conjugate is internalized in the cell. The cell may be in vivo, ex vivo or in vitro.

Sialoadhesin is expressed primarily by macrophages. Thus, in one embodiment of an inventive method, a drug delivery system targeting macrophages is provided. Thus, in such an embodiment, a cell contacted with a conjugated sialoadhesin binding moiety and cargo moiety is a macrophage.

A cell contacted with a conjugate composition in a method according to the present invention expresses sialoadhesin naturally or may be induced to do so. In such a method, cells other than macrophages may be targeted.

For example, a cell may be transfected with an expression construct encoding sialoadhesin such that sialoadhesin is expressed in the cell. An expression construct includes a nucleic acid encoding full-length sialoadhesin, or a portion thereof, operably linked to a regulatory element. Full-length nucleic acids encoding sialoadhesin have been isolated from various species and exemplary nucleic acid sequences and encoded sialoadhesin proteins are described herein. A regulatory element operably linked to the nucleic acid encoding sialoadhesin illustratively includes a promoter, an enhancer, an origin of replication, a polyadenylation signal, and a transcription termination sequence. Expression constructs and methods for their generation are known in the art, as described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

In particular embodiments, an expression construct encoding a sialoadhesin protein encodes a sialoadhesin protein identified herein as SEQ ID No. 5, SEQ ID No. 7, SEQ ID No. 9, or a biologically active homologue thereof. In particular embodiments, an expression construct encoding a sialoadhesin protein includes a nucleotide sequence identified herein as SEQ ID No. 6, SEQ ID No. 6, or SEQ ID No. 10.

Biological activity of a putative sialoadhesin homologue is readily determined by one of skill in the art, for instance using any of the functional assays described herein or other functional assays known in the art.

An expression construct encoding sialoadhesin is generated according to methods known in the art. For example, a pcDNA3.1/Sn plasmid containing the porcine sialoadhesin cDNA cloned into the pcDNA3.1 vector (Invitrogen) described in Vanderheijden, N. et al., 2003, J. Virol. 77:8207-15 is a sialoadhesin expression construct.

A cell transfected with an expression construct to induce or enhance sialoadhesin expression in the cell may be transiently transfected in particular embodiments. Alternatively, a stable cell line expressing sialoadhesin is produced.

Any of various cells may be used to produce a cell line stably expressing sialoadhesin. Particular examples include, but are not limited to THP-1 cells, PK-15 cells, 3D4/31 cells, and HEK293T cells.

Methods of producing a stable cell line expressing a desired protein are known in the art, as exemplified in standard molecular biology references such as S. Ozturk and W.-S. Hu (Eds.), Cell Culture Technology for Pharmaceutical and Cell-Based Therapies, Biotechnology and Bioprocessing Series, CRC Press, 2005.

Briefly described, cells are transfected with an expression construct encoding sialoadhesin. For example, cells are transfected with an expression construct including SEQ ID No. 6, SEQ ID No. 6, or SEQ ID No. 10 or another sequence encoding SEQ ID No. 5, SEQ ID No. 7, or SEQ ID No. 9 or a homologue thereof. A transfected expression construct further encodes resistance to a selection agent, including, but not limited to, resistance to neomycin (G418). Expression constructs conferring resistance to a selection agent are known in the art and are commercially available or may be constructed using standard molecular biology techniques.

Cells are transfected according to standard transfection methods illustratively including, but not limited to, calcium phosphate techniques and lipofectin techniques such as described in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

Following transfection, cells are incubated, on cell culture plates or in cell culture wells for instance, in medium containing a selection agent, such as 0.5 g/L neomycin. Cells not transfected or not expressing the resistance marker die following incubation with the selection agent, generally after several days. Dead cells are removed from the vicinity of living transfected cells in order to select for particular clones. Transfected cells are typically disposed individually, in wells or in cloning cylinders for example, in order to select one or more stably transfected cell lines. Once individual colonies have grown, they can be assayed for sialoadhesin expression, such as by ELISA. Stably transfected cells are further assayed for binding of a sialoadhesin binding moiety and/or conjugate and uptake of the binding moiety and/or conjugate into the cell.

Stably transfected cells may be used in methods of the present invention. For example, a stable cell line expressing sialoadhesin is used in a method of the present invention for transfection of a cell by delivery of a conjugate including a sialoadhesin binding moiety and a nucleic acid.

In further embodiments of methods according to the present invention a cell is treated with an agent effective to induce or enhance expression of sialoadhesin in the cell. In particular embodiments of methods according to the present invention a cell is treated with a cytokine effective to induce or enhance expression of sialoadhesin in the cell. For example, a cell treated with a cytokine effective to induce or enhance expression of sialoadhesin is a monocyte, a monocyte cell line, a macrophage and a macrophage cell line.

In particular embodiments, a human cell and/or a human-derived cell line is treated with a cytokine effective to induce or enhance expression of sialoadhesin. An example of a human-derived cell line is human monocyte cell line THP-1. A suitable cytokine effective to induce or enhance expression of sialoadhesin is interferon-alpha (INF-alpha).

Human monocytes are treated with INF-alpha to induce or enhance expression of sialoadhesin in a particular embodiment. The monocytes may be isolated, for instance from blood, and treated in vitro with INF-alpha. Sialoadhesin expression may be assessed by assays illustratively including, but not limited to, immunoassay.

In further embodiments, an effective amount of INF-alpha is administered to a subject such that sialoadhesin expression is induced or enhanced in cells in vivo. An effective amount is illustratively between 10 to 500 units IFN-alpha per ml of blood of the subject.

Methods are provided for transfection of a cell using a conjugate according to the present invention including a cargo nucleic acid, particularly a cargo expression construct. Cells expressing sialoadhesin are contacted with a conjugate including a sialoadhesin binding moiety and a cargo expression construct in a particular embodiment in order to express an encoded protein or peptide in the cells. Transfection using a sialoadhesin binding moiety and a cargo expression construct is used in sialoadhesin expressing cells in vitro or in vivo. Transfection using a conjugate provided by the present invention is useful to increase the level of a desired protein or peptide in a cell, for instance, to produce recombinantly expressed protein, for instance, to study function of the protein.

A method according to the present invention which includes contacting a cell expressing sialoadhesin with a conjugate composition may be used to stimulate an immune response in a subject, for instance to vaccinate the subject.

Vaccination is one of the earliest used and most powerful tools for stimulating an organism to defend against infection. Broadly described, vaccination is a method of administering an antigen to an organism in order to stimulate the organism's immune system to provide a cellular and/or molecular defensive response.

While vaccination by non-cell targeted administration of an antigen to an organism can be effective, in some cases large amounts of antigen must be administered in order to achieve a desired response. Further, a non-cell targeted administration may require a longer time and/or more booster administrations of the antigen to achieve an effective immune response. Thus, compositions and methods for stimulating an immune response in a subject are needed. Such a method is provided according to the present invention and includes administering to a subject an effective amount of a conjugate composition according to the present invention which includes a sialoadhesin binding moiety conjugated to an antigen. An immune response may be stimulated in order to inhibit infection by a pathogen, or to stimulate an antitumoral response for instance.

An immune response may be measured, for instance, by assay of the subject's serum for antibodies to an antigen administered as part of an inventive conjugate. Applicable immunoassays include ELISA performed on a sample before and at one or more times following administration of the conjugate, for example.

In one embodiment, administration of a composition effective to target an antigen to an antigen presenting cell, particularly a macrophage, is included in a method provided according to the present invention.

In a specific example, vaccination of swine against Porcine Reproductive and Respiratory Syndrome (PRRS) virus is an embodiment of a method according to the present invention. PRRS virus is an infectious disease of swine which can cause severe respiratory disorders, as well as abortion. The viral agent has been identified, as described in Weensvoort, G., et al., 1991, Veterinary Review. 13: 121-130. However, there is currently no effective treatment for this disease which can frequently only be controlled by destruction of the herd, resulting in considerable cost to swine producers.

A vaccine and method for vaccination of a pig against PRRS virus is provided. A conjugate composition including a sialoadhesin binding moiety which binds to porcine sialoadhesin is conjugated to a PRRS virus, a PRRS protein, or an antigenic portion of a PRRS virus or protein. The conjugate composition is administered to a pig in an amount effective to stimulate an immune response. The route of administration may be any convenient route, illustratively including, but not limited to, intravenous, intramuscular, intraperitoneal, subcutaneous, oral, mucosal, and any combination thereof.

In a further example, vaccination of a subject against an influenza virus is an embodiment of a method according to the present invention. Influenza virus is an infectious disease of numerous species which can cause severe respiratory symptoms and death.

A vaccine and method for vaccination of a subject against influenza virus is provided. A conjugate composition including a sialoadhesin binding moiety which binds to sialoadhesin is conjugated to an influenza virus, an influenza virus protein or an antigenic portion of an influenza virus or protein. In particular embodiments, compositions and methods for vaccination of a subject against a type A influenza virus are provided. The conjugate composition is administered to a subject in an amount effective to stimulate an immune response against influenza virus. The route of administration may be any convenient route, illustratively including, but not limited to, intravenous, intramuscular, intraperitoneal, subcutaneous, oral, mucosal, and any combination thereof.

In specific embodiments, compositions and methods for vaccination of a porcine subject against an influenza virus are provided. Inventive methods and compositions for vaccination against influenza virus are not limited to porcine subjects and may be used in other subjects susceptible to influenza virus infection, illustratively including, but not limited to, humans and birds.

A conjugate composition for vaccination of a subject against an influenza virus includes a sialoadhesin binding moiety and an influenza virus hemagglutinin protein or antigenic portion thereof in particular embodiments. In a specific example, a conjugate composition for vaccination of a subject against an influenza virus includes the protein encoded by SEQ ID No. 3 or a homologue thereof. In a further specific example, a conjugate composition for vaccination of a subject against an influenza virus includes the protein identified as SEQ ID No. 4 or a homologue thereof.

Traditionally, achieving desired antibody titers can be difficult with some antigens, such as inactivated or subunit vaccines, requiring multiple administrations of the antigen. Targeted delivery of an antigen to sialoadhesin expressing macrophages using an inventive composition including antigen coupled to a sialoadhesin-specific mAb allows increased titers of antigen-specific antibodies. Targeted delivery elicits an immune response which is more efficient in comparison to administration of an unconjugated antigen, since antibodies appear earlier after administration and higher titers are reached.

Thus, in one embodiment, a method for stimulating the immune system of a subject includes a single administration of a conjugate composition having an antigen cargo moiety according to the invention. Additional administrations of such a conjugate may be performed in alternative embodiment of the present invention.

The term "subject" refers to a vertebrate to which an inventive conjugate is to be administered. A subject is preferably a mammal, and more preferably a human in particular embodiments. In further embodiments, a preferred subject is porcine. However, the term subject is not limited to either human or porcine subjects and methods and compositions of the present invention may be used in conjunction with any of various animals illustratively including cows, horses, chickens and other poultry, goats, rodents, cats, dogs and birds.

An effective amount is an amount sufficient to achieve an intended beneficial or desired result. In general, an effective amount is in the range of about 0.001 to 100 milligrams per kilogram of a subject's body weight.

In a further embodiment of a method according to the present invention, a cell expressing sialoadhesin is targeted in order to eliminate or inhibit the cell. For example, elimination or inhibition of sialoadhesin expressing macrophages is desirable in certain disease states, such as, but not limited to, rheumatoid arthritis. Rheumatoid arthritis is characterized by presence of activated synovial macrophages which induce development of synovitis and joint destruction.

Another embodiment of a method according to the present invention relates to delivery of a therapeutic agent to inhibit pathogenic infection. Thus, one embodiment of an inventive method includes targeted delivery to macrophages of a conjugate composition according to the present invention including an antimicrobial drug cargo moiety. Such targeted delivery allows the use of antimicrobial drugs that have undesirable side effects when a non-targeted delivery system is used, such as systemic administration of free antimicrobial drug.

Embodiments of inventive compositions and methods are illustrated in the following examples. These examples are provided for illustrative purposes and are not considered limitations on the scope of inventive compositions and methods.

EXAMPLES

Example 1

An assay for assessment of binding of a sialoadhesin binding moiety to sialoadhesin is described in this example along with an assay for assessing uptake of the bound sialoadhesin binding moiety into a cell.

In this example, primary porcine alveolar macrophages, cells which express sialoadhesin, are used to assess binding and/or uptake of a sialoadhesin binding moiety.

Porcine alveolar macrophages are isolated from 4- to 6-week old conventional Belgian Landrace pigs from a PRRSV negative herd as described in Wensvoort, G., C. et al., 1991, Vet Q 13:121-30. Briefly, the main bronchus of each lung half was clamped and a needle was inserted distally. Cold PBS (3×20 ml) was injected, followed by massage of the lung tissue and aspiration. About 75% of the BAL fluid could be aspirated and was kept on ice. BAL cells were separated from fluids by centrifugation and cells were used in the experiments. Staining with mAb 41D3 showed that this procedure routinely resulted in a purity of more than 95% of sialoadhesin expressing macrophages.

The cells are cultivated in Earle's MEM, supplemented with 10% fetal bovine serum (FBS), 2 mM L-glutamine (BDH Chemicals Ltd.), 1% non-essential amino acids (Gibco BRL), 1 mM sodium pyruvate and antibiotics in a humidified 5% $CO_2$ atmosphere at 37° C. Macrophages are preferably cultivated for 24 hours before use.

Control cells, such as non-sialoadhesin-expressing cells, may be used to assess specificity of binding and uptake. Such cells include, for example, HEK293T cells, a human embryonic kidney cell line transfected with SV40 large T-Ag (SV40TtsA1609) described in DuBridge, R. B. et al., 1987, Mol Cell Biol 7:379-8. HEK293T cells are maintained in DMEM supplemented with 10% FBS, 2 mM L-glutamine and a mixture of antibiotics.

Antibodies used in this example include Mab 41D3 directed against sialoadhesin. Control antibodies include isotype matched (IgG1) mAb 13D12, directed against PRV glycoprotein gD described further in Nauwynck, H. J., and M. B. Pensaert, 1995, Arch Virol 140:1137-46; and mAb 74-22-15, reactive with SWC3, a membrane/surface protein used as a marker of porcine monocytes, macrophages and neutrophils described in Pescovitz, M. D. et al., 1984, J Immunol 133:368-75.

Antibodies are purified using protein G sepharose column chromatography (Amersham Biosciences), dialyzed to PBS and stored at 4° C. or −70° C. prior to use.

In an assay to assess characteristics of a sialoadhesin binding moiety, cells are incubated with a sialoadhesin binding moiety under various conditions and at various concentrations. In this example, primary macrophages are incubated with purified antibodies at a concentration of 25 micrograms/milliliter for 1 hour at 4° C. to allow only attachment, but no internalization. Cells are then washed to remove unbound antibody and shifted to 37° C. to start endocytosis. After different times, cells are fixed with 3% paraformaldehyde (PF), permeabilized with 0.1% Triton X-100, and stained with FITC-labelled goat-anti-mouse IgG to visualize antibodies bound to and internalized in the cells. As a control, cells are fixed after the 4° C. incubation (time 0). The number of vesicles internalized in the macrophages and control cells incubated under various conditions may be counted using an appropriate technique, such as confocal microscopy.

Confocal analysis is performed using a scanning spectral confocal system, such as a Leica TCS SP2 laser linked to a Leica DM IRBE inverted microscope, from Leica Microsystems GmbH. Image acquisition is performed using a Leica TCS SP2 confocal software package and overlay images are produced with Adobe Photoshop CS.

In a particular example, macrophages are incubated for 60 min at 4° C. with the sialoadhesin-specific mAb 41D3 to allow antibody binding, but no internalization. Cells are then washed to remove unbound antibody, and shifted to 37° C. to allow internalization. Cells are fixed and stained at different times for analysis of binding and uptake into cells.

FIG. 1 shows that incubation of primary porcine macrophages with mAb 41D3 induces sialoadhesin and antibody internalization. FIG. 1 is a graph illustrating specific binding and internalization of a sialoadhesin binding moiety at different times after incubation of macrophages at 37° C. with mAb 41D3. Kinetics of uptake are demonstrated by the percentage of cells with internalized sialoadhesin at different times after incubation of macrophages at 37° C. with mAb 41D3. Data in FIG. 1 represent the means±standard deviations of 3 independent experiments. At time 0, a clear membrane staining is observed, and none of the macrophages contain sialoadhesin positive vesicles in the cytoplasm, as indicated by the point at the origin of the graph.

With increasing time at 37° C., the number of cells which internalized sialoadhesin and antibody increases to a maximum of 90% at 90 min after the 37° C. shift (FIG. 1), and then declines to 61% at 120 min and 50% at 180 min. At early time points, endocytic vesicles are mainly present in the vicinity of the plasma membrane, while with increasing time, endocytosed sialoadhesin is mainly localized to the perinuclear region. As a control, primary porcine macrophages are incubated with a non-sialoadhesin binding antibody, isotype matched mAb 13D12, or mAb 74-22-15. Cells incubated with mAb 13D12 show no staining (data not shown), while mAb 74-22-15 incubated cells show exclusive plasma membrane staining at all timepoints examined. Further, when mAb 41D3 is added to macrophages directly at 37° C., this results in similar internalization kinetics.

Example 2

Various cells may be used in an assay to assess uptake and/or internalization of a sialoadhesin binding moiety. A cell line expressing sialoadhesin may be used for assay of binding and/or uptake of a sialoadhesin binding moiety.

A porcine cell line, PK-15, may be used in an assay to assess uptake and/or internalization of a sialoadhesin binding moiety. PK-15 cells are maintained as described by Vanderheijden, N. et al., 2003, J. Virol. 77:8207-15. About 25% of PK-15 cells usually express sialoadhesin. PK-15 cells are optionally transfected with a sialoadhesin expression construct to enhance expression of sialoadhesin in the cells for use in an assay to assess uptake and/or internalization of a sialoadhesin binding moiety.

The porcine alveolar macrophage cell line 3D4/31 (37) is maintained in RPMI/MEM (50/50) supplemented with 10% FBS, 2 mM L-glutamine, 1% non-essential amino acids (Gibco) and a mixture of antibiotics. About 5% of 3D4/31 cells usually express sialoadhesin. 3D4/31 are optionally transfected with a sialoadhesin expression construct to enhance expression of sialoadhesin in the cells for use in an assay to assess uptake and/or internalization of a sialoadhesin binding moiety.

HEK293T cells are transfected using calcium phosphate (Cellphect transfection kit, Amersham Biosciences), and PK-15 and 3D4 cells are transfected using Lipofectamine Plus (Invitrogen), following the manufacturers instructions. Cells are used for experiments 24 hours after transfection.

Example 3

A primary cell or cell line characterized by little or no expression of sialoadhesin may be treated to express sialoadhesin and/or to enhance sialoadhesin expression. In particular embodiments, a cell is transfected with a sialoadhesin expression construct in order to provide a cell used in an assay for assessment of binding and/or uptake of a sialoadhesin binding moiety. An expression construct including a nucleotide sequence encoding pig, mouse or human sialoadhesin detailed herein is optionally used. A pcDNA3.1/Sn plasmid containing the porcine sialoadhesin cDNA cloned into the pcDNA3.1 vector (Invitrogen) is described in Vanderheijden, N. et al., 2003, J. Virol. 77:8207-15.

Example 4

In further particular embodiments, a cell is treated with a stimulator of sialoadhesin expression in order to provide a cell used in an assay for assessment of binding and/or uptake of a sialoadhesin binding moiety. Stimulators of sialoadhesin expression include interferon-alpha. In this example, human peripheral blood mononuclear cells (PBMC) are isolated from heparinized blood from a healthy donor via centrifugation on Ficoll-paque according to the manufacturer's instructions (Amersham Biosciences). Monocytes are semi-purified by plastic adhesion and several washing steps to remove non-adherent lymphocytes. Flow cytometric analysis with a mouse-anti-human CD14 antibody shows that this procedure routinely results in a purity of the monocytes of >90%. Cells are cultivated for 3 days in RPMI medium with 10% FBS (RPMI-FBS) or RPMI-FBS with interferon-gamma, 500

U/ml and Tumor Necrosis Factor-alpha (TNF-alpha), 10 ng/nl, as described in Hartnell, A., et al., Blood, 2001. 97(1): p. 288-96, or in RPMI-FBS supplemented with interferon-alpha (100 U/ml).

Figure 5:
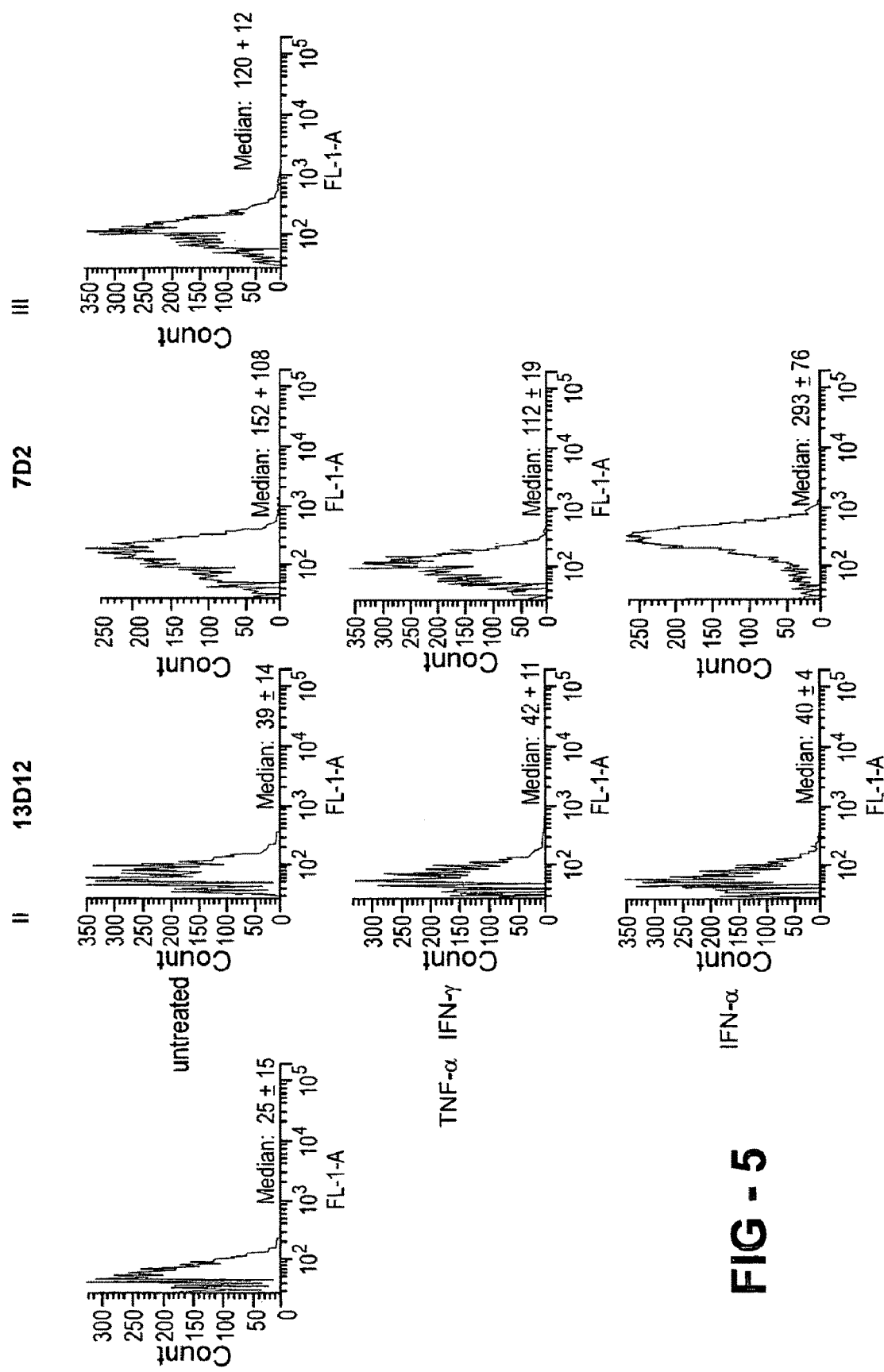
FIG. 5 is a set of histograms generated from flow cytometric analysis showing binding and internalization of a particular sialoadhesin binding moiety.

Cells are lifted from a plastic substrate to which they have adhered by incubation with ice-cold PBS for 30 min at 4° C. Cells are first incubated at 4° C. with a mouse anti-human-sialoadhesin specific antibody, 7D2, or a isotype-matched irrelevant control antibody, 13D12. Next, cells are fixed with paraformaldehyde (3% in PBS) or incubated at 37° C. for 1 hr for the internalization of the bound antibodies followed by paraformaldehyde fixation. Cells are washed 3 times and subsequently incubated with FITC-labeled goat-anti-mouse Ab (Molecular Probes). Some of the cells are double stained with APC-labeled mouse-anti-human CD14 (BD Pharmingen). Finally, the cells are washed 2 times, resuspended in PBS and analyzed with a Becton-Dickinson (San Jose, Calif.) FACScalibur. Ten thousand cells are analyzed for each sample, and four parameters are stored for further analysis: forward light scatter, sideward light scatter, green and red fluorescence, and results of this analysis are shown in FIG. 5.

Flow cytometric analysis of sialoadhesin expression yields data representative of three experiments. The control sample (shown at I in FIG. 5) is treated as the others during staining but without antibodies. Untreated and cytokine treated cells are stained with a control antibody 13D12 and with a human sialoadhesin-specific antibody 7D2, shown at II in FIG. 5. After the binding of 7D2, one sample was incubated for 1 hr at 37° C. to enable the receptor, sialoadhesin, to internalize the antibodies, shown at III in FIG. 5. IFN-alpha treatment clearly induces Sn expression and the induced Sn is able to internalize monoclonal antibody 7D2. Internalization of monoclonal antibody 7D2 is demonstrated by the reduction in the median fluorescence intensity upon surface staining of interferon-alpha treated cells incubated at 37° C. with FITC labeled goat-anti-mouse IgG (Molecular Probes, Invitrogen), as shown in FIG. 5.

In 2 of the 3 experiments using human monocytes, low levels of sialoadhesin is present on the untreated cells, in the third experiment it is absent. Treatment of the cells with TNF-alpha and IFN-gamma induces Sn expression, however treatment with IFN-alpha leads to a significantly higher expression of sialoadhesin. Similar results are obtained using monocytes isolated from peripheral blood from pigs and treated with IFN-alpha to induce Sn expression.

Sialoadhesin induced by IFN-alpha treatment is biologically active as shown by sialic acid binding capacity of IFN-alpha treated monocytes. Red blood cells contain sialic acids on their surface which allows them to bind to monocytes if these have functional expression of sialoadhesin. Monocytes are grown in 96-well plates for 3 days as described above. Next, they are incubated for 30 min at 37° C. with normal medium or medium supplemented with neuraminidase (Roche) 30 U/ml to remove sialic acids present on the surface. After removal of the neuraminidase, monocytes are incubated for 1 hr at room temperature with a 0.1% solution of human erythrocytes. Excess erythrocytes are washed away and binding of red blood cells to sialoadhesin is visualized via light microscopy. When sialic acids present on the surface of the monocytes are not removed, red blood cells are unable to bind to the monocytes under any conditions tested. However when sialic acids are removed from monocytes, red blood cells are able to bind in some conditions. Little binding is observed in cells grown in normal medium. Cells treated with TNF-alpha and IFN-gamma do not bind RBC. However, in the IFN-alpha treated cells clear formation of rosettes, that is, red blood cells bound to monocytes are observed. These data confirm the results obtained in the flowcytometric analysis showing that biologically active sialoadhesin is induced in monocytes by IFN-alpha treatment.

The ability of cytokine-induced sialoadhesin expression on human monocytes to internalize a sialoadhesin binding moiety is also shown in this example. Human monocytes are isolated as described above and treated with IFN-alpha for 3 days to induce human sialoadhesin. Cells are then incubated with human sialoadhesin-specific mAb 7D2 for 60 min at 37° C. to allow binding and internalization. As a control, the cells are incubated with mAb 7D2 at 4° C. At 4° C., cells are no longer capable of mediating internalization, thus this control should only binding of the sialoadhesin binding moiety mAb 7D2. After 60 min, the cells are fixed with 3% paraformaldehyde in PBS and permeabilized by incubation with 0.1% Triton X-100 in PBS for 2 min. MAb 7D2 is visualized by incubation with FITC-labelled goat-anti-mouse (Invitrogen). Cortical actin is also visualized, using TexasRed labelled Phalloidin, to allow discrimination of surface bound and internalized sialoadhesin. Surface expression of sialoadhesin and binding of sialoadhesin binding moiety mAb 7D2 is observed at time 0. Following incubation for 60 minutes at 37° C., internalized sialoadhesin and sialoadhesin binding moiety mAb 7D2 is observed in the IFN-alpha treated human monocytes.

Thus, an in vitro system for evaluation of human sialoadhesin binding moieties and conjugates of human sialoadhesin binding moieties is provided which is analogous to the in vitro and in vivo pig system for evaluation of sialoadhesin binding moieties and conjugates of sialoadhesin binding moieties.

Example 5

The effect of interferon-alpha on sialoadhesin expression in human THP-1 cells, a monocytic continuous cell line, is tested to determine if sialoadhesin is internalized in these cells upon stimulation with an antibody as a sialoadhesin binding moiety. THP-1 cells are deposited with the American Type Culture Collection (ATCC) and are identified by ATCC Number TIB-202. THP-1 cells are cultivated for 3 days in RPMI medium with 10% FBS (RPMI-FBS) or RPMI-FBS with interferon-gamma (500 U/ml) and TNF-alpha (10 ng/ml) or in RPMI-FBS supplemented with interferon-alpha (100 U/ml).

Figure 10:
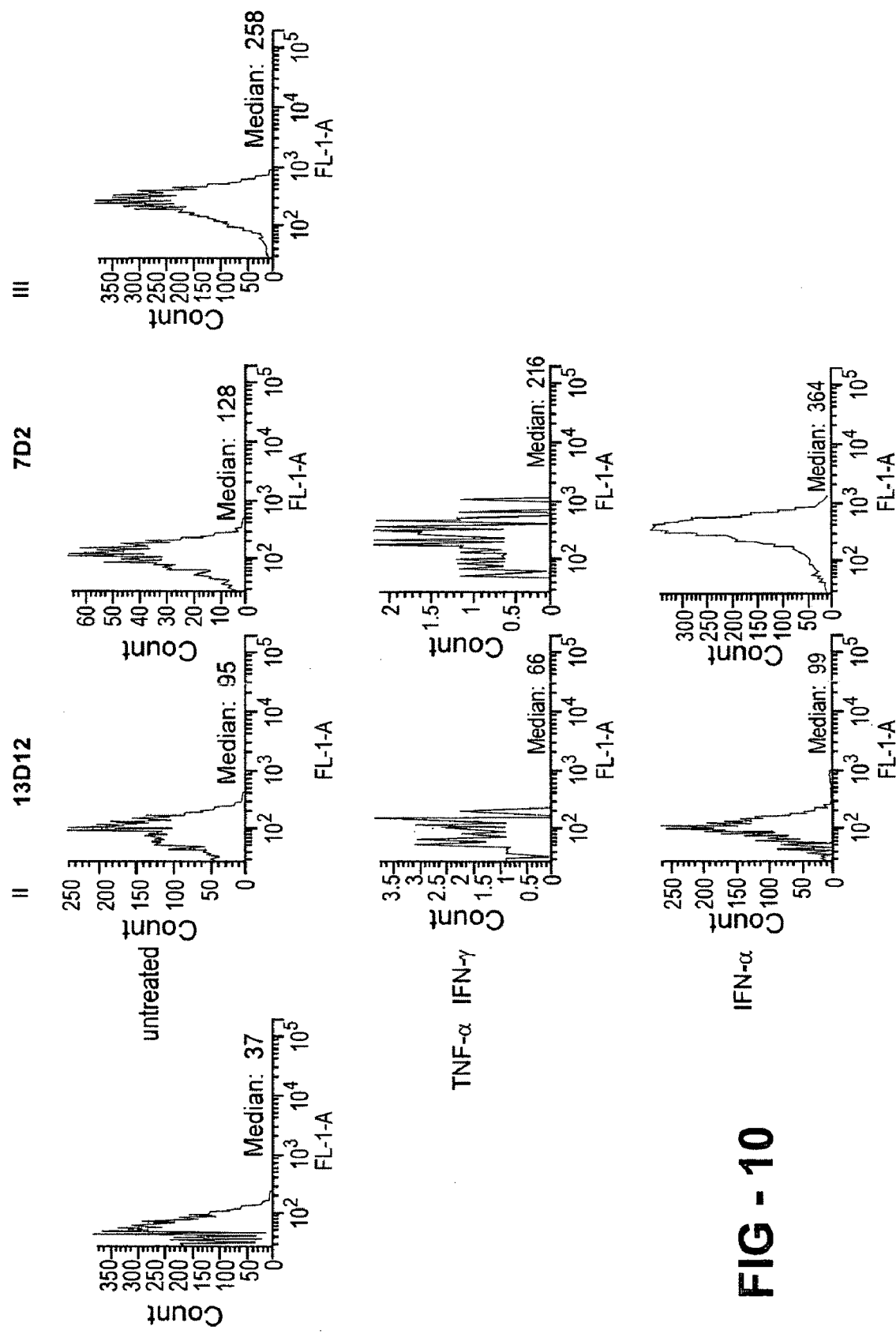
FIG. 10 is a set of histograms generated from flow cytometric analysis showing binding and internalization of a particular sialoadhesin binding moiety.

THP-1 cells are incubated at 4° C. with a human-sialoadhesin specific antibody, 7D2, or an isotype-matched irrelevant control antibody, 13D12. Next, cells are fixed with paraformaldehyde (3% in PBS) or incubated at 37° C. for 1 hour to allow antibody induced internalization of sialoadhesin and the bound antibody followed by paraformaldehyde fixation and permeabilization of the cells with 0.1% Triton X-100. Cells are washed 3 times and subsequently incubated with FITC-labeled goat-anti-mouse Ab (Molecular Probes). Some of the cells are double stained with APC-labeled mouse-anti-human CD14 (BD Pharmingen). The cells are washed 2 times, resuspended in PBS and analyzed with a Becton-Dickinson (San Jose, Calif.) FACScalibur. Ten thousand cells are analyzed for each sample, and four parameters were stored for further analysis: forward light scatter, sideward light scatter, green and red fluorescence (FIG. 10). These data show that IFN-alpha treatment induces human sialoadhesin on THP-1 cells, and that upon stimulation with mAb 7D2 at 37° C., a decrease in cell surface sialoadhesin fluorescence is observed, indicative of internalization of the antibody bound to sialoadhesin.

FIG. 10 shows flow cytometric analysis of sialoadhesin expression and antibody induced sialoadhesin internalization. Histograms are representative for three experiments. The control sample (I) is treated as the others during staining but without antibodies. Untreated and cytokine treated cells are stained with a control antibody 13D12 and with a human sialoadhesin-specific antibody 7D2 (II). After the binding of 7D2, one sample was incubated for 1 hr at 37° C. to enable the receptor to internalize the antibodies (III). IFN-alpha treatment clearly induces sialoadhesin expression and the induced sialoadhesin is able to internalize monoclonal antibody 7D2 as shown by the decreased median which lowers from 364 to 258 upon incubation at 37° C.

Confocal microscopy is used in this example to visualize internalization of sialoadhesin and bound sialoadhesin binding moiety mAb 7D2. THP-1 cells are incubated with human sialoadhesin—specific mAb 7D2 for 60 min at 37° C. to allow internalization. As a control, a time 0 was analyzed by incubating the cells with mAb 7D2 at 4° C. At 4° C., cells are no longer capable of mediating internalization, thus this control should only show binding to sialoadhesin at the cell surface without internalization. After 60 min, the cells are fixed with 3% paraformaldehyde in PBS and permeabilized by incubation with 0.1% Triton X-100 in PBS for 2 min. Internalized antibodies are visualized by incubation and staining with FITC-labelled goat-anti-mouse (Invitrogen). Surface labeling of these cells is observed at time 0, while at time 60, sialoadhesin and bound antibody is observed internalized in the THP-1 cells.

Thus, an in vitro system is provided including the human monocytic THP-1 cell line, allowing further analysis of antibody-induced human sialoadhesin internalization without the need of isolating primary blood monocytes or macrophages.

Example 6

Chemical cross-linking of a sialoadhesin binding moiety and a cargo moiety is described. In this example, human serum albumin (HSA) is a cargo moiety which is an antigen to be conjugated to mAb 41D3, a sialoadhesin binding moiety, to form an inventive conjugate composition. In addition, as a control, human serum albumin (HSA) is conjugated to a non-sialoadhesin binding antibody, mAb 13D12.

For chemical cross-linking of HSA and the mAb in this example, a two step cross-linking protocol is used. The amine reactive cross-linker LC-SMCC (Pierce) is coupled to the purified mAb 41D3 by incubating 600 micrograms of LC-SMCC with 20 milligrams of mAb in 8 milliliters phosphate buffered saline (PBS) for 30 minutes at room temperature. The amine-reactive cross-linker SPDP (Pierce) is coupled to the purified HSA by incubating 2 milligrams SPDP with 40 milligrams HSA in 8 milliliters PBS, for 30 minutes at 37° C. The SPDP-HSA is then activated by addition of 125 micrograms DTT, which results in the formation of a thiol activated protein. Both the mAb-LC-SMCC and the thiol activated HSA are then dialyzed to PBS at 4° C. using a membrane with a 10-14 kDa cutoff to remove residual unreacted LC-SMMC, SPDP and DTT. The mAb-LC-SMCC and the thiol activated HSA are then mixed together and incubated at 37° C. for 30 minutes to allow the thiol group on HSA to react with the maleimide end of the LC-SMCC on the mAb, resulting in the formation of a covalent thio-ether bond. After the coupling reaction, the mixture is dialyzed again towards PBS using a membrane with a 100 kDa cut off, to remove any unreacted HSA from the mixture.

A similar reaction is performed to generate a control conjugate including human serum albumin (HSA) conjugated to a non-sialoadhesin binding antibody, mAb 13D12.

Samples taken in between different steps of the cross-linking protocol may be analyzed to confirm formation of a conjugate. For example, such samples may be separated by SDS-PAGE on a 7% gel and proteins stained with a reagent such as Coomassie blue in order to visualize the reactants and reaction products.

Example 7

Internalization of a conjugate composition including a sialoadhesin binding moiety and a cargo moiety is demonstrated in primary macrophages. In this example, the HSA-mAb 41D3 conjugate and HSA-mAb 13D12 conjugate are incubated for 1 hour at 37° C. with sialoadhesin expressing primary porcine macrophages. Cells in separate culture dishes are incubated for 1 hour at 37° C. with mAb 41D3, mAb 13D12 or with HSA alone. Cells are then washed, fixed by incubating with 3% paraformaldehyde for 10 minutes and permeabilized by incubating with 0.1% Triton X-100 for 2 minutes.

HSA is detected in these preparations by incubating the cells with a HSA-specific biotinylated polyclonal pig serum, followed by incubation with FITC-labeled streptavidin FITC (Molecular Probes). The monoclonal antibodies are detected with TxRed-labeled goat-anti-mouse Ig (Molecular Probes). The cells are then analyzed using an appropriate technique, such as confocal microscopy.

Confocal analysis is performed using a scanning spectral confocal system, such as a Leica TCS SP2 laser linked to a Leica DM IRBE inverted microscope, from Leica Microsystems GmbH. Image acquisition is performed using a Leica TCS SP2 confocal software package and overlay images are produced with Adobe Photoshop CS.

Analysis demonstrates mAb 41D3 internalization both when it is coupled to HSA or not, indicating that the coupling reaction had no effect on the ability of mAb 41D3 to bind to sialoadhesin and to induce internalization. Internalization of free HSA is either absent, or at very low levels when it is added to macrophages not coupled to mAb 41D3, but a clear internalization of HSA is observed when it is coupled to mAb 41D3. Further, internalized HSA co-localizes with mAb 41D3 in confocal images of cells treated with the HSA-mAb 41D3 conjugate. Coupling HSA to mAb 41D3 results thus in co-internalization of HSA with mAb 41D3 via the sialoadhesin receptor.

Thus, contact of an inventive conjugate including HSA coupled to the sialoadhesin-specific mAb 41D3 with primary, sialoadhesin expressing macrophages, results in sialoadhesin-dependent uptake of HSA into macrophages, while addition of non-coupled HSA to macrophages did not result in efficient HSA uptake.

Example 8

Immunization is performed using conjugate compositions according to the present invention in this example. Six week old conventional pigs are purchased from a porcine arterivirus negative farm and housed in isolation units with HEPA filtered air following the recommendations of the ethical committee of the Faculty of Veterinary Medicine, Ghent University. Six pigs are immunized with one milligram of an inventive conjugate having HSA coupled to the sialoadhesin-specific mAb 41D3. Three pigs are immunized with one milligram of a control conjugate having HSA coupled to the control mAb 13D12. Each immunization includes administration of the conjugate in 3 milliliters PBS, of which 1.5 milliliters is administered intravenously and 1.5 milliliters is administered intramuscularly. As a control, six pigs are immunized with one milligram unconjugated HSA.

Blood samples are collected before immunization and at days 10, 17, 24, 32 and 38 after immunization. Three months later, blood is sampled again and the pigs are boostered with one milligram HSA by intramuscular injection.

Serum obtained from immunized pigs is analyzed for the presence of HSA-specific IgM and IgG antibodies by ELISA. The HSA-specific IgM, and IgG antibody titers are determined with an indirect ELISA as described in Van der Stede, Y., E. et al., 2001, Vaccine 19:1870-8; and Verdonck, F. et al., 2005, J Control Release 104:243-58. Briefly, the wells of a 96-well Polysorb Immuno microtiter plate (NUNC) are coated with HSA at a concentration of 30 micrograms/milliliter in PBS for 2 hours at 37° C. The plates are then washed and the remaining binding sites are blocked overnight at 4° C. with PBS supplemented with 0.2% Tween®80. Two-fold serial dilutions of the serum samples (starting from 1/10) in ELISA dilution buffer (PBS+0.05% Tween®20) are added to the plate, followed by the swine-specific IgM, or IgG MAb, such as described in Van Zaane, D., and M. M. Hulst, 1987, Vet Immunol Immunopathol 16:23-36, and peroxidase-conjugated rabbit-anti-mouse polyclonal antibodies (Dako) supplemented with 2% pig serum. ABTS and $H_2O_2$ are used as chromogen and substrate and the optical density is spectrophotometrically measured at 405 nm (OD405). The cut-off values are calculated as the mean $OD_{405}$-value of all sera (dilution 1/10) at day 0, increased with 3 times the standard deviation. The antibody titer is the inverse of the highest dilution that still had an $OD_{405}$ higher than the calculated cut-off value.

Figure 2A:
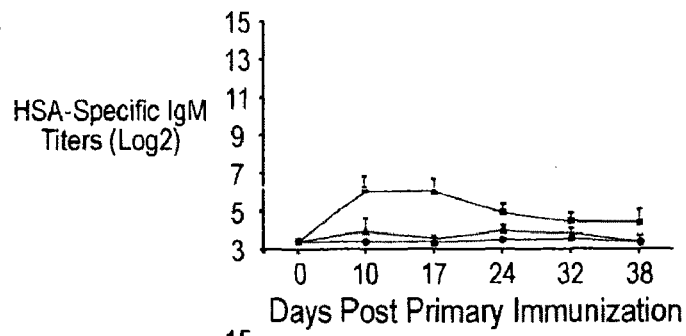
FIG. 2A is a graph showing the mean±SEM of antigen-specific IgM serum titers after primary immunization with a sialoadhesin binding moiety/antigen conjugate according to the present invention in which square symbols indicate pigs immunized with HSA coupled to Sn-specific mAb 41D3; triangle symbols indicate pigs immunized with HSA coupled to irrelevant control mAb; and circle symbols indicate pigs immunized with free HSA.
Figure 2B:
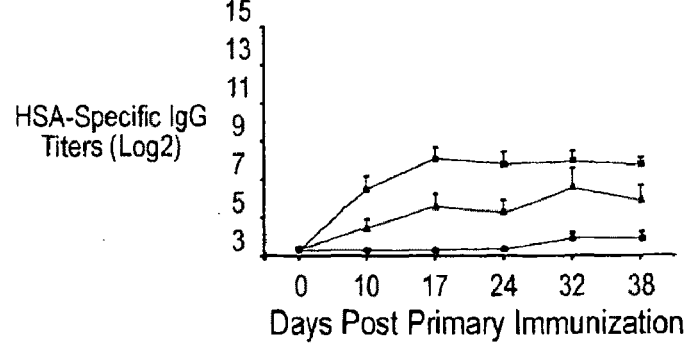
FIG. 2B is a graph showing the mean±SEM of antigen-specific IgG serum titers after primary immunization with a sialoadhesin binding moiety/antigen conjugate according to the present invention in which square symbols indicate pigs immunized with HSA coupled to Sn-specific mAb 41D3; triangle symbols indicate pigs immunized with HSA coupled to irrelevant control mAb; and circle symbols indicate pigs immunized with free HSA.
Figure 2C:
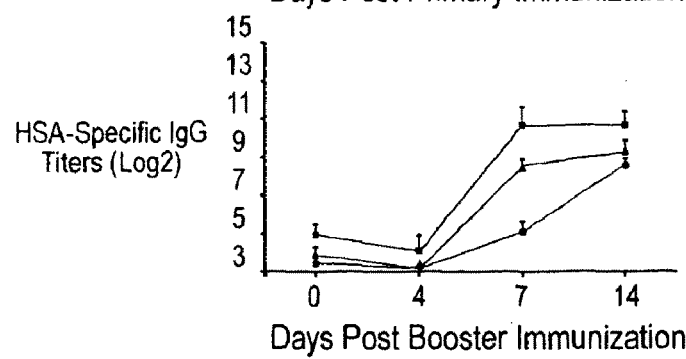
FIG. 2C is a graph illustrating means±SEM of antigen-specific IgG serum titers after booster immunization in which square symbols indicate pigs immunized with HSA coupled to Sn-specific mAb 41D3; triangle symbols indicate pigs immunized with HSA coupled to irrelevant control mAb; and circle symbols indicate pigs immunized with free HSA.
Figure 3:
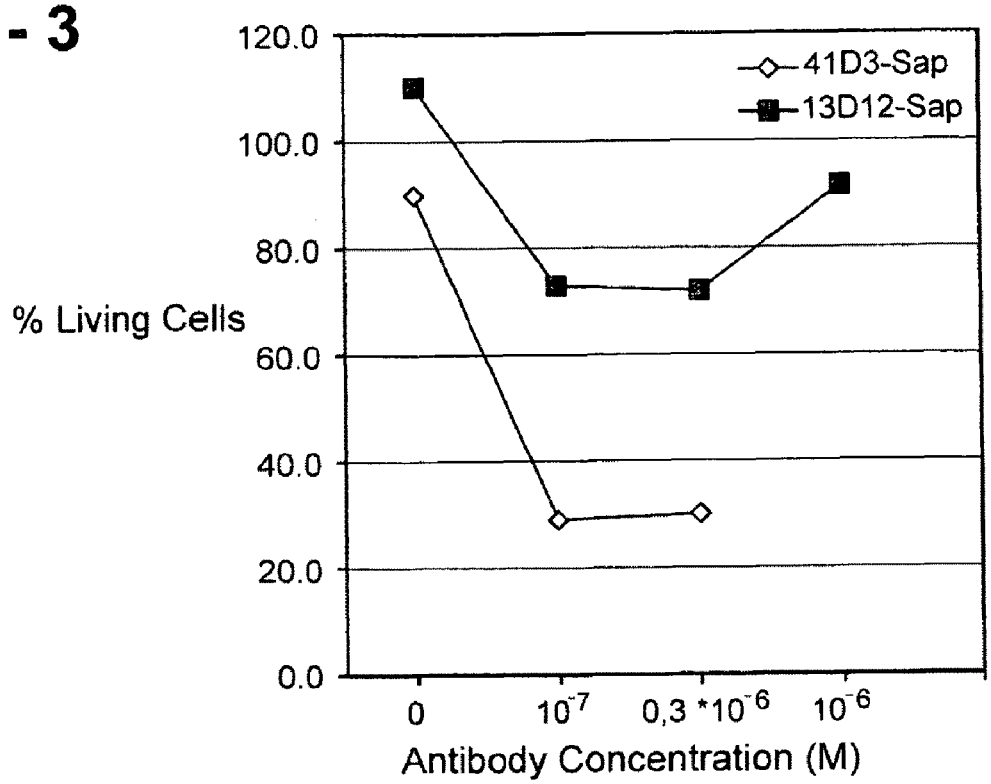
FIG. 3 is a graph illustrating the percentage of living cells in a population of sialoadhesin expressing cells treated with sialoadhesin binding moiety/cytotoxic agent conjugate compared to cells treated with a non-sialoadhesin binding moiety/cytotoxic agent conjugate.

FIG. 2 shows means of HSA specific IgM (FIG. 2A) and IgG (FIG. 2B) serum titers (±SEM) after primary immunization. FIG. 2C shows means of HSA specific IgG serum titers after booster immunization. Square symbols indicate pigs immunized with HSA coupled to Sn-specific mAb 41D3; triangle symbols indicate pigs immunized with HSA coupled to irrelevant control mAb; and circle symbols indicate pigs immunized with free HSA.

After primary immunization, low to undetectable titers of IgM antibodies are detected in the pigs immunized with HSA alone, or with HSA coupled to the control mAb 13D12. In contrast, IgM antibodies are present starting from 10 days post immunization (dpi) in the pigs immunized with HSA coupled to the sialoadhesin-specific mAb 41D3. These antibodies remained at a nearly constant level until 17 dpi, and started to decline from 24 dpi as illustrated in FIG. 2A.

Similarly, HSA-specific IgG antibodies are undetectable in pigs immunized with HSA alone until 24 dpi, and low titers are detected from 32 dpi. In pigs immunized with HSA coupled to the control mAb 13D12, low titers of HSA-specific IgG antibodies could be detected from 10 dpi which reached maximum titers at 32 dpi. Cross-linking of HSA and a non-sialoadhesin binding antibody stimulates some HSA-specific IgG antibody response. In contrast, pigs immunized with HSA coupled to the sialoadhesin-specific mAb developed high titers of IgG antibodies already starting at 10 dpi. Maximum antibody titers are detected at 17 dpi and these remained constant until 38 dpi as illustrated in FIG. 2B.

To investigate if immunization with HSA coupled to the sialoadhesin-specific mAb 41D3 had an effect on the induction of HSA-specific memory cells, all animals are boosted 3 months after primary immunization with HSA alone. At the time of the booster immunization and at 4 dpi, all animals had low to undetectable HSA-specific IgG titers. Starting from 7 dpi, an IgG antibody response is detected in all animals, but the highest titers are detected in the animals which received HSA coupled to the sialoadhesin-specific mAb 41D3 as the primary immunization as is shown in FIG. 2C.

Pigs immunized with the HSA-mAb41D3 constructs showed the highest IgG and IgM antibody titers throughout the study, which indicates that coupling HSA to the sialoadhesin-specific mAb greatly enhances both the speed of induction and the titers of HSA-specific IgG and IgM antibodies.

Thus, targeted delivery of an immunogen to macrophages is possible by coupling the immunogen to the sialoadhesin-specific mAb, and this affects the humoral immune response, enhancing both the speed of induction and the titers of antigen-specific antibodies.

Example 9

Sialoadhesin binding moiety/viral protein conjugate, administration and immune response. In this example, influenza virus haemagglutinin (HA) is conjugated to sialoadhesin binding moiety monoclonal antibody (mAb) 41D3. Influenza virus haemagglutinin conjugated to sialoadhesin binding moiety monoclonal antibody 41D3 is either the native protein purified from virus or a recombinant form produced in eukaryotic cells. Haemagglutinin conjugated to sialoadhesin binding moiety monoclonal antibody 41D3 is chemically cross-linked with mAb 41D3 in this example and injected in pigs to demonstrate and evaluate the capacity of the conjugates to induce HA-specific antibodies.

Purification of Native Haemagglutinin

In order to obtain native haemagglutinin, a split H1N1 component is prepared essentially as described by Van Reeth, K., S. et al., Vet Rec, 2003. 153(1): p. 9-13. Ten-day-old embryonated SPF chicken eggs are inoculated with the H1N1 swine influenza strain A/swine/Belgium/1/98. Allantoic fluid is collected 72 h post inoculation and red blood cells and cell debris are removed via centrifugation. The clarified allantoic fluid is then centrifuged to pellet the virus, 70,000 g at 4° C. for 90 min. Virus pellets are resuspended overnight at 4° C. in TSE buffer, 10 mM Tris-HCl pH7.4, 100 mM NaCl and 1 mM EDTA. Presence of influenza virus is confirmed with a haemagglutination (HA) test such as described by Van Reeth, K., S. et al., Vet Rec, 2003. 153(1): p. 9-13 followed by concentration and purification via ultracentrifugation on a linear 20 to 60% (w/v) sucrose gradient, 130,000 g at 4° C. for 14 hrs. Gradient fractions containing virus are identified with an HA test, pooled, dialysed in a slide-a-lyzer dialysis cassette, 10,000 MWCO, against phosphate buffered saline (PBS) to remove sucrose and concentrated by dialysis in a 20% polyethylene glycol (PEG-20,000) solution. Finally, the haemagglutinin is released from the purified and concentrated virus by centrifugation on a linear denaturing 20 to 60% (w/v) sucrose gradient consisting of 0.1% Tween 80 and 1.2% sodium deoxycholate in TSE buffer, 130,000 g at 4° C. for 14 hrs. Fractions containing haemagglutinin are identified with an HA test, pooled, dialysed in a slide-a-lyzer cassette (10,000 MWCO) against PBS and concentrated by dialysis in a 20% PEG solution. Residual infectious virus is inactivated by UV treatment of the solution (5 J/cm²). Complete inactivation is confirmed by inoculation on MDCK cells and two blind passages in 10-day old embryonated SPF chicken eggs.

Figure 6A:
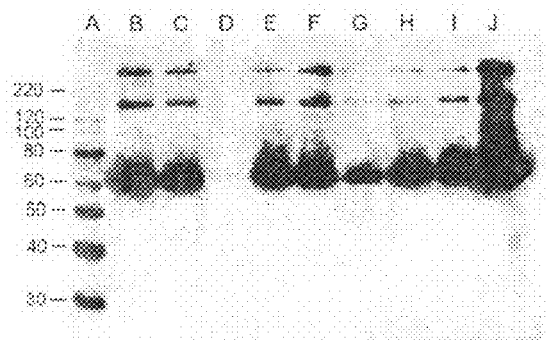
FIG. 6A is a xerographic reproduction of a digital image showing SDS-PAGE analysis of the presence and purity of native influenzavirus haemagglutinin in different fractions obtained during purification includes detection of HA via western blotting using a monoclonal antibody directed against HA of the H1N1 virus.
Figure 6B:
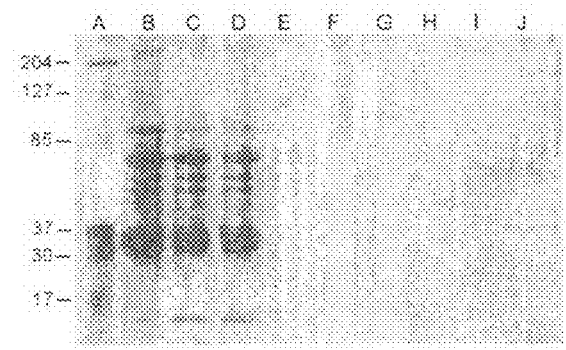
FIG. 6B is a xerographic reproduction of a digital image showing detection of total protein in the samples shown in FIG. 6A using Coomassie blue staining.

The purification process is analysed via SDS-PAGE followed by western blotting and coomassie blue staining. HA is clearly present in the original allantoic fluid, but also in the purified solution after the denaturing sucrose gradient. HA can be detected as a monomer and as two different multimers, most likely a dimer and a trimer during all steps of the purification process. FIG. 6A shows SDS-PAGE analysis of the presence and purity of native influenzavirus haemagglutinin in different fractions obtained during purification includes detection of HA via western blotting using a monoclonal antibody directed against HA of the H1N1 virus. FIG. 6B shows detection of all proteins in the samples is accomplished via coomassie blue staining. In both FIGS. 6A and 6B: Lane A: marker, lane B: allantoic fluid after removal of RBC, lane C: allantoic fluid after removal of cell debris, lane D: supernatant after pelleting the virus, lane E: the virus pellet (1/100 dilution), lane F: virus after the first sucrose gradient and after removal of sucrose (1/100 dilution), lane G-J: virus after denaturing sucrose gradient: lane G: fraction with HAU 64 and 128 (1/100), lane H: fraction with HAU≧256 (1/100), lane I: fraction with HAU 64 and 128 (undiluted), lane J: fraction with HAU≧256 (undiluted). HA can be detected as a monomer and as two different multimers, most likely a dimer and a trimer.

Production of Recombinant Haemagglutinin

In further embodiments, a recombinant influenza virus haemagglutinin protein is produced. The recombinant influenza virus haemagglutinin protein used in this example includes the extracellular domain of haemagglutinin fused to the V5-His tag in the pcDNA3.1D/V5-His vector (Invitrogen). Viral RNA is isolated from H1N1 swine influenza strain A/swine/Belgium/1/98 via the RNeasy mini kit (Qiagen) and subsequently converted into cDNA via random primers (Invitrogen) and SuperScript II reverse transcriptase (Invitrogen) followed by an RNase H (Gibco) treatment. The obtained single stranded cDNA serves as template for PCR amplification of the HA sequence using following primers: forward primer 5'GAA GAT CTC ACC ATG GAA GCA AAA CTG TTT GTA TTA TTC TG3' (SEQ ID No. 1) and reverse primer 5'TCC CCG CGG AAT CTG GTA AAC TCC CAT TGA TTC3' (SEQ ID NO. 2) (Invitrogen). The PCR fragment is then cloned in the pcDNA3.1D/V5-His vector. The sequence is verified via restriction digest and sequencing. The isolated and verified nucleotide sequence encoding the extracellular domain of influenza virus haemagglutinin is shown and referred to as SEQ ID NO. 3 herein.

Extracellular domain of influenza virus haemagglutinin—SEQ ID NO. 3

```
5'-ATGGAAGCAAAACTGTTTGTATTATTCTGTGTATTCAATGCGCTGAA
AGCTGACACCATTTGTGTAGGCTACCATGCTAACAATTCCACAGACACTG
TCGACACAATACTGGAGAAAAATGTGACTGTTACCCATTCAGTTAATTTA
CTAGAAAACAGCCATAATGGAAAACTCTGCAGCCTGAATGGAAAAGCCCC
CCTACAACTGGGGAACTGCAACGTAGCAGGATGGATCCTTGGCAACCCAG
AATGTGACTTGTTGCTCACAGCGAATTCATGGTCTTACATAATAGAGACT
TCAAATTCAAAAAATGGAAAATGCTACCCCGGAGAATTCGCTGATTATGA
GGAATTAAGGGAGCAGCTGAGTACAGTTTCTTCATTTGAAAGATTTGAAA
TTTTCCCAAAAGCAACCTCATGGCCAGATCATGAGACAACCAAAGGTACC
ACAACTGCATGCTCCCACTCTGGAACCAGCAGTTTTTACCGGAACTTGCT
ATGGATAGTAAAGAAGGGAAACTCCTATCCTAAGCTCAGCAAGTCATACA
CAAACAACAAAGGAAAAGAAGTGCTTGTAATCTGGGGAGTGCACCACCCT
CCGACTAACAGTGACCAACAAACCCTCTACCAGAATGCTTATACATATGT
TTCAGTTGAATCATCAAAATACTACCGAAGGTTCACACCAGAAATAGCAG
CTAGACCCTAAAGTCAGAGGACAAGCAGGCAGAATGAATTATTATTGGACA
CTGTTAGATCAAGGAGACACCATAACATTTGAAGCCACTGGGAACTTAAT
AGCACCATGGTACGCATTTGCTTTGAATAAGGGCTCTAATTCTGGAATTA
TGATGTCGGATGCTCATGTTCACAATTGCACTACAAAGTGCCAAACTCCT
CATGGGGCCTTGAAAAGTAATCTTCCTTTTCAgAACGTACATCCCATCAC
TATTGGAGAATGCCCTAAATATGTTAAAAGCACCCAACTAAGAATGGCAA
CAGGATTAAGAAACGTCCCCTCTATCCAATCCAGAGGACTTTTTGGAGCA
ATTGCTGGGTTCATTGAAGGAGGATGGACAGGAATGATAGATGGATGGTA
TGGATATCACCATCAAAATGAGCAGGGATCTGGTTACGCAGCAGATCAGA
AAAGCACACAAATTGCAATTGATGGGATCAGCAACAAAGTGAACTCAGTA
ATTGAAAAAATGAACATTCAATTTACTTCAGTGGGCAAGGAGTTCAATAA
TCTGGAGAAAAGGATTGAGAATTTGAATAAGAAGGTCGATGATGGGTTTT
TGGATATATGGACATATAATGCTGAGTTGCTCATTTTGCTCGAGAATGAA
AGGACTCTAGATTTCCATGACTTTAACGTAAAAAATTTATATGAAAAGGT
CAAATCACAATTGAGAAACAATGCCAAGGAAGTCGGTAATGGTTGTTTTG
AGTTCTATCACAAATGTGATAATGAATGCATGGAGAGCGTAAAGAATGGC
ACATACAATTATCCCAAATATTCAGAAGAATCCAAATTGAATAGAGAGGA
AATAGACGGTGTGAAATTAGAATCAATGGGAGTTTACCAGATT-3'
```

Figure 7A:
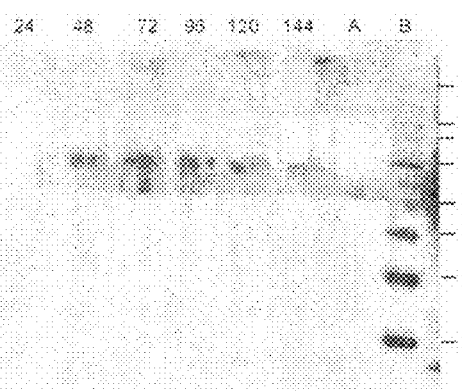
FIG. 7A is a xerographic reproduction of a digital image showing SDS-PAGE analysis of the production of recombinant HA with a V5-His tag where the protein is produced in the absence of fetal bovine serum.
Figure 7B:
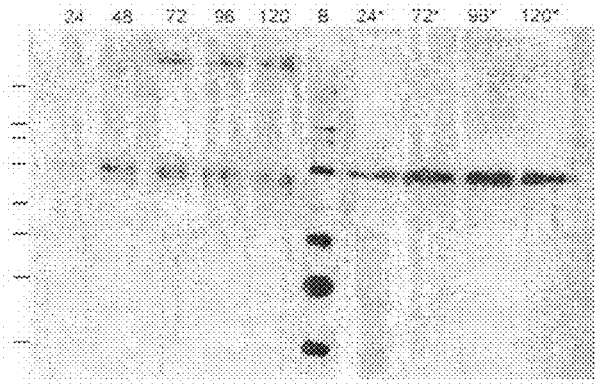
FIG. 7B is a xerographic reproduction of a digital image showing SDS-PAGE analysis of the production of recombinant HA with a V5-His tag where the protein is produced in the presence of fetal bovine serum.

Production and purification of the recombinant, soluble HA is demonstrated in a human embryonic kidney cell line, HEK293T. HEK293T cells are transfected using calcium phosphate to produce the soluble haemagglutinin. Sixteen hours post transfection, medium is replaced by fresh medium with or without fetal bovine serum (FBS). Samples are taken every 24 hrs post transfection and analyzed via SDS-PAGE and western blotting to determine at what time post transfection the supernatant contains the highest concentrations of soluble HA (FIGS. 7A and 7B). The recombinant, soluble HA is produced in HEK293T cells, no matter whether FBS is present in the serum or not. In the absence of FBS, the maximum amount of HA in the serum is reached at 72 hrs post transfection. In the presence of FBS, the amount of HA stays the same until 120 hrs post transfection. The recombinant HA is produced as a monomer and, to a lesser extent as a trimer, which is confirmed by the disulfide-reducing agent beta-mercaptoethanol.

FIGS. 7A and 7B show SDS-PAGE analysis of the production of recombinant HA with a V5-His tag. The recombinant HA is produced in the absence, FIG. 7A or in the presence FIG. 7B of fetal bovine serum. Samples are taken every 24 hrs post transfection as indicated above the lanes in FIGS. 7A and 7B. HA is detected via a monoclonal antibody recognizing the V5 tag. Under non-reducing conditions, HA is mainly present in the supernatant as a monomer, although it also forms trimers. In the presence of the disulfide-reducing agent beta-mercaptoethanol, indicated with an asterix* in FIGS. 7A and 7B, HA is only present as a monomer, confirming that the high molecular weight protein was indeed an HA trimer. The molecular weight of the proteins is determined via a marker in lane A (prestained) and B.

Figure 8A:
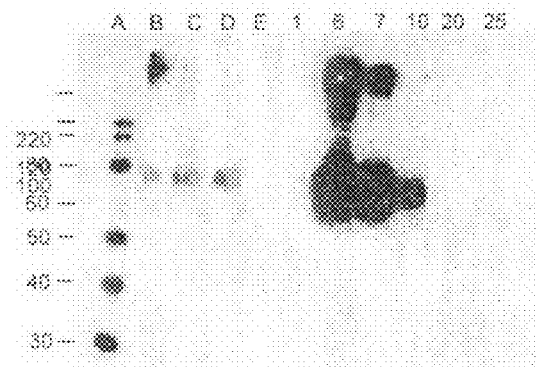
FIG. 8A is a xerographic reproduction of a digital image showing SDS-PAGE Western blot analysis of different fractions taken during the purification process of HA.
Figure 8B:
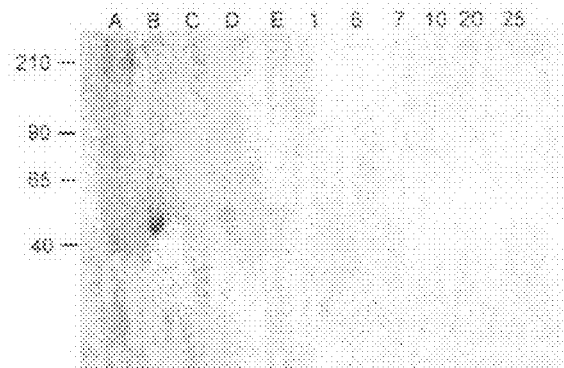
FIG. 8B is a xerographic reproduction of a digital image showing SDS-PAGE Coomassie blue analysis of the same fractions taken during the purification process of HA shown in FIG. 8A.

After collection of the supernatant, the recombinant HA is purified via Ni-NTA beads according to the manufacturers instructions (Qiagen). Because of interference of the FBS with this purification step, HA is further produced without FBS and the supernatant is collected at 72 hrs post transfection. Different fractions are taken during the purification process and HA is visualized via SDS-PAGE followed by western blot or coomassie blue staining as shown in FIGS. 8A and 8B, respectively. The recombinant HA is present in the original supernatant, but not in the flow through. HA is clearly concentrated, both the monomer and the trimer. FIGS. 8A and 8B show SDS-PAGE analysis of the purification process of recombinant HA-V5-His via Ni-NTA beads. SDS-PAGE is followed by western blotting and detection of HA via a monoclonal antibody directed against the V5-tag to identify the fractions containing HA, FIG. 8A, or by coomassie blue staining to visualize the purity of the HA, FIG. 8B. Lane A: marker, lane B: original supernatant with FBS, lane C and D: original supernatant from 2 different productions without FBS, lane E: flow through of purification, following lanes: elution fractions of 0.8 ml, fractions are indicated with their respective number above the lanes. HA is present in all original supernatants but not in the flow through. HA is clearly concentrated, both the monomer and the trimer.

Conjugation of Antibodies with HA

Hybridomas producing monoclonal antibody 41D3, described in Duan, X., et al., Adv Exp Med Biol, 1998. 440: p. 81-8, or monoclonal antibody 13D12, described in Nauwynck, H. J. and M. B. Pensaert, Arch Virol, 1995. 140(6): p. 1137-46, directed against porcine sialoadhesin or an isotype matched (IgG1) irrelevant control antibody, respectively, are cultivated and supernatant is collected every 72 hrs. Antibodies are purified via protein G sepharose columns as described by the manufacturer (GE Healthcare).

Influenza virus hemagglutinin Type A/swine/Belgium/1/98 having protein sequence identified as GenPept Accession number AY590824, and herein as SEQ ID No. 4, is used in this example as a cargo moiety conjugated to mAb 41D3.

```
SEQ ID No. 4:
MEAKLFVLFCVFNALKADTICVGYHANNSTDTVDTILEKNVTVTHSVNLL

ENSHNGKLCSLNGKAPLQLGNCNVAGWILGNPECDLLLTANSWSYIIETS

NSKNGKCYPGEFADYEELREQLSTVSSFERFEIFPKATSWPDHETTKGTT

TACSHSGTSSFYRNLLWIVKKGNSYPKLSKSYTNNKGKEVLVIWGVHHPP

TNSDQQTLYQNAYTYVSVESSKYYRRFTPEIAARPKVRGQAGRMNYYWTL

LDQGDTITFEATGNLIAPWYAFALNKGSNSGIMMSDAHVHNCTTKCQTPH

GALKSNLPFQNVHPITIGECPKYVKSTQLRMATGLRNVPSIQSRGLFGAI

AGFIEGGWTGMIDGWYGYHHQNEQGSGYAADQKSTQIAIDGISNKVNSVI

EKMNIQFTSVGKEFNNLEKRIENLNKKVDDGFLDIWTYNAELLILLENER

TLDFHDFNVKNLYEKVKSQLRNNAKEVGNGCFEFYHKCDNECMESVKNGT

YNYPKYSEESKLNREEIDGVKLESMGVYQI
```

The purified antibodies are coupled to influenza haemagglutinin (HA) SEQ ID No. 4 via a disulfide-bridge. To accomplish this, the 41D3 monoclonal antibody, the isotype matched control monoclonal antibody and HA are activated with the cross-linker SPDP (N-succinimidyl-3-(2-pyridyldithio)-propionate) according to the manufacturers instructions (Pierce Biotechnology). For HA, the SPDP is activated via dithiothreitol (DTT). The activated proteins are purified from the unreacted cross-linkers via PD-10 desalting columns (Amersham Biosciences). The activated proteins are mixed in a 1:1 antibody:HA ratio. The uncoupled HA is removed from the coupled products, 41D3-HA and control monoclonal antibody-HA, by dialysis with a float-a-lyzer (Spectra/Por) with a MWCO 100,000.

Figure 9A:
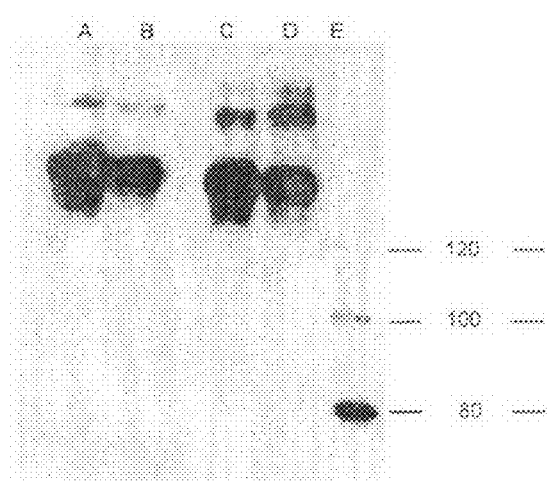
FIG. 9A is a xerographic reproduction of a digital image showing SDS-PAGE Western blot analysis showing visualization of coupling of antibody 13D12 with isolated native HA.
Figure 9B:
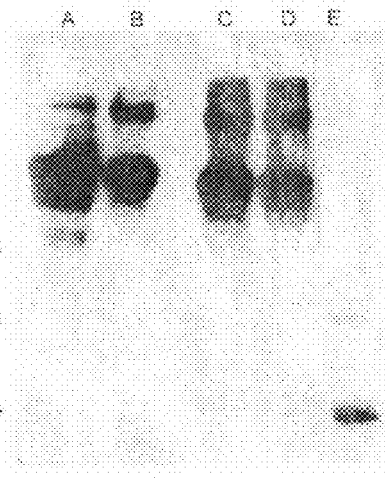
FIG. 9B is a xerographic reproduction of a digital image showing SDS-PAGE Western blot analysis showing visualization of coupling of antibody 41D3 with isolated native HA.
Figure 11:
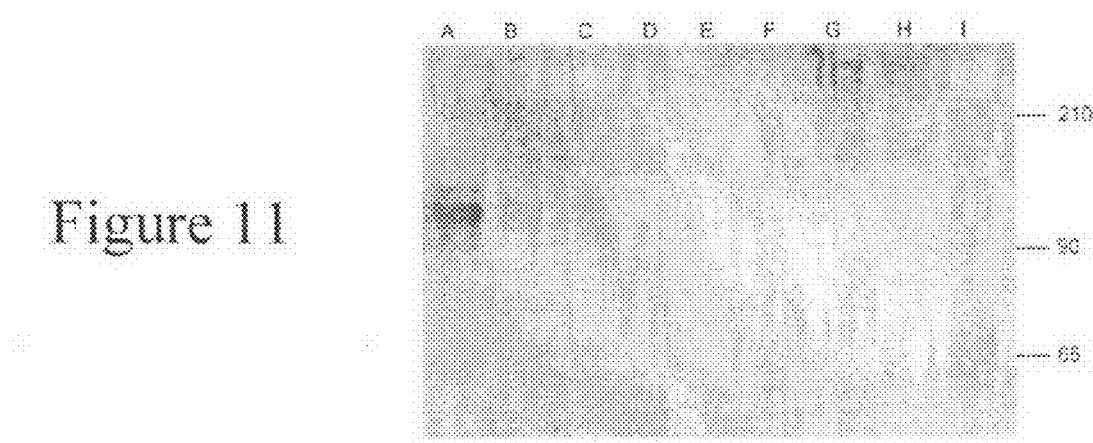
FIG. 11 is a xerographic reproduction of a digital image showing SDS-PAGE and Coomassie blue staining of different samples taken during the antibody-saporin conjugation protocol.

Coupling of the antibodies and HA to form conjugates is verified via SDS-PAGE followed by western blotting and by analysis of uptake of the coupling products by primary alveolar macrophages. For both antibodies there is a clear shift towards a bigger protein, which confirms that each antibody is coupled with HA. FIGS. 9A and 9B show visualization of coupling of antibodies 13D12, FIG. 9A, or 41D3, FIG. 9B, with isolated native HA. Samples taken during the coupling process are analyzed via SDS-PAGE followed by western blotting and detection via a mixture of 3 monoclonal antibodies recognizing HA of H1N1. Lane A: original antibody, lane B: SPDP treated antibody after PD-10 desalting column, lane C: HA coupled with antibody, lane D: HA coupled with antibody after dialysis and lane E: marker.

Vaccinations

Twelve six-week-old pigs are obtained from an influenza virus-seronegative farm and randomly assigned to 3 groups of 4 pigs. The animals are housed in isolation units with high efficiency particulate air (HEPA) filters. Water and feed are provided ad libitum. The first group of 4 pigs is immunized with 1 mg HA-13D12 conjugate per pig, the second group with 1 mg HA-41D3 conjugate per pig and the control group with the same volume of PBS without any protein. For each pig, the conjugate is diluted in 3 ml PBS. Half of the conjugate is injected intravenously and the other half intramuscularly in the neck.

Blood samples are collected from all pigs at the time of immunization and on day 4, 7, 11, 14 and 18 after immunization. The sera are examined in haemagglutination inhibition (HI) tests, virus neutralization (VN) test and in immunoperoxidase monolayer assays (IPMA) as described in Van Reeth, K., S. Van Gucht, and M. Pensaert, Vet Rec. 2003. 153(1): p. 9-13.

Haemagglutination Assay (HA)

Samples containing influenzavirus haemagglutinin are serially diluted and mixed with 0.5% chicken erythrocytes for one hour at room temperature. The highest dilution of that still shows haemaglutination is considered to be the haemagglutinating titer.

Haemagglutination Inhibition (HI)

The sera are examined in a haemagglutination inhibition (HI) test against H1N1 strain A/swine/Belgium/1/98. The inactivated sera are first treated with receptor-destroying enzyme (RDE) from *Vibrio cholera*, followed by inactivation of the enzyme via sodium citrate treatment. Afterwards, the sera are absorbed on chicken erythrocytes to remove non-specific inhibitors of influenza haemagglutination. The HI test is carried out according to standard procedures including positive and negative controls. Because of the pretreatments, the starting dilution of the sera was 1:10 followed by two-fold serum dilutions. Furthermore, each well was mixed with four haemagglutination units of the H1N1 strain and 0.5% chicken erythrocytes. After 1 hour incubation, the results are interpreted. In the presence of HA recognizing antibodies, no haemagglutination can be observed and the RBC will all be together in one spot on the bottom of the plate. The HI titer is the reverse of the titer needed for complete inhibition of haemagglutination. As a reference, positive and negative control sera are included in the HI tests.

Virus Neutralization (VN)

Sera are also examined in a virus neutralization (VN) test for the presence of H1N1 neutralizing antibodies. Two-fold serum dilutions are incubated with 100 tissue culture infectious doses (TCID$_{50}$) of A/swine/Belgium/1/98 virus. Madin-Darby canine kidney (MDCK) cells are then added at a concentration of 600,000 cells per ml. After 24 hours incubation, virus-positive cells are detected by immuno-peroxidase staining. Starting dilution of the sera was 1:2.

Immuno-Peroxidase Monolayer Assay (IPMA)

Figure 12:
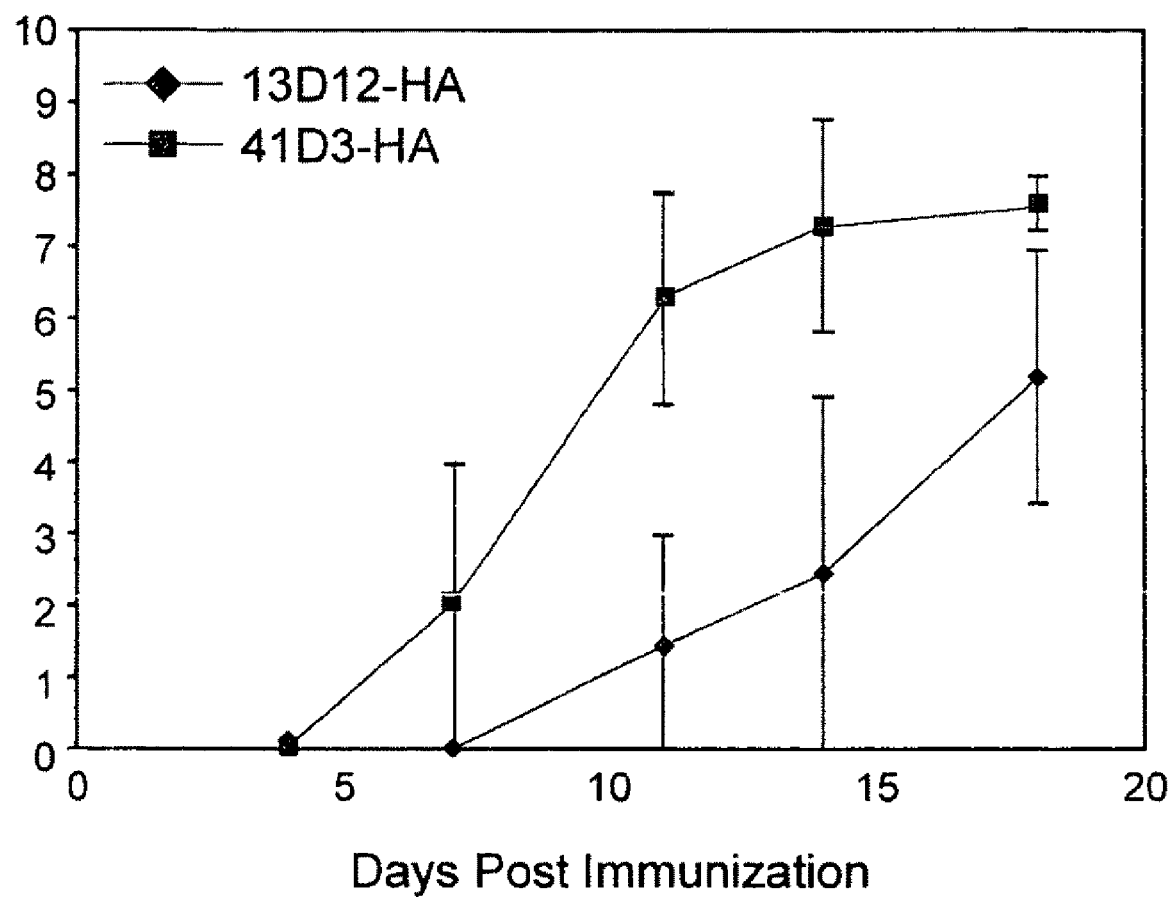
FIG. 12 is a graph showing mean immuno-peroxidase monolayer assay titers of pigs immunized with 13D12-HA or 41D3-HA.

Finally, sera are analysed via an immuno-peroxidase monolayer assay (IPMA) for the presence of influenza recognizing antibodies. Therefore, MDCK cells are grown for 24 hours in the presence of 1000 $TCID_{50}$ of A/swine/Belgium/1/98 virus. After fixation, cells were incubated with two-fold serum dilutions followed by immuno-peroxidase staining for antibody detection. Starting dilution of the sera is 1:2. Results are shown in FIG. 12. FIG. 12 shows mean immuno-peroxidase monolayer assay (IPMA) titers of pigs immunized with 13D12-HA or 41D3-HA. For each group, 4 pigs are immunized with native haemagglutinin (HA) coupled with the isotype matched (IgG1) control antibody 13D12, or HA coupled with 41D3, a monoclonal antibody directed against porcine sialoadhesin. Serum is collected at day 0, 4, 7, 11, 14 and 18 after immunization and analysed via an IPMA. Pigs immunized with HA coupled to the sialoadhesin specific mAb 41D3 show a faster induction and higher titers of IPMA antibodies.

Example 10

A conjugate composition including a sialoadhesin binding moiety and a cytotoxic agent is generated in this example. The cytotoxic agent saporin is a 30 kDa plant enzyme, belonging to the family of ribosome inactivating proteins (RIP). Saporin may be isolated from seeds of the plant *Saponaria officinalis* according to methods known in the art or obtained commercially. Saporin is used in this example as a representative of cytotoxic agents which may be included in a conjugate according to the present invention.

Saporin alone has no cell binding moiety and can thus not enter the cell. However, following conjugation with a sialoadhesin binding moiety to produce a conjugate, saporin is co-internalized in the cell along with the sialoadhesin binding moiety. Saporin is also representative of cytotoxic agents which are capable of linkage to a sialoadhesin binding moiety by a disulfide bond between the sialoadhesin binding moiety and saporin. Further cytotoxic agents are described in Thrush, G. R., et al., Annu Rev Immunol, 1996. 14: p. 49-71. The disulfide bond between the sialoadhesin binding moiety and saporin allows dissociation of toxin.

Conjugation of a Cytotoxic Agent with a Sialoadhesin Binding Moiety

The purified antibody 41D3 is conjugated to saporin (Sigma) via a disulfide-bridge. Therefore, the antibody and saporin are activated with the cross-linker SPDP (N-succinimidyl-3-(2-pyridyldithio)-propionate) according to the manufacturers instructions (Pierce Biotechnology). For saporin, the SPDP is activated with dithiothreitol and the proteins are purified from the unreacted cross-linkers with PD-10 desalting columns (Amersham Biosciences). The activated proteins are mixed in a 1:1 antibody:saporin ratio. The uncoupled saporin was removed from the coupling products by dialysis with a float-a-lyzer (Spectra/Por) with a MWCO 100,000.

Coupling of saporin and antibody 41D3 is verified via SDS-PAGE followed by coomassie blue staining and by analysis of uptake of the coupling products by primary alveolar macrophages. Coomassie blue staining of an SDS-PAGE shows a clear, upwards shift after conjugation, indicating an increased size, which confirms that part of the antibodies are coupled with saporin. The uncoupled proteins are clearly removed after dialysis. FIG. 11 shows SDS-PAGE and Coomassie blue staining of different samples taken during the antibody-saporin conjugation protocol. Lane I: marker, lane A: original antibody, lane B: SPDP treated antibody, lane C: SPDP treated antibody after PD-10 desalting column, lane D: original saporin, lane E: SPDP and DTT treated saporin, lane F: SPDP and DTT treated saporin after PD-10 desalting column, lane G: saporin coupled with antibody, lane H: saporin coupled with antibody after dialysis, and finally lane J: saporin coupled with antibody in the presence of the disulfide-reducing agent beta-mercapto-ethanol in the loading dye. For both antibodies there is a clear shift towards a bigger protein, which confirms that part of the antibodies are coupled with saporin. The uncoupled proteins are clearly removed after dialysis.

Saporin is conjugated to the mAb 41D3, resulting in a conjugate composition according to the present invention A control conjugate including a non-sialoadhesin recognizing antibody, mAb 13D12 and saporin is also generated.

The mAb 41D3/saporin conjugate and the control mAB 13D12/saporin conjugate are each separately incubated with sialoadhesin expressing primary porcine macrophages. After an appropriate time, the cells are immunostained and analyzed by confocal microscopy to determine whether the conjugate binds and is internalized into the cells. Incubation of cells with the mAb 41D3/saporin conjugate results in internalization of the conjugate, indicating that the 41D3 mAb is still functional to bind and stimulate internalization of the conjugate. In contrast, the mAb 41D3/saporin conjugate is observed not to be internalized.

Example 11

Cytotoxic effects of the mAb 41D3/saporin conjugate and the mAB 13D12/saporin conjugate on primary porcine macrophages are tested. Macrophages are incubated with various concentrations of either the mAb 41D3/saporin conjugate or the mAB 13D12/saporin conjugate for various periods of time. An MTT assay is used to colorimetrically assay cell populations and differentiate living and dead cells.

The following table shows OD values as a function of time and the percentage of living cells as a function of conjugate concentration as a result of these treatments:

| Macrophages | | | | | | |
|---|---|---|---|---|---|---|
| OD values: | 0 | 10 | 30 | 100 | APOP | Levend |
| 41D3-Sap | 0.772 | 0.537 | 0.541 | | 0.401 | 2.644 |
| 13D12-Sap | 0.851 | 0.708 | 0.703 | 0.780 | 0.445 | 2.824 |
| Average | 0.389 | | | | 0.423 | |
| % Living cells | 0 | $10^{-7}$ | $0.3*10^{-6}$ | $10^{-6}$ | | |
| 41D3-Sap | 89.8 | 29.3 | 30.4 | | | |
| 13D12-Sap | 110.2 | 73.4 | 72.1 | 91.9 | | |

FIG. 3 depicts the percentage of living cells as a function of conjugate concentration in graphical form.

Example 12

A mAb 41D3/saporin conjugate is incubated with various cells to assess the effect of the cytotoxic agent saporin. CHO cells that express recombinant sialoadhesin and CHO cells do not express sialoadhesin are each incubated with various amounts of the mAb 41D3/saporin conjugate and effects on cell viability are measured at various times following addition of the conjugate. An MTT assay is used to colorimetrically assay cell populations and differentiate living and dead cells.

The following table shows OD values as a function of time and the percentage of living cells as a function of conjugate concentration as a result of these treatments:

| CHO (41D3-Sap) | | | | | |
|---|---|---|---|---|---|
| OD values: | 0 | 6.25 | 12.5 | 25 | 50 |
| CHO-K1 | 3.475 | 3.379 | 3.299 | 2.873 | 2.822 |
| CHO-Sn | 2.054 | 1.45 | 1.474 | 1.354 | 1.47 |
| % Living cells | 0 | $10^{-7}$ | $0.1*10^{-6}$ | $0.25*10^{-6}$ | $0.5*10^{-6}$ |
| CHO-K1 | 100.0 | 96.9 | 94.2 | 80.3 | 78.6 |
| CHO-Sn | 100.0 | 63.0 | 64.4 | 57.1 | 64.2 |

Figure 4:
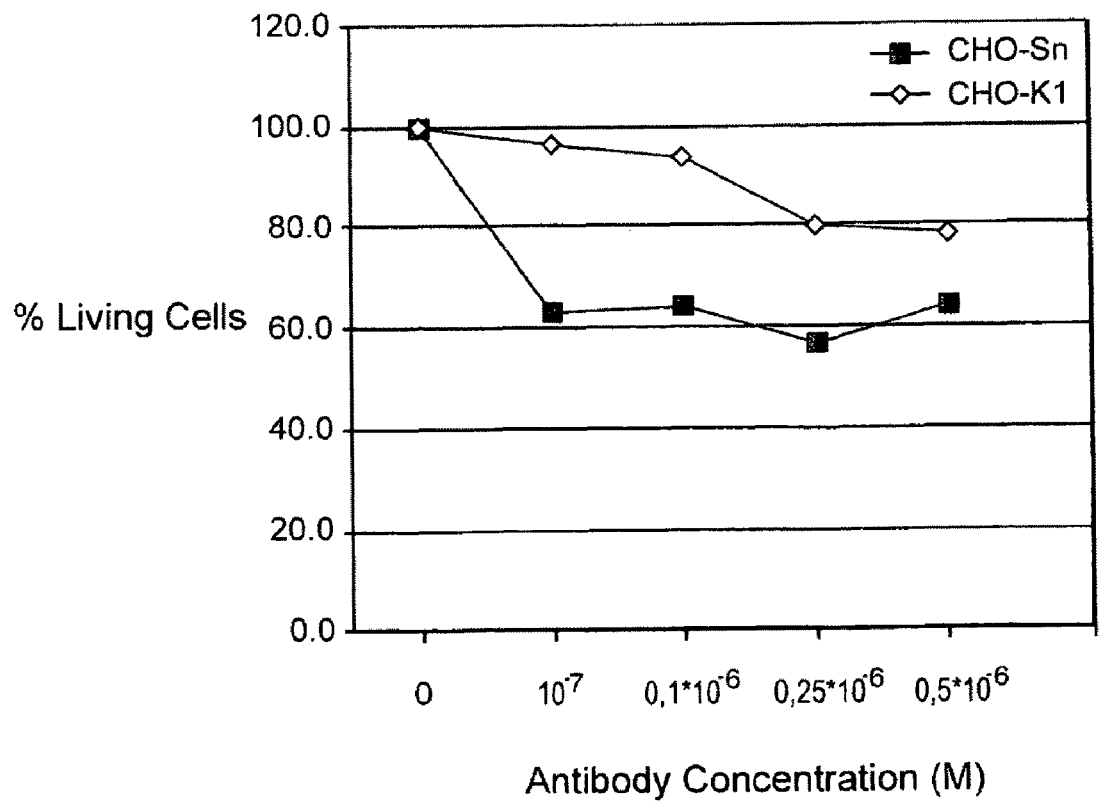
FIG. 4 is a graph illustrating the percentage of living cells in a population of sialoadhesin expressing cells treated with sialoadhesin binding moiety/cytotoxic agent conjugate compared to non-sialoadhesin expressing cells treated with a sialoadhesin binding moiety/cytotoxic agent conjugate.

FIG. 4 depicts the percentage of living cells as a function of conjugate concentration in graphical form. CHO-Sn indicates CHO cells expressing sialoadhesin. CHO-K1 indicates CHO cells which do not express sialoadhesin.

In Vivo Treatment of Pigs with Saporin-41D3 Immunotoxin

Pigs are injected intramuscularly with 0.1 or 1 mg saporin-41D3 conjugate in 1 ml of PBS/kg body weight, either as a single dose, or divided in two doses injected with an interval of 6 hours. Four pigs are used for each saporin-41D3 conjugate condition, four control pigs injected with PBS alone; twenty pigs in total. The pigs are euthanized 24 hours after the first injection and the local, draining lymph nodes are collected analyzed.

Flow Cytometry Analysis of Lymph Node Immune Cells

Changes in the immune cell population of the lymph nodes are analyzed by flow cytometry. Total immune cells are prepared from lymph nodes by mechanical dissociation or collagenase D digestion. For mechanical dissociation, lymph node samples are dissociation with needles and filtered on a 40 micron pore size nylon filter. Cells are collected into a 50-ml conical tube and washed twice in RPMI. For collagenase D digestion, lymph nodes are incubated for 1 h at 37° C. in RPMI with 1 mg collagenase D (Sigma)/ml. Cell suspensions are then filtered through a 40 micron pore size nylon filter and collected in RPMI with 30% FBS. After centrifugation for 15 min at 400×g, cells are washed three times with RPMI with 5% FBS. For erythrocyte lysis, cells are incubated for 5 min in 5 ml lysis solution (NH4Cl [0.15 M], KHC03 [1 mM], $Na^{2+}$EDTA [0.1 mM]) and washed three times in RPMI with 5% FBS. Monocyte/macrophage cells are identified with FITC-labelled SWC3 specific mAb 74-22-15. Sialoadhesin expressing macrophages are stained with biotinylated mAb 41D3, followed by FITC labelled streptavidin. Total T-cells are quantified by staining with a FITC-labelled CD3-specific mAb, while subpopulations of T-cells are quantified by staining with either FITC-labelled CD4 or CD8. B cells are identified with a FITC-labelled mouse monoclonal anti-pig IgM antibody (Clone M160).

Analysis of Lymph Node Micro-Anatomy

Samples of lymph nodes are fixed in a phosphate-buffered 3.5% formaldehyde solution for 24 h. After fixation, the samples are embedded in paraffin using an automated system (Shandon Citadel Tissue Processor, Cheshire, UK). Sections of 8 microns in thickness are made, deparaffinised in xylene, rehydrated in descending grades of alcohol, stained, dehydrated in ascending grades of alcohol and xylene, and mounted on slides with DPX. Haematoxylin-eosin staining is done to analyze the morphology and micro-anatomy of the lymph nodes of treated and untreated pigs.

Immunohistochemical Analysis

Samples from the draining lymph nodes are embedded in methylcellulose medium and frozen at −70° C. Cryostat sections (5 to 8 microns in thickness) are made and fixed in acetone for 20 min at −20° C. Sections are stained with one or more of the following:

(1) FITC labelled goat-anti-mouse IgG antibodies to detect the injected immunotoxin;

(2) biotinylated mAb 41D3 followed by FITC labelled streptavidin to allow quantification of sialoadhesin expressing cells and evaluate the effect of the immunotoxin on the numbers of sialoadhesin expressing cells;

(3) biotinylated antibody 74-22-15, an anti-SWC3 antibody which stains all monocytes and macrophages, not only the sialoadhesin expressing cells, followed by FITC-labelled streptavidin to assess the effect of the toxin on all cells of the monocyte macrophage lineage; and (4) biotinylated mAb 41D3 followed by FITC labelled streptavidin together with a staining with a goat polyclonal antibody specific for activated caspase-3 (apoptosis marker) followed by TexasRed labelled rabbit-anti-goat antibodies to quantify the total level of apoptosis and the number of apoptotic sialoadhesin expressing macrophages in the draining local lymph nodes of saporin-41D3 conjugate immunotoxin treated pigs.

In vivo administration of a sialoadhesin binding moiety/cytotoxic agent conjugate, such as a saporin-41D3 conjugate allows for assessment of the in vivo functionality of a sialoadhesin specific immunotoxin and assessment of the capacity of the conjugate to selectively kill sialoadhesin expressing macrophages in lymph nodes. Both in vitro and in vivo assay provide information on the dose and manner of administration that is optimal for depletion of sialoadhesin expressing macrophages in lymph nodes. Depletion of sialoadhesin expressing macrophages may have utility in treatment of specific diseases that involve macrophages, such as rheumatoid arthritis, inflammatory skin diseases, persistent infections and others.

Sialoadhesin Protein sand Nucleotide Sequences

Sequence ID No. 5 is a protein sequence for pig sialoadhesin identified by GenBank Accession number AF509585.1. Sequence ID No. 5:

```
MDFLLLLLLLASSALAGLASWTVSSPETVQGIKGSCLIIPCTFGFPANVEVPHGITAIWYYDYSGKRLVV

SHSRNPKVVENHFQGRALLLGQVEQRTCSLLLKDLQPQDSGSYNFRFEISEGNRWSDVKGTVVTVTEVPS

VPTIALPAKLHEGMEVDFNCSTPYVCPTEPVNLQWQGQDPTRSVTSHLQKLEPSGTSHMETLHMALSWQD

HGRILSCQVSAAERRMQKEIHLQVQYAPKGVEILFSHSGRNVLPGDLVTLSCQVNSSNPQVSSVQWVKDG

TKLKDQKRVLQLRRAAWADAGVYTCQAGNAVGSSVSPPVSLHVFMAEVQVSPVGSILENQTVTLACNTPK

EAPSELRYSWYKNHALLEGSHSRTLRLHSVTRADSGFYFCEVQNARGRERSPPVSVVVSHPPLTPDLTAF
```

-continued

```
LETQAGLVGILQCSVVSEPPATLVLSHGGLILASTSGEGDHSPRFSVASAPNSLRLEIQDLGPTDSGEYM
CSASSSLGNASSTLDFHANAARLLISPAAEVVEGQAVTLSCRSSLSLMPDTRFSWYLNGALILEGPSSSL
LLPAASSTDAGSYHCRAQNSHSTSGPSSPAVLTVLYAPRQPVFTAQLDPDTAGAGARQGLLLCRVDSDP
PAQLQLLHRGRVVASSLSWGGGCCTCGGCFHRMKVTKAPNLLRVEIRDPVLEDEGVYLCEASSALGNASA
SATLDAQATVLVITPSHTLQEGIEANLTCNVSREASGPANFSWFRDGALWAQGPLDTVTLLPVARTDAAL
YACRIVTEAGAGLSTPVALNVLYPPDPPKLSALLDVDQGHTAVFVCTVDSRPLAQLALFRGEHLLAASSA
LRLPPRGRLQAKASANSLQLEVRDLSLGDSGSYHCEATNILGSANTSLTFQVRGAWVRVSPSPELQEGQA
VVLSCQVPIGVLEGTSYRWYRDGQPLQESTSATLRFAAITLSQAGAYHCQAQAPGSATTDLAAPVSLHVT
YAPRQATLTTLMDSGLGRLGLLLCRVNSDPPAQLRLLHGSRLVASTLQGVEELAGSSPRLQVATAPNTLR
LEIHNAVLEDEGVYTCEATNTLGQTLASAAFDAQAMRVQVWPNATVQEGQLVNLTCLVWTTHLAQLTYTW
YRDQQQLPGAAHSILLPNVTVTDAASYRCGILIPGQALRLSRPVALDVLYAPRRLRLTHLLESRGGQLAV
VLCTVDSRPAAQLTLSHAGRLLASSTAASVPNTLRLELWEPRPSDEGLYSCSARSPLGQANTSLELRLEG
VQVALAPSATVPEGAPVTVTCEDPAARPPTLYVWYHNSRWLQEGSAASLSFPAATRAHAGAYTCQVQDAQ
GTRISQPAALHILYAPRDAVLSSFWDSRASPMAVVQCTVDSEPPAEMTLSHDGKVLATSHGVHGLAVGTG
HVQVARNALQLRVQNVPSRDKDTYVCMDRNSLGSVSTMGQLPEGVHVVAEPGLDVPEGTALNLSCRLPS
GPGHIGNSTFAWFRNGRQLHTESVPTLTFTHVARAQAGLYHCQAELPAGAATSAPVLLRVLYPPKTPTMT
VFVEPEGGIQGILDCRVDSEPLASLTLHLGSRLVASSQPQAAPAKPHIRVSASPNALRVDMEELKPSDQG
EYVCSASNALGSASAATYFGTRALHRLHLFQHLLWFLGLLASLLFLLLGLGVWYAWRRGNFYKLRMGEYS
VEMVSRKETTQMSTDQEEVTGIGDDAGSVNQAAFDPAHLCENTQSVKSTV
```

Sequence ID No. 6 is a nucleotide sequence encoding pig sialoadhesin identified by GenBank Accession number AF509585.1. Sequence ID No. 6:

```
   1 atggacttcc tgctcctgct cctcctcctg gcttcatctg ctctagcagg cctggcctcg
  61 tggacggttt ccagcccccga ccgtgcag ggcatcaagg gctcctgcct catcatcccc
 121 tgcaccttcg gcttcccggc caacgtggag gtgccccatg gcatcacagc catctggtac
 181 tatgactact caggcaagcg cctggtagtg agccactcca ggaacccaaa ggtggtggag
 241 aaccacttcc aaggccgggc cctgctgttg ggcaggttg aacagaggac gtgcagcctg
 301 ctgctgaagg acctgcagcc ccaggactcg gctcctata acttccgctt tgagatcagc
 361 gagggcaacc gctggtcaga tgtcaaaggc acagttgtca ccgtgacaga ggtgcccagc
 421 gtgcccacca ttgccttgcc agccaagctg catgagggca tggaggtgga cttcaactgc
 481 tccactccct atgtgtgccc gacggagccg gtcaacctac agtggcaagg ccaggatccc
 541 acccgctccg tcacctccca cctccagaag cttgagccct cgggcaccag ccacatggag
 601 accctgcaca tggccctgtc ctggcaggac catggccgga tcctgagctg ccaggtctca
 661 gcagccgaac gcaggatgca gaaggagatt cacctccaag tgcagtatgc ccccaagggt
 721 gtggagatcc ttttcagcca ctccggacgg aacgtccttc caggtgatct ggtcaccctc
 781 agctgccagg tgaatagcag caaccctcag gtcagttccg tgcagtgggt caaggatggg
 841 acgaagctca agaccagaa acgtgtactg cagttgcgcc gggcagcctg gctgatgct
 901 ggcgtctaca cctgccaagc cgggaatgcc gtgggctctt cagtctcacc ccggtcagc
 961 ctccacgtct tcatggctga ggtccaggta agcctgtgg gctccatcct ggagaaccag
1021 acggtgacgc tggcctgcaa tacacctaag gaagcgccca gcgagctgcg ctacagctgg
1081 tacaagaacc acgccctgct ggagggctct cacagccgca cctccggct gcactcagtt
1141 accagggcgg attcgggctt ctacttctgc gaggtgcaga acgcccgggg cagagagcgc
1201 tctccccctg tcagcgtggt ggtcagccac ccacccctca ccccggacct aactgccttc
```

-continued

```
1261 ctggagacac aggcggggct ggtgggcatc ctccaatgct ctgtggtcag cgagccccca
1321 gctactctgg tgttgtcaca cggggggcctc atcttggcct ctacctccgg ggagggtgac
1381 cacagcccac gcttcagtgt cgcctctgcc cccaactccc tgcgcctgga gattcaagac
1441 ctggggccaa cagacagtgg ggaatacatg tgctcagcca gcagttctct tgggaatgcg
1501 tcctccaccc tggacttcca tgccaatgca gcccgcctcc tcatcagccc agcagcagag
1561 gtggtggaag gcaggcggt gacactgagc tgcaggagca gcctgagcct gatgcctgac
1621 acccgttttt cctggtacct gaacggggcc ctgattctcg aggggcccag cagcagcctc
1681 ctgctcccag cagcctccag cacagatgcc ggctcatacc actgccgggc cagaacagc
1741 cacagcacca gcgggccctc ctcacctgct gttctcaccg tgctctacgc cccacgccag
1801 cccgtgttca ctgcccagct ggaccctgat actgcaggag ctggggccgg acgccaaggc
1861 ctcctcttgt gccgtgtgga cagcgacccc ccagcccagc tgcagctgct ccacaggggc
1921 cgtgttgtgg cctcttctct gtcatggggg ggcggctgct gcacctgcgg aggctgtttc
1981 caccgcatga aggtcaccaa agcacccaac ctactgcgtg tagagatccg agacccggtg
2041 ctggaggatg agggtgtgta cctgtgcgag gccagcagcg ccctgggcaa cgcctccgcc
2101 tctgcaacct tggatgccca ggccactgtc ctggtcatca caccgtcaca cacgctgcag
2161 gaaggcattg aagccaacct gacttgcaac gtgagccgtg aagccagcgg ccctgccaac
2221 ttctcctggt tccgagatgg ggcgctatgg gcccagggcc ctctggacac cgtgacgctg
2281 ctacctgtgg ccagaactga tgctgccctc tatgcttgcc gcatcgtcac cgaggctggt
2341 gctggcctct ccacccctgt ggccctgaat gtgctctatc ccccgatcc tccaaagttg
2401 tcagccctcc tggacgtgga ccagggccac acggctgtgt tcgtctgtac tgtggacagt
2461 cgccctcttg cccagttggc cctgttccgt ggggaacacc tcctggccgc cagctcggca
2521 ctccggctcc ccctcgtgg ccgcctccag gccaaagcct cggccaactc cttgcagcta
2581 gaggtccgag acttgagcct tggggactct ggcagctacc actgtgaggc caccaacatc
2641 cttggatcag ccaacacttc tcttaccttc caggtccgag agcctgggt ccgggtgtca
2701 ccgtcgcctg agctccagga gggccaggct gtggtcctga ctgccaggt acccatggg
2761 gtcctggagg ggacctcata tcgttggtat cgggatggcc agcccctcca ggagtccact
2821 tcggccacgc tccgttttgc agccataact ctgagccagg ctggagccta ccattgccaa
2881 gcccaagctc caggctcagc caccacggac ctggctgccc ctgtcagcct ccacgtgacc
2941 tacgcacctc gccaggccac actcaccacc ctgatggact caggcctcgg gcgactgggc
3001 ctccttctgt gccgtgtgaa cagtgaccct cctgcccagc tccgactgct ccatgggagc
3061 cgcctcgtgg cctctactct acaaggtgtg gaggagcttg caggcagctc tccccgccta
3121 caggtggcca cagcccccaa cacgctgcgc ctggagatcc acaacgcagt gctggaggat
3181 gaaggcgtct acacctgcga ggccaccaac acctgggtc agaccttggc ctccgccgcc
3241 ttcgatgccc aggctatgag agtgcaggtg tggcccaatg ccaccgtgca agaggggcag
3301 ctggtgaacc tgacctgcct tgtatggacc acgcacctgg cccagctcac ctacacgtgg
3361 taccgagacc agcagcagct cccaggtgct gcccactcca tcctcctgcc caatgtcact
3421 gtcacagatg ccgcctccta ccgctgtggc atattgatcc ctggccaggc actccgcctc
3481 tccagacctg tcgccctgga tgtcctctac gcaccccgca gactgcgcct gacccatctc
3541 ttggagagcc gtggtgggca gctggccgtg gtgctgtgca ctgtggacag tcgcccagct
3601 gcccagctga ccctcagcca tgctggccgc ctcctggcct cctcaaccgc agcctctgtc
```

-continued

```
3661 cccaacaccc tgcgcctgga gctgtgggag cccggccca gtgatgaggg tctctacagc
3721 tgctcggccc gcagtcctct gggccaggcc aacacatccc tggagctgcg gctagagggc
3781 gtgcaggtgg cactggctcc atcggccact gtgccggagg gggcccctgt cacagtgacc
3841 tgtgaagacc ctgctgcccg cccacccact ctctatgtct ggtaccacaa cagccgttgg
3901 ctgcaggagg ggtcggctgc ctccctctcg tttccagcgg ctacacgggc tcacgcgggc
3961 gcctatacct gccaggtcca ggatgcccag ggcacacgca tctcccagcc cgcagcactg
4021 cacatcctct atgcccctcg ggatgctgtc ctttcctcct tctgggactc aagggccagc
4081 ccctatgccg tggtacagtg cactgtggac agcgagccac ctgccgagat gaccctgtcc
4141 catgatggca aggtgctggc caccagccat ggggtccacg gcttagcagt ggggacaggc
4201 catgtccagg tggcccgcaa cgccctgcag ctgcgggtgc agaatgtgcc ctcacgtgac
4261 aaggacacct acgtctgcat ggaccgcaac tccttgggct cagtcagcac catggggcag
4321 ctgcagccag aaggtgtgca cgtggtagct gagccagggc tggatgtgcc tgaaggcaca
4381 gcgctgaacc tgagctgtcg cctccctagt ggccctgggc acataggcaa ctccacccttt
4441 gcttggttcc ggaacggtcg gcagctacac acagagtctg tgcccaccct taccttcacc
4501 catgtggccc gcgcccaagc tggcttgtac cactgccagg ctgagctccc cgccggggct
4561 gccacctctg ctccagtctt gctccgggtg ctctaccctc ccaagacgcc caccatgact
4621 gtttttgtgg agcccgaggg tggcatccag ggcattctgg actgccgagt ggacagtgag
4681 cccctagcca gcctgaccct ccacctgggc agtcggctgg tggcctccag ccagcctcag
4741 gctgcccctg ccaagccgca catccgcgtc tcagccagtc ccaatgcctt gcgagtggac
4801 atggaggagc tgaagcccag tgaccagggg gagtatgtgt gctcggcctc caatgccctg
4861 ggctctgcct ctgctgccac ctactcggga accagagccc tgcatcgcct gcatctgttc
4921 cagcaccttc tctggttcct ggggctgctg gcgagcctcc tcttcctact gttgggcctg
4981 ggggtctggt acgcctggag acggggaaat ttttacaagc tgagaatggg cgaatattca
5041 gtagagatgg tatctcggaa ggaaaccacg cagatgtcca ctgaccagga agaagttact
5101 ggaatcggtg atgatgcggg ctctgtgaac caggcggcat tgatcctgc ccacctctgt
5161 gaaaacacac agtctgtgaa aagcacagtc tga
```

Sequence ID No. 7 is a protein sequence for mouse sialoadhesin identified by GenBank Accession number NM_011426. Sequence ID No. 7

MCVLFSLLLLASVFSLGQTTWGVSSPKNVQGLSGSGLLIPCIFSYPADVPVSNGITAIWYYDYSGKRQVV

IHSGDPKLVDKRFRGRAELMGNMDHKVCNLLLKDLKPEDSGTYNFRFEISDNRWLDVKGTTVTVTTDPS

PPTITIPEELREGMERNFNCSTPYLCLQEKQVSLQWRGQDPTHSVTSSFQSLEPTGVYHQTTLHMALSWQ

DHGRTLLCQFSLGAHSSRKEVYLQVPHAPKGVEILLSSSGRNILPGDPVTLTCRVNSSYPAVSAVQWARD

GVNLGVTGHVLRLFSAAWNDSGAYTCQATNDMGSLVSSPLSLHVFMAEVKMNPAGPVLENETVTLLCSTP

KEAPQELRYSWYKNHILLEDAHASTLHLPAVTRADTGFYFCEVQNAQGSERSSPLSVVRYPPLTPDLTT

FLETQAGLVGILHCSVVSEPLATVVLSHGGLTLASNSGENDFNPRFRISSAPNSLRLEIRDLQPADSGEY

TCLAVNSLGNSTSSLDFYANVARLLINPSAEVVEGQAVTLSCRSGLSPAPDTRFSWYLNGALLLEGSSSS

LLLPAASSTDAGSYYCRTQAGPNTSGPSLPTVLTVFYPPRKPTFTARLDLDTSGVGDGRRGILLCHVDSD

PPAQLRLLHKGHVVATSLPSRCGSCSQRTKVSRTSNSLHVEIQKPVLEDEGVYLCEASNTLGNSSAAASF

NAKATVLVITPSNTLREGTEANLTCNVNQEVAVSPANFSWFRNGVLWTQGSLETVRLQPVARTDAAVYAC

RLLTEDGAQLSAPVVLSVLYAPDPPKLSALLDVGQGHMAVFICTVDSYPLAHLSLFRGDHLLATNLEPQR

PSHGRIQAKATANSLQLEVRELGLVDSGNYHCEATNILGSANSSLFFQVRGAWVQVSPSPELREGQAVVL

SCQVPTGVSEGTSYSWYQDGRPLQESTSSTLRIAAISLRQAGAYHCQAQAPDTAIASLAAPVSLHVSYTP

-continued

RHVTLSALLSTDPERLGHLVCSVQSDPPAQLQLFHRNRLVASTLQGADELAGSNPRLHVTVLPNELRLQI

HFPELEDDGTYTCEASNTLGQASAAADFDAQAVRVTVWPNATVQEGQQVNLTCLVWSTHQDSLSYTWYKG

GQQLLGARSITLPSVKVLDATSYRCGVGLPGHAPHLSRPVTLDVLHAPRNLRLTYLLETQGRQLALVLCT

VDSRPPAQLTLSHGDQLVASSTEASVPNTLRLELQDPRPSNEGLYSCSAHSPLGKANTSLELLLEGVRVK

MNPSGSVPEGEPVTVTCEDPAALSSALYAWFHNGHWLQEGPASSLQFLVTTRAHAGAYFCQVHDTQGTRS

SRPASLQILYAPRDAVLSSFRDSRTRLMVVIQCTVDSEPPAEMVLSHNGKVLAASHERHSSASGIGHIQV

ARNALRLQVQDVTLGDGNTYVCTAQNTLGSISTTQRLLTETDIRVTAEPGLDVPEGTALNLSCLLPGGSG

PTGNSSFTWFWNRHRLHSAPVPTLSFTPVVRAQAGLYHCRADLPTGATTSAPVMLRVLYPPKTPTLIVFV

EPQGGHQGILDCRVDSEPLAILTLHRGSQLVASNQLHDAPTKPHIRVTAPPNALRVDIEELGPSNQGEYV

CTASNTLGSASASAYFGTRALHQLQLFQRLLWVLGFLAGFLCLLLGLVAYHTWRKKSSTKLNEDENSAEM

ATKKNTIQEEVVAAL

Sequence ID No. 8 is a nucleotide sequence encoding mouse sialoadhesin
identified by GenBank Accession number NM_011426. Sequence ID No. 8:

```
   1 agacaagatt aggcctagag taagtctatg aaacacagag aaaggggaca gcataggggt
  61 taagaaatga ggtctttcaa aatctcaggg ggcaatgagg agttttttga gagaggaagg
 121 actctttaaa ggaagttgaa ggaggattct gtgaacttga gaccaccctg agctgccaag
 181 ttgagaactt tgtctacaaa caagccaggc agcctcagcg tgtgctcagt ccgacttgta
 241 gctggagagg caggagacca atttccggtg cttacggtgc ttgctggatg ccctggagta
 301 agtgacaggg tctcactgga ctccaggttc tgttggtttg agtaatagga ggcggcaggg
 361 gagaagtgaa gagagacatg cactgctgat ctgccttgag gctgtgtcct taaggggtgg
 421 agccaagggg cacagaagac tctctgggac atgccaccaa gtgagagcat ttccaatcac
 481 tccctgagcc aggaacaggg gcttctggtt ccctgctggt ggctgccaca gcagtccttc
 541 ctgttgggtt gaccaacaca gcaggtgaga taaaccctat agacttgggc cctggagtgc
 601 tccaggcagt ctctgtgtgc ctacccaccc ggcttcccta ggcacctgaa tgcacctggg
 661 cactgggatg tgtgtcctgt tctccctgct cctgctggcc tctgtcttct cactaggcca
 721 gaccacatgg ggtgtctcca gtcccaagaa tgtgcagggc ttgtcgggat cctgcctgct
 781 cattccctgc atcttcagct accctgccga tgtcccagtg tccaatggca tcacagccat
 841 ctggtactat gactactcgg gcaagcggca ggtggtaatc cactcagggg accccaagct
 901 ggtggacaag cgtttcaggg gtcgagctga actgatgggg aacatggacc acaaggtgtg
 961 caacctgttg ctcaaagact tgaagcctga agactctggc acctacaact tccgcttgga
1021 gatcagtgat agcaaccgct ggttagatgt caaaggcacc acggtcactg tgacaacgga
1081 tcccagcccc cccactatta ccattcctga ggagctgcgt gaaggcatgg agaggaactt
1141 caactgttcc acaccctacc tgtgcctgca ggagaagcaa gtcagcctgc agtggcgagg
1201 ccaggacccc acccactctg tcacctccag cttccagagc ctcgagccca ctggcgtcta
1261 tcaccagacg accctacata tggccctatc ctggcaggac cacggtcgga ccctgctctg
1321 ccagttctca ttgggcgcac acagtagtcg gaaagaggtt tacctgcaag tgccacatgc
1381 ccccaaaggt gtggagatcc tcctcagctc ctcaggagg aacatccttc ccggggatcc
1441 agtcacactc acctgcagag tgaacagcag ctatcctgct gtcagtgccg tgcagtgggc
1501 cagggacgga gtgaacctcg gagtcacggg acatgtgctt cggctgttct cagcagcctg
1561 gaatgattct ggggcctaca cctgccaagc aacaaatgat atgggctctc tggtgtcatc
1621 cccgctcagc ctccatgttt ttatggctga agtcaaaatg aaccccgcag ggcccgtctt
```

```
1681 ggaaaatgag acagtgactc tgctctgtag cacgccgaag gaggctcccc aggagctccg 1741 ctatagctgg tacaagaacc acattctcct ggaagatgcc catgcctcaa ccttgcacct 1801 gcctgcagtc accagggctg atactggctt ctacttctgt gaagtgcaga atgcccaggg 1861 cagtgagcgc tccagtccat tgagtgtggt ggtcagatat ccaccccta ctccagacct 1921 gaccaccttc ctggagacac aggccggact tgtgggcatc ttgcattgct ccgtggtcag 1981 tgagccctg gctactgtgg tgctgtcaca cggaggcctc acgttggcct ccaactctgg 2041 agaaaatgac ttcaaccccc gattcaggat ctcctctgcc cccaactccc tgcgcctaga 2101 aatccgagac ttgcagccag cagacagcgg agagtacaca tgcttagctg tcaactccct 2161 tggaaactca acgtccagcc tagacttcta tgctaatgtg gcccgactcc tcatcaaccc 2221 ttcagcagag gttgtggaag ggcaggcggt gaccctgagc tgcaggagtg gcctgagccc 2281 agctcctgac actcgcttct cctggtacct gaacggagct ctacttctgg aaggatccag 2341 cagcagcctc ctgcttcctg cggcttccag cactgatgcg ggctcatact actgtaggac 2401 gcaggctggc cccaacacca gcggcccctc cctgcctact gtcctcactg tgttctatcc 2461 cccaagaaag cccacattca ctgccaggct ggatttggat acctctggag tcggggatgg 2521 acgacggggc atcctcttgt gccacgtaga cagcgatccc ccagcccagc tacggcttct 2581 ccacaaaggc catgttgtgg ccacttctct gccatcaagg tgtgggagct gttcccagcg 2641 cacaaaagtc agcagaacct ccaactcact gcacgtggag atccagaagc ctgtattaga 2701 ggatgagggc gtgtacctgt gtgaggctag caacacattg ggcaactcct cagccgcagc 2761 ctctttcaat gctaaggcca ctgtactggt catcacaccg tcaaatacac tgcgtgaagg 2821 cacagaggcc aacctaactt gcaacgtgaa ccaggaggtt gctgtcagcc ctgccaactt 2881 ctcctggttc cggaatggag tgctgtggac ccagggatca ctggagactg tgaggctgca 2941 gcctgtggcc agaactgatg ctgctgtcta tgcctgccgc ctcctcaccg aggatggggc 3001 tcagctctcg gctcctgtgg tcctaagtgt gctgtatgcc ccagaccctc caaagctgtc 3061 agccctccta gatgtgggtc agggccacat ggccgtgttc atctgcactg tggacagcta 3121 tccctggct cacctgtctc tgttccgtgg ggaccatctc ctggccacca acttggaacc 3181 ccagcgtccc tccatggca ggatccaggc caaggccaca gccaactccc tgcagctaga 3241 ggtccgagaa ctaggtcttg tggactctgg aaactaccac tgtgaagcca ccaatattct 3301 tgggtcagcc aacagttcac tcttcttcca ggtcagagga gcctgggtcc aggtttcacc 3361 atcacctgag ctccgggagg ccaggctgt ggtcctgagc tgccaggtgc cacaggagt 3421 ctctgagggg acctcataca gctggtatca ggatggccgc cccctccagg agtcaacctc 3481 atctacactc cgcattgcag ccataagtct gaggcaagct ggtgcctacc attgccaagc 3541 tcaggcccca gacacagcta ttgccagcct ggctgcccct gtcagcctcc atgtgtccta 3601 taccccacgt catgttacac tcagtgccct gctgagcacg gaccctgagc gactaggcca 3661 cctggtgtgc agtgtacaaa gtgaccctcc agcgcagctg caactgtttc accggaatcg 3721 cctcgtggcc tctaccctac aaggcgcgga cgaattggca ggcagtaatc cccggctgca 3781 tgtgactgtg ctccccaatg agctgcgcct gcagatccac tttccagagc tggaggatga 3841 cgggacctat acatgcgaag ccagcaacac actgggccag gcctcggctg cagctgactt 3901 cgatgcccag gctgtgcgag tgactgtgtg gcccaatgcc actgtgcaag aggggcagca 3961 ggtgaacctg acctgcttgg tgtggagcac ccaccaggac tcactcagct acacatggta 4021 caagggcggg caacaactcc ttggtgccag atccatcacc ctgcccagtg ttaaggtttt 4081 ggatgctacc tcctaccgct gtggtgtggg gctccccggc cacgcacccc atctctccag
```

```
4141 acccgtgacc ctggatgtcc tccatgctcc ccgaaacctg cggctgacct acctcctaga
4201 gacccagggc aggcagctgg ccctggtact gtgtacggtg gatagtcgtc cacctgccca
4261 gctaactctc agccatggtg accagcttgt agcctcctca actgaagcct ctgtccccaa
4321 caccctgcgc ctagagcttc aggatccaag gcctagtaat gagggctct atagctgctc
4381 tgcccacagc ccattgggca aggccaacac gtccctggaa cttctgctgg aaggtgtccg
4441 agtgaaaatg aatccctctg gtagtgtacc cgagggagag cctgtcacag tgacctgcga
4501 ggaccctgct gccctctcat ccgccctcta tgcctggttt cacaatggcc attggcttca
4561 ggagggaccg gcttcctcac tccagttcct ggtgactaca cgggctcacg ctggtgctta
4621 cttttgccag gtgcatgata cacaaggcac acggagctcc agacctgcca gcctgcaaat
4681 tctctatgcc ccccgggatg ctgtcctgtc ttcctttcga gactcaagga ccaggctcat
4741 ggtcgtgatt cagtgcaccg tggacagtga gccacctgct gagatggtcc tatcccacaa
4801 tggcaaggtg ctagctgcca gccacgagcg tcacagctca gcatcaggga taggccacat
4861 ccaggtagcc cgaaatgctc ttcgactaca agtgcaagat gtgactctgg gtgatggcaa
4921 cacctatgtt tgcacagccc agaatacact gggctccatc agtaccaccc agaggcttct
4981 gacggagact gatatacgtg tgacagctga gccaggcttg gatgtgccag agggcacagc
5041 tctgaactta agctgcctcc tccctggtgg ctctgggccc acgggcaact cttccttcac
5101 gtggttctgg aatcgccacc gactacattc agctcctgtg cccacactct ccttcaccccc
5161 tgtggtccgg gctcaggctg ggctgtacca ctgcagggct gatctcccca ccggggccac
5221 tacctctgct ccagttatgc tccgtgtcct ctatcccccc aagacgccca ctctcatagt
5281 gtttgtggag cctcagggtg gccaccaggg catcctcgac tgtcgagtgg acagtgagcc
5341 cctggccatc ctcactcttc accggggcag tcaactagta gcctccaacc aacttcacga
5401 tgctcccacc aagccccaca tccgagtcac tgctcctccc aatgccttga gagtggacat
5461 agaggagctc ggccctagca atcaagggga gtatgtgtgc actgcctcca acactctggg
5521 ctctgcctca gcctctgcct actttgggac cagagctctg caccaactgc agctgttcca
5581 gaggctgctc tgggtcctgg gatttctggc aggcttcctg tgcctgctgc tgggtctggt
5641 ggcctatcac acctggagaa agaagagttc taccaagctg aatgaggatg agaattcagc
5701 agagatggcc actaagaaaa atactatcca ggaggaagtg gttgctgctc tctgacaact
5761 caggtgctgt gaacaagatc ctgcctacct ctgtataagc agtacagaga catctggctt
5821 tcctgacctg cccgacttgc cttccaagcc tcttgatcct aagaaaaatg gacgaaggga
5881 ggtttgggt tggaggtcaa cctgccgcct ccagggctct gagacggact cagccatgtt
5941 gcccacgtct ctctgtgtgg ttttcctctg tatcccttg cctttctctt caaagctcac
6001 cttggacttt cttggtgggt tagagcaaca tccagtttct cacagacttt ctaagacggt
6061 ctgtaccagc caggatatca gtcaggttgc tctaacagag actcaataca gtgaccacag
6121 catgacaggg tcttagtttt ccctcctggc ctggttatgt tgttgtggta tcagaatcct
6181 tcttgcttga ttttctccat tccccaagtg ttgcctttga ttatgaagct caggtaactg
6241 cagtgcccat ggaccctaca gggagaagga agagtgaagg gaagacatac ccatccccat
6301 ggtccatgga ctgtgtgtgc aattgcaccc cacccaactt ctcatccgct agaaactggt
6361 cacataaaca taccatgctg aaaggga Sequence ID No. 9 is a protein sequence for human sialoadhesin identi-
fied by GenBank Accession number NM_023068. Sequence ID No. 9
MGFLPKLLLLASFFPAGQASWGVSSPQDVQGVKGSCLLIPCIFSFPADVEVPDGITAIWYYDYSGQRQVV
```

-continued

SHSADPKLVEARFRGRTEFMGNPEHRVCNLLLKDLQPEDSGSYNFRFEISEVNRWSDVKGTLVTVTEEPR

VPTIASPVELLEGTEVDFNCSTPYVCLQEQVRLQWQGQDPARSVTFNSQKFEPTGVGHLETLHMAMSWQD

HGRILRCQLSVANHRAQSEIHLQVKYAPKGVKILLSPSGRNILPGELVTLTCQVNSSYPAVSSIKWLKDG

VRLQTKTGVLHLPQAAWSDAGVYTCQAENGVGSLVSPPISLHIFMAEVQVSPAGPILENQTVTLVCNTPN

EAPSDLRYSWYKNHVLLEDAHSHTLRLHLATRADTGFYFCEVQNVHGSERSGPVSVVVNHPPLTPVLTAF

LETQAGLVGILHCSVVSEPLATLVLSHGGHILASTSGDSDHSPRFSGTSGPNSLRLEIRDLEETDSGEYK

CSATNSLGNATSTLDFHANAARLLISPAAEVVEGQAVTLSCRSGLSPTPDARFSWYLNGALLHEGPGSSL

LLPAASSTDAGSYHCRARDGHSASGPSSPAVLTVLYPPRQPTFTTRLDLDAAGAGAGRRGLLLCRVDSDP

PARLQLLHKDRVVATSLPSGGGCSTCGGCSPRMKVTKAPNLLRVEIHNPLLEEEGLYLCEASNALGNAST

SATFNGQATVLAIAPSHTLQEGTEANLTCNVSREAAGSPANFSWFRNGVLWAQGPLETVTLLPVARTDAA

LYACRILTEAGAQLSTPVLLSVLYPPDRPKLSALLDMGQGHMALFICTVDSRPLALLALFHGEHLLATSL

GPQVPSHGRFQAKAEANSLKLEVRELGLGDSGSYRCEATNVLGSSNTSLFFQVRGAWVQVSPSPELQEGQ

AVVLSCQVHTGVPEGTSYRWYRDGQPLQESTSATLRFAAITLTQAGAYHCQAQAPGSATTSLAAPISLHV

SYAPRHVTLTTLMDTGPGRLGLLLCRVDSDPPAQLRLLHGDRLVASTLQGVGGPEGSSPRLHVAVAPNTL

RLEIHGAMLEDEGVYICEASNTLGQASASADFDAQAVNVQVWPGATVREGQLVNLTCLVWTTHPAQLTYT

WYQDGQQRLDAHSIPLPNVTVRDATSYRCGVGPPGRAPRLSRPITLDVLYAPRNLRLTYLLESHGGQLAL

VLCTVDSRPPAQLALSHAGRLLASSTAASVPNTLRLELRGPQPRDEGFYSCSARSPLGQANTSLELRLEG

VRVILAPEAAVPEGAPITVTCADPAAHAPTLYTWYHNGRWLQEGPAASLSFLVATRAHAGAYSCQAQDAQ

GTRSSRPAALQVLYAPQDAVLSSFRDSRARSMAVIQCTVDSEPPAELALSHDGKVLATSSGVHSLASGTG

HVQVARNALRLQVQDVPAGDDTYVCTAQNLLGSISTIGRLQVEGARVVAEPGLDVPEGAALNLSCRLLGG

PGPVGNSTFAWFWNDRRLHAEPVPTLAFTHVARAQAGMYHCLAELPTGAAASAPVMLRVLYPPKTPTMMV

FVEPEGGLRGILDCRVDSEPLASLTLHLGSRLVASSQPQGAPAEPHIHVLASPNALRVDIEALRPSDQGE

YICSASNVLGSASTSTYFGVRALHRLHQFQQLLWVLGLLVGLLLLLLGLGACYTWRRRRVCKQSMGENSV

EMAFQKETTQLIDPDAATCETSTCAPPLG

```
Sequence ID No. 10 is a nucleotide sequence encoding mouse
sialoadhesin identified by GenBank Accession number NM_023068.
Sequence ID No. 10:
    1 atgggcttct tgcccaagct tctcctcctg gcctcattct tcccagcagg ccaggcctca 61 tggggcgtct ccagtcccca ggacgtgcag ggtgtgaagg ggtcttgcct gcttatcccc 121 tgcatcttca gcttccctgc cgacgtggag gtgcccgacg gcatcacggc catctggtac 181 tacgactact cgggccagcg gcaggtggtg agccactcgg cggaccccaa gctggtggag 241 gcccgcttcc gcggccgcac cgagttcatg gggaacccccg agcacagggt gtgcaacctg 301 ctgctgaagg acctgcagcc cgaggactct ggttcctaca cttccgcttc gagatcagt 361 gaggtcaacc gccggtcaga tgtgaaaggc accttggtca cagtaacaga ggagcccagg 421 gtgcccacca ttgcctcccc ggtggagctt ctcgagggca cagaggtgga cttcaactgc 481 tccactccct acgtatgcct gcaggagcag gtcagactgc agtggcaagg ccaggaccct 541 gctcgctctg tcaccttcaa cagccagaag tttgagccca ccggcgtcgg ccacctggag 601 accctccaca tggccatgtc ctggcaggac acggccgga tcctgcgctg ccagctctcc 661 gtggccaatc acagggctca gagcgagatt cacctccaag tgaagtatgc ccccaagggt 721 gtgaagatcc tcctcagccc ctcggggagg aacatccttc aggtgagct ggtcacactc 781 acctgccagg tgaacagcag ctaccctgca gtcagttcca ttaagtggct caaggatggg 841 gtacgcctcc aaaccaagac tggtgtgctg cacctgcccc aggcagcctg gagcgatgct
```

-continued

```
 901 ggcgtctaca cctgccaagc tgagaacggc gtgggctctt tggtctcacc ccccatcagc 961 ctccacatct tcatggctga ggtccaggtg agcccagcag gtcccatcct ggagaaccag 1021 acagtgacac tagtctgcaa cacacccaat gaggcaccca gtgatctccg ctacagctgg 1081 tacaagaacc atgtcctgct ggaggatgcc cactcccata ccctccggct gcacttggcc 1141 actagggctg atactggctt ctacttctgt gaggtgcaga acgtccatgg cagcgagcgc 1201 tcgggccctg tcagcgtggt agtcaaccac ccgcctctca ctccagtcct gacagccttc 1261 ctggagaccc aggcgggact tgtgggcatc cttcactgct ctgtggtcag tgagccctg 1321 gccacactgg tgctgtcaca tgggggtcat atcctggcct ccacctccgg gacagtgat 1381 cacagcccac gcttcagtgg tacctctggt cccaactccc tgcgcctgga gatccgagac 1441 ctggaggaaa ctgacagtgg ggagtacaag tgctcagcca ccaactccct tggaaatgca 1501 acctccaccc tggacttcca tgccaatgcc gcccgtctcc tcatcagccc ggcagccgag 1561 gtggtggaag acaggcagt gacactgagc tgcagaagcg gcctaagccc cacacctgat 1621 gcccgcttct cctggtacct gaatggagcc ctgcttcacg agggtcccgg cagcagcctc 1681 ctgctccccg cggcctccag cactgacgcc ggctcatacc actgccgggc ccgggacggc 1741 cacagtgcca gtggccctc ttcgccagct gttctcactg tgctctaccc ccctcgacaa 1801 ccaacattca ccaccaggct ggaccttgat gccgctgggg ccggggctgg acggcgaggc 1861 ctccttttgt gccgtgtgga cagcgacccc ccgccaggc tgcagctgct ccacaaggac 1921 cgtgttgtgg ccacttccct gccatcaggg ggtggctgca gcacctgtgg gggctgttcc 1981 ccacgcatga aggtcaccaa agccccccaac ttgctgcgtg tggagattca caaccctttg 2041 ctggaagagg agggcttgta cctctgtgag gccagcaatg ccctgggcaa cgcctccacc 2101 tcagccacct tcaatggcca ggccactgtc ctggccattg caccatcaca cacacttcag 2161 gagggcacag aagccaactt gacttgcaac gtgagccggg aagctgctgg cagccctgct 2221 aacttctcct ggttccgaaa tgggtgtctg tgggcccagg gtcccctgga gaccgtgaca 2281 ctgctgcccg tggccagaac tgatgctgcc ctttacgcct gccgcatcct gactgaggct 2341 ggtgcccagc tctccactcc cgtgctcctg agtgtactct atcccccgga ccgtccaaag 2401 ctgtcagccc tcctagacat gggccagggc cacatggctc tgttcatctg cactgtggac 2461 agccgccccc tggccttgct ggccttgttc catggggagc acctcctggc caccagcctg 2521 ggtcccagg tccatccca tggtcggttc caggctaaag ctgaggccaa ctccctgaag 2581 ttagaggtcc gagaaccggg ccttggggac tctggcagct accgctgtga ggccacaaat 2641 gttcttggat catccaacac ctcactcttc ttccaggtcc gaggagcctg gtccaggtg 2701 tcaccatcac ctgagctcca agagggccag gctgtggtcc tgagctgcca ggtacacaca 2761 ggagtcccag aggggacctc atatcgttgg tatcgggatg ccagcccct ccaggagtcg 2821 acctcggcca cgctccgctt tgcagccata actttgacac aagctgggc ctatcattgc 2881 caagcccagg ccccaggctc agccaccacg agcctagctg cacccatcag cctccacgtg 2941 tcctatgccc cacgccacgt cacactcact accctgatgg acacaggccc tggacgactg 3001 ggcctcctcc tgtgccgtgt ggacagtgac cctccgcc agctgcggct gctccacggg 3061 gatcgccttg tggcctccac cctacaaggt gtgggggac ccgaaggcag ctctcccagg 3121 ctgcatgtgg ctgtggcccc caacacactg cgtctggaga tccacgggc tatgctggag 3181 gatgagggtg tctatatctg tgaggcctcc aacacccctgg ccaggcctc ggcctcagct 3241 gacttcgacg ctcaagctgt gaatgtgcag gtgtggcccg ggctaccgt gcgggagggg 3301 cagctggtga acctgacctg ccttgtgtgg accactcacc cggcccagct cacctacaca
```

```
3361 tggtaccagg atgggcagca gcgcctggat gcccactcca tcccctgcc caacgtcaca
3421 gtcagggatg ccacctccta ccgctgcggt gtgggccccc ctggtcgggc accccgcctc
3481 tccagaccta tcaccttgga cgtcctctac gcgccccgca acctgcgcct gacctacctc
3541 ctggagagcc atggcgggca gctggccctg gtactgtgca ctgtggacag ccgcccgccc
3601 gcccagctgg ccctcagcca cgccggtcgc ctcttggcct cctcgacagc agcctctgtc
3661 cccaacaccc tgcgcctgga gctgcgaggg ccacagccca gggatgaggg tttctacagc
3721 tgctctgccc gcagccctct gggccaggcc aacacgtccc tggagctgcg gctggagggt
3781 gtgcgggtga tcctggctcc ggaggctgcc gtgcctgaag tgcccccat cacagtgacc
3841 tgtgcggacc ctgctgccca cgcacccaca ctctatactt ggtaccacaa cggtcgttgg
3901 ctgcaggagg tccagctgc ctcactctca ttcctggtgg ccacgcgggc tcatgcaggc
3961 gcctactctt gccaggccca ggatgcccag ggcacccgca gctcccgtcc tgctgccctg
4021 caagtcctct atgcccctca ggacgctgtc ctgtcctcct tccgggactc cagggccaga
4081 tccatggctg tgatacagtg cactgtggac agtgagccac ctgctgagct ggccctatct
4141 catgatggca aggtgctggc cacgagcagc ggggtccaca gcttggcatc agggacaggc
4201 catgtccagg tggcccgaaa cgccctacgg ctgcaggtgc aagatgtgcc tgcaggtgat
4261 gacacctatg tttgcacagc ccaaaacttg ctgggctcaa tcagcaccat cgggcggttg
4321 caggtagaag gtgcacgcgt ggtggcagag cctggcctgg acgtgcctga gggcgctgcc
4381 ctgaacctca gctgccgcct cctgggtggc cctgggcctg tgggcaactc cacctttgca
4441 tggttctgga atgaccggcg gctgcacgcg gagcctgtgc ccactctcgc cttcacccac
4501 gtggctcgtg ctcaagctgg gatgtaccac tgcctggctg agctcccac tggggctgct
4561 gcctctgctc cagtcatgct ccgtgtgctc taccctccca agacgcccac catgatggtc
4621 ttcgtggagc tgagggtgg cctccgggc atcctggatt gccgagtgga cagcgagccg
4681 ctcgccagcc tgactctcca ccttggcagt cgactggtgg cctccagtca gccccagggt
4741 gctcctgcag agccacacat ccatgtcctg gcttcccca atgccctgag ggtggacatc
4801 gaggcgctga ggcccagcga ccaaggggaa tacatctgtt ctgcctcaaa tgtcctgggc
4861 tctgcctcta cctccaccta ctttggggtc agagccctgc accgcctgca tcagttccag
4921 cagctgctct gggtcctggg actgctggtg gcctcctgc tcctgctgtt gggcctgggg
4981 gcctgctaca cctggagaag gaggcgtgtt tgtaagcaga gcatgggcga gaattcggtg
5041 gagatggctt ttcagaaaga gaccacgcag ctcattgatc ctgatgcagc cacatgtgag
5101 acctcaacct gtgccccacc cctgggctga ccagtggtgt tgcctgccct ccggaggaga
5161 aagtggccag aatctgtgat gactccagcc tatgaatgtg aatgaggcag tgttgagtcc
5221 tgcccgcctc tacgaaaaca gctctgtgac atctgacttt ttatgacctg gccccaagcc
5281 tcttgccccc ccaaaaatgg gtggtgagag gtctgcccag gagggtgttg accctggagg
5341 acactgaaga gcactgagct gatctcgctc tctcttctct ggatctcctc ccttctctcc
5401 atttctcccct caaaggaagc cctgccctt cacatccttc tcctcgaaag tcaccctgga
5461 ctttggttgg attgcagcat cctgcatcct cagaggctca ccaaggcatt ctgtattcaa
5521 cagagtatca gtcagcctgc tctaacaaga gaccaaatac agtgacttca acatgataga
5581 attttatttt tctctcccac gctagtctgg ctgtlacgat ggtttatgat gttggggctc
5641 aggatccttc tatcttcctt ttctctatcc ctaaaatgat gcctttgatt gtgaggctca
5701 ccatggcccc gctttgtcca catgccctcc agccagaaga aggaagagtg gaggtagaag
```

-continued

```
5761 cacacccatg cccatggtgg acgcaactca gaagctgcac aggacttttc cactcacttc 5821 ccattggctg gagtattgtc acatggctac tgcaagctac aagggagact gggaaatgta 5881 gtttttattt tgagtccaga ggacatttgg aattggactt ccaaaggact cccaactgtg 5941 agctcatccc tgagactttt gacattgttg ggaatgccac cagcaggcca tgttttgtct 6001 cagtgcccat ctactgaggg ccagggtgtg ccoctggcca ttctggttgt gggcttcctg 6061 gaagaggtga tcactctcac actaagactg aggaaataaa aaaggtttgg tgttttccta 6121 gggagagagc atgccaggca gtggagttgc ctaagcagac atccttgtgc cagatttggc 6181 ccctgaaaga agagatgccc tcattcccac caccaccccc cctaccccca gggactgggt 6241 actaccttac tggcccttac aagagtggag ggcagacaca gatgttgtca gcatccttat 6301 tcctgctcca gatgcatctc tgttcatgac tgtgtgagct cctgtcctt tcctggagac 6361 cctgtgtcgg gctgttaaag agaatgagtt accaagaagg aatgacgtgc ccctgcgaat 6421 cagggaccaa caggagagag ctcttgagtg ggctagtgac tcccctgca gctggtgga 6481 gatggtgtga ggagcgaaga gccctctgct ctaggatttg ggttgaaaaa cagagagaga 6541 agtggggagt tgccacagga gctaacacgc tgggaggcag ttgggggcgg gtgaactttg 6601 tgtagccgag gccgcaccct ccctcattcc aggctcattc attttcatgc tccattgcca 6661 gactcttgct gggagcccgt ccagaatgtc ctcccaataa aactccatcc tatgacgcaa 6721 aaaaaaaaaa aaaaaa
```

Any patents or publications mentioned in this specification are incorporated herein by reference to the same extent as if each individual publication is specifically and individually indicated to be incorporated by reference. Protein and nucleic acid sequences identified by a database accession number are incorporated herein by reference in their entirety. This application claims priority to U.S. Provisional Patent Application Ser. No. 60/799,566, filed May 11, 2006, the entire content of which is incorporated herein by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of delivering a cargo moiety to a cell, the method comprising:
   contacting a cell expressing sialoadhesin with a conjugate, the conjugate comprising a sialoadhesin binding moiety and a cargo moiety, and
   treating the cell with interferon-alpha to induce or enhance expression of sialoadhesin, wherein the sialoadhesin binding moiety binds to the sialoadhesin expressed by the cell,
   thereby delivering the cargo moiety to the cell.

2. The method of claim 1 wherein the cell is a macrophage.

3. The method of claim 1 wherein the sialoadhesin binding moiety is an antibody.

4. The method of claim 1 wherein the sialoadhesin binding moiety is a sialoadhesin ligand.

5. The method of claim 1 wherein the cargo moiety is an antigen.

6. The method of claim 1 wherein the cargo moiety is an inhibitor of the cell.

7. The method of claim 1 wherein the cargo moiety is a cytotoxic agent.

8. The method of claim 7 wherein the cytotoxic agent is a ribosome inactivating protein.

9. The method of claim 7 wherein the cytotoxic agent is saporin.

10. The method of claim 1, wherein the cargo moiety is an antimicrobial agent effective to inhibit a microbe selected from the group consisting of: a bacterium, a virus, a fungus, a protozoan, and a combination thereof.

11. The method of claim 1, wherein the cargo moiety comprises a nucleic acid.

12. The method of claim 5 wherein the antigen is selected from the group consisting of: a protein, a peptide, a glycoprotein and a glycopeptide.

13. A method of delivering a cargo moiety to a cell, the method comprising:
contacting a cell expressing sialoadhesin with a conjugate, the conjugate comprising a sialoadhesin binding moiety and a cargo moiety,
wherein the sialoadhesin binding moiety binds to sialoadhesin expressed by the cell, thereby delivering the cargo moiety to the cell, and wherein the cargo moiety is an antigen and the antigen is an influenza virus hemagglutinin or an antigenic portion thereof.

14. The method of claim 13 wherein the antigenic portion of an influenza virus hemagglutinin is SEQ ID NO: 4.

15. The method of claim 13, wherein the cell is in vitro.

16. The method of claim 13, wherein the cell is in vivo.

17. The method of claim 13, further comprising treating the cell with a cytokine effective to induce or enhance expression of sialoadhesin.

18. The method of claim 17 wherein the cell is selected from the group consisting of: a monocyte, a monocyte cell line, a macrophage and a macrophage cell line.

19. The method of claim 18 wherein the cell is selected from the group consisting of: a human cell and a human-derived cell line.

20. The method of claim 19 wherein the human-derived cell line is human monocyte cell line THP-1.

21. The method of claim 1 wherein the cell is transfected with an expression construct encoding sialoadhesin.

22. The method of claim 1 wherein the cell is a mammalian cell.

23. A method of stimulating an immune response to an antigen in a subject, comprising:
administering a composition comprising a sialoadhesin binding moiety conjugated to a cargo moiety, wherein the cargo moiety thereof is an antigen comprising influenza virus hemagglutinin, to the subject.

24. The method of claim 23 wherein the is influenza virus hemagglutinin is isolated from an influenza virus.

25. The method of claim 23 wherein the influenza virus hemagglutinin is recombinant.

26. The method of claim 25, wherein the recombinant influenza virus protein is an extracellular portion of an influenza virus hemagglutinin made by expression of the nucleic acid sequence of SEQ ID NO: 3.

27. The method of claim 23, wherein the influenza virus hemagglutinin is SEQ ID NO: 4.

28. A method of stimulating an immune response to an antigen in a subject, comprising:
administering to the subject a composition comprising a sialoadhesin binding moiety conjugated to a cargo moiety, wherein the cargo moiety thereof is an antigen and wherein the sialoadhesin binding moiety is an antibody.

29. The method of claim 28 wherein the sialoadhesin binding moiety is selected from the group consisting of: monoclonal antibody 41D3, monoclonal antibody 7D2 and monoclonal antibody MCA2316.

30. The method according to claim 28, wherein the antigen is selected from the group consisting of a protein, a peptide, a glycoprotein, and a glycopeptide.

31. The method according to claim 28, wherein the antigen is influenza virus hemagglutinin isolated from an influenza virus.

32. The method according to claim 28, wherein the antigen is recombinant influenza virus hemagglutinin.

33. The method according to claim 32, wherein the recombinant influenza protein is an extracellular portion of an influenza virus hemagglutinin made by expression of the nucleic acid sequence of SEQ ID NO: 3.

34. The method according to claim 31, wherein the antigen is SEQ ID NO: 4.

35. The method according to claim 29, wherein the antigen is influenza virus hemagglutinin isolated from an influenza virus.

36. The method according to claim 29, wherein the antigen is recombinant influenza virus hemagglutinin.

37. The method according to claim 36, wherein the recombinant influenza protein is an extracellular portion of an influenza virus hemagglutinin made by expression of the nucleic acid sequence of SEQ ID NO: 3.

38. The method according to claim 35, wherein the antigen is SEQ ID NO: 4.

* * * * *

UNITED STATES PATENT AND TRADEMARK OFFICE
CERTIFICATE OF CORRECTION

PATENT NO. : 7,998,485 B2  Page 1 of 1
APPLICATION NO. : 12/227106
DATED : August 16, 2011
INVENTOR(S) : Nauwynck et al.

It is certified that error appears in the above-identified patent and that said Letters Patent is hereby corrected as shown below:

On the title page:
In ITEM [56] References Cited
    FOREIGN PATENT DOCUMENTS
    LINE 6,                     change "WO 99/61463" to --WO 99/24078--

In the claims:
CLAIM 24, COLUMN 170, LINE 1,    change "the is influenza" to --the influenza--

Signed and Sealed this
Twenty-fourth Day of December, 2013

Margaret A. Focarino
*Commissioner for Patents of the United States Patent and Trademark Office*

SEQUENCE LISTING

```
<160> NUMBER OF SEQ ID NOS: 10

<210> SEQ ID NO 1
<211> LENGTH: 41
<212> TYPE: DNA
<213> ORGANISM: Artificial Sequence
<220> FEATURE:
<223> OTHER INFORMATION: primer

<400> SEQUENCE: 1
gaagatctca ccatggaagc aaaactgttt gtattattct g                        41

<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2
tccccgcgga atctggtaaa ctcccattga ttc                                 33

<210> SEQ ID NO 3
<211> LENGTH: 1590
<212> TYPE: DNA
```

<213> ORGANISM: Influenza virus

<400> SEQUENCE: 3

```
atggaagcaa aactgtttgt attattctgt gtattcaatg cgctgaaagc tgacaccatt      60
tgtgtaggct accatgctaa caattccaca gacactgtcg acacaatact ggagaaaaat     120
gtgactgtta cccattcagt taatttacta gaaaacagcc ataatggaaa actctgcagc     180
ctgaatggaa agcccccct acaactgggg aactgcaacg tagcaggatg gatccttggc      240
aacccagaat gtgacttgtt gctcacagcg aattcatggt cttacataat agagacttca     300
aattcaaaaa atggaaaatg ctaccccgga gaattcgctg attatgagga attaagggag     360
cagctgagta cagtttcttc atttgaaaga tttgaaattt tcccaaaagc aacctcatgg     420
ccagatcatg agacaaccaa aggtaccaca actgcatgct cccactctgg aaccagcagt     480
ttttaccgga acttgctatg gatagtaaag aagggaaact cctatcctaa gctcagcaag     540
tcatacacaa acaacaaagg aaaagaagtg cttgtaatct ggggagtgca ccaccctccg     600
actaacagtg accaacaaac cctctaccag aatgcttata catatgtttc agttgaatca     660
tcaaaatact accgaaggtt cacaccagaa atagcagcta gacctaaagt cagaggacaa     720
gcaggcagaa tgaattatta ttggacactg ttagatcaag agacaccat aacatttgaa      780
gccactggga acttaatagc accatggtac gcatttgctt tgaataaggg ctctaattct     840
ggaattatga tgtcggatgc tcatgttcac aattgcacta caaagtgcca aactcctcat     900
ggggccttga aaagtaatct ccttttcag aacgtacatc ccatcactat ggagaatgc       960
cctaaatatg ttaaaagcac ccaactaaga atggcaacag gattaagaaa cgtcccctct    1020
atccaatcca gaggactttt tggagcaatt gctgggttca ttgaaggagg atggacagga    1080
atgatagatg gatggtatgg atatcaccat caaaatgagc agggatctgg ttacgcagca    1140
gatcagaaaa gcacacaaat tgcaattgat gggatcagca acaaagtgaa ctcagtaatt    1200
gaaaaaatga acattcaatt tacttcagtg ggcaaggagt tcaataatct ggagaaaagg    1260
attgagaatt tgaataagaa ggtcgatgat gggttttttgg atatatggac atataatgct    1320
gagttgctca ttttgctcga gaatgaaagg actctagatt tccatgactt taacgtaaaa    1380
aatttatatg aaaaggtcaa atcacaattg agaaacaatg ccaaggaagt cggtaatggt    1440
tgttttgagt tctatcacaa atgtgataat gaatgcatgg agagcgtaaa gaatggcaca    1500
tacaattatc ccaaatattc agaagaatcc aaattgaata gagaggaaat agacggtgtg    1560
aaattagaat caatgggagt ttaccagatt                                     1590
```

<210> SEQ ID NO 4
<211> LENGTH: 530
<212> TYPE: PRT
<213> ORGANISM: Influenza virus

<400> SEQUENCE: 4

```
Met Glu Ala Lys Leu Phe Val Leu Phe Cys Val Phe Asn Ala Leu Lys
1               5                   10                  15

Ala Asp Thr Ile Cys Val Gly Tyr His Ala Asn Asn Ser Thr Asp Thr
            20                  25                  30

Val Asp Thr Ile Leu Glu Lys Asn Val Thr Val Thr His Ser Val Asn
        35                  40                  45

Leu Leu Glu Asn Ser His Asn Gly Lys Leu Cys Ser Leu Asn Gly Lys
    50                  55                  60

Ala Pro Leu Gln Leu Gly Asn Cys Asn Val Ala Gly Trp Ile Leu Gly
65                  70                  75                  80
```

```
Asn Pro Glu Cys Asp Leu Leu Leu Thr Ala Asn Ser Trp Ser Tyr Ile
                85                  90                  95

Ile Glu Thr Ser Asn Ser Lys Asn Gly Lys Cys Tyr Pro Gly Glu Phe
            100                 105                 110

Ala Asp Tyr Glu Glu Leu Arg Glu Gln Leu Ser Thr Val Ser Ser Phe
            115                 120                 125

Glu Arg Phe Glu Ile Phe Pro Lys Ala Thr Ser Trp Pro Asp His Glu
            130                 135                 140

Thr Thr Lys Gly Thr Thr Thr Ala Cys Ser His Ser Gly Thr Ser Ser
145                 150                 155                 160

Phe Tyr Arg Asn Leu Leu Trp Ile Val Lys Lys Gly Asn Ser Tyr Pro
                165                 170                 175

Lys Leu Ser Lys Ser Tyr Thr Asn Asn Lys Gly Lys Glu Val Leu Val
            180                 185                 190

Ile Trp Gly Val His His Pro Pro Thr Asn Ser Asp Gln Gln Thr Leu
            195                 200                 205

Tyr Gln Asn Ala Tyr Thr Tyr Val Ser Val Glu Ser Ser Lys Tyr Tyr
        210                 215                 220

Arg Arg Phe Thr Pro Glu Ile Ala Ala Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp Tyr Ala Phe
            260                 265                 270

Ala Leu Asn Lys Gly Ser Asn Ser Gly Ile Met Met Ser Asp Ala His
            275                 280                 285

Val His Asn Cys Thr Thr Lys Cys Gln Thr Pro His Gly Ala Leu Lys
        290                 295                 300

Ser Asn Leu Pro Phe Gln Asn Val His Pro Ile Thr Ile Gly Glu Cys
305                 310                 315                 320

Pro Lys Tyr Val Lys Ser Thr Gln Leu Arg Met Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Ile Ala Ile Asp Gly Ile Ser Asn Lys Val Asn Ser Val Ile
385                 390                 395                 400

Glu Lys Met Asn Ile Gln Phe Thr Ser Val Gly Lys Glu Phe Asn Asn
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Ile Leu Leu Glu Asn
            435                 440                 445

Glu Arg Thr Leu Asp Phe His Asp Phe Asn Val Lys Asn Leu Tyr Glu
        450                 455                 460

Lys Val Lys Ser Gln Leu Arg Asn Asn Ala Lys Glu Val Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asn Tyr Pro Lys Tyr Ser Glu Glu Ser Lys Leu
```

```
                         500                 505                 510
Asn Arg Glu Glu Ile Asp Gly Val Lys Leu Glu Ser Met Gly Val Tyr
            515                 520                 525

Gln Ile
    530

<210> SEQ ID NO 5
<211> LENGTH: 1730
<212> TYPE: PRT
<213> ORGANISM: Sus scrofa

<400> SEQUENCE: 5

Met Asp Phe Leu Leu Leu Leu Leu Ala Ser Ser Ala Leu Ala
1               5                   10                  15

Gly Leu Ala Ser Trp Thr Val Ser Pro Glu Thr Val Gln Gly Ile
            20                  25                  30

Lys Gly Ser Cys Leu Ile Ile Pro Cys Thr Phe Gly Phe Pro Ala Asn
            35                  40                  45

Val Glu Val Pro His Gly Ile Thr Ala Ile Trp Tyr Tyr Asp Tyr Ser
50                  55                  60

Gly Lys Arg Leu Val Val Ser His Ser Arg Asn Pro Lys Val Val Glu
65                  70                  75                  80

Asn His Phe Gln Gly Arg Ala Leu Leu Leu Gly Gln Val Glu Gln Arg
                85                  90                  95

Thr Cys Ser Leu Leu Leu Lys Asp Leu Gln Pro Gln Asp Ser Gly Ser
            100                 105                 110

Tyr Asn Phe Arg Phe Glu Ile Ser Glu Gly Asn Arg Trp Ser Asp Val
            115                 120                 125

Lys Gly Thr Val Val Thr Val Thr Glu Val Pro Ser Val Pro Thr Ile
130                 135                 140

Ala Leu Pro Ala Lys Leu His Glu Gly Met Glu Val Asp Phe Asn Cys
145                 150                 155                 160

Ser Thr Pro Tyr Val Cys Pro Thr Glu Pro Val Asn Leu Gln Trp Gln
                165                 170                 175

Gly Gln Asp Pro Thr Arg Ser Val Thr Ser His Leu Gln Lys Leu Glu
            180                 185                 190

Pro Ser Gly Thr Ser His Met Glu Thr Leu His Met Ala Leu Ser Trp
            195                 200                 205

Gln Asp His Gly Arg Ile Leu Ser Cys Gln Val Ser Ala Ala Glu Arg
        210                 215                 220

Arg Met Gln Lys Glu Ile His Leu Gln Val Gln Tyr Ala Pro Lys Gly
225                 230                 235                 240

Val Glu Ile Leu Phe Ser His Ser Gly Arg Asn Val Leu Pro Gly Asp
                245                 250                 255

Leu Val Thr Leu Ser Cys Gln Val Asn Ser Ser Asn Pro Gln Val Ser
            260                 265                 270

Ser Val Gln Trp Val Lys Asp Gly Thr Lys Leu Lys Asp Gln Lys Arg
            275                 280                 285

Val Leu Gln Leu Arg Arg Ala Ala Trp Ala Asp Ala Gly Val Tyr Thr
        290                 295                 300

Cys Gln Ala Gly Asn Ala Val Gly Ser Ser Val Ser Pro Pro Val Ser
305                 310                 315                 320

Leu His Val Phe Met Ala Glu Val Gln Val Ser Pro Val Gly Ser Ile
                325                 330                 335

Leu Glu Asn Gln Thr Val Thr Leu Ala Cys Asn Thr Pro Lys Glu Ala
```

```
                    340             345             350
Pro Ser Glu Leu Arg Tyr Ser Trp Tyr Lys Asn His Ala Leu Leu Glu
            355                 360                 365
Gly Ser His Ser Arg Thr Leu Arg Leu His Ser Val Thr Arg Ala Asp
        370                 375                 380
Ser Gly Phe Tyr Phe Cys Glu Val Gln Asn Ala Arg Gly Arg Glu Arg
385                 390                 395                 400
Ser Pro Pro Val Ser Val Val Ser His Pro Pro Leu Thr Pro Asp
                405                 410                 415
Leu Thr Ala Phe Leu Glu Thr Gln Ala Gly Leu Val Gly Ile Leu Gln
            420                 425                 430
Cys Ser Val Val Ser Glu Pro Pro Ala Thr Leu Val Leu Ser His Gly
            435                 440                 445
Gly Leu Ile Leu Ala Ser Thr Ser Gly Glu Gly Asp His Ser Pro Arg
        450                 455                 460
Phe Ser Val Ala Ser Ala Pro Asn Ser Leu Arg Leu Glu Ile Gln Asp
465                 470                 475                 480
Leu Gly Pro Thr Asp Ser Gly Glu Tyr Met Cys Ser Ala Ser Ser
                485                 490                 495
Leu Gly Asn Ala Ser Ser Thr Leu Asp Phe His Ala Asn Ala Ala Arg
            500                 505                 510
Leu Leu Ile Ser Pro Ala Ala Glu Val Val Glu Gly Gln Ala Val Thr
            515                 520                 525
Leu Ser Cys Arg Ser Ser Leu Ser Leu Met Pro Asp Thr Arg Phe Ser
        530                 535                 540
Trp Tyr Leu Asn Gly Ala Leu Ile Leu Glu Gly Pro Ser Ser Ser Leu
545                 550                 555                 560
Leu Leu Pro Ala Ala Ser Ser Thr Asp Ala Gly Ser Tyr His Cys Arg
                565                 570                 575
Ala Gln Asn Ser His Ser Thr Ser Gly Pro Ser Ser Pro Ala Val Leu
            580                 585                 590
Thr Val Leu Tyr Ala Pro Arg Gln Pro Val Phe Thr Ala Gln Leu Asp
            595                 600                 605
Pro Asp Thr Ala Gly Ala Gly Ala Gly Arg Gln Gly Leu Leu Leu Cys
        610                 615                 620
Arg Val Asp Ser Asp Pro Pro Ala Gln Leu Gln Leu Leu His Arg Gly
625                 630                 635                 640
Arg Val Val Ala Ser Ser Leu Ser Trp Gly Gly Gly Cys Cys Thr Cys
                645                 650                 655
Gly Gly Cys Phe His Arg Met Lys Val Thr Lys Ala Pro Asn Leu Leu
            660                 665                 670
Arg Val Glu Ile Arg Asp Pro Val Leu Glu Asp Glu Gly Val Tyr Leu
        675                 680                 685
Cys Glu Ala Ser Ser Ala Leu Gly Asn Ala Ser Ala Ser Ala Thr Leu
            690                 695                 700
Asp Ala Gln Ala Thr Val Leu Val Ile Thr Pro Ser His Thr Leu Gln
705                 710                 715                 720
Glu Gly Ile Glu Ala Asn Leu Thr Cys Asn Val Ser Arg Glu Ala Ser
                725                 730                 735
Gly Pro Ala Asn Phe Ser Trp Phe Arg Asp Gly Ala Leu Trp Ala Gln
            740                 745                 750
Gly Pro Leu Asp Thr Val Thr Leu Leu Pro Val Ala Arg Thr Asp Ala
        755                 760                 765
```

-continued

Ala Leu Tyr Ala Cys Arg Ile Val Thr Glu Ala Gly Ala Gly Leu Ser
770                 775                 780

Thr Pro Val Ala Leu Asn Val Leu Tyr Pro Pro Asp Pro Pro Lys Leu
785                 790                 795                 800

Ser Ala Leu Leu Asp Val Asp Gln Gly His Thr Ala Val Phe Val Cys
                805                 810                 815

Thr Val Asp Ser Arg Pro Leu Ala Gln Leu Ala Leu Phe Arg Gly Glu
        820                 825                 830

His Leu Leu Ala Ala Ser Ser Ala Leu Arg Leu Pro Pro Arg Gly Arg
            835                 840                 845

Leu Gln Ala Lys Ala Ser Ala Asn Ser Leu Gln Leu Glu Val Arg Asp
    850                 855                 860

Leu Ser Leu Gly Asp Ser Gly Ser Tyr His Cys Glu Ala Thr Asn Ile
865                 870                 875                 880

Leu Gly Ser Ala Asn Thr Ser Leu Thr Phe Gln Val Arg Gly Ala Trp
                885                 890                 895

Val Arg Val Ser Pro Ser Pro Glu Leu Gln Glu Gly Gln Ala Val Val
            900                 905                 910

Leu Ser Cys Gln Val Pro Ile Gly Val Leu Gly Thr Ser Tyr Arg
    915                 920                 925

Trp Tyr Arg Asp Gly Gln Pro Leu Gln Glu Ser Thr Ser Ala Thr Leu
930                 935                 940

Arg Phe Ala Ala Ile Thr Leu Ser Gln Ala Gly Ala Tyr His Cys Gln
945                 950                 955                 960

Ala Gln Ala Pro Gly Ser Ala Thr Thr Asp Leu Ala Ala Pro Val Ser
                965                 970                 975

Leu His Val Thr Tyr Ala Pro Arg Gln Ala Thr Leu Thr Thr Leu Met
            980                 985                 990

Asp Ser Gly Leu Gly Arg Leu Gly Leu Leu Leu Cys Arg Val Asn Ser
                995                 1000                1005

Asp Pro Pro Ala Gln Leu Arg Leu Leu His Gly Ser Arg Leu Val
        1010                1015                1020

Ala Ser Thr Leu Gln Gly Val Glu Glu Leu Ala Gly Ser Ser Pro
    1025                1030                1035

Arg Leu Gln Val Ala Thr Ala Pro Asn Thr Leu Arg Leu Glu Ile
    1040                1045                1050

His Asn Ala Val Leu Glu Asp Glu Gly Val Tyr Thr Cys Glu Ala
    1055                1060                1065

Thr Asn Thr Leu Gly Gln Thr Leu Ala Ser Ala Ala Phe Asp Ala
    1070                1075                1080

Gln Ala Met Arg Val Gln Val Trp Pro Asn Ala Thr Val Gln Glu
    1085                1090                1095

Gly Gln Leu Val Asn Leu Thr Cys Leu Val Trp Thr Thr His Leu
    1100                1105                1110

Ala Gln Leu Thr Tyr Thr Trp Tyr Arg Asp Gln Gln Gln Leu Pro
    1115                1120                1125

Gly Ala Ala His Ser Ile Leu Leu Pro Asn Val Thr Val Thr Asp
    1130                1135                1140

Ala Ala Ser Tyr Arg Cys Gly Ile Leu Ile Pro Gly Gln Ala Leu
    1145                1150                1155

Arg Leu Ser Arg Pro Val Ala Leu Asp Val Leu Tyr Ala Pro Arg
    1160                1165                1170

Arg Leu Arg Leu Thr His Leu Leu Glu Ser Arg Gly Gly Gln Leu
    1175                1180                1185

-continued

```
Ala Val Val Leu Cys Thr Val Asp Ser Arg Pro Ala Ala Gln Leu
    1190            1195                1200
Thr Leu Ser His Ala Gly Arg Leu Leu Ala Ser Ser Thr Ala Ala
    1205            1210                1215
Ser Val Pro Asn Thr Leu Arg Leu Glu Leu Trp Glu Pro Arg Pro
    1220            1225                1230
Ser Asp Glu Gly Leu Tyr Ser Cys Ser Ala Arg Ser Pro Leu Gly
    1235            1240                1245
Gln Ala Asn Thr Ser Leu Glu Leu Arg Leu Gly Val Gln Val
    1250            1255                1260
Ala Leu Ala Pro Ser Ala Thr Val Pro Glu Gly Ala Pro Val Thr
    1265            1270                1275
Val Thr Cys Glu Asp Pro Ala Ala Arg Pro Pro Thr Leu Tyr Val
    1280            1285                1290
Trp Tyr His Asn Ser Arg Trp Leu Gln Glu Gly Ser Ala Ala Ser
    1295            1300                1305
Leu Ser Phe Pro Ala Ala Thr Arg Ala His Ala Gly Ala Tyr Thr
    1310            1315                1320
Cys Gln Val Gln Asp Ala Gln Gly Thr Arg Ile Ser Gln Pro Ala
    1325            1330                1335
Ala Leu His Ile Leu Tyr Ala Pro Arg Asp Ala Val Leu Ser Ser
    1340            1345                1350
Phe Trp Asp Ser Arg Ala Ser Pro Met Ala Val Val Gln Cys Thr
    1355            1360                1365
Val Asp Ser Glu Pro Pro Ala Glu Met Thr Leu Ser His Asp Gly
    1370            1375                1380
Lys Val Leu Ala Thr Ser His Gly Val His Gly Leu Ala Val Gly
    1385            1390                1395
Thr Gly His Val Gln Val Ala Arg Asn Ala Leu Gln Leu Arg Val
    1400            1405                1410
Gln Asn Val Pro Ser Arg Asp Lys Asp Thr Tyr Val Cys Met Asp
    1415            1420                1425
Arg Asn Ser Leu Gly Ser Val Ser Thr Met Gly Gln Leu Gln Pro
    1430            1435                1440
Glu Gly Val His Val Val Ala Glu Pro Gly Leu Asp Val Pro Glu
    1445            1450                1455
Gly Thr Ala Leu Asn Leu Ser Cys Arg Leu Pro Ser Gly Pro Gly
    1460            1465                1470
His Ile Gly Asn Ser Thr Phe Ala Trp Phe Arg Asn Gly Arg Gln
    1475            1480                1485
Leu His Thr Glu Ser Val Pro Thr Leu Thr Phe Thr His Val Ala
    1490            1495                1500
Arg Ala Gln Ala Gly Leu Tyr His Cys Gln Ala Glu Leu Pro Ala
    1505            1510                1515
Gly Ala Ala Thr Ser Ala Pro Val Leu Leu Arg Val Leu Tyr Pro
    1520            1525                1530
Pro Lys Thr Pro Thr Met Thr Val Phe Val Glu Pro Glu Gly Gly
    1535            1540                1545
Ile Gln Gly Ile Leu Asp Cys Arg Val Asp Ser Glu Pro Leu Ala
    1550            1555                1560
Ser Leu Thr Leu His Leu Gly Ser Arg Leu Val Ala Ser Ser Gln
    1565            1570                1575
Pro Gln Ala Ala Pro Ala Lys Pro His Ile Arg Val Ser Ala Ser
```

|                |                |                |                |                |
| -------------- | -------------- | -------------- | -------------- | -------------- |
| 1580           |                | 1585           |                | 1590           |

Pro Asn Ala Leu Arg Val Asp Met Glu Glu Leu Lys Pro Ser Asp
1595                1600                1605

Gln Gly Glu Tyr Val Cys Ser Ala Ser Asn Ala Leu Gly Ser Ala
1610                1615                1620

Ser Ala Ala Thr Tyr Phe Gly Thr Arg Ala Leu His Arg Leu His
1625                1630                1635

Leu Phe Gln His Leu Leu Trp Phe Leu Gly Leu Leu Ala Ser Leu
1640                1645                1650

Leu Phe Leu Leu Leu Gly Leu Gly Val Trp Tyr Ala Trp Arg Arg
1655                1660                1665

Gly Asn Phe Tyr Lys Leu Arg Met Gly Glu Tyr Ser Val Glu Met
1670                1675                1680

Val Ser Arg Lys Glu Thr Thr Gln Met Ser Thr Asp Gln Glu Glu
1685                1690                1695

Val Thr Gly Ile Gly Asp Asp Ala Gly Ser Val Asn Gln Ala Ala
1700                1705                1710

Phe Asp Pro Ala His Leu Cys Glu Asn Thr Gln Ser Val Lys Ser
1715                1720                1725

Thr Val
1730

<210> SEQ ID NO 6
<211> LENGTH: 5193
<212> TYPE: DNA
<213> ORGANISM: Sus scrofa

<400> SEQUENCE: 6

| | |
|---|---|
| atggacttcc tgctcctgct cctcctcctg gcttcatctg ctctagcagg cctggcctcg | 60 |
| tggacggttt ccagccccga gaccgtgcag ggcatcaagg gctcctgcct catcatcccc | 120 |
| tgcaccttcg gcttcccggc caacgtggag gtgcccatg gcatcacagc catctggtac | 180 |
| tatgactact caggcaagcg cctggtagtg agccactcca ggaacccaaa ggtggtggag | 240 |
| aaccacttcc aaggccgggc cctgctgttg ggcaggttg aacagaggac gtgcagcctg | 300 |
| ctgctgaagg acctgcagcc ccaggactcg gctcctata acttccgctt tgagatcagc | 360 |
| gagggcaacc gctggtcaga tgtcaaaggc acagttgtca ccgtgacaga ggtgcccagc | 420 |
| gtgcccacca ttgccttgcc agccaagctg catgagggca tggaggtgga cttcaactgc | 480 |
| tccactccct atgtgtgccc gacgagccg gtcaacctac agtggcaagg ccaggatccc | 540 |
| acccgctccg tcacctccca cctccagaag cttgagccct cgggcaccag ccacatggag | 600 |
| accctgcaca tggccctgtc ctggcaggac atggccgga tcctgagctg ccaggtctca | 660 |
| gcagccgaac gcaggatgca gaaggagatt cacctccaag tgcagtatgc ccccaagggt | 720 |
| gtggagatcc ttttcagcca ctccggacgg aacgtccttc aggtgatct ggtcaccctc | 780 |
| agctgccagg tgaatagcag caaccctcag gtcagttccg tgcagtgggt caaggatggg | 840 |
| acgaagctca agaccagaa acgtgtactg cagttgcgcc gggcagcctg ggctgatgct | 900 |
| ggcgtctaca cctgccaagc cgggaatgcc gtgggctctt cagtctcacc cccggtcagc | 960 |
| ctccacgtct tcatggctga ggtccaggta agccctgtgg gctccatcct ggagaaccag | 1020 |
| acggtgacgc tggcctgcaa tacacctaag gaagcgccca gcgagctgcg ctacagctgg | 1080 |
| tacaagaacc acgccctgct ggagggctct cacagccgca cctccggct gcactcagtt | 1140 |
| accagggcgg attcgggctt ctacttctgc gaggtgcaga acgcccgggg cagagagcgc | 1200 |

```
tctcccctg tcagcgtggt ggtcagccac ccaccctca ccccggacct aactgccttc    1260
ctggagacac aggcgggct ggtgggcatc ctccaatgct ctgtggtcag cgagccccca    1320
gctactctgg tgttgtcaca cgggggcctc atcttggcct ctacctccgg ggagggtgac    1380
cacagcccac gcttcagtgt cgcctctgcc cccaactccc tgcgcctgga gattcaagac    1440
ctggggccaa cagacagtgg ggaatacatg tgctcagcca gcagttctct tgggaatgcg    1500
tcctccaccc tggacttcca tgccaatgca gcccgcctcc tcatcagccc agcagcagag    1560
gtggtggaag ggcaggcggt gacactgagc tgcaggagca gcctgagcct gatgcctgac    1620
acccgttttt cctggtacct gaacgggcc ctgattctcg aggggcccag cagcagcctc    1680
ctgctcccag cagcctccag cacagatgcc ggctcatacc actgccgggc ccagaacagc    1740
cacagcacca gcgggccctc ctcacctgct gttctcaccg tgctctacgc cccacgccag    1800
cccgtgttca ctgcccagct ggaccctgat actgcaggag ctggggccgg acgccaaggc    1860
ctcctcttgt gccgtgtgga cagcgacccc ccagcccagc tgcagctgct ccacaggggc    1920
cgtgttgtgg cctcttctct gtcatggggg ggcggctgct gcacctgcgg aggctgtttc    1980
caccgcatga aggtcaccaa agcacccaac ctactgcgtg tagagatccg agacccggtg    2040
ctggaggatg agggtgtgta cctgtgcgag gccagcagcg ccctgggcaa cgcctccgcc    2100
tctgcaacct tggatgccca ggccactgtc ctggtcatca ccgtcaca cacgctgcag    2160 gaaggcattg aagccaacct gacttgcaac gtgagccgtg aagccagcgg ccctgccaac    2220
ttctcctggt tccagatggg ggcgctatgg gcccagggcc ctctggacac cgtgacgctg    2280
ctacctgtgg ccagaactga tgctgccctc tatgcttgcc gcatcgtcac cgaggctggt    2340
gctggcctct ccacccctgt ggccctgaat gtgctctatc cccccgatcc tccaaagttg    2400
tcagccctcc tggacgtgga ccagggccac acggctgtgt tcgtctgtac tgtggacagt    2460
cgccctcttg cccagttggc cctgttccgt ggggaacacc tcctggccgc cagctcggca    2520
ctccggctcc ccctcgtgg ccgcctccag gccaaagcct cggccaactc cttgcagcta    2580
gaggtccgag acttgagcct tgggactct ggcagctacc actgtgaggc caccaacatc    2640
cttggatcag ccaacacttc tcttaccttc caggtccgag gagcctgggt ccgggtgtca    2700
ccgtcgcctg agctccagga gggccaggct gtggtcctga gctgccaggt acccataggg    2760
gtcctggagg ggacctcata tcgttggtat cgggatggcc agccctcca ggagtccact    2820 tcggccacgc tccgtttgc agccataact ctgagccagg ctggagccta ccattgccaa    2880
gcccaagctc caggctcagc caccacggac ctggctgccc ctgtcagcct ccacgtgacc    2940
tacgcacctc gccaggccac actcaccacc ctgatggact caggcctcgg gcgactgggc    3000
ctccttctgt gccgtgtgaa cagtgaccct cctgcccagc tccgactgct ccatgggagc    3060
cgcctcgtgg cctctactct acaaggtgtg gaggagcttg caggcagctc tccccgccta    3120
caggtggcca cagcccccaa cacgctgcgc ctggagatcc acaacgcagt gctggaggat    3180
gaaggcgtct acacctgcga ggccaccaac accctgggtc agaccttggc ctccgccgcc    3240
ttcgatgccc aggctatgag agtgcaggtg tggcccaatg ccaccgtgca agagggggcag    3300 ctggtgaacc tgacctgcct tgtatggacc acgcacctgg cccagctcac ctacacgtgg    3360
taccgagacc agcagcagct cccaggtgct gcccactcca tcctcctgcc caatgtcact    3420
gtcacagatg ccgcctccta ccgctgtggc atattgatcc ctggccaggc actccgcctc    3480
tccagacctg tcgccctgga tgtcctctac gcacccgca gactgcgcct gacccatctc    3540
ttggagagcc gtggtgggca gctggccgtg gtgctgtgca ctgtggacag tcgcccagct    3600
```

```
gcccagctga ccctcagcca tgctggccgc ctcctggcct cctcaaccgc agcctctgtc    3660
cccaacaccc tgcgcctgga gctgtgggag ccccggccca gtgatgaggg tctctacagc    3720
tgctcggccc gcagtcctct gggccaggcc aacacatccc tggagctgcg gctagagggc    3780
gtgcaggtgg cactggctcc atcggccact gtgccgaggg ggcccctgt cacagtgacc     3840 tgtgaagacc ctgctgcccg cccacccact ctctatgtct ggtaccacaa cagccgttgg    3900
ctgcaggagg ggtcggctgc ctccctctcg tttccagcgg ctacacgggc tcacgcgggc    3960
gcctatacct gccaggtcca ggatgcccag ggcacacgca tctcccagcc cgcagcactg    4020
cacatcctct atgcccctcg ggatgctgtc ctttcctcct tctgggactc aagggccagc    4080
cctatggccg tggtacagtg cactgtggac agcgagccac ctgccgagat gaccctgtcc    4140
catgatggca aggtgctggc caccagccat ggggtccacg gcttagcagt ggggacaggc    4200
catgtccagg tggcccgcaa cgccctgcag ctgcgggtgc agaatgtgcc ctcacgtgac    4260
aaggacacct acgtctgcat ggaccgcaac tccttgggct cagtcagcac catggggcag    4320
ctgcagccag aaggtgtgca cgtggtagct gagccagggc tggatgtgcc tgaaggcaca    4380
gcgctgaacc tgagctgtcg cctccctagt ggccctgggc acataggcaa ctccacccttt   4440 gcttggttcc ggaacggtcg gcagctacac acagagtctg tgcccaccct taccttcacc    4500
catgtggccc gcgcccaagc tggcttgtac cactgccagg ctgagctccc cgccggggct    4560
gccacctctg ctccagtctt gctccgggtg ctctaccctc ccaagacgcc caccatgact    4620
gtttttgtgg agcccgaggg tggcatccag ggcattctgg actgccgagt ggacagtgag    4680
cccctagcca gcctgaccct ccacctgggc agtcggctgg tggcctccag ccagcctcag    4740 gctgccccctg ccaagccgca catccgcgtc tcagccagtc ccaatgcctt gcgagtggac    4800
atggaggagc tgaagcccag tgaccagggg gagtatgtgt gctcggcctc caatgccctg    4860
ggctctgcct ctgctgccac ctacttcgga accagagccc tgcatcgcct gcatctgttc    4920
cagcaccttc tctggttcct ggggctgctg gcgagcctcc tcttcctact gttgggcctg    4980
ggggtctggt acgcctggag acggggaaat ttttacaagc tgagaatggg cgaatattca    5040
gtagagatgg tatctcggaa ggaaaccacg cagatgtcca ctgaccagga agaagttact    5100
ggaatcggtg atgatgcggg ctctgtgaac caggcggcat tgatcctgc ccacctctgt     5160 gaaaacacac agtctgtgaa aagcacagtc tga                                  5193
```

<210> SEQ ID NO 7
<211> LENGTH: 1695
<212> TYPE: PRT
<213> ORGANISM: Mus musculus

<400> SEQUENCE: 7

```
Met Cys Val Leu Phe Ser Leu Leu Leu Ala Ser Val Phe Ser Leu
1               5                   10                  15

Gly Gln Thr Thr Trp Gly Val Ser Pro Lys Asn Val Gln Gly Leu
            20                  25                  30

Ser Gly Ser Cys Leu Leu Ile Pro Cys Ile Phe Ser Tyr Pro Ala Asp
        35                  40                  45

Val Pro Val Ser Asn Gly Ile Thr Ala Ile Trp Tyr Tyr Asp Tyr Ser
    50                  55                  60

Gly Lys Arg Gln Val Val Ile His Ser Gly Asp Pro Lys Leu Val Asp
65                  70                  75                  80

Lys Arg Phe Arg Gly Arg Ala Glu Leu Met Gly Asn Met Asp His Lys
                85                  90                  95
```

```
Val Cys Asn Leu Leu Leu Lys Asp Leu Lys Pro Glu Asp Ser Gly Thr
            100                 105                 110

Tyr Asn Phe Arg Phe Glu Ile Ser Asp Ser Asn Arg Trp Leu Asp Val
            115                 120                 125

Lys Gly Thr Thr Val Thr Val Thr Thr Asp Pro Ser Pro Pro Thr Ile
130                 135                 140

Thr Ile Pro Glu Glu Leu Arg Glu Gly Met Glu Arg Asn Phe Asn Cys
145                 150                 155                 160

Ser Thr Pro Tyr Leu Cys Leu Gln Glu Lys Gln Val Ser Leu Gln Trp
                165                 170                 175

Arg Gly Gln Asp Pro Thr His Ser Val Thr Ser Ser Phe Gln Ser Leu
            180                 185                 190

Glu Pro Thr Gly Val Tyr His Gln Thr Thr Leu His Met Ala Leu Ser
            195                 200                 205

Trp Gln Asp His Gly Arg Thr Leu Leu Cys Gln Phe Ser Leu Gly Ala
    210                 215                 220

His Ser Ser Arg Lys Glu Val Tyr Leu Gln Val Pro His Ala Pro Lys
225                 230                 235                 240

Gly Val Glu Ile Leu Leu Ser Ser Gly Arg Asn Ile Leu Pro Gly
                245                 250                 255

Asp Pro Val Thr Leu Thr Cys Arg Val Asn Ser Ser Tyr Pro Ala Val
            260                 265                 270

Ser Ala Val Gln Trp Ala Arg Asp Gly Val Asn Leu Gly Val Thr Gly
        275                 280                 285

His Val Leu Arg Leu Phe Ser Ala Ala Trp Asn Asp Ser Gly Ala Tyr
    290                 295                 300

Thr Cys Gln Ala Thr Asn Asp Met Gly Ser Leu Val Ser Ser Pro Leu
305                 310                 315                 320

Ser Leu His Val Phe Met Ala Glu Val Lys Met Asn Pro Ala Gly Pro
                325                 330                 335

Val Leu Glu Asn Glu Thr Val Thr Leu Leu Cys Ser Thr Pro Lys Glu
            340                 345                 350

Ala Pro Gln Glu Leu Arg Tyr Ser Trp Tyr Lys Asn His Ile Leu Leu
        355                 360                 365

Glu Asp Ala His Ala Ser Thr Leu His Leu Pro Ala Val Thr Arg Ala
    370                 375                 380

Asp Thr Gly Phe Tyr Phe Cys Glu Val Gln Asn Ala Gln Gly Ser Glu
385                 390                 395                 400

Arg Ser Ser Pro Leu Ser Val Val Val Arg Tyr Pro Pro Leu Thr Pro
                405                 410                 415

Asp Leu Thr Thr Phe Leu Glu Thr Gln Ala Gly Leu Val Gly Ile Leu
            420                 425                 430

His Cys Ser Val Val Ser Glu Pro Leu Ala Thr Val Val Leu Ser His
        435                 440                 445

Gly Gly Leu Thr Leu Ala Ser Asn Ser Gly Glu Asn Asp Phe Asn Pro
    450                 455                 460

Arg Phe Arg Ile Ser Ser Ala Pro Asn Ser Leu Arg Leu Glu Ile Arg
465                 470                 475                 480

Asp Leu Gln Pro Ala Asp Ser Gly Glu Tyr Thr Cys Leu Ala Val Asn
                485                 490                 495

Ser Leu Gly Asn Ser Thr Ser Ser Leu Asp Phe Tyr Ala Asn Val Ala
            500                 505                 510

Arg Leu Leu Ile Asn Pro Ser Ala Glu Val Val Glu Gly Gln Ala Val
        515                 520                 525
```

```
Thr Leu Ser Cys Arg Ser Gly Leu Ser Pro Ala Pro Asp Thr Arg Phe
    530                 535                 540

Ser Trp Tyr Leu Asn Gly Ala Leu Leu Glu Gly Ser Ser Ser Ser Ser
545                 550                 555                 560

Leu Leu Leu Pro Ala Ala Ser Ser Thr Asp Ala Gly Ser Tyr Tyr Cys
                565                 570                 575

Arg Thr Gln Ala Gly Pro Asn Thr Ser Gly Pro Ser Leu Pro Thr Val
            580                 585                 590

Leu Thr Val Phe Tyr Pro Pro Arg Lys Pro Thr Phe Thr Ala Arg Leu
        595                 600                 605

Asp Leu Asp Thr Ser Gly Val Gly Asp Gly Arg Arg Gly Ile Leu Leu
    610                 615                 620

Cys His Val Asp Ser Asp Pro Ala Gln Leu Arg Leu Leu His Lys
625                 630                 635                 640

Gly His Val Val Ala Thr Ser Leu Pro Ser Arg Cys Gly Ser Cys Ser
                645                 650                 655

Gln Arg Thr Lys Val Ser Arg Thr Ser Asn Ser Leu His Val Glu Ile
            660                 665                 670

Gln Lys Pro Val Leu Glu Asp Glu Gly Val Tyr Leu Cys Glu Ala Ser
        675                 680                 685

Asn Thr Leu Gly Asn Ser Ser Ala Ala Ala Ser Phe Asn Ala Lys Ala
    690                 695                 700

Thr Val Leu Val Ile Thr Pro Ser Asn Thr Leu Arg Glu Gly Thr Glu
705                 710                 715                 720

Ala Asn Leu Thr Cys Asn Val Asn Gln Glu Val Ala Val Ser Pro Ala
                725                 730                 735

Asn Phe Ser Trp Phe Arg Asn Gly Val Leu Trp Thr Gln Gly Ser Leu
            740                 745                 750

Glu Thr Val Arg Leu Gln Pro Val Ala Arg Thr Asp Ala Ala Val Tyr
        755                 760                 765

Ala Cys Arg Leu Leu Thr Glu Asp Gly Ala Gln Leu Ser Ala Pro Val
    770                 775                 780

Val Leu Ser Val Leu Tyr Ala Pro Asp Pro Pro Lys Leu Ser Ala Leu
785                 790                 795                 800

Leu Asp Val Gly Gln Gly His Met Ala Val Phe Ile Cys Thr Val Asp
                805                 810                 815

Ser Tyr Pro Leu Ala His Leu Ser Leu Phe Arg Gly Asp His Leu Leu
            820                 825                 830

Ala Thr Asn Leu Glu Pro Gln Arg Pro Ser His Gly Arg Ile Gln Ala
        835                 840                 845

Lys Ala Thr Ala Asn Ser Leu Gln Leu Glu Val Arg Glu Leu Gly Leu
    850                 855                 860

Val Asp Ser Gly Asn Tyr His Cys Glu Ala Thr Asn Ile Leu Gly Ser
865                 870                 875                 880

Ala Asn Ser Ser Leu Phe Phe Gln Val Arg Gly Ala Trp Val Gln Val
                885                 890                 895

Ser Pro Ser Pro Glu Leu Arg Glu Gly Gln Ala Val Val Leu Ser Cys
            900                 905                 910

Gln Val Pro Thr Gly Val Ser Glu Gly Thr Ser Tyr Ser Trp Tyr Gln
        915                 920                 925

Asp Gly Arg Pro Leu Gln Glu Ser Thr Ser Ser Thr Leu Arg Ile Ala
    930                 935                 940

Ala Ile Ser Leu Arg Gln Ala Gly Ala Tyr His Cys Gln Ala Gln Ala
```

-continued

```
            945                 950                 955                 960
        Pro Asp Thr Ala Ile Ala Ser Leu Ala Ala Pro Val Ser Leu His Val
                        965                 970                 975
        Ser Tyr Thr Pro Arg His Val Thr Leu Ser Ala Leu Leu Ser Thr Asp
                        980                 985                 990
        Pro Glu Arg Leu Gly His Leu Val Cys Ser Val Gln Ser Asp Pro Pro
                        995                 1000                1005
        Ala Gln Leu Gln Leu Phe His Arg Asn Arg Leu Val Ala Ser Thr
            1010                1015                1020
        Leu Gln Gly Ala Asp Glu Leu Ala Gly Ser Asn Pro Arg Leu His
            1025                1030                1035
        Val Thr Val Leu Pro Asn Glu Leu Arg Leu Gln Ile His Phe Pro
            1040                1045                1050
        Glu Leu Glu Asp Asp Gly Thr Tyr Thr Cys Glu Ala Ser Asn Thr
            1055                1060                1065
        Leu Gly Gln Ala Ser Ala Ala Ala Asp Phe Asp Ala Gln Ala Val
            1070                1075                1080
        Arg Val Thr Val Trp Pro Asn Ala Thr Val Gln Glu Gly Gln Gln
            1085                1090                1095
        Val Asn Leu Thr Cys Leu Val Trp Ser Thr His Gln Asp Ser Leu
            1100                1105                1110
        Ser Tyr Thr Trp Tyr Lys Gly Gly Gln Gln Leu Leu Gly Ala Arg
            1115                1120                1125
        Ser Ile Thr Leu Pro Ser Val Lys Val Leu Asp Ala Thr Ser Tyr
            1130                1135                1140
        Arg Cys Gly Val Gly Leu Pro Gly His Ala Pro His Leu Ser Arg
            1145                1150                1155
        Pro Val Thr Leu Asp Val Leu His Ala Pro Arg Asn Leu Arg Leu
            1160                1165                1170
        Thr Tyr Leu Leu Glu Thr Gln Gly Arg Gln Leu Ala Leu Val Leu
            1175                1180                1185
        Cys Thr Val Asp Ser Arg Pro Pro Ala Gln Leu Thr Leu Ser His
            1190                1195                1200
        Gly Asp Gln Leu Val Ala Ser Ser Thr Glu Ala Ser Val Pro Asn
            1205                1210                1215
        Thr Leu Arg Leu Glu Leu Gln Asp Pro Arg Pro Ser Asn Glu Gly
            1220                1225                1230
        Leu Tyr Ser Cys Ser Ala His Ser Pro Leu Gly Lys Ala Asn Thr
            1235                1240                1245
        Ser Leu Glu Leu Leu Leu Glu Gly Val Arg Val Lys Met Asn Pro
            1250                1255                1260
        Ser Gly Ser Val Pro Glu Gly Glu Pro Val Thr Val Thr Cys Glu
            1265                1270                1275
        Asp Pro Ala Ala Leu Ser Ser Ala Leu Tyr Ala Trp Phe His Asn
            1280                1285                1290
        Gly His Trp Leu Gln Glu Gly Pro Ala Ser Ser Leu Gln Phe Leu
            1295                1300                1305
        Val Thr Thr Arg Ala His Ala Gly Ala Tyr Phe Cys Gln Val His
            1310                1315                1320
        Asp Thr Gln Gly Thr Arg Ser Ser Arg Pro Ala Ser Leu Gln Ile
            1325                1330                1335
        Leu Tyr Ala Pro Arg Asp Ala Val Leu Ser Ser Phe Arg Asp Ser
            1340                1345                1350
```

| | | | | | | | | | | |
|---|---|---|---|---|---|---|---|---|---|---|
| Arg | Thr | Arg | Leu | Met | Val | Val | Ile | Gln | Cys | Thr | Val | Asp | Ser | Glu |
| | 1355 | | | | 1360 | | | | 1365 | | | | | |

Pro Pro Ala Glu Met Val Leu Ser His Asn Gly Lys Val Leu Ala
1370           1375                1380

Ala Ser His Glu Arg His Ser Ser Ala Ser Gly Ile Gly His Ile
1385           1390                1395

Gln Val Ala Arg Asn Ala Leu Arg Leu Gln Val Gln Asp Val Thr
1400           1405                1410

Leu Gly Asp Gly Asn Thr Tyr Val Cys Thr Ala Gln Asn Thr Leu
1415           1420                1425

Gly Ser Ile Ser Thr Thr Gln Arg Leu Leu Thr Glu Thr Asp Ile
1430           1435                1440

Arg Val Thr Ala Glu Pro Gly Leu Asp Val Pro Glu Gly Thr Ala
1445           1450                1455

Leu Asn Leu Ser Cys Leu Leu Pro Gly Gly Ser Gly Pro Thr Gly
1460           1465                1470

Asn Ser Ser Phe Thr Trp Phe Trp Asn Arg His Arg Leu His Ser
1475           1480                1485

Ala Pro Val Pro Thr Leu Ser Phe Thr Pro Val Val Arg Ala Gln
1490           1495                1500

Ala Gly Leu Tyr His Cys Arg Ala Asp Leu Pro Thr Gly Ala Thr
1505           1510                1515

Thr Ser Ala Pro Val Met Leu Arg Val Leu Tyr Pro Pro Lys Thr
1520           1525                1530

Pro Thr Leu Ile Val Phe Val Glu Pro Gln Gly Gly His Gln Gly
1535           1540                1545

Ile Leu Asp Cys Arg Val Asp Ser Glu Pro Leu Ala Ile Leu Thr
1550           1555                1560

Leu His Arg Gly Ser Gln Leu Val Ala Ser Asn Gln Leu His Asp
1565           1570                1575

Ala Pro Thr Lys Pro His Ile Arg Val Thr Ala Pro Pro Asn Ala
1580           1585                1590

Leu Arg Val Asp Ile Glu Glu Leu Gly Pro Ser Asn Gln Gly Glu
1595           1600                1605

Tyr Val Cys Thr Ala Ser Asn Thr Leu Gly Ser Ala Ser Ala Ser
1610           1615                1620

Ala Tyr Phe Gly Thr Arg Ala Leu His Gln Leu Gln Leu Phe Gln
1625           1630                1635

Arg Leu Leu Trp Val Leu Gly Phe Leu Ala Gly Phe Leu Cys Leu
1640           1645                1650

Leu Leu Gly Leu Val Ala Tyr His Thr Trp Arg Lys Lys Ser Ser
1655           1660                1665

Thr Lys Leu Asn Glu Asp Glu Asn Ser Ala Glu Met Ala Thr Lys
1670           1675                1680

Lys Asn Thr Ile Gln Glu Glu Val Val Ala Ala Leu
1685           1690                1695

<210> SEQ ID NO 8
<211> LENGTH: 6387
<212> TYPE: DNA
<213> ORGANISM: Mus musculus

<400> SEQUENCE: 8
agacaagatt aggcctagag taagtctatg aaacacagag aaaggggaca gcatagggt      60 taagaaatga ggtctttcaa aatctcaggg ggcaatgagg agttttttga gagaggaagg    120

```
actctttaaa ggaagttgaa ggaggattct gtgaacttga gaccaccctg agctgccaag      180
ttgagaactt tgtctacaaa caagccaggc agcctcagcg tgtgctcagt ccgacttgta      240
gctggagagg caggagacca atttccggtg cttacggtgc ttgctggatg ccctggagta      300
agtgacaggg tctcactgga ctccaggttc tgttggtttg agtaatagga ggcggcaggg      360
gagaagtgaa gagagacatg cactgctgat ctgccttgag gctgtgtcct taagggtgg       420 agccaagggg cacagaagac tctctgggac atgccaccaa gtgagagcat ttccaatcac      480
tccctgagcc aggaacaggg gcttctgtt ccctgctggt ggctgccaca gcagtccttc       540
ctgttgggtt gaccaacaca gcaggtgaga taaaccctat agacttgggc cctggagtgc      600
tccaggcagt ctctgtgtgc ctacccaccc ggcttcccta ggcacctgaa tgcacctggg      660
cactgggatg tgtgtcctgt tctccctgct cctgctggcc tctgtcttct cactaggcca      720
gaccacatgg ggtgtctcca gtcccaagaa tgtgcagggc ttgtcgggat cctgcctgct      780
cattccctgc atcttcagct accctgccga tgtcccagtg tccaatggca tcacagccat      840
ctggtactat gactactcgg gcaagcggca ggtggtaatc cactcagggg accccaagct      900
ggtggacaag cgtttcaggg gtcgagctga actgatgggg aacatggacc acaaggtgtg      960
caacctgttg ctcaaagact tgaagcctga agactctggc acctacaact tccgctttga      1020
gatcagtgat agcaaccgct ggttagatgt caaaggcacc acggtcactg tgacaacgga      1080
tcccagcccc ccactatta ccattcctga ggagctgcgt gaaggcatgg agaggaactt       1140
caactgttcc acaccctacc tgtgcctgca ggagaagcaa gtcagcctgc agtggcgagg      1200
ccaggacccc accactctg tcacctccag cttccagagc ctcgagccca ctggcgtcta       1260
tcaccagacg accctacata tggccctatc ctggcaggac cacggtcgga ccctgctctg      1320
ccagttctca ttgggcgcac acagtagtcg gaaagaggtt tacctgcaag tgccacatgc      1380
ccccaaaggt gtggagatcc tcctcagctc tcaggaggg aacatccttc ccggggatcc       1440
agtcacactc acctgcagag tgaacagcag ctatcctgct gtcagtgccg tgcagtgggc      1500
cagggacgga gtgaacctcg gagtcacggg acatgtgctt cggctgttct cagcagcctg      1560
gaatgattct ggggcctaca cctgccaagc aacaaatgat atgggctctc tggtgtcatc      1620
cccgctcagc ctccatgttt ttatggctga agtcaaaatg aaccccgcag ggcccgtctt      1680
ggaaaatgag acagtgactc tgctctgtag cacgccgaag gaggctcccc aggagctccg      1740
ctatagctgg tacaagaacc acattctcct ggaagatgcc catgcctcaa ccttgcacct      1800
gcctgcagtc accagggctg atactggctt ctacttctgt gaagtgcaga atgcccaggg      1860
cagtgagcgc tccagtccat tgagtgtggt ggtcagatat ccaccccctta ctccagacct      1920 gaccaccttc ctggagacac aggccggact tgtgggcatc ttgcattgct ccgtggtcag      1980
tgagcccctg gctactgtgg tgctgtcaca cggaggcctc acgttggcct ccaactctgg      2040
agaaaatgac ttcaacccccc gattcaggat ctcctctgcc cccaactccc tgcgcctaga     2100
aatccgagac ttgcagccag cagacagcgg agagtacaca tgcttagctg tcaactccct      2160
tggaaactca acgtccagcc tagacttcta tgctaatgtg gcccgactcc tcatcaaccc      2220
ttcagcagag gttgtggaag gcaggcggt gaccctgagc tgcaggagtg gcctgagccc       2280
agctcctgac actcgcttct cctggtacct gaacggagct ctacttctgg aaggatccag      2340
cagcagcctc ctgcttcctg cggcttccag cactgatgcg ggctcatact actgtaggac      2400
gcaggctggc cccaacacca gcggcccctc cctgcctact gtcctcactg tgttctatcc      2460
cccaagaaag cccacattca ctgccaggct ggatttggat acctctggag tcggggatgg      2520
```

```
acgacgggc atcctcttgt gccacgtaga cagcgatccc ccagcccagc tacggcttct   2580
ccacaaaggc catgttgtgg ccacttctct gccatcaagg tgtgggagct gttcccagcg   2640
cacaaaagtc agcagaacct ccaactcact gcacgtggag atccagaagc ctgtattaga   2700
ggatgagggc gtgtacctgt gtgaggctag caacacattg ggcaactcct cagccgcagc   2760
ctctttcaat gctaaggcca ctgtactggt catcacaccg tcaaatacac tgcgtgaagg   2820
cacagaggcc aacctaactt gcaacgtgaa ccaggaggtt gctgtcagcc ctgccaactt   2880
ctcctggttc cggaatggag tgctgtggac ccagggatca ctggagactg tgaggctgca   2940
gcctgtggcc agaactgatg ctgctgtcta tgcctgccgc ctcctcaccg aggatggggc   3000
tcagctctcg gctcctgtgg tcctaagtgt gctgtatgcc ccagaccctc caaagctgtc   3060
agccctccta gatgtgggtc agggccacat ggccgtgttc atctgcactg tggacagcta   3120 tccccctggct cacctgtctc tgttccgtgg ggaccatctc ctggccacca acttggaacc   3180
ccagcgtccc tcccatggca ggatccaggc caaggccaca gccaactccc tgcagctaga   3240
ggtccgagaa ctaggtcttg tggactctgg aaactaccac tgtgaagcca ccaatattct   3300
tgggtcagcc aacagttcac tcttcttcca ggtcagagga gcctgggtcc aggtttcacc   3360
atcacctgag ctccgggagg gccaggctgt ggtcctgagc tgccaggtgc cacaggagt   3420 ctctgagggg acctcataca gctggtatca ggatggccgc cccctccagg agtcaacctc   3480
atctacactc cgcattgcag ccataagtct gaggcaagct ggtgcctacc attgccaagc   3540
tcaggcccca gacacagcta ttgccagcct ggctgcccct gtcagcctcc atgtgtccta   3600
taccccacgt catgttacac tcagtgccct gctgagcacg gaccctgagc gactaggcca   3660
cctggtgtgc agtgtacaaa gtgaccctcc agcgcagctg caactgtttc accggaatcg   3720
cctcgtggcc tctaccctac aaggcgcgga cgaattggca ggcagtaatc cccggctgca   3780
tgtgactgtg ctccccaatg agctgcgcct gcagatccac tttccagagc tggaggatga   3840
cgggacctat acatgcgaag ccagcaacac actgggccag gcctcggctg cagctgactt   3900
cgatgcccag gctgtgcgag tgactgtgtg gcccaatgcc actgtgcaag aggggcagca   3960
ggtgaacctg acctgcttgg tgtggagcac ccaccaggac tcactcagct acacatggta   4020
caagggcggg caacaactcc ttggtgccag atccatcacc ctgcccagtg ttaaggtttt   4080
ggatgctacc tcctaccgct gtggtgtggg gctccccggc cacgcacccc atctctccag   4140
acccgtgacc ctggatgtcc tccatgctcc ccgaaacctg cggctgacct acctcctaga   4200
gacccagggc aggcagctgg ccctggtact gtgtacggtg gatagtcgtc cacctgccca   4260
gctaactctc agccatggtg accagcttgt agcctcctca actgaagcct ctgtccccaa   4320 cacccctgcgc ctagagcttc aggatccaag gcctagtaat gaggggctct atagctgctc   4380
tgcccacagc ccattgggca aggccaacac gtccctggaa cttctgctgg aaggtgtccg   4440
agtgaaaatg aatccctctg gtagtgtacc cgagggagag cctgtcacag tgacctgcga   4500
ggaccctgct gccctctcat ccgccctcta tgcctggttt cacaatggcc attggcttca   4560
ggagggaccg gcttcctcac tccagttcct ggtgactaca cgggctcacg ctggtgctta   4620
cttttgccag gtcatgata cacaaggcac acggagctcc agacctgcca gcctgcaaat   4680
tctctatgcc ccccgggatg ctgtcctgtc ttcctttcga gactcaagga ccaggctcat   4740
ggtcgtgatt cagtgcaccg tggacagtga gccacctgct gagatggtcc tatcccacaa   4800
tggcaaggtg ctagctgcca gccacgagcg tcacagctca gcatcaggga taggccacat   4860
ccaggtagcc cgaaatgctc ttcgactaca agtgcaagat gtgactctgg gtgatggcaa   4920
```

```
cacctatgtt tgcacagccc agaatacact gggctccatc agtaccaccc agaggcttct    4980
gacggagact gatatacgtg tgacagctga gccaggcttg gatgtgccag agggcacagc    5040
tctgaactta agctgcctcc tccctggtgg ctctgggccc acgggcaact cttccttcac    5100
gtggttctgg aatcgccacc gactacattc agctcctgtg cccacactct ccttcacccc    5160
tgtggtccgg gctcaggctg gctgtaccac tgcagggct gatctcccca ccggggccac     5220
tacctctgct ccagttatgc tccgtgtcct ctatccccc aagacgccca ctctcatagt     5280
gtttgtggag cctcagggtg gccaccaggg catcctcgac tgtcgagtgg acagtgagcc    5340
cctggccatc ctcactcttc accggggcag tcaactagta gcctccaacc aacttcacga    5400
tgctcccacc aagccccaca tccgagtcac tgctcctccc aatgccttga gagtggacat    5460
agaggagctc ggccctagca atcaagggga gtatgtgtgc actgcctcca acactctggg    5520
ctctgcctca gcctctgcct actttgggac cagagctctg caccaactgc agctgttcca    5580
gaggctgctc tgggtcctgg gatttctggc aggcttcctg tgcctgctgc tgggtctggt    5640
ggcctatcac acctggagaa agaagagttc taccaagctg aatgaggatg agaattcagc    5700
agagatggcc actaagaaaa atactatcca ggaggaagtg gttgctgctc tctgacaact    5760
caggtgctgt gaacaagatc ctgcctacct ctgtataagc agtacagaga catctggctt    5820
tcctgacctg cccgacttgc cttccaagcc tcttgatcct aagaaaaatg gacgaaggga    5880
ggtttggggt tggaggtcaa cctgccgcct ccagggctct gagacggact cagccatgtt    5940
gcccacgtct ctctgtgtgg ttttcctctg tatcccttg cctttctctt caaagctcac     6000
cttggacttt cttggtgggt tagagcaaca tccagtttct cacagacttt ctaagacggt    6060
ctgtaccagc caggatatca gtcaggttgc tctaacagag actcaataca gtgaccacag    6120
catgacaggg tcttagtttt ccctcctggc ctggttatgt tgttgtggta tcagaatcct    6180
tcttgcttga ttttctccat tccccaagtg ttgcctttga ttatgaagct caggtaactg    6240
cagtgcccat ggaccctaca gggagaagga agagtgaagg gaagacatac ccatccccat    6300
ggtccatgga ctgtgtgtgc aattgcaccc cacccaactt ctcatccgct agaaactggt    6360
cacataaaca taccatgctg aaaggga                                       6387
```

<210> SEQ ID NO 9
<211> LENGTH: 1709
<212> TYPE: PRT
<213> ORGANISM: Homo sapiens

<400> SEQUENCE: 9

```
Met Gly Phe Leu Pro Lys Leu Leu Leu Ala Ser Phe Phe Pro Ala
1               5                   10                  15

Gly Gln Ala Ser Trp Gly Val Ser Ser Pro Gln Asp Val Gln Gly Val
            20                  25                  30

Lys Gly Ser Cys Leu Leu Ile Pro Cys Ile Phe Ser Phe Pro Ala Asp
        35                  40                  45

Val Glu Val Pro Asp Gly Ile Thr Ala Ile Trp Tyr Tyr Asp Tyr Ser
    50                  55                  60

Gly Gln Arg Gln Val Val Ser His Ser Ala Asp Pro Lys Leu Val Glu
65                  70                  75                  80

Ala Arg Phe Arg Gly Arg Thr Glu Phe Met Gly Asn Pro Glu His Arg
                85                  90                  95

Val Cys Asn Leu Leu Leu Lys Asp Leu Gln Pro Glu Asp Ser Gly Ser
            100                 105                 110
```

```
Tyr Asn Phe Arg Phe Glu Ile Ser Glu Val Asn Arg Trp Ser Asp Val
            115                 120                 125

Lys Gly Thr Leu Val Thr Val Thr Glu Glu Pro Arg Val Pro Thr Ile
130                 135                 140

Ala Ser Pro Val Glu Leu Leu Glu Gly Thr Glu Val Asp Phe Asn Cys
145                 150                 155                 160

Ser Thr Pro Tyr Val Cys Leu Gln Glu Gln Val Arg Leu Gln Trp Gln
                165                 170                 175

Gly Gln Asp Pro Ala Arg Ser Val Thr Phe Asn Ser Gln Lys Phe Glu
                180                 185                 190

Pro Thr Gly Val Gly His Leu Glu Thr Leu His Met Ala Met Ser Trp
                195                 200                 205

Gln Asp His Gly Arg Ile Leu Arg Cys Gln Leu Ser Val Ala Asn His
210                 215                 220

Arg Ala Gln Ser Glu Ile His Leu Gln Val Lys Tyr Ala Pro Lys Gly
225                 230                 235                 240

Val Lys Ile Leu Leu Ser Pro Ser Gly Arg Asn Ile Leu Pro Gly Glu
                245                 250                 255

Leu Val Thr Leu Thr Cys Gln Val Asn Ser Ser Tyr Pro Ala Val Ser
            260                 265                 270

Ser Ile Lys Trp Leu Lys Asp Gly Val Arg Leu Gln Thr Lys Thr Gly
275                 280                 285

Val Leu His Leu Pro Gln Ala Ala Trp Ser Asp Ala Gly Val Tyr Thr
290                 295                 300

Cys Gln Ala Glu Asn Gly Val Gly Ser Leu Val Ser Pro Pro Ile Ser
305                 310                 315                 320

Leu His Ile Phe Met Ala Glu Val Gln Val Ser Pro Ala Gly Pro Ile
                325                 330                 335

Leu Glu Asn Gln Thr Val Thr Leu Val Cys Asn Thr Pro Asn Glu Ala
                340                 345                 350

Pro Ser Asp Leu Arg Tyr Ser Trp Tyr Lys Asn His Val Leu Leu Glu
                355                 360                 365

Asp Ala His Ser His Thr Leu Arg Leu His Leu Ala Thr Arg Ala Asp
            370                 375                 380

Thr Gly Phe Tyr Phe Cys Glu Val Gln Asn Val His Gly Ser Glu Arg
385                 390                 395                 400

Ser Gly Pro Val Ser Val Val Asn His Pro Leu Thr Pro Val
                405                 410                 415

Leu Thr Ala Phe Leu Glu Thr Gln Ala Gly Leu Val Gly Ile Leu His
                420                 425                 430

Cys Ser Val Val Ser Glu Pro Leu Ala Thr Leu Val Leu Ser His Gly
            435                 440                 445

Gly His Ile Leu Ala Ser Thr Ser Gly Asp Ser Asp His Ser Pro Arg
450                 455                 460

Phe Ser Gly Thr Ser Gly Pro Asn Ser Leu Arg Leu Glu Ile Arg Asp
465                 470                 475                 480

Leu Glu Glu Thr Asp Ser Gly Glu Tyr Lys Cys Ser Ala Thr Asn Ser
                485                 490                 495

Leu Gly Asn Ala Thr Ser Thr Leu Asp Phe His Ala Asn Ala Ala Arg
                500                 505                 510

Leu Leu Ile Ser Pro Ala Ala Glu Val Val Glu Gly Gln Ala Val Thr
            515                 520                 525

Leu Ser Cys Arg Ser Gly Leu Ser Pro Thr Pro Asp Ala Arg Phe Ser
530                 535                 540
```

```
Trp Tyr Leu Asn Gly Ala Leu Leu His Glu Gly Pro Gly Ser Ser Leu
545                 550                 555                 560

Leu Leu Pro Ala Ala Ser Ser Thr Asp Ala Gly Ser Tyr His Cys Arg
            565                 570                 575

Ala Arg Asp Gly His Ser Ala Ser Gly Pro Ser Ser Pro Ala Val Leu
            580                 585                 590

Thr Val Leu Tyr Pro Pro Arg Gln Pro Thr Phe Thr Thr Arg Leu Asp
            595                 600                 605

Leu Asp Ala Ala Gly Ala Gly Ala Gly Arg Arg Gly Leu Leu Leu Cys
    610                 615                 620

Arg Val Asp Ser Asp Pro Pro Ala Arg Leu Gln Leu Leu His Lys Asp
625                 630                 635                 640

Arg Val Val Ala Thr Ser Leu Pro Ser Gly Gly Cys Ser Thr Cys
                645                 650                 655

Gly Gly Cys Ser Pro Arg Met Lys Val Thr Lys Ala Pro Asn Leu Leu
            660                 665                 670

Arg Val Glu Ile His Asn Pro Leu Glu Glu Gly Leu Tyr Leu
    675                 680                 685

Cys Glu Ala Ser Asn Ala Leu Gly Asn Ala Ser Ser Ala Thr Phe
    690                 695                 700

Asn Gly Gln Ala Thr Val Leu Ala Ile Ala Pro Ser His Thr Leu Gln
705                 710                 715                 720

Glu Gly Thr Glu Ala Asn Leu Thr Cys Asn Val Ser Arg Glu Ala Ala
            725                 730                 735

Gly Ser Pro Ala Asn Phe Ser Trp Phe Arg Asn Gly Val Leu Trp Ala
            740                 745                 750

Gln Gly Pro Leu Glu Thr Val Thr Leu Pro Val Ala Arg Thr Asp
            755                 760                 765

Ala Ala Leu Tyr Ala Cys Arg Ile Leu Thr Glu Ala Gly Ala Gln Leu
    770                 775                 780

Ser Thr Pro Val Leu Leu Ser Val Leu Tyr Pro Pro Asp Arg Pro Lys
785                 790                 795                 800

Leu Ser Ala Leu Leu Asp Met Gly Gln Gly His Met Ala Leu Phe Ile
            805                 810                 815

Cys Thr Val Asp Ser Arg Pro Leu Ala Leu Leu Ala Leu Phe His Gly
            820                 825                 830

Glu His Leu Leu Ala Thr Ser Leu Gly Pro Gln Val Pro Ser His Gly
    835                 840                 845

Arg Phe Gln Ala Lys Ala Glu Ala Asn Ser Leu Lys Leu Glu Val Arg
    850                 855                 860

Glu Leu Gly Leu Gly Asp Ser Gly Ser Tyr Arg Cys Glu Ala Thr Asn
865                 870                 875                 880

Val Leu Gly Ser Ser Asn Thr Ser Leu Phe Phe Gln Val Arg Gly Ala
            885                 890                 895

Trp Val Gln Val Ser Pro Ser Pro Glu Leu Gln Glu Gly Gln Ala Val
            900                 905                 910

Val Leu Ser Cys Gln Val His Thr Gly Val Pro Glu Gly Thr Ser Tyr
    915                 920                 925

Arg Trp Tyr Arg Asp Gly Gln Pro Leu Gln Glu Ser Thr Ser Ala Thr
    930                 935                 940

Leu Arg Phe Ala Ala Ile Thr Leu Thr Gln Ala Gly Ala Tyr His Cys
945                 950                 955                 960

Gln Ala Gln Ala Pro Gly Ser Ala Thr Thr Ser Leu Ala Ala Pro Ile
```

```
                      965                 970                 975
Ser Leu His Val Ser Tyr Ala Pro Arg His Val Thr Leu Thr Thr Leu
              980                 985                 990
Met Asp Thr Gly Pro Gly Arg Leu  Gly Leu Leu Leu Cys  Arg Val Asp
          995                 1000                1005
Ser Asp Pro Pro Ala Gln Leu Arg Leu Leu His Gly  Asp Arg Leu
    1010                1015                1020
Val Ala Ser Thr Leu Gln Gly Val Gly Gly Pro Glu  Gly Ser Ser
    1025                1030                1035
Pro Arg Leu His Val Ala Val Ala Pro Asn Thr Leu  Arg Leu Glu
    1040                1045                1050
Ile His Gly Ala Met Leu Glu Asp Glu Gly Val Tyr  Ile Cys Glu
    1055                1060                1065
Ala Ser Asn Thr Leu Gly Gln Ala Ser Ala Ser Ala  Asp Phe Asp
    1070                1075                1080
Ala Gln Ala Val Asn Val Gln Val Trp Pro Gly Ala  Thr Val Arg
    1085                1090                1095
Glu Gly Gln Leu Val Asn Leu Thr Cys Leu Val Trp  Thr Thr His
    1100                1105                1110
Pro Ala Gln Leu Thr Tyr Thr Trp Tyr Gln Asp Gly  Gln Gln Arg
    1115                1120                1125
Leu Asp Ala His Ser Ile Pro Leu Pro Asn Val Thr  Val Arg Asp
    1130                1135                1140
Ala Thr Ser Tyr Arg Cys Gly Val Gly Pro Pro Gly  Arg Ala Pro
    1145                1150                1155
Arg Leu Ser Arg Pro Ile Thr Leu Asp Val Leu Tyr  Ala Pro Arg
    1160                1165                1170
Asn Leu Arg Leu Thr Tyr Leu Leu Glu Ser His Gly  Gly Gln Leu
    1175                1180                1185
Ala Leu Val Leu Cys Thr Val Asp Ser Arg Pro Pro  Ala Gln Leu
    1190                1195                1200
Ala Leu Ser His Ala Gly Arg Leu Leu Ala Ser Ser  Thr Ala Ala
    1205                1210                1215
Ser Val Pro Asn Thr Leu Arg Leu Glu Leu Arg Gly  Pro Gln Pro
    1220                1225                1230
Arg Asp Glu Gly Phe Tyr Ser Cys Ser Ala Arg Ser  Pro Leu Gly
    1235                1240                1245
Gln Ala Asn Thr Ser Leu Glu Leu Arg Leu Glu Gly  Val Arg Val
    1250                1255                1260
Ile Leu Ala Pro Glu Ala Ala Val Pro Glu Gly Ala  Pro Ile Thr
    1265                1270                1275
Val Thr Cys Ala Asp Pro Ala Ala His Ala Pro Thr  Leu Tyr Thr
    1280                1285                1290
Trp Tyr His Asn Gly Arg Trp Leu Gln Glu Gly Pro  Ala Ala Ser
    1295                1300                1305
Leu Ser Phe Leu Val Ala Thr Arg Ala His Ala Gly  Ala Tyr Ser
    1310                1315                1320
Cys Gln Ala Gln Asp Ala Gln Gly Thr Arg Ser Ser  Arg Pro Ala
    1325                1330                1335
Ala Leu Gln Val Leu Tyr Ala Pro Gln Asp Ala Val  Leu Ser Ser
    1340                1345                1350
Phe Arg Asp Ser Arg Ala Arg Ser Met Ala Val Ile  Gln Cys Thr
    1355                1360                1365
```

| Val | Asp | Ser | Glu | Pro | Ala | Glu | Leu | Ala | Leu | Ser | His | Asp | Gly |
| | 1370 | | | | 1375 | | | | 1380 | | | | |

| Lys | Val | Leu | Ala | Thr | Ser | Ser | Gly | Val | His | Ser | Leu | Ala | Ser | Gly |
| 1385 | | | | | 1390 | | | | | 1395 | | | | |

| Thr | Gly | His | Val | Gln | Val | Ala | Arg | Asn | Ala | Leu | Arg | Leu | Gln | Val |
| 1400 | | | | | 1405 | | | | | 1410 | | | | |

| Gln | Asp | Val | Pro | Ala | Gly | Asp | Asp | Thr | Tyr | Val | Cys | Thr | Ala | Gln |
| 1415 | | | | | 1420 | | | | | 1425 | | | | |

| Asn | Leu | Leu | Gly | Ser | Ile | Ser | Thr | Ile | Gly | Arg | Leu | Gln | Val | Glu |
| 1430 | | | | | 1435 | | | | | 1440 | | | | |

| Gly | Ala | Arg | Val | Val | Ala | Glu | Pro | Gly | Leu | Asp | Val | Pro | Glu | Gly |
| 1445 | | | | | 1450 | | | | | 1455 | | | | |

| Ala | Ala | Leu | Asn | Leu | Ser | Cys | Arg | Leu | Leu | Gly | Gly | Pro | Gly | Pro |
| 1460 | | | | | 1465 | | | | | 1470 | | | | |

| Val | Gly | Asn | Ser | Thr | Phe | Ala | Trp | Phe | Trp | Asn | Asp | Arg | Arg | Leu |
| 1475 | | | | | 1480 | | | | | 1485 | | | | |

| His | Ala | Glu | Pro | Val | Pro | Thr | Leu | Ala | Phe | Thr | His | Val | Ala | Arg |
| 1490 | | | | | 1495 | | | | | 1500 | | | | |

| Ala | Gln | Ala | Gly | Met | Tyr | His | Cys | Leu | Ala | Glu | Leu | Pro | Thr | Gly |
| 1505 | | | | | 1510 | | | | | 1515 | | | | |

| Ala | Ala | Ala | Ser | Ala | Pro | Val | Met | Leu | Arg | Val | Leu | Tyr | Pro | Pro |
| 1520 | | | | | 1525 | | | | | 1530 | | | | |

| Lys | Thr | Pro | Thr | Met | Met | Val | Phe | Val | Glu | Pro | Glu | Gly | Gly | Leu |
| 1535 | | | | | 1540 | | | | | 1545 | | | | |

| Arg | Gly | Ile | Leu | Asp | Cys | Arg | Val | Asp | Ser | Glu | Pro | Leu | Ala | Ser |
| 1550 | | | | | 1555 | | | | | 1560 | | | | |

| Leu | Thr | Leu | His | Leu | Gly | Ser | Arg | Leu | Val | Ala | Ser | Ser | Gln | Pro |
| 1565 | | | | | 1570 | | | | | 1575 | | | | |

| Gln | Gly | Ala | Pro | Ala | Glu | Pro | His | Ile | His | Val | Leu | Ala | Ser | Pro |
| 1580 | | | | | 1585 | | | | | 1590 | | | | |

| Asn | Ala | Leu | Arg | Val | Asp | Ile | Glu | Ala | Leu | Arg | Pro | Ser | Asp | Gln |
| 1595 | | | | | 1600 | | | | | 1605 | | | | |

| Gly | Glu | Tyr | Ile | Cys | Ser | Ala | Ser | Asn | Val | Leu | Gly | Ser | Ala | Ser |
| 1610 | | | | | 1615 | | | | | 1620 | | | | |

| Thr | Ser | Thr | Tyr | Phe | Gly | Val | Arg | Ala | Leu | His | Arg | Leu | His | Gln |
| 1625 | | | | | 1630 | | | | | 1635 | | | | |

| Phe | Gln | Gln | Leu | Leu | Trp | Val | Leu | Gly | Leu | Leu | Val | Gly | Leu | Leu |
| 1640 | | | | | 1645 | | | | | 1650 | | | | |

| Leu | Leu | Leu | Leu | Gly | Leu | Gly | Ala | Cys | Tyr | Thr | Trp | Arg | Arg | Arg |
| 1655 | | | | | 1660 | | | | | 1665 | | | | |

| Arg | Val | Cys | Lys | Gln | Ser | Met | Gly | Glu | Asn | Ser | Val | Glu | Met | Ala |
| 1670 | | | | | 1675 | | | | | 1680 | | | | |

| Phe | Gln | Lys | Glu | Thr | Thr | Gln | Leu | Ile | Asp | Pro | Asp | Ala | Ala | Thr |
| 1685 | | | | | 1690 | | | | | 1695 | | | | |

| Cys | Glu | Thr | Ser | Thr | Cys | Ala | Pro | Pro | Leu | Gly |
| 1700 | | | | | 1705 | | | | | |

<210> SEQ ID NO 10
<211> LENGTH: 6736
<212> TYPE: DNA
<213> ORGANISM: Homo sapiens

<400> SEQUENCE: 10

```
atgggcttct tgcccaagct tctcctcctg gcctcattct tcccagcagg ccaggcctca    60
tggggcgtct ccagtcccca ggacgtgcag ggtgtgaagg ggtcttgcct gcttatcccc   120
```

-continued

```
tgcatcttca gcttccctgc cgacgtggag gtgcccgacg gcatcacggc catctggtac      180
tacgactact cgggccagcg gcaggtggtg agccactcgg cggaccccaa gctggtggag      240
gcccgcttcc gcggccgcac cgagttcatg gggaacccccg agcacagggt gtgcaacctg     300
ctgctgaagg acctgcagcc cgaggactct ggttcctaca acttccgctt cgagatcagt     360
gaggtcaacc gctggtcaga tgtgaaaggc accttggtca cagtaacaga ggagcccagg      420
gtgcccacca ttgcctcccc ggtggagctt ctcgagggca cagaggtgga cttcaactgc      480
tccactccct acgtatgcct gcaggagcag gtcagactgc agtggcaagg ccaggaccct      540
gctcgctctg tcaccttcaa cagccagaag tttgagccca ccggcgtcgg ccacctggag      600
accctccaca tggccatgtc ctggcaggac acggccggaa tcctgcgctg ccagctctcc      660
gtggccaatc acagggctca gagcgagatt cacctccaag tgaagtatgc ccccaagggt      720
gtgaagatcc tcctcagccc ctcggggagg aacatccttc caggtgagct ggtcacactc      780
acctgccagg tgaacagcag ctaccctgca gtcagttcca ttaagtggct caaggatggg      840
gtacgcctcc aaaccaagac tggtgtgctg cacctgcccc aggcagcctg agcgatgct      900 ggcgtctaca cctgccaagc tgagaacggc gtgggctctt tggtctcacc ccccatcagc      960
ctccacatct tcatggctga ggtccaggtg agcccagcag gtcccatcct ggagaaccag     1020
acagtgacac tagtctgcaa cacacccaat gaggcaccca gtgatctccg ctacagctgg     1080
tacaagaacc atgtcctgct ggaggatgcc cactcccata ccctccggct gcacttggcc     1140
actagggctg atactggctt ctacttctgt gaggtgcaga acgtccatgg cagcgagcgc     1200
tcgggccctg tcagcgtggt agtcaaccac ccgcctctca ctccagtcct gacagccttc     1260
ctggagaccc aggcgggact tgtgggcatc cttcactgct ctgtggtcag tgagcccctg     1320
gccacactgg tgctgtcaca tgggggtcat atcctggcct ccacctccgg ggacagtgat     1380
cacagcccac gcttcagtgg tacctctggt cccaactccc tgcgcctgga gatccgagac     1440
ctggaggaaa ctgacagtgg ggagtacaag tgctcagcca ccaactccct tggaaatgca     1500
acctccaccc tggacttcca tgccaatgcc gcccgtctcc tcatcagccc ggcagccgag     1560
gtggtggaag acaggcagt gacactgagc tgcagaagcg gcctaagccc cacacctgat     1620
gcccgcttct cctggtacct gaatggagcc ctgcttcacg agggtcccgg cagcagcctc     1680
ctgctccccg cggcctccag cactgacgcc ggctcatacc actgccgggc ccgggacggc     1740
cacagtgcca gtggccccctc ttcgccagct gttctcactg tgctctaccc ccctcgacaa     1800
ccaacattca ccaccaggct ggaccttgat gccgctgggg ccggggctgg acggcgaggc     1860
ctccttttgt gccgtgtgga cagcgacccc ccgccaggc tgcagctgct ccacaaggac      1920
cgtgttgtgg ccacttccct gccatcaggg ggtggctgca gcacctgtgg gggctgttcc     1980
ccacgcatga aggtcaccaa agccccccaac ttgctgcgtg tggagattca caacccttg     2040 ctggaagagg agggcttgta cctctgtgag gccagcaatg ccctgggcaa cgcctccacc     2100
tcagccacct tcaatggcca ggccactgtc ctggccattg caccatcaca cacacttcag     2160
gagggcacag aagccaactt gacttgcaac gtgagccggg aagctgctgg cagccctgct     2220
aacttctcct ggttccgaaa tggggtgctg tgggccagg gtccccctgga gaccgtgaca    2280 ctgctgcccg tggccagaac tgatgctgcc ctttacgcct gccgcatcct gactgaggct    2340
ggtgcccagc tctccactcc cgtgctcctg agtgtactct atccccccgga ccgtccaaag    2400 ctgtcagccc tcctagacat gggccagggc cacatgctc tgttcatctg cactgtggac     2460
agccgccccc tggccttgct ggccttgttc catggggagc acctcctggc caccagcctg     2520
```

```
ggtccccagg tcccatccca tggtcggttc caggctaaag ctgaggccaa ctccctgaag   2580
ttagaggtcc gagaactggg ccttggggac tctggcagct accgctgtga ggccacaaat   2640
gttcttggat catccaacac ctcactcttc ttccaggtcc gaggagcctg gtccaggtg    2700 tcaccatcac ctgagctcca agagggccag gctgtggtcc tgagctgcca ggtacacaca   2760
ggagtcccag aggggacctc atatcgttgg tatcggatg  ccagcccct ccaggagtcg    2820 acctcggcca cgctccgctt tgcagccata actttgacac aagctggggc ctatcattgc   2880
caagcccagg ccccaggctc agccaccacg agcctagctg cacccatcag cctccacgtg   2940
tcctatgccc cacgccacgt cacactcact accctgatgg acacaggccc tggacgactg   3000
ggcctcctcc tgtgccgtgt ggacagtgac cctccggccc agctgcggct gctccacggg   3060
gatcgccttg tggcctccac cctacaaggt gtgggggac  ccgaaggcag ctctcccagg   3120
ctgcatgtgg ctgtggcccc caacacactg cgtctggaga tccacggggc tatgctggag   3180
gatgagggtg tctatatctg tgaggcctcc aacaccctgg gccaggcctc ggcctcagct   3240
gacttcgacg ctcaagctgt gaatgtgcag gtgtggcccg ggctaccgt  gcgggagggg   3300 cagctggtga acctgacctg ccttgtgtgg accactcacc cggcccagct cacctacaca   3360
tggtaccagg atgggcagca gcgcctggat gcccactcca tcccctgcc  caacgtcaca   3420 gtcagggatg ccacctccta ccgctgcggt gtgggccccc tggtcgggc  accccgcctc   3480 tccagaccta tcaccttgga cgtcctctac gcgccccgca acctgcgcct gacctacctc   3540
ctggagagcc atggcgggca gctggccctg gtactgtgca ctgtggacag ccgcccgccc   3600
gcccagctgg ccctcagcca cgccggtcgc ctcttggcct cctcgacagc agcctctgtc   3660
cccaacaccc tgcgcctgga gctgcgaggg ccacagccca gggatgaggg tttctacagc   3720
tgctctgccc gcagccctct gggccaggcc aacacgtccc tggagctgcg gctggagggt   3780
gtgcgggtga tcctggctcc ggaggctgcc gtgcctgaag tgcccccat  cacagtgacc   3840 tgtgcggacc ctgctgccca cgcacccaca ctctatactt ggtaccacaa cggtcgttgg   3900
ctgcaggagg gtccagctgc ctcactctca ttcctggtgg ccacgcgggc tcatgcaggc   3960
gcctactctt gccaggccca ggatgcccag ggcacccgca gctccgtcc  tgctgccctg   4020 caagtcctct atgcccctca ggacgctgtc ctgtcctcct tccgggactc cagggccaga   4080
tccatggctg tgatacagtg cactgtggac agtgagccac ctgctgagct ggccctatct   4140
catgatggca aggtgctggc cacgagcagc ggggtccaca gcttggcatc agggacaggc   4200
catgtccagg tggcccgaaa cgccctacgg ctgcaggtgc aagatgtgcc tgcaggtgat   4260
gacacctatg tttgcacagc ccaaaacttg ctgggctcaa tcagcaccat cgggcggttg   4320
caggtagaag gtgcacgcgt ggtggcagag cctggcctgg acgtgcctga gggcgctgcc   4380
ctgaacctca gctgccgcct cctggtggc  cctgggcctg tggcaactc  cacctttgca   4440 tggttctgga atgaccggcg gctgcacgcg gagcctgtgc ccactctcgc cttcacccac   4500
gtggctcgtg ctcaagctgg gatgtaccac tgcctggctg agctcccac  tggggctgct   4560 gcctctgctc cagtcatgct ccgtgtgctc taccctccca agacgccac  catgatggtc   4620 ttcgtggagc ctgagggtgg cctccggggc atcctggatt gccgagtgga cagcgagccg   4680
ctcgccagcc tgactctcca ccttggcagt cgactggtgg cctccagtca gcccagggt   4740 gctcctgcag agccacacat ccatgtcctg gcttccccca tgccctgag  ggtggacatc   4800 gaggcgctga ggcccagcga ccaaggggaa tacatctgtt ctgcctcaaa tgtcctgggc   4860
tctgcctcta cctccaccta ctttggggtc agagccctgc accgcctgca tcagttccag   4920
```

-continued

```
cagctgctct gggtcctggg actgctggtg ggcctcctgc tcctgctgtt gggcctgggg      4980
gcctgctaca cctggagaag gaggcgtgtt tgtaagcaga gcatgggcga gaattcggtg      5040
gagatggctt ttcagaaaga gaccacgcag ctcattgatc ctgatgcagc cacatgtgag      5100
acctcaacct gtgccccacc cctgggctga ccagtggtgt tgcctgccct ccggaggaga      5160
aagtggccag aatctgtgat gactccagcc tatgaatgtg aatgaggcag tgttgagtcc      5220
tgcccgcctc tacgaaaaca gctctgtgac atctgacttt ttatgacctg gccccaagcc      5280
tcttgccccc ccaaaaatgg gtggtgagag gtctgcccag gagggtgttg accctggagg      5340
acactgaaga gcactgagct gatctcgctc tctcttctct ggatctcctc ccttctctcc      5400
atttctccct caaaggaagc cctgcccttt cacatccttc tcctcgaaag tcaccctgga      5460
ctttggttgg attgcagcat cctgcatcct cagaggctca ccaaggcatt ctgtattcaa      5520
cagagtatca gtcagcctgc tctaacaaga gaccaaatac agtgacttca acatgataga      5580
attttatttt tctctcccac gctagtctgg ctgttacgat ggtttatgat gttgggctc       5640
aggatccttc tatcttcctt ttctctatcc ctaaaatgat gcctttgatt gtgaggctca      5700
ccatggcccc gctttgtcca catgcccctcc agccagaaga aggaagagtg gaggtagaag     5760
cacacccatg cccatggtgg acgcaactca gaagctgcac aggacttttc cactcacttc      5820
ccattggctg gagtattgtc acatggctac tgcaagctac aagggagact gggaaatgta      5880
gtttttattt tgagtccaga ggacatttgg aattggactt ccaaaggact cccaactgtg      5940
agctcatccc tgagactttt gacattgttg ggaatgccac cagcaggcca tgttttgtct      6000
cagtgcccat ctactgaggg ccagggtgtg ccctggcca ttctggttgt gggcttcctg        6060
gaagaggtga tcactctcac actaagactg aggaaataaa aaaggtttgg tgttttccta      6120
gggagagagc atgccaggca gtggagttgc ctaagcagac atccttgtgc cagatttggc      6180
ccctgaaaga agagatgccc tcattcccac caccaccccc cctaccccca gggactgggt      6240
actaccttac tggcccttac aagagtggag ggcagacaca gatgttgtca gcatccttat      6300
tcctgctcca gatgcatctc tgttcatgac tgtgtgagct cctgtccttt tcctggagac      6360
cctgtgtcgg gctgttaaag agaatgagtt accaagaagg aatgacgtgc ccctgcgaat      6420
cagggaccaa caggagagag ctcttgagtg ggctagtgac tcccctgca gcctggtgga       6480
gatggtgtga ggagcgaaga gccctctgct ctaggatttg ggttgaaaaa cagagagaga      6540
agtggggagt tgccacagga gctaacacgc tgggaggcag ttgggggcgg gtgaactttg      6600
tgtagccgag gccgcaccct ccctcattcc aggctcattc attttcatgc tccattgcca      6660
gactcttgct gggagcccgt ccagaatgtc ctcccaataa aactccatcc tatgacgcaa      6720
aaaaaaaaaa aaaaaa                                                      6736
```